(12) United States Patent
Powers et al.

(10) Patent No.: US 8,772,296 B2
(45) Date of Patent: *Jul. 8, 2014

(54) BENZAMIDE DERIVATIVES AND USES RELATED THERETO

(75) Inventors: Jay P. Powers, Pacifica, CA (US); Michael Degraffenreid, San Francisco, CA (US); Lisa Julian, Redwood City, CA (US); Jacob Kaizerman, Redwood City, CA (US); Dustin McMinn, Pacifica, CA (US); Yosup Rew, Foster City, CA (US); Daqing Sun, Foster City, CA (US); Xuelei Yan, Foster City, CA (US); Zhulun Wang, Palo Alto, CA (US); Felix Gonzalez Lopez De Turiso, San Mateo, CA (US)

(73) Assignee: Amgen Inc., Thousands Oaks, CA (US)

( * ) Notice: Subject to any disclaimer, the term of this patent is extended or adjusted under 35 U.S.C. 154(b) by 1132 days.

This patent is subject to a terminal disclaimer.

(21) Appl. No.: 11/806,461

(22) Filed: May 31, 2007

(65) Prior Publication Data

US 2007/0299080 A1 Dec. 27, 2007

Related U.S. Application Data

(60) Provisional application No. 60/811,758, filed on Jun. 8, 2006, provisional application No. 60/879,539, filed on Jan. 10, 2007.

(51) Int. Cl.

| | | |
|---|---|---|
| *A61K 31/166* | (2006.01) | |
| *A61K 31/381* | (2006.01) | |
| *A61K 31/42* | (2006.01) | |
| *A61K 31/426* | (2006.01) | |
| *A61K 31/44* | (2006.01) | |
| *A61K 31/4965* | (2006.01) | |
| *A61K 31/50* | (2006.01) | |
| *A61K 31/505* | (2006.01) | |
| *A61P 3/04* | (2006.01) | |
| *A61P 3/10* | (2006.01) | |
| *C07C 235/42* | (2006.01) | |
| *C07C 271/12* | (2006.01) | |
| *C07D 213/56* | (2006.01) | |
| *C07D 237/08* | (2006.01) | |
| *C07D 239/26* | (2006.01) | |
| *C07D 241/12* | (2006.01) | |
| *C07D 261/08* | (2006.01) | |
| *C07D 277/30* | (2006.01) | |
| *C07D 333/24* | (2006.01) | |
| *C07D 333/38* | (2006.01) | |
| *C07D 277/22* | (2006.01) | |
| *C07C 237/24* | (2006.01) | |
| *C07C 237/42* | (2006.01) | |
| *C07C 237/22* | (2006.01) | |
| *C07C 255/31* | (2006.01) | |
| *C07C 255/46* | (2006.01) | |
| *C07C 271/20* | (2006.01) | |
| *C07C 307/06* | (2006.01) | |
| *C07D 213/30* | (2006.01) | |
| *C07D 213/53* | (2006.01) | |

(52) U.S. Cl.
CPC ............ *C07C 235/42* (2013.01); *C07D 277/22* (2013.01); *C07C 237/24* (2013.01); *C07C 237/42* (2013.01); *C07C 237/22* (2013.01); *C07D 237/08* (2013.01); *C07C 255/31* (2013.01); *C07C 255/46* (2013.01); *C07C 271/12* (2013.01); *C07C 271/20* (2013.01); *C07C 307/06* (2013.01); *C07D 213/30* (2013.01); *C07D 213/53* (2013.01); *C07D 239/26* (2013.01); *C07D 241/12* (2013.01); *C07D 261/08* (2013.01); *C07C 2101/02* (2013.01); *C07C 2101/14* (2013.01); *C07C 2103/94* (2013.01); *A61K 31/166* (2013.01); *A61K 31/381* (2013.01); *A61K 31/42* (2013.01); *A61K 31/426* (2013.01); *A61K 31/44* (2013.01); *A61K 31/4965* (2013.01); *A61K 31/50* (2013.01); *A61K 31/505* (2013.01)
USPC ........ 514/252.1; 514/247; 514/256; 514/357; 514/365; 514/378; 514/438; 514/448; 514/616; 514/622; 544/224; 544/335; 544/336; 546/330; 548/204; 548/247; 549/72; 549/77; 560/164; 564/153; 564/158; 564/176

(58) Field of Classification Search
CPC .. C07C 235/42; C07C 237/24; C07C 237/42; C07C 255/31; C07C 255/46; C07C 271/12; C07C 271/20; C07C 307/06; C07C 237/22; C07C 2101/02; C07C 2101/14; C07C 2103/94; C07D 277/22; C07D 213/30; C07D 213/53; C07D 237/08; C07D 239/26; C07D 241/12; C07D 261/08; A61K 31/166; A61K 31/381; A61K 31/42; A61K 31/426; A61K 31/44; A61K 31/4965; A61K 31/50
See application file for complete search history.

(56) References Cited

U.S. PATENT DOCUMENTS

| | | | |
|---|---|---|---|
| 3,536,809 A | 10/1970 | Allplezwqeig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,098,904 A | 7/1978 | Szmuszkovicz | |
| 4,148,914 A | 4/1979 | Szmuszkovicz | |
| 4,152,459 A | 5/1979 | Szmuszkovicz | |
| 4,153,717 A | 5/1979 | Szmuszkovicz | |
| 4,179,501 A | 12/1979 | Szmuszkovicz | |
| 4,192,885 A | 3/1980 | Szmuszkovicz | |
| 4,197,308 A | 4/1980 | Szmuszkovicz | |
| 4,215,114 A | 7/1980 | Szmuszkovicz | |
| 4,765,539 A | 8/1988 | Noakes et al. | |
| 4,914,108 A | 4/1990 | Khanna et al. | |
| 4,962,885 A | 10/1990 | Coffee | |
| 5,019,581 A | 5/1991 | Khanna et al. | |
| 5,059,595 A | 10/1991 | Le Grazie et al. | |
| 5,073,543 A | 12/1991 | Marshall et al. | |
| 5,112,598 A | 5/1992 | Biesalski | |
| 5,120,548 A | 6/1992 | McClelland et al. | |
| 5,223,539 A | 6/1993 | Nosal et al. | |
| 5,227,384 A | 7/1993 | Khanna et al. | |
| 5,262,426 A | 11/1993 | Weier et al. | |
| 5,302,601 A | 4/1994 | Khannal et al. | |
| 5,354,556 A | 10/1994 | Sparks et al. | |

| | | | |
|---|---|---|---|
| 5,359,073 | A | 10/1994 | Weier et al. |
| 5,360,907 | A | 11/1994 | Lentz et al. |
| 5,455,273 | A | 10/1995 | Maier et al. |
| 5,556,611 | A | 9/1996 | Biesalski |
| 5,591,767 | A | 1/1997 | Mohr et al. |
| 5,639,476 | A | 6/1997 | Oshlack et al. |
| 5,652,363 | A | 7/1997 | Khanna et al. |
| 5,674,533 | A | 10/1997 | Santus et al. |
| 5,733,566 | A | 3/1998 | Lewis |
| 5,861,403 | A | 1/1999 | Khanna et al. |
| 5,950,619 | A | 9/1999 | van der Linden et al. |
| 5,954,047 | A | 9/1999 | Armer et al. |
| 5,970,974 | A | 10/1999 | van der Linden et al. |
| 6,008,215 | A | 12/1999 | Flockerzi |
| 6,831,193 | B2 | 12/2004 | Lee et al. |
| 6,858,651 | B2 | 2/2005 | Ackermann et al. |
| 7,605,289 | B2 * | 10/2009 | Powers et al. .......... 564/177 |

FOREIGN PATENT DOCUMENTS

| | | |
|---|---|---|
| WO | WO 94/12285 | 6/1994 |
| WO | WO 94/14543 | 7/1994 |
| WO | WO 95/26234 | 10/1995 |
| WO | WO 95/26235 | 10/1995 |
| WO | WO 95/32807 | 12/1995 |
| WO | WO 97/39745 | 10/1997 |
| WO | WO 99/47196 | 9/1999 |
| WO | WO 02/058690 | 8/2002 |
| WO | WO 2004/011410 | 2/2004 |
| WO | WO 2004/033427 | 4/2004 |
| WO | WO 2004/065351 | 8/2004 |
| WO | WO 2004/072034 | 8/2004 |
| WO | WO 2004/089896 | 10/2004 |
| WO | WO 2004/111003 | 12/2004 |
| WO | WO 2006/138508 | 12/2006 |

OTHER PUBLICATIONS

Draper et al. "11b-Hydroxysteroid dehydrogenase and the pre-receptor regulation of corticosteroid hormone action" J. Endocrinology, 2005, 186, 251-271.*
Barf et al., *J. Med. Chem.*, 2002, 45: pp. 3813/3815.
Bellows et al., Bone 1998, 23: pp. 119/125.
Billaudel et al., Horm. Metab. Res. 1979, 11: pp. 555/560.
Biology of Reproduction 1999, 60: pp. 855/860.
Buchwald et al., Surgery, 1980, 88, p. 507.
Bujalska et al., Lancet 1997, 349: pp. 1210/1213.
*Burger's Medicinal Chemistry and Drug Discovery* 6th ed. (Donald J. Abraham ed., 2001, Wiley).
Cheney et al., Factors affecting binding of trans/N/[2/(methylamino) cyclohexyl]benzamides at the primary morphine receptor, J. Medicinal Chem., 1985, pp. 1853/1864, vol. 28, No. 12.
Cheney, V.B., Structure/activity relationships for drugs binding to the agonist and antagonist states of the primary morphine receptor, J. Medicinal Chem., 1988, pp. 521/531, vol. 31, No. 3.
*Controlled Drug Bioavailability, Drug Product Design and Performance*, Smolen and Ball (eds.), Wiley, New York (1984).
Cooper et al., Bone 2000, 27: pp. 375/381.
Dahl et al., Poster 524 at American Association of Cancer Research, San Francisco, Calif., Apr. 1/5, 2000.
Davani et al., J. Biol. Chem. 2000, 275: pp. 34841/34844.
de Quervain et al., Nature 1998, 394: pp. 787/790.
*Design and Application of Prodrugs* (H. Bundgaard ed., 1985, Harwood Academic Publishers Gmfh).
During et al., Ann. Neurol., 1989,25, p. 351.
Engelke et al., Poster 342 at American Association of Cancer Research, San Francisco, Calif., Apr. 1/5, 2000.
Fraser et al., Hypertension 1999, 33: pp. 1364/1368.
Geissler et al., Nat. Genet. 1994, 7: pp. 34/39.
Goodson, in Medical Applications of Controlled Release, supra, vol. 2, pp. 115 (1984).
Houssay, Endocrinology 1942, vol. 30: pp. 884/892.
Howard et al., 1989, J. Neurosurg. 71, p. 105.
Ishii et al. (2000) J. Org. Chem. 65: pp. 1597/1599.
Jamieson et al., J. Endocrinol. 2000, vol. 165: pp. 685/692.
Jens T. Carstensen, Drug Stability: Principles & Practice, 2d. Ed., Marcel Dekker, NY, NY, 1995, pp. 379/380.

Khanna et al., Facile, Regioselective Syntheses of N/Alkylated 2,3/Diaminopyridines and Imidazo[4,5/b]pyridines, J. Org. Chem., 1995, pp. 960/965, vol. 60, No. 4.
Kim et al., J. Endocrinol. 1999, 162: pp. 371 379.
Kitawaki et al., J. Clin. Endocrin. Metab., 2000, 85: pp. 3292/3296.
Kotelevtsev et al., Proc. Natl. Acad. Sci. USA 1997, vol. 94: pp. 14924/14929.
Labrie et al., Mol. Cell. Endocrinol. 1991, 78: pp. C113/C118.
Langer and Peppas, J Macromol. Sci. Rev. Macromol. Chem., 1983, 23, p. 61.
Langer, Science, 1990, 249, 1527.
Levy et al., Science 1985, 228, p. 190.
Long et al., J. Exp. Med. 1936, vol. 63, pp. 465/490.
Mason, Immunology Today 1991, 12: pp. 57/60.
*Medical Applications of Controlled Release*, Langer and Wise (eds.), CRC Pres., Boca Raton, Fla. (1974).
Montague et al., Diabetes 2000, vol. 49: pp. 883/888.
Nobel et al., Eur. J. Biochem. 2001, vol. 268, pp. 4113/4125.
Peltoketo, et al., J. Mol. Endocrinol. 1999, 23: pp. 1/11.
Penning et al., Biochem. J. 2000, 351: pp. 67/77.
Quattropani et al., J. Clin. Invest. Nov. 2001, 108: pp. 1299/1305.
Rajan et al., Neuroscience 1996, 16: pp. 65/70.
Raleigh et al., Proc. Amer. Assoc. Cancer Research Annual Meeting, 1999, 40, pp. 397.
Remington's Pharmaceutical Sciences, 18th ed., Mack Publishing, Easton PA (1990).
Rook, Baillier's Clin. Endocrinol. Metab. 2000, 13: pp. 576/581.
Saudek et al., N. Engl. J Med, 1989, 321, p. 574.
Seckl et al., Neuroendocrinol. 2000, 18: pp. 49/99.
Seckl, et al., Endocrinology, 2001, vol. 142: pp. 1371/1376.
Sefton, CRC Crit. Ref Biomed Eng., 1987, 14, p. 201.
Stokes et al., Invest. Ophthalmol. 2000, 41: pp. 1629/1638.
*The Practice of Medicinal Chemistry*; Wermuth, C.G., Ed.; Academic Press: New York, 1996; p. 203.
Thompson et al. (1995) *Tetrahedron Lett.* 49: pp. 8937/8940.
Tronche et al., Nature Genetics 1999, 23: pp. 99/103.
Walker et al., Hypertension 1998, 31: pp. 891/895.
Woods et al., Science 1998, 280: pp. 1378/1383.
Yau et al., Proc Natl. Acad. Sci. USA 2001, 98: pp. 4716/4721.
Zhu et al., Comparison of pyrrolidinyl and piperidinyl benzamides for their anticonvulsant activity and inhibitory action on sodium channel, British J. Pharm., 1992, pp. 49/54, vol. 106, No. 1.
Zhuang et al. (2001) *J. Org. Chem.* 66: pp. 1009/1013.
International Report on Patentability received in the corresponding International Patent Application No. PCT/US2007/012808, dated Dec. 24, 2008.
Kim et al., "Identification of Substituted 4-Aminopiperidines and 3-Aminopyrrolidines as Potent MCH-R1 Antagonists for the Treatment of Obesity"; *Bioorganic & Medicinal Chemistry Letters*, 2006, 16( 20), pp. 5445-5450.
Tokita et al., "FK962, a Novel Enhancer of Somatostatin Release, Exerts Cognitive-Enhancing Actions in Rats", *European Journal of Pharmacology*, 2005, 527 (1-3), pp. 111-120.
Vasudevan et al., "Identification of Aminopiperidine Benzamides as MCHr1 Antagonists", *Bioorganic & Medicinal Chemistry Letters*, 2005, 15(14), pp. 3412-3416.
McMinn, et al., "Optimization of novel di-substituted cyclohexylbenzamide derivatives as potent 11β-HSD1 inhibitors", *Bioorganic & Medicinal Chemistry Letters*, vol. 19, 2009, pp. 1446-1450.

* cited by examiner

*Primary Examiner* — Kortney L Klinkel
(74) *Attorney, Agent, or Firm* — Elsa D. Lemoine

(57) ABSTRACT

Benzamide derivatives of formula I are described and have therapeutic utility, particularly in the treatment of diabetes, obesity and related conditions and disorders:

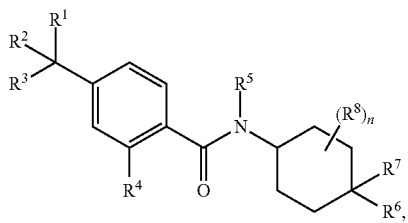
(I) wherein $R^1$, $R^2$, $R^3$, $R^4$, $R^5$, $R^6$, $R^7$, $R^8$, and n are as defined herein.
23 Claims, No Drawings

BENZAMIDE DERIVATIVES AND USES RELATED THERETO

This application claims the benefit of priority of U.S. Provisional Patent Application No. 60/811,758, which was filed on Jun. 8, 2006, and No. 60/879,539, which was filed on Jan. 10, 2007.

BACKGROUND OF THE INVENTION

This invention is generally directed to novel compounds, compositions, and the use of either in methods for modulating hydroxysteroid dehydrogenases, such as 11β-HSD1, and for treating or preventing diseases associated with the modulation of hydroxysteroid dehydrogenases, such as diabetes and obesity. The methods comprise the administration, to a patient in need thereof, of a therapeutically effective amount of a benzamide derivative. Novel benzamide derivatives or pharmaceutically acceptable salts, solvates, stereoisomers, or prodrugs thereof are presented herein.

Hydroxysteroid dehydrogenases (HSDs) regulate the occupancy and activation of steroid hormone receptors by converting steroid hormones into their inactive metabolites. For a recent review, see Nobel et al., Eur. J. Biochem. 2001, 268:4113-4125.

There exist numerous classes of HSDs. The 11-beta-hydroxysteroid dehydrogenases (11β-HSDs) catalyze the interconversion of active glucocorticoids (such as cortisol and corticosterone), and their inert forms (such as cortisone and 11-dehydrocorticosterone). The isoform 11-beta-hydroxysteroid dehydrogenase type 1 (11β-HSD1) is expressed in liver, adipose tissue, brain, lung and other glucocorticoid tissue and is a potential target for therapy directed at numerous disorders that may be ameliorated by reduction of glucocorticoid action, such as diabetes, obesity and age-related cognitive dysfunction. Seckl, et al., Endocrinology, 2001, 142:1371-1376.

It is well known that glucocorticoids play a central role in the development of diabetes and that glucocorticoids enable the effect of glucagon on the liver. Long et al., J. Exp. Med. 1936, 63: 465~490; and Houssay, Endocrinology 1942, 30: 884~892. In addition, it has been well substantiated that 11β-HSD1 plays an important role in the regulation of local glucocorticoid effect and of glucose production in the liver. Jamieson et al., J. Endocrinol. 2000, 165:685~692.

Furthermore, the hypothesized mechanism of action of HSDs in the treatment of diabetes has been supported by various experiments conducted in mice and rats. These studies showed that the mRNA levels and activities of two key enzymes in hepatic glucose production, phosphoenolpyruvate carboxykinase (PEPCK), and glucose-6-phosphatase (G6Pase) were reduced upon administration of HSD inhibitors. In addition, blood glucose levels and hepatic glucose production were shown to be reduced in 11β-HSD1 knockout mice. Additional data gathered using this murine knockout model also confirm that inhibition of 11β-HSD1 will not cause hypoglycemia, since the basal levels of PEPCK and G6Pase are regulated independently of glucocorticoids. Kotelevtsev et al., Proc. Natl. Acad. Sci. USA 1997, 94: 14924~14929.

HSDs also play a role in obesity. Obesity is an important factor in Syndrome X as well as type II (non-insulin dependent) diabetes, and omental fat appears to be of central importance in the development of both of these disease, as abdominal obesity has been linked with glucose intolerance, hyperinsulinemia, hypertriglyceridemia, and other factors of Syndrome X (e.g., raised blood pressure, decreased levels of HDL and increased levels of VLDL). Montague et al., Diabetes 2000, 49:883-888, 2000. It has also been reported that inhibition of the 11β-HSDs in pre-adipocytes (stromal cells) resulted in a decreased rate of differentiation into adipocytes. This is predicted to result in diminished expansion (possibly reduction) of the omental fat depot, which may lead to reduced central obesity. Bujalska et al., Lancet 1997, 349: 1210-1213.

Inhibition of 11β-HSD1 in mature adipocytes is expected to attenuate secretion of the plasminogen activator inhibitor 1 (PAI-1), which is an independent cardiovascular risk factor, as reported in Halleux et al., J. Clin. Endocrinol. Metab. 1999, 84:4097-4105. In addition, a correlation has been shown to exist between glucocorticoid activity and certain cardiovascular risk factors. This suggests that a reduction of the glucocorticoid effects would be beneficial in the treatment or prevention of certain cardiovascular diseases. Walker et al., Hypertension 1998, 31:891-895; and Fraser et al., Hypertension 1999, 33:1364-1368.

HSDs have also been implicated in the process of appetite control and therefore are believed to play an additional role in weight-related disorders. It is known that adrenalectomy attenuates the effect of fasting to increase both food intake and hypothalamic neuropeptide Y expression. This suggests that glucocorticoids play a role in promoting food intake and that inhibition of 11β-HSD1 in the brain may increase satiety, thus resulting in a decreased food intake. Woods et al., Science 1998, 280:1378-1383.

Another possible therapeutic effect associated with modulation of HSDs is that which is related to various pancreatic aliments. It is reported that inhibition of 11β-HSD1 in murine pancreatic β-cells results in increased insulin secretion. Davani et al., J. Biol. Chem. 2000, 275:34841-34844. This follows from the discovery that glucocorticoids were previously found to be responsible for reduced pancreatic insulin release in vivo, Billaudel et al., Horm. Metab. Res. 1979, 11:555-560. Thus, it is suggested that inhibition of 11β-HSD1 would yield other beneficial effects in the treatment of diabetes other than the predicted effects on the liver and fat reduction.

11β-HSD1 also regulates glucocorticoid activity in the brain and thus contributes to neurotoxicity. Rajan et al., Neuroscience 1996, 16:65-70; and Seckl et al., Neuroendocrinol. 2000, 18:49-99. Stress and/or glucocorticoids are known to influence cognitive function (de Quervain et al., Nature 1998, 394:787-790), and unpublished results indicate significant memory improvement in rats treated with a non-specific 11β-HSD inhibitor. These reports, in addition to the known effects of glucocorticoids in the brain, suggest that inhibiting HSDs in the brain may have a positive therapeutic effect against anxiety and related conditions. Tronche et al., Nature Genetics 1999, 23:99-103. 11β-HSD1 reactivates 11-DHC to corticosterone in hippocampal cells and can potentiate kinase neurotoxicity, resulting in age-related learning impairments. Therefore, selective inhibitors of 11β-HSD1 are believed to protect against hippocampal function decline with age. Yau et al., Proc Natl. Acad. Sci. USA 2001, 98:4716-4721. Thus, it has been hypothesized that inhibition of 11β-HSD1 in the human brain would protect against deleterious glucocorticoid-mediated effects on neuronal function, such as cognitive impairment, depression, and increased appetite.

HSDs are believed to play a role in immunomodulation based on the general perception that glucocorticoids suppress the immune system. There is known to be a dynamic interaction between the immune system and the HPA (hypothalamo-pituitary-adrenal) axis (Rook, Baillier's Clin. Endocrinol. Metab. 2000, 13: 576-581), and glucocorticoids help balance between cell-mediated responses and humoral responses. Increased glucocorticoid activity, which may be induced by stress, is associated with a humoral response and as such, the inhibition of 11β-HSD1 may result in shifting the response towards a cell-based reaction. In certain disease states, such as tuberculosis, leprosy, and psoriasis, the immune reaction is typically biased towards a humoral response when a cell-based response might be more appropriate. Inhibition of 11β-HSD1 is being studied for use to direct a cell-based response in these instances. Mason, Immunology Today 1991, 12:57-60. It follows then, that an alternative utility of 11β-HSD1 inhibition would be to bolster a temporal immune response in association with immunization to ensure that a cell based response would be obtained.

Recent reports suggest that the levels of glucocorticoid target receptors and of HSDs are connected with the risks of developing glaucoma. Stokes et al., Invest. Opthalmol. 2000, 41:1629-1638. Further, a connection between inhibition of 11β-HSD1 and a lowering of the intraocular pressure was reported. Walker et al., poster P3-698 at the Endocrine society meeting Jun. 12-15, 1999, San Diego. It was shown that administration of the nonspecific 11β-HSD1 inhibitor, carbenoxolone, resulted in the reduction of the intraocular pressure by 20% in normal patients. In the eye, 11β-HSD1 is expressed exclusively in the basal cells of the corneal epithelium, the non-pigmented epithelialium of the cornea (the site of aqueous production), ciliary muscle, and the sphincter and dilator muscles of the iris. In contrast, the distant isoenzyme 11β-hydroxysteroid dehydrogenase type 2 ("11β-HSD2") is highly expressed in the non-pigmented ciliary epithelium and corneal endothelium. No HSDs have been found at the trabecular meshwork, which is the site of drainage. Therefore, 11β-HSD1 is suggested to have a role in aqueous production.

Glucocorticoids also play an essential role in skeletal development and function but are detrimental to such development and function when present in excess. Glucocorticoid-induced bone loss is partially derived from suppression of osteoblast proliferation and collagen synthesis, as reported in Kim et al., J. Endocrinol. 1999, 162:371 379. It has been reported that the detrimental effects of glucocorticoids on bone nodule formation can be lessened by administration of carbenoxolone, which is a non-specific 11β-HSD1 inhibitor. Bellows et al., Bone 1998, 23:119-125. Additional reports suggest that 11β-HSD1 may be responsible for providing increased levels of active glucocorticoid in osteoclasts, and thus in augmenting bone resorption. Cooper et al., Bone 2000, 27:375-381. This data suggests that inhibition of 11β-HSD1 may have beneficial effects against osteoporosis via one or more mechanisms which may act in parallel.

It is known that bile acids inhibit 11β-HSD2 and that such inhibition results in a shift in the cortisol/cortisone equilibrium in the favor of cortisol. Quattropani et al., J. Clin. Invest. November 2001, 108:1299-305. A reduction in the hepatic activity of 11β-HSD2 is therefore predicted to reverse the cortisol/cortisone equilibrium to favor cortisone, which could provide therapeutic benefit in diseases such as hypertension.

The various isozymes of the 17-beta-hydroxysteroid dehydrogenases (17β-HSDs) bind to androgen receptors or estrogen receptors and catalyze the interconversion of various sex hormones including estradiol/estrone and testosterone/androstenedione. To date, six isozymes have been identified in humans and are expressed in various human tissues including endometrial tissue, breast tissue, colon tissue, and in the testes. 17-beta-Hydroxysteroid dehydrogenase type 2 (17β-HSD2) is expressed in human endometrium and its activity has been reported to be linked to cervical cancer. Kitawaki et al., J. Clin. Endocrin. Metab., 2000, 85:1371-3292-3296. 17-beta-Hydroxysteroid dehydrogenase type 3 (17β-HSD3) is expressed in the testes and its modulation may be useful for the treatment of androgen-related disorders.

Androgens and estrogens are active in their 17β-hydroxy configurations, whereas their 17-keto derivatives do not bind to androgen and estrogen receptors and are thus inactive. The conversion between the active and inactive forms (estradiol/estrone and testosterone/androstenedione) of sex hormones is catalyzed by members of the 17β-HSD family. 17β-HSD1 catalyzes the formation of estradiol in breast tissue, which is important for the growth of malignant breast tumors. Labrie et al., Mol. Cell. Endocrinol. 1991, 78:C113-C118. A similar role has been suggested for 17β-HSD4 in colon cancer. English et al., J. Clin. Endocrinol. Metab. 1999, 84:2080-2085. 17β-HSD3 is almost exclusively expressed in the testes and converts androstenedione into testosterone. Deficiency of this enzyme during fetal development leads to male pseudohermaphroditism. Geissler et al., Nat. Genet. 1994, 7:34-39. Both 17β-HSD3 and various 3α-HSD isozymes are involved in complex metabolic pathways which lead to androgen shuffles between inactive and active forms. Penning et al., Biochem. J. 2000, 351:67-77. Thus, modulation of certain HSDs can have potentially beneficial effects in the treatment of androgen- and estrogen-related disorders.

The 20-alpha-hydroxysteroid dehydrogenases (20α-HSDs) catalyze the interconversion of progestins (such as between progesterone and 20α-hydroxy progesterone). Other substrates for 20α-HSDs include 17α-hydroxypregnenolone or 17α-hydroxyprogesterone, leading to 20α-OH steroids. Several 20α-HSD isoforms have been identified and 20α-HSDs are expressed in various tissues, including the placenta, ovaries, testes and adrenals. Peltoketo, et al., J. Mol. Endocrinol. 1999, 23:1-11.

The 3-alpha-hydroxysteroid dehydrogenases (3α-HSDs) catalyze the interconversion of the androgens dihydrotestosterone (DHT) and 5α-androstane-3α,17β-diol and the interconversion of the androgens DHEA and androstenedione and therefore play an important role in androgen metabolism. Ge et al., Biology of Reproduction 1999, 60:855-860.

International Publications Nos. WO 2004/089896 and WO 2004/065351 disclose benzamide derivatives and their use as 11β-HSD1 modulators.

Despite the previous research done in the field of HSD inhibition, there remains a need for novel compounds that are potent inhibitors of the various families of HSDs and efficacious for the treatment of HSD-mediated conditions such as diabetes, obesity, glaucoma, osteoporosis, cognitive disorders, immune disorders, depression, hypertension, and others.

BRIEF SUMMARY OF THE INVENTION

In brief, the present invention relates to novel compounds, compositions thereof and methods for modulating the activity of hydroxysteroid dehydrogenases (HSDs), such as 11β-hydroxysteroid dehydrogenases, 17β-hydroxysteroid dehydrogenases, 20α-hydroxysteroid dehydrogenases, and 3α-hydroxysteroid dehydrogenases, including all isoforms thereof, including but not limited to 11β-hydroxysteroid dehydrogenase type 1 (hereinafter "11β-HSD1"), 11β-hydroxysteroid dehydrogenase type 2 (hereinafter "11β-HSD2"), and 17β-hydroxysteroid dehydrogenase type 3 (hereinafter "17β-HSD3"). In one embodiment, the compounds of the invention inhibit HSD activity.

The present invention also relates to methods for treating or preventing diseases or disorders associated with the action of hydroxysteroid dehydrogenases, comprising administering to a patient in need thereof a therapeutically effective amount of a benzamide derivative or a pharmaceutically acceptable salt, solvate, stereoisomer, or prodrug thereof. The invention encompasses both selective and non-selective inhibitors of hydroxysteroid dehydrogenases.

It should be understood that selective and non-selective inhibitors of hydroxysteroid dehydrogenases each have benefits in the treatment or prevention of diseases associated with, for example, abnormal glucose levels or hypothalmic function. The invention also encompasses selective inhibitors of HSDs. Two types of selectivity are contemplated, that with respect to selectivity for HSDs as a class over other types of receptors or gene targets related to glucose metabolism, or those which are selective for various HSDs or specific isoforms thereof compared to other HSDs or specific isoforms thereof.

In one embodiment, the benzamide derivatives can act as selective or non-selective 11β-HSD inhibitors. The compounds may inhibit the interconversion of inactive 11-keto steroids with their active hydroxy equivalents. The present invention provides methods by which the conversion of the inactive to the active form may be controlled, and to useful therapeutic effects which may be obtained as a result of such control. More specifically, but not exclusively, the invention is concerned with interconversion between cortisone and cortisol in humans.

In another embodiment, the benzamide derivatives of the present invention may be orally active.

The benzamide derivatives are also useful for modulation of numerous metabolic functions including, but not limited to, one or more of: (i) regulation of carbohydrate metabolism, (ii) regulation of protein metabolism, (iii) regulation of lipid metabolism, (iv) regulation of normal growth and/or development, (v) influence on cognitive function, (vi) resistance to stress and mineralocorticoid activity.

The benzamide derivatives may also be useful for inhibiting hepatic gluconeogenesis, and may also be effective to relieve the effects of endogenous glucocorticoids in diabetes mellitus, obesity (including entripetal obesity), neuronal loss and/or the cognitive impairment of old age. Thus, in a further embodiment, the invention provides the use of an inhibitor of HSDs in methods directed to producing one or more therapeutic effects in a patient to whom the benzamide derivative is administered, said therapeutic effects selected from the group consisting of inhibition of hepatic gluconeogenesis, an increase in insulin sensitivity in adipose tissue and muscle, and the prevention of or reduction in neuronal loss/cognitive impairment due to glucocorticoid-potentiated neurotoxicity or neural dysfunction or damage.

The invention further provides methods for treating a condition selected from the group consisting of: hepatic insulin resistance, adipose tissue insulin resistance, muscle insulin resistance, neuronal loss or dysfunction due to glucocorticoid potentiated neurotoxicity, and any combination of the aforementioned conditions, the methods comprising administering to a patient in need thereof a therapeutically effective amount of a benzamide derivative.

The benzamide derivatives of the invention are compounds having Formula (I)

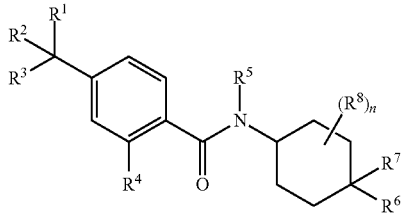

(I)

or pharmaceutically acceptable salts, solvates, stereoisomers or prodrugs thereof.

n is 0, 1, or 2.

$R^1$ is a member selected from the group consisting of —OH, halogen and $(C_1\text{-}C_8)$haloalkyl.

$R^2$ and $R^3$ are members independently selected from the group consisting of halogen, $(C_1\text{-}C_8)$alkyl, $(C_2\text{-}C_8)$alkenyl, $(C_2\text{-}C_8)$alkynyl, $(C_1\text{-}C_8)$alkoxy, $(C_1\text{-}C_8)$haloalkyl, $(C_2\text{-}C_8)$hydroxyalkyl and $(C_3\text{-}C_8)$cycloalkyl, wherein no more than two of $R^1$, $R^2$ and $R^3$ are halogen.

$R^4$ is a member selected from the group consisting of hydrogen, halogen, $(C_1\text{-}C_8)$alkyl and $(C_3\text{-}C_8)$cycloalkyl.

$R^5$ is selected from the group consisting of $(C_1\text{-}C_8)$alkyl, $(C_1\text{-}C_8)$haloalkyl, $(C_2\text{-}C_8)$hydroxyalkyl, $(C_3\text{-}C_8)$cycloalkyl, and $(C_3\text{-}C_8)$heterocycloalkyl.

$R^6$ is selected from the group consisting of $(C_1\text{-}C_8)$alkyl, $(C_2\text{-}C_8)$alkenyl, $(C_1\text{-}C_8)$haloalkyl, aryl$(C_1\text{-}C_6)$alkyl, $(C_3\text{-}C_8)$cycloalkyl, $(C_3\text{-}C_8)$heterocycloalkyl, heteroaryl, and aryl.

$R^5$ or $R^6$ is optionally substituted with from one to two members selected from the group consisting of halogen, —CN, —NO₂, $(C_1\text{-}C_4)$alkyl, $(C_2\text{-}C_8)$alkenyl, $(C_2\text{-}C_8)$alkynyl, $(C_1\text{-}C_4)$alkoxy, $(C_1\text{-}C_4)$haloalkyl, $(C_2\text{-}C_4)$hydroxyalkyl, —C(O)R', —C(O)OR', —NR'C(O)OR', —OR', —SR', —OC(O)R', —C(O)N(R')₂, —S(O)R', —SO₂R', —SO₂N(R')₂, —N(R')₂, —NR'C(O)R' and —NR'SO₂R'.

$R^7$ is selected from the group consisting of halogen, —CN, $(C_1\text{-}C_8)$alkyl, $(C_2\text{-}C_8)$alkenyl, $(C_2\text{-}C_8)$alkynyl, $(C_1\text{-}C_8)$haloalkyl, $(C_1\text{-}C_8)$hydroxyalkyl, —C(O)R', —C(O)OR', —NR'C(O)OR', —OR', —OC(O)R', —C(O)N(R')₂, —S(O)R', —SO₂R', —SO₂N(R')₂, —N(R')₂, —NR'C(O)R', —NR'SO₂R', —X—CN, —X—C(O)R', —X—C(O)OR', —X—NR'C(O)OR', —X—OR', —X—OC(O)R', —X—C(O)N(R')₂, —X—S(O)R', —X—SO₂R', —X—SO₂N(R')₂, —X—N(R')₂, —X—NR'C(O)R', $R^6$ and $R^7$ may be combined to form a $(C_3\text{-}C_8)$cycloalkyl or $(C_3\text{-}C_8)$heterocycloalkyl.

$R^8$ is selected from the group consisting of halogen, —CN, $(C_1\text{-}C_6)$alkyl, $(C_1\text{-}C_6)$alkyloxy, and —OH.

X is a branched or straight chain $(C_1\text{-}C_8)$alkylene group.

Each occurrence of R' is independently hydrogen or an unsubstituted member selected from the group consisting of $(C_1\text{-}C_8)$alkyl, $(C_2\text{-}C_8)$alkenyl, $(C_2\text{-}C_8)$alkynyl, $(C_1\text{-}C_4)$alkoxy$(C_1\text{-}C_4)$alkyl, $(C_1\text{-}C_9)$haloalkyl, $(C_2\text{-}C_8)$hydroxyalkyl, $(C_3\text{-}C_8)$cycloalkyl, $(C_3\text{-}C_8)$heterocycloalkyl, heteroaryl, aryl, $(C_3\text{-}C_8)$cycloalkyl$(C_1\text{-}C_6)$alkyl, $(C_3\text{-}C_8)$heterocycloalkyl$(C_1\text{-}C_6)$alkyl, heteroaryl$(C_1\text{-}C_6)$alkyl, aryl$(C_1\text{-}C_6)$alkyl, or two R groups, when attached to the same nitrogen atom, can be combined with the nitrogen atom to which they are attached to form a heterocycle or heteroaryl group.

It should be understood that a compound where $R^1$ is —OH and $R^2$ and $R^3$ are both $CF_3$ is excluded from the scope of the present invention.

In one embodiment, the invention provides pharmaceutical compositions comprising a benzamide derivatives and a pharmaceutically acceptable vehicle, carrier, excipient or diluent.

In another embodiment, the invention provides methods of treating a disease or condition selected from the group consisting of diabetes, obesity, dyslipidemia, hyperinsulinemia, glaucoma, osteoporosis, cognitive disorders, atherosclerosis, immune disorders, hypertension and wound healing in a patient in need thereof comprising administering to the patient a therapeutically effective amount of the compound of Formula (I).

In another embodiment, the invention provides methods for treating insulin-dependent diabetes mellitus comprising administering to a patient in need thereof a therapeutically effective amount of a benzamide derivative of Formula (I).

In another embodiment, the invention provides methods for treating non-insulin-dependent diabetes mellitus comprising administering to a patient in need thereof a therapeutically effective amount of a benzamide derivative of Formula (I).

In another embodiment, the invention provides methods for treating insulin resistance comprising administering to a patient in need thereof a therapeutically effective amount of a benzamide derivative of Formula (I).

In another embodiment, the invention provides methods for treating obesity comprising administering to a patient in need thereof a therapeutically effective amount of a benzamide derivative of Formula (I).

In another embodiment, the invention provides methods for modulating cortisol production comprising administering to a patient in need thereof a therapeutically effective amount of a benzamide derivative of Formula (I).

In another embodiment, the invention provides methods for modulating hepatic glucose production comprising administering to a patient in need thereof a therapeutically effective amount of a benzamide derivative of Formula (I).

In another embodiment, the invention provides methods for modulating hypothalamic function comprising administering to a patient in need thereof a therapeutically effective amount of a benzamide derivative of Formula (I).

In one embodiment, the invention provides methods for treating a hydroxysteroid dehydrogenase-mediated condition or disorder comprising administering to a patient in need thereof a therapeutically effective amount of a benzamide derivative of Formula (I).

In a further embodiment, the invention provides methods for modulating a hydroxysteroid dehydrogenase, comprising administering to a patient in need thereof a therapeutically effective amount of a benzamide derivative of Formula (I).

In still another embodiment, the invention provides methods for treating an 11β-HSD1-mediated condition or disorder comprising administering to a patient in need thereof a therapeutically effective amount of a benzamide derivative of Formula (I).

In yet another embodiment, the invention provides method for modulating the function of 11β-HSD1 in a cell comprising administering to a patient in need thereof a therapeutically effective amount of a benzamide derivative of Formula (I).

In a further embodiment, the invention provides methods for modulating 11β-HSD1, comprising administering to a patient in need thereof a therapeutically effective amount of a benzamide derivative of Formula (I).

In one embodiment, the invention provides methods for treating an 11β-HSD2-mediated condition or disorder comprising administering to a patient in need thereof a therapeutically effective amount of a benzamide derivative of Formula (I).

In another embodiment, the invention provides method for modulating the function of 11β-HSD2 in a cell comprising administering to a patient in need thereof a therapeutically effective amount of a benzamide derivative of Formula (I).

In a further embodiment, the invention provides methods for modulating 11β-HSD2, comprising administering to a patient in need thereof a therapeutically effective amount of a benzamide derivative of Formula (I).

In one embodiment, the invention provides methods for treating an 17β-HSD3-mediated condition or disorder comprising administering to a patient in need thereof a therapeutically effective amount of a benzamide derivative of Formula (I).

In another embodiment, the invention provides method for modulating the function of 17β-HSD3 in a cell comprising administering to a patient in need thereof a therapeutically effective amount of a benzamide derivative of Formula (I).

In a further embodiment, the invention provides methods for modulating 17β-HSD3, comprising administering to a patient in need thereof a therapeutically effective amount of a benzamide derivative of Formula (I).

These and other embodiments of this invention will be evident upon reference to the following detailed description. To that end, certain patent and other documents are cited herein to more specifically set forth various embodiments of this invention. Each of these documents are hereby incorporated by reference in their entirety.

DETAILED DESCRIPTION OF THE INVENTION

As used herein, the terms have the following meanings:

The term "alkyl" as used herein refers to a straight or branched chain, saturated hydrocarbon having the indicated number of carbon atoms. For example, ($C_1$-$C_6$)alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein below.

The term "alkenyl" as used herein refers to a straight or branched chain unsaturated hydrocarbon having the indicated number of carbon atoms and at least one double bond. Examples of a ($C_2$-$C_8$)alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein below.

The term. "alkynyl" as used herein refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkylene" refers to a divalent alkyl group (e.g., an alkyl group attached to two other moieties, typically as a linking group). Examples of a ($C_1$-$C_7$)alkylene include —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, and —CH$_2$CH$_2$CH$_2$CH$_2$CH$_2$CH$_2$CH$_2$—, as well as branched versions thereof. An alkylene group can be unsubstituted or optionally substituted with one or more substituents as described herein below.

The term "alkoxy" as used herein refers to an —O-alkyl group having the indicated number of carbon atoms. For example, a ($C_1$-$C_6$)alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl," as used herein, refers to an alkyl group (typically one to six carbon atoms) wherein from one or more of the $C_1$-$C_6$ alkyl group's hydrogen atoms is replaced with an amine of formula —N($R^a$)$_2$, wherein each occurrence of $R^a$ is independently —H or ($C_1$-$C_6$)alkyl. Examples of aminoalkyl groups include, but are not limited to, —CH$_2$NH$_2$, —CH$_2$CH$_2$NH$_2$, —CH$_2$CH$_2$CH$_2$NH$_2$, —CH$_2$CH$_2$CH$_2$CH$_2$NH$_2$, —CH$_2$CH$_2$CH$_2$CH$_2$CH$_2$NH$_2$, —CH$_2$CH$_2$CH$_2$CH$_2$CH$_2$CH$_2$NH$_2$, —CH$_2$CH$_2$CH$_2$N(CH$_3$)$_2$, t-butylaminomethyl, isopropylaminomethyl and the like.

The term "aryl" as used herein refers to a 6- to 14-membered monocyclic, bicyclic or tricyclic aromatic hydrocarbon ring system. Examples of an aryl group include phenyl and naphthyl. An aryl group can be unsubstituted or optionally substituted with one or more substituents as described herein below.

The term "cycloalkyl" as used herein refers to a 3- to 14-membered saturated or unsaturated non-aromatic monocyclic, bicyclic or tricyclic hydrocarbon ring system. The bicyclic or tricyclic hydrocarbon ring systems may be spiro-fused. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, spiro[5,4]decane, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene. A cycloalkyl group can be unsubstituted or optionally substituted with one or more substituents as described herein below.

The term "halo" as used herein refers to —F, —Cl, —Br or —I.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" or "heterocycloalkyl" as used herein refers to 5- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including monocyclic, bicyclic, and tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "hydroxyalkyl," as used herein, refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

Substituents for the groups referred to as alkyl, heteroalkyl, alkylene, alkenyl, alkynyl, cycloalkyl, heterocycloalkyl, cycloalkenyl and heterocycloalkenyl can be a variety of groups selected from: —OR', =O, =NR', =N—OR', —NR'R", —SR', -halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$, in a number ranging from zero to three, with those groups having zero, one or two substituents being exemplary. R', R" and R'" each independently refer to hydrogen, unsubstituted ($C_1$-$C_8$)alkyl, unsubstituted hetero($C_1$-$C_8$) alkyl, unsubstituted aryl and aryl substituted with one to three substituents selected from -halo, unsubstituted alkyl, unsubstituted alkoxy, unsubstituted thioalkoxy and unsubstituted aryl($C_1$-$C_4$)alkyl. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. An alkyl or heteroalkyl group will have from zero to three substituents, with those groups having two or fewer substituents being exemplary in the present invention. In some embodiments, an alkyl or heteroalkyl radical will be unsubstituted or monosubstituted. An alkyl or heteroalkyl radical can be unsubstituted.

Exemplary substituents for the alkyl and heteroalkyl radicals are selected from: —OR', =O, —NR'R", —SR', -halo, —SiR'R"R'", —OC(O)R', —C(O)R', —CO$_2$R', —C(O)NR'R", —OC(O)NR'R", —NR"C(O)R', —NR"CO$_2$R', —NR'"SO$_2$NR'R", —S(O)R', —SO$_2$R', —SO$_2$NR'R", —NR"SO$_2$R', —CN and —NO$_2$, where R', R" and R'" are as defined above. Typically, substituents are selected from: —OR', =O, —NR'R", -halo, —OC(O)R', —CO$_2$R', —C(O) NR'R", —OC(O)NR'R", —NR"C(O)R', —NR"CO$_2$R', —NR'"SO$_2$NR'R", —SO$_2$R', —SO$_2$NR'R", —NR"SO$_2$R'— CN and —NO$_2$.

Similarly, substituents for the aryl and heteroaryl groups are varied and selected from: -halo, —OR', —OC(O)R', —NR'R", —SR', —R', —CN, —NO$_2$, —CO$_2$R', —C(O) NR'R", —C(O)R', —OC(O)NR'R", —NR"C(O)R', —NR"CO$_2$R', —NR'"C(O)NR'R", —NR'"SO$_2$NR'R", —NHC(NH$_2$)=NH, —NR'C(NH$_2$)=NH, —NH—C(NH$_2$) =NR', —S(O)R', —SO$_2$R', —SO$_2$NR'R", —NR"SO$_2$R', —N$_3$, —CH(Ph)$_2$, perfluoroalkoxy and perfluoro($C_1$-$C_4$) alkyl, in a number ranging from zero to the total number of open valences on the aromatic ring system; and where R', R" and R'" are independently selected from hydrogen, unsubstituted ($C_1$-$C_8$)alkyl, unsubstituted hetero($C_1$-$C_8$)alkyl, unsubstituted aryl, unsubstituted heteroaryl, unsubstituted aryl($C_1$-

$C_4$)alkyl and unsubstituted aryloxy($C_1$-$C_4$)alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Exemplary substituents for aryl and heteroaryl groups are selected from: -halo, —OR', —OC(O)R', —NR'R", —SR', —R', —CN, —$NO_2$, —$CO_2$R', —CONR'R", —C(O)R', —OC(O)NR'R", —NR"C(O)R', —S(O)R', —$SO_2$R', —$SO_2$NR'R", —NR"$SO_2$R', —$N_3$, —CH(Ph)$_2$, perfluoroalkoxy and perfluoro($C_1$-$C_4$)alkyl, where R' and R" are as defined above. Typically, substituents are selected from: -halo, —OR', —OC(O)R', —NR'R", —R', —CN, —$NO_2$, —$CO_2$R', —CONR'R", —NR"C(O)R', —$SO_2$R', —$SO_2$NR'R", —NR"$SO_2$R', perfluoroalkoxy and perfluoro ($C_1$-$C_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

It is to be understood that the substituent —$CO_2$H, as used herein, may be optionally replaced with bioisosteric replacements such as:

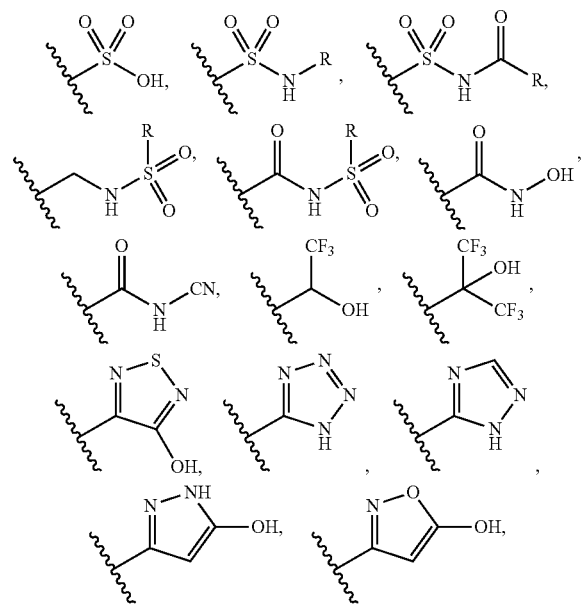

and the like. See, e.g., *The Practice of Medicinal Chemistry*; Wermuth, C. G., Ed.; Academic Press: New York, 1996; p. 203.

The benzamide derivative can also exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a benzamide derivative, including tautomeric forms of the compound.

Certain benzamide derivatives may have asymmetric centers and therefore exist in different enantiomeric and diastereomeric forms. A benzamide derivative can be in the form of an optical isomer or a diastereomer. Accordingly, the invention encompasses benzamide derivatives and their uses as described herein in the form of their optical isomers, diastereomers and mixtures thereof, including a racemic mixture. Optical isomers of the benzamide derivatives can be obtained by known techniques such as asymmetric synthesis, chiral chromatography, simulated moving bed technology or via chemical separation of stereoisomers through the employment of optically active resolving agents.

As used herein and unless otherwise indicated, the term "stereoisomer" or means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

It should be noted that if there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

A benzamide derivative can be in the form of a pharmaceutically acceptable salt. Depending on the its structure, the phrase "pharmaceutically acceptable salt," as used herein, refers to a pharmaceutically acceptable organic or inorganic acid or base salt of a benzamide derivative. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. Furthermore, a pharmaceutically acceptable salt can have more than one charged atom in its structure. In this instance the pharmaceutically acceptable salt can have multiple counterions. Hence, a pharmaceutically acceptable salt can have one or more charged atoms and/or one or more counterions.

As used herein, the term "isolated and purified form" means that when isolated (e.g., from other components of a synthetic organic chemical reaction mixture), the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a benzamide derivative by weight of the isolate. In one embodiment, the isolate contains at least 95% of a benzamide derivative by weight of the isolate.

As used herein, the term "prodrug" means a derivative of a compound that can hydrolyze, oxidize, or otherwise react under biological conditions (in vitro or in vivo) to provide an active compound, particularly a benzamide derivative. Examples of prodrugs include, but are not limited to, derivatives and metabolites of a benzamide derivative that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, the terms "treat", "treating" and "treatment" refer to the eradication or amelioration of a disease or symptoms associated with a disease. In certain embodiments, such terms refer to minimizing the spread or worsening of the disease resulting from the administration of one or more prophylactic or therapeutic agents to a patient with such a disease.

As used herein, the terms "prevent", "preventing" and "prevention" refer to the prevention of the onset, recurrence or spread of the disease in a patient resulting from the administration of a prophylactic or therapeutic agent.

The term "effective amount" as used herein refers to an amount of a benzamide derivative or other active ingredient sufficient to provide a therapeutic or prophylactic benefit in the treatment or prevention of a disease or to delay or minimize symptoms associated with a disease. Further, a therapeutically effective amount with respect to a benzamide derivative means that amount of therapeutic agent alone, or in combination with other therapies, that provides a therapeutic benefit in the treatment or prevention of a disease. Used in connection with a benzamide derivative, the term can encompass an amount that improves overall therapy, reduces or avoids symptoms or causes of disease, or enhances the therapeutic efficacy of or synergies with another therapeutic agent.

As used herein, "syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

The terms "modulate", "modulation" and the like refer to the ability of a compound to increase or decrease the function, or activity of, for example, 11β-HSD1. "Modulation", as used herein in its various forms, is intended to encompass inhibition, antagonism, partial antagonism, activation, agonism and/or partial agonism of the activity associated with 11β-HSD1. 11β-HSD1 inhibitors are compounds that, e.g., bind to, partially or totally block stimulation, decrease, prevent, delay activation, inactivate, desensitize, or down regulate signal transduction. 11β-HSD1 activators are compounds that, e.g., bind to, stimulate, increase, open, activate, facilitate, enhance activation, sensitize or up regulate signal transduction. The ability of a compound to modulate 11β-HSD1 can be demonstrated in an enzymatic assay or a cell-based assay. For example, the inhibition of 11β-HSD1 may decrease cortisol levels in a patient and/or increase cortisone levels in a patient by blocking the conversion of cortisone to cortisol. Alternatively, the inhibition of 11β-HSD2 can increase cortisol levels in a patient and/or decrease cortisone levels in a patient by blocking the conversion of cortisol to cortisone.

A "patient" includes an animal (e.g., cow, horse, sheep, pig, chicken, turkey, quail, cat, dog, mouse, rat, rabbit or guinea pig), in one embodiment a mammal such as a non-primate and a primate (e.g., monkey and human), and in another embodiment a human. In one embodiment, a patient is a human. In specific embodiments, the patient is a human infant, child, adolescent or adult.

The term "HSD" as used herein, refers to hydroxysteroid dehydrogenase enzymes in general, including, but not limited to, 11-beta-hydroxysteroid dehydrogenases (11β-HSDs), 17-beta-hydroxysteroid dehydrogenases (17β-HSDs), 20-alpha-hydroxysteroid dehydrogenases (20α-HSDs), 3-alpha-hydroxysteroid dehydrogenases (3α-HSDs), and all isoforms thereof.

The term "11β-HSD1" as used herein, refers to the 11-beta-hydroxysteroid dehydrogenase type 1 enzyme, variant, or isoform thereof. 11β-HSD1 variants include proteins substantially homologous to native 11β-HSD1, i.e., proteins having one or more naturally or non-naturally occurring amino acid deletions, insertions or substitutions (e.g., 11β-HSD1 derivatives, homologs and fragments). The amino acid sequence of a 11β-HSD1 variant is, for example, at least about 80% identical to a native 11β-HSD1, or at least about 90% identical, or at least about 95% identical.

The term "11β-HSD2" as used herein, refers to the 11-beta-hydroxysteroid dehydrogenase type 2 enzyme, variant, or isoform thereof. 11β-HSD2 variants include proteins substantially homologous to native 11β-HSD2, i.e., proteins having one or more naturally or non-naturally occurring amino acid deletions, insertions or substitutions (e.g., 11β-HSD2 derivatives, homologs and fragments). The amino acid sequence of a 11β-HSD2 variant is, for example, at least about 80% identical to a native 11β-HSD2, or at least about 90% identical, or at least about 95% identical. (see Bart et al., *J. Med. Chem.*, 2002, 45:3813-3815).

The term "17β-HSD3" as used herein, refers to the 17-beta-hydroxysteroid dehydrogenase type 3 enzyme, variant, or isoform thereof. 17β-HSD3 variants include proteins substantially homologous to native 17β-HSD3, i.e., proteins having one or more naturally or non-naturally occurring amino acid deletions, insertions or substitutions (e.g., 17β-HSD3 derivatives, homologs and fragments). The amino acid sequence of a 17β-HSD3 variant is, for example, at least about 80% identical to a native 17β-HSD3, or at least about 90% identical, or at least about 95% identical.

As used herein, the term "HSD-responsive condition or disorder" and related terms and phrases refer to a condition or disorder that responds favorably to modulation of a hydroxysteroid dehydrogenase enzyme (HSD). Favorable responses to HSD modulation include alleviation or abrogation of the disease and/or its attendant symptoms, inhibition of the disease, i.e., arrest or reduction of the development of the disease, or its clinical symptoms, and regression of the disease or its clinical symptoms. An HSD-responsive condition or disease may be completely or partially responsive to HSD modulation. An HSD-responsive condition or disorder may be associated with inappropriate, e.g., less than or greater than normal, HSD activity and at least partially responsive to or affected by HSD modulation (e.g., an HSD inhibitor results in some improvement in patient well-being in at least some patients). Inappropriate HSD functional activity might arise as the result of HSD expression in cells which normally do not express HSD, decreased HSD expression or increased HSD expression. An HSD-responsive condition or disorder may include condition or disorder mediated by any HSD or isoform thereof.

As used herein, the term "11β-HSD1-responsive condition or disorder" and related terms and phrases refer to a condition or disorder that responds favorably to modulation of 11β-HSD1 activity. Favorable responses to 11β-HSD1 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD1-responsive condition or disease may be completely or partially responsive to 11β-HSD1 modulation. An 11β-HSD1-responsive condition or disorder may be associated with inappropriate, e.g., less than or greater than normal, 11β-HSD1 activity and at least partially responsive to or affected by 11β-HSD1 modulation (e.g., a 11β-HSD1 inhibitor results in some improvement in patient well-being in at least some patients). Inappropriate 11β-HSD1 functional activity might arise as the result of 11β-HSD1 expression in cells which normally do not express 11β-HSD1, decreased 11β-HSD1 expression or increased 11β-HSD1 expression. A 11β-HSD1-responsive condition or disorder may include a 11β-HSD1-mediated condition or disorder.

As used herein, the term "11β-HSD2-responsive condition or disorder" and related terms and phrases refer to a condition or disorder that responds favorably to modulation of 11β-HSD2 activity. Favorable responses to 11β-HSD2 modulation include alleviation or abrogation of the disease and/or its attendant symptoms, inhibition of the disease, i.e., arrest or reduction of the development of the disease, or its clinical symptoms, and regression of the disease or its clinical symptoms. An 11β-HSD2-responsive condition or disease may be completely or partially responsive to 11β-HSD2 modulation. An 11β-HSD2-responsive condition or disorder may be associated with inappropriate, e.g., less than or greater than normal, 11β-HSD2 activity and at least partially responsive to or affected by 11β-HSD2 modulation (e.g., a 11β-HSD2 inhibitor results in some improvement in patient well-being in at least some patients).

As used herein, the term "17β-HSD3-responsive condition or disorder" and related terms and phrases refer to a condition or disorder that responds favorably to modulation of 17β-HSD3 activity. Favorable responses to 17β-HSD3 modulation include alleviation or abrogation of the disease and/or its attendant symptoms, inhibition of the disease, i.e., arrest or reduction of the development of the disease, or its clinical symptoms, and regression of the disease or its clinical symptoms. An 17β-HSD3-responsive condition or disease may be completely or partially responsive to 17β-HSD3 modulation. An 17β-HSD3-responsive condition or disorder may be associated with inappropriate, e.g., less than or greater than normal, 17β-HSD3 activity and at least partially responsive to or affected by 17β-HSD3 modulation (e.g., a 17β-HSD3 inhibitor results in some improvement in patient well-being in at least some patients). Inappropriate 17β-HSD3 functional activity might arise as the result of 17β-HSD3 expression in cells which normally do not express 17β-HSD3, decreased 17β-HSD3 expression or increased 17β-HSD3 expression. A 17β-HSD3-responsive condition or disorder may include a 17β-HSD3-mediated condition or disorder.

As used herein, the term "HSD-mediated condition or disorder" and related terms and phrases refer to a condition or disorder characterized by inappropriate, e.g., less than or greater than normal, activity of a hydroxysteroid dehydrogenase (HSD). An HSD-mediated condition or disorder may be completely or partially characterized by inappropriate HSD activity. However, an HSD-mediated condition or disorder is one in which modulation of an HSD results in some effect on the underlying condition or disease (e.g., an HSD inhibitor results in some improvement in patient well-being in at least some patients).

As used herein, the term "11β-HSD1-mediated condition or disorder" and related terms and phrases refer to a condition or disorder characterized by inappropriate, e.g., less than or greater than normal, 11β-HSD1 activity. A 11β-HSD1-mediated condition or disorder may be completely or partially characterized by inappropriate 11β-HSD1 activity. However, a 11β-HSD1-mediated condition or disorder is one in which modulation of 11β-HSD1 results in some effect on the underlying condition or disease (e.g., a 11β-HSD1 inhibitor results in some improvement in patient well-being in at least some patients).

As used herein, the term "11β-HSD2-mediated condition or disorder" and related terms and phrases refer to a condition or disorder characterized by inappropriate, e.g., less than or greater than normal, 11β-HSD2 activity. A 11β-HSD2-mediated condition or disorder may be completely or partially characterized by inappropriate 11β-HSD2 activity. However, a 11β-HSD2-mediated condition or disorder is one in which modulation of 11β-HSD2 results in some effect on the underlying condition or disease (e.g., a 11β-HSD2 inhibitor results in some improvement in patient well-being in at least some patients).

As used herein, the term "17β-HSD3-mediated condition or disorder" and related terms and phrases refer to a condition or disorder characterized by inappropriate, e.g., less than or greater than normal, 17β-HSD3 activity. A 17β-HSD3-mediated condition or disorder may be completely or partially characterized by inappropriate 17β-HSD3 activity. However, a 17β-HSD3-mediated condition or disorder is one in which modulation of 17θ-HSD3 results in some effect on the underlying condition or disease (e.g., a 17β-HSD3 inhibitor results in some improvement in patient well-being in at least some patients).

The following abbreviations are used herein and have the indicated definitions: DMEM is Dulbecco's Modified Eagle Medium; Et$_3$N is triethylamine; EtOAc is ethyl acetate; MeOH is methanol; MS is mass spectrometry; NMR is nuclear magnetic resonance; PBS is phosphate-buffered saline; SPA is scintillation proximity assay; THF is tetrahydrofuran; and TMS is trimethylsilyl.

Compounds of the Invention

The present invention provides compounds of Formula (I) as well as their pharmaceutically acceptable salts, solvates, stereoisomers, or prodrugs thereof, collectively referred to as the "the benzamide derivatives"

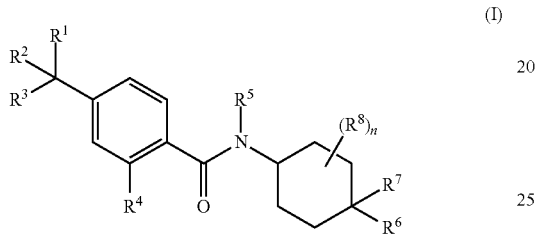

(I)

wherein all the variables are defined as above.

In one embodiment, n is 0, $R^1$ is —OH, $R^2$ is ($C_1$-$C_3$)alkyl, and $R^3$ is ($C_1$-$C_3$)haloalkyl, $R^5$ is selected from the group consisting of ($C_1$-$C_4$)alkyl, ($C_3$-$C_6$)cycloalkyl, ($C_1$-$C_3$)haloalkyl, and $R^6$ is selected from the group consisting of ($C_3$-$C_8$)cycloalkyl, aryl, and heteroaryl.

In one embodiment, $R^6$ is aryl, in particular, optionally substituted phenyl. In still another embodiment, $R^6$ is heteroaryl, in particular, pyridinyl.

In another embodiment, $R^6$ is ($C_3$-$C_6$)cycloalkyl, in particular, cyclopropyl.

In one embodiment $R^1$ is —OH, $R^2$ is methyl, $R^3$ is trifluoromethyl, and $R^5$ is cyclopropyl.

In another embodiment, the $R^1$-$R^3$ moiety is:

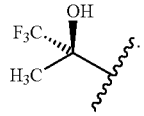

In another embodiment, the $R^1$-$R^3$ moiety is:

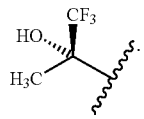

The benzamide derivatives can have asymmetric centers and therefore exist in different enantiomeric and diastereomeric forms. This invention relates to the use of all optical isomers and stereoisomers of the benzamide derivatives, and mixtures thereof, and to all pharmaceutical compositions and methods of treatment that may employ or contain them.

It should be noted that racemates, racemic mixtures, and stereoisomers, particularly diastereomeric mixtures or diastereomerically pure compounds and enantiomers or enantiomerically pure compounds of the above are all encompassed.

Specific examples of compounds of Formula (I) are provided below:

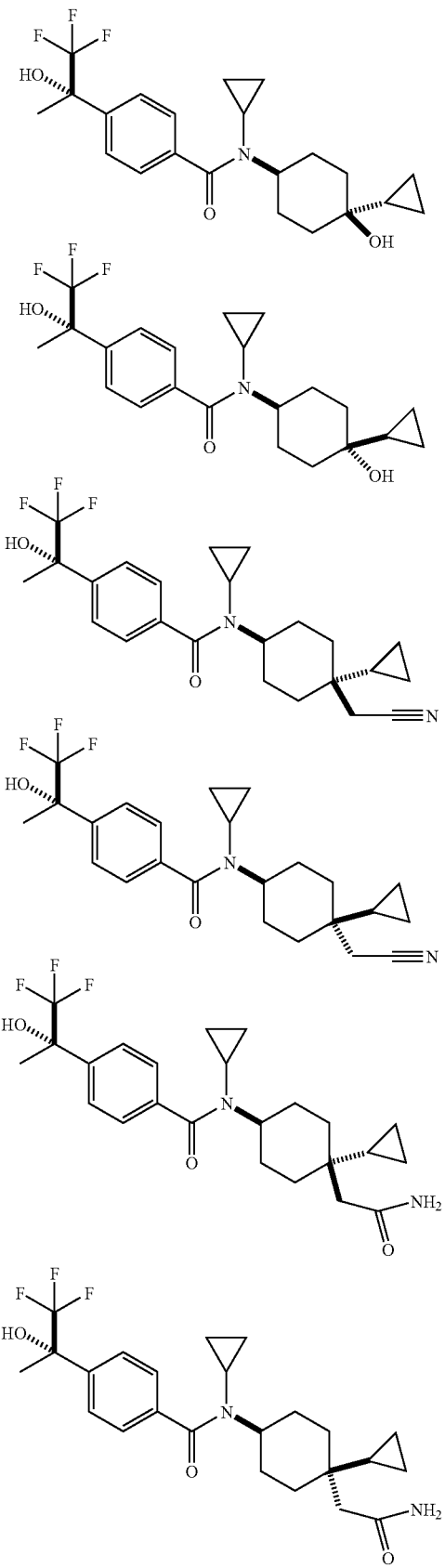

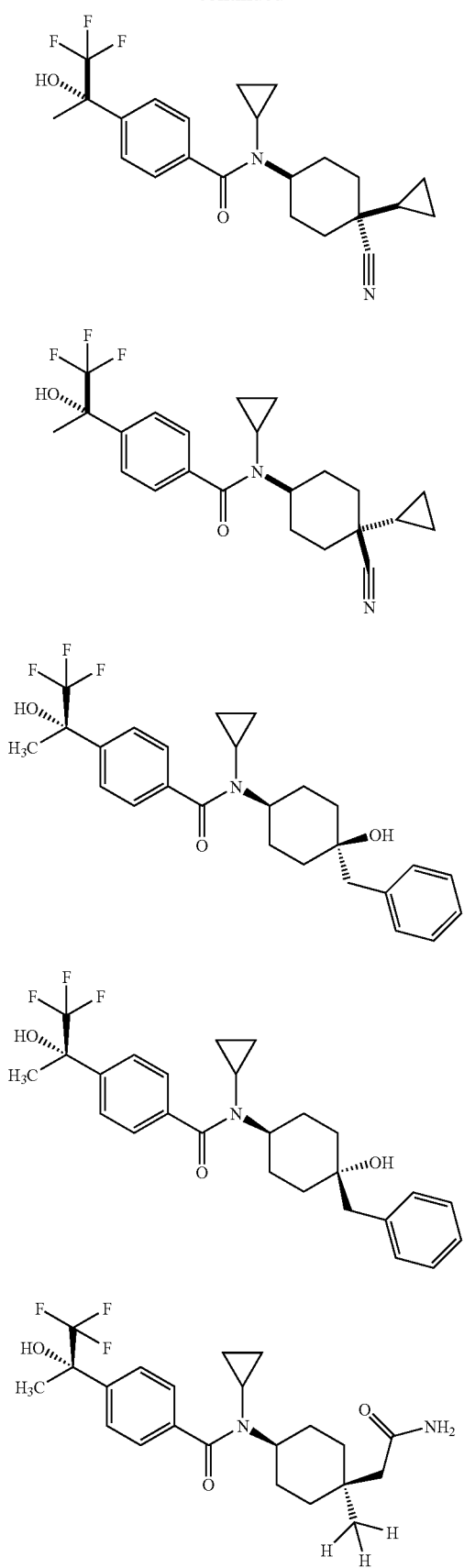
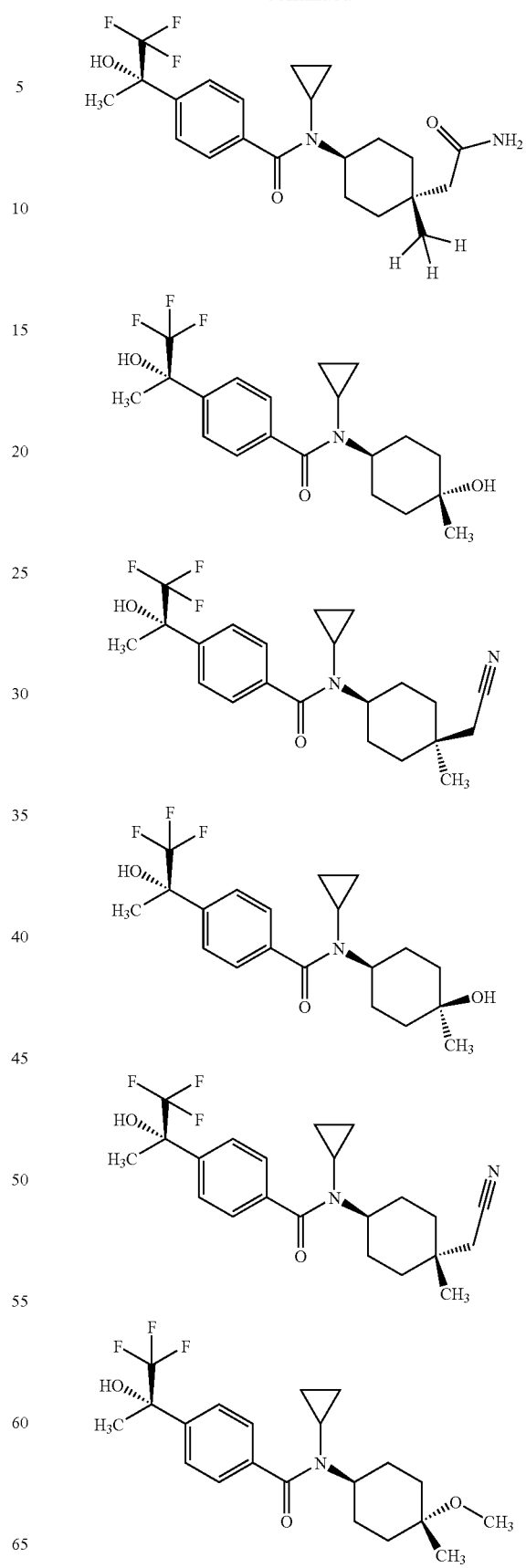

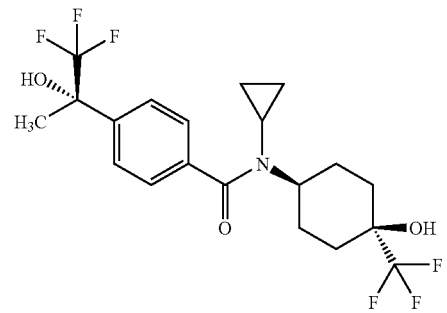
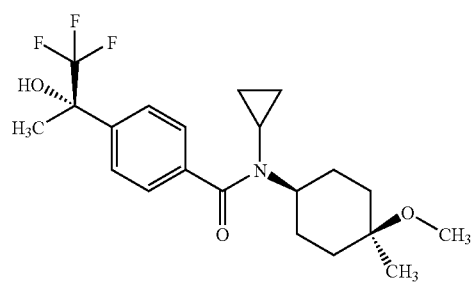
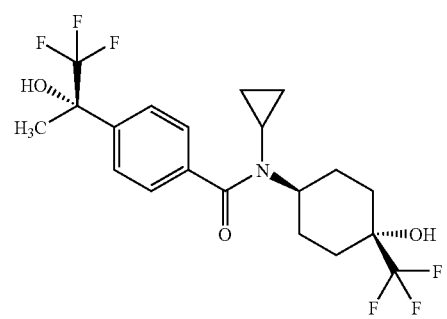
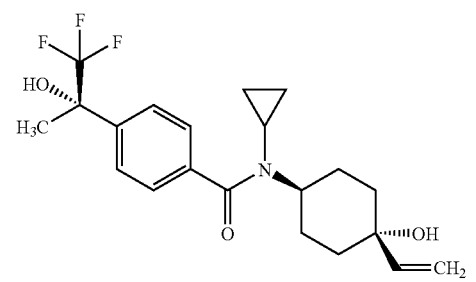
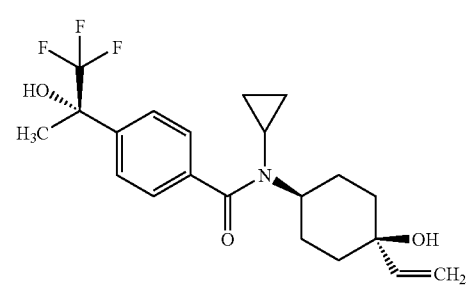
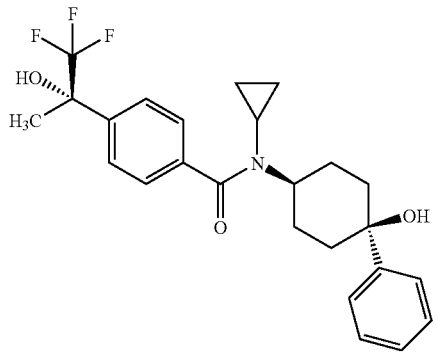
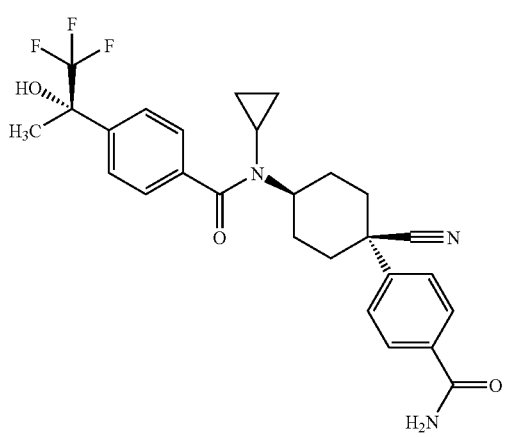
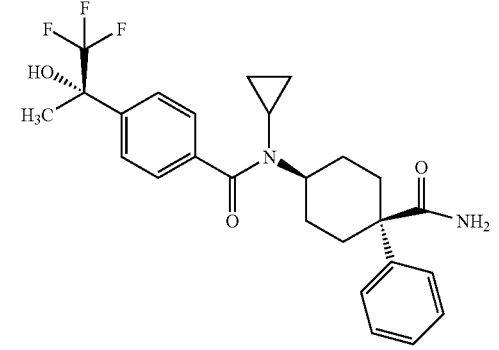
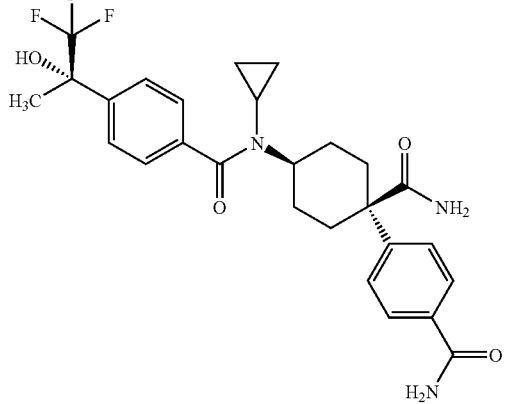

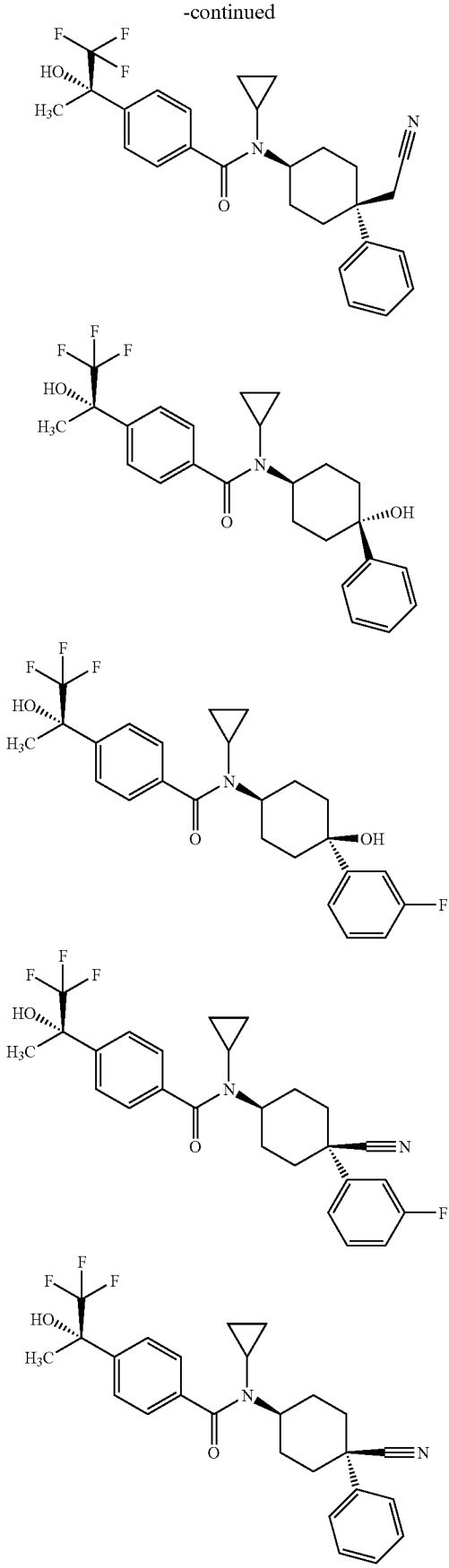
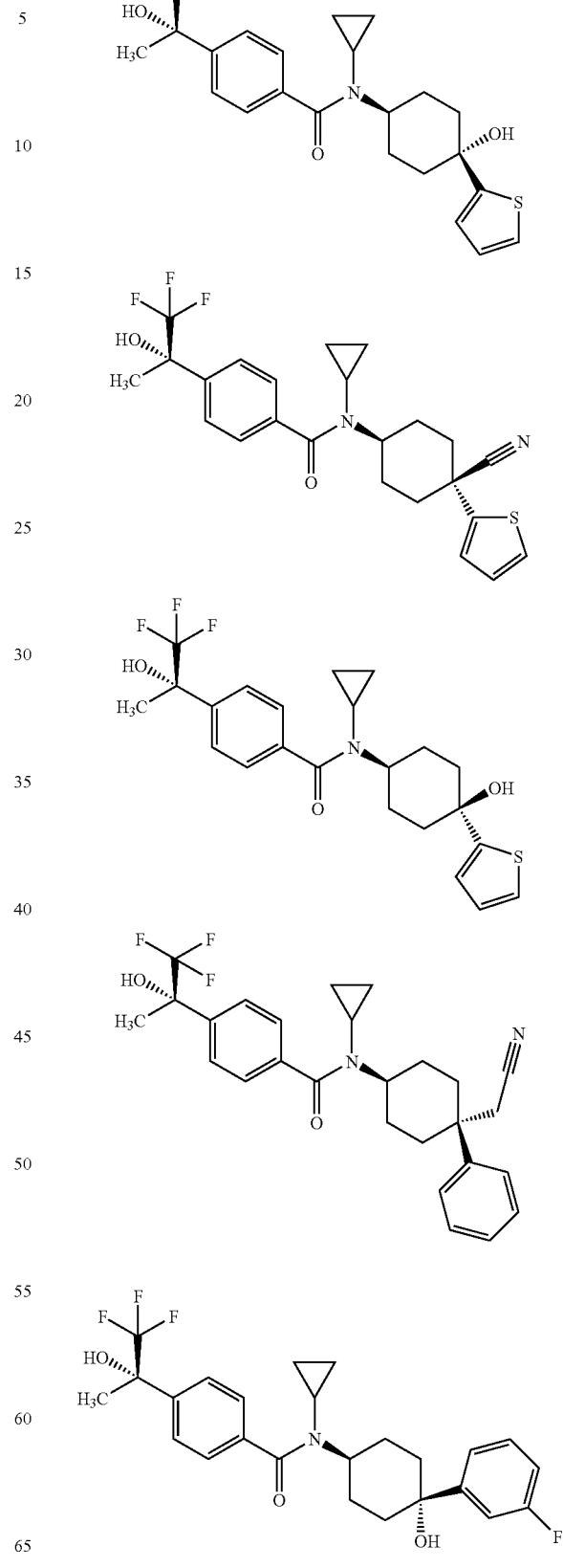

-continued
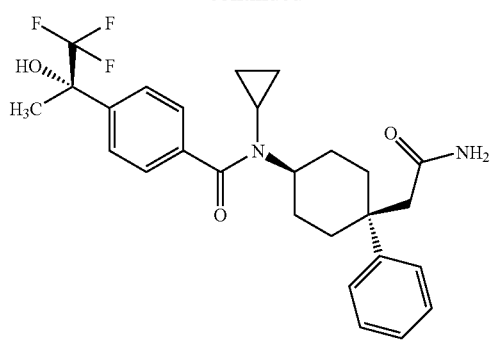
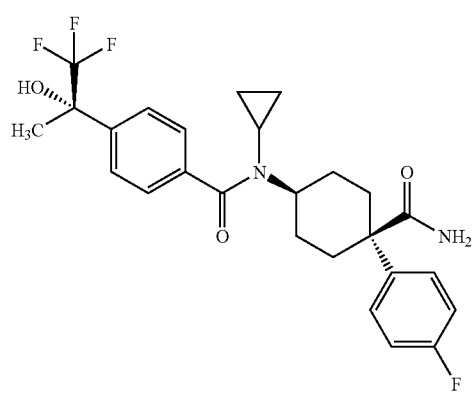
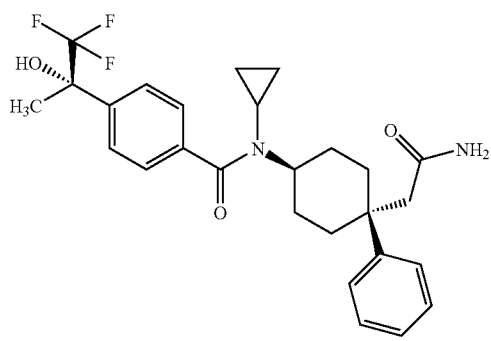
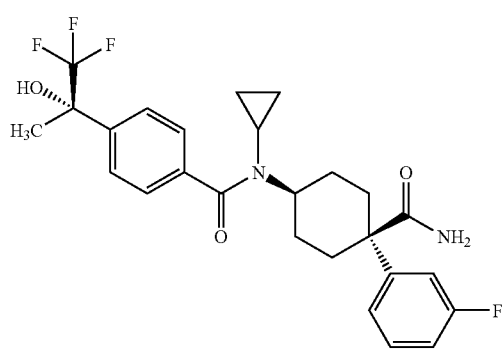
-continued
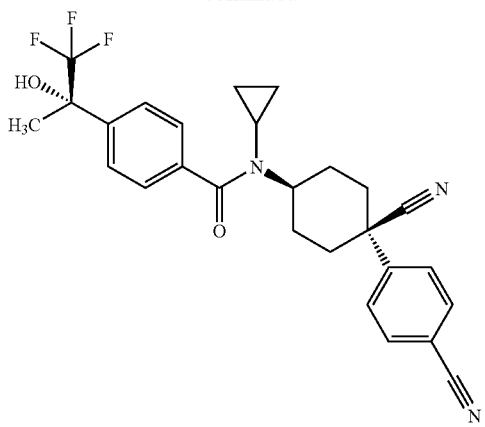
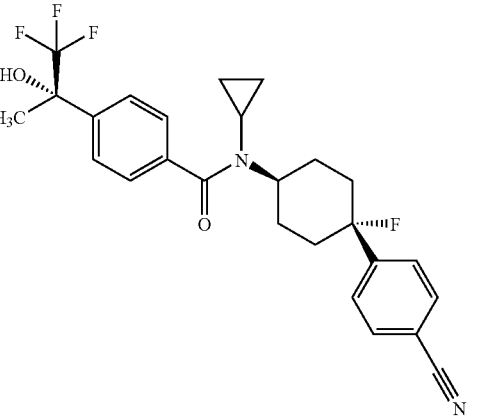

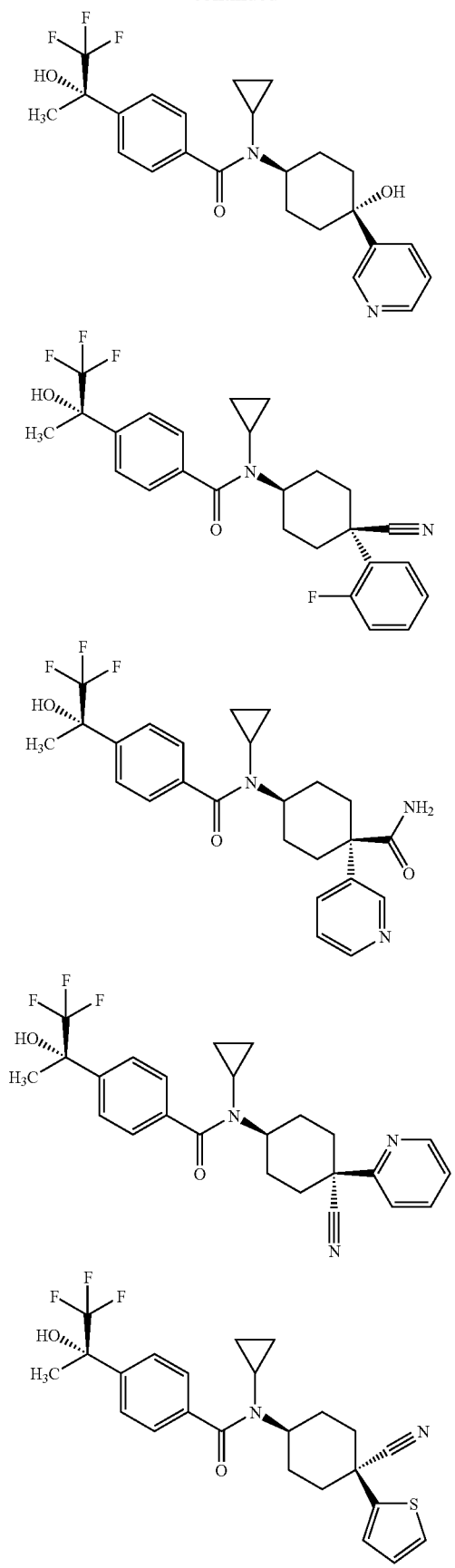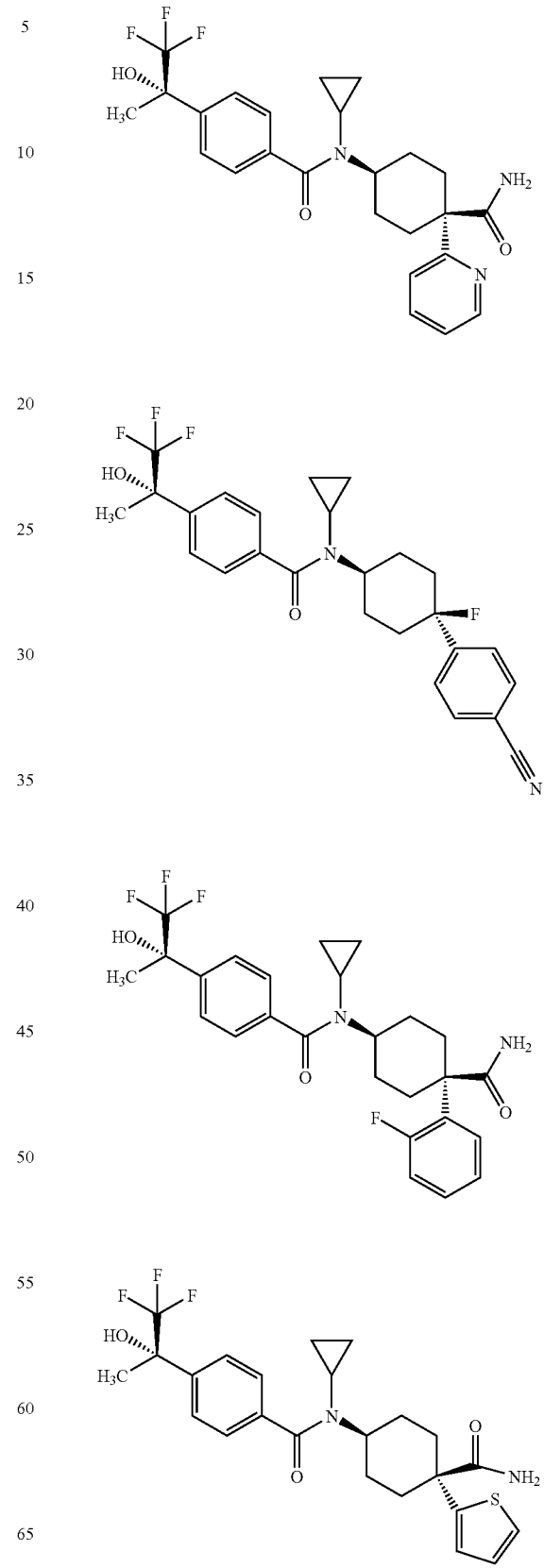

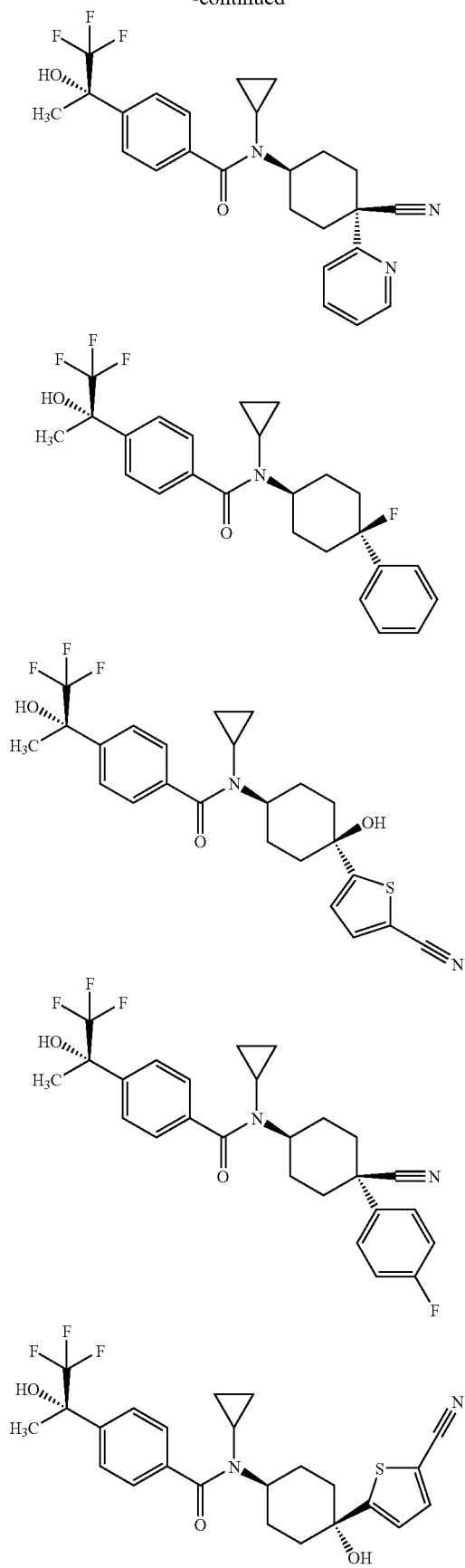
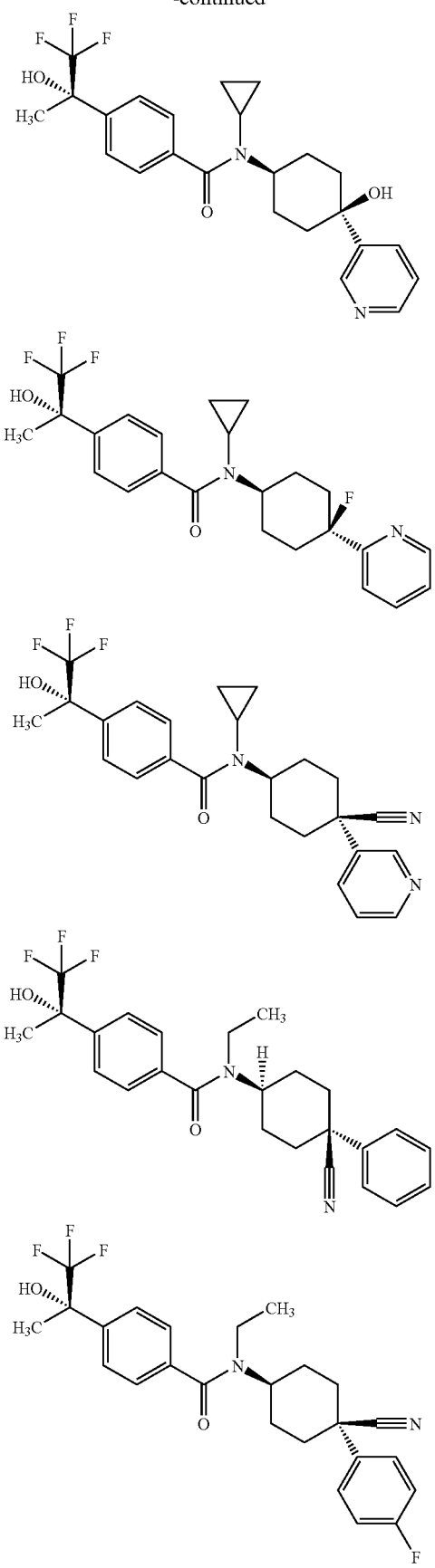

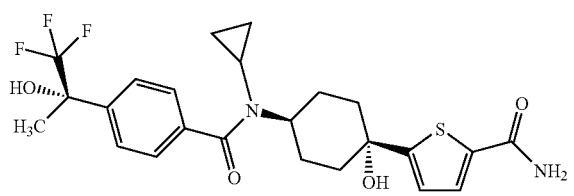
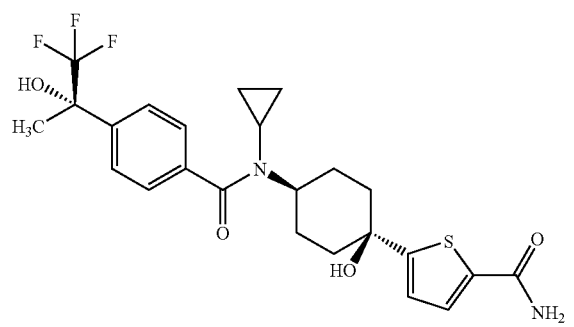
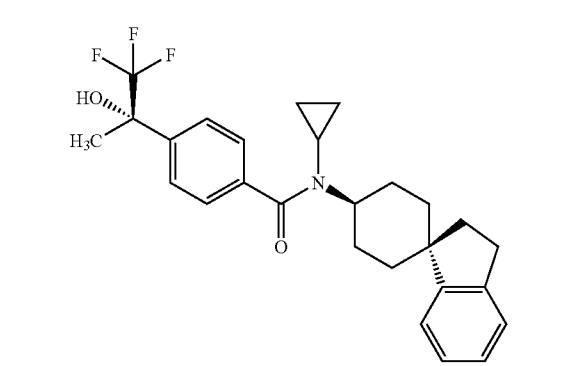
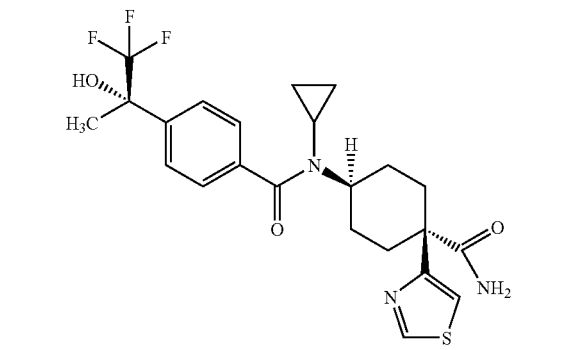
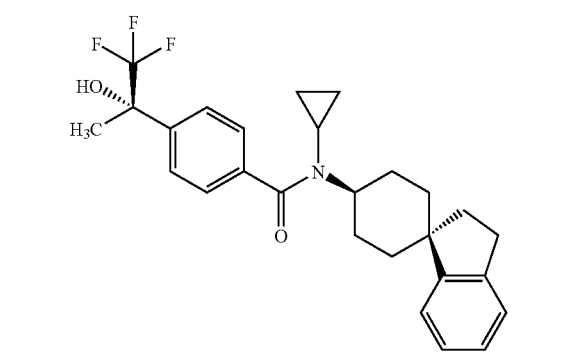
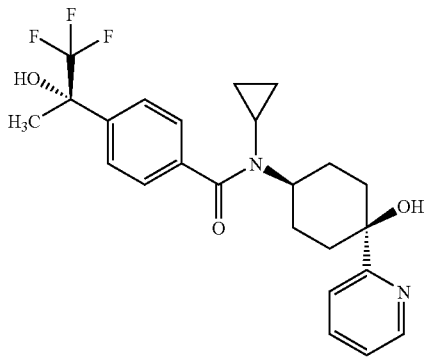
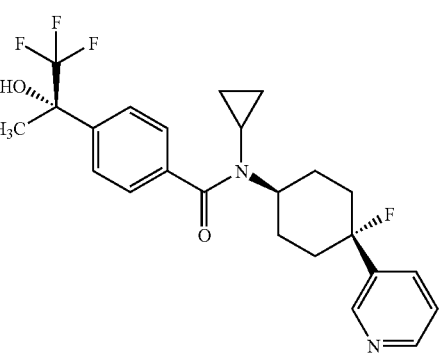
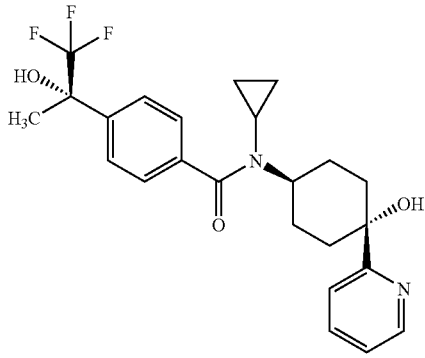
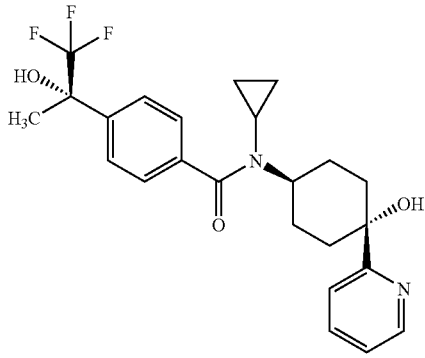

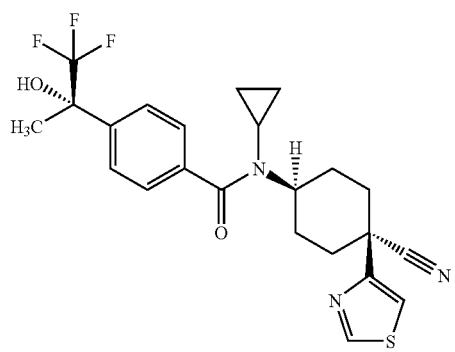
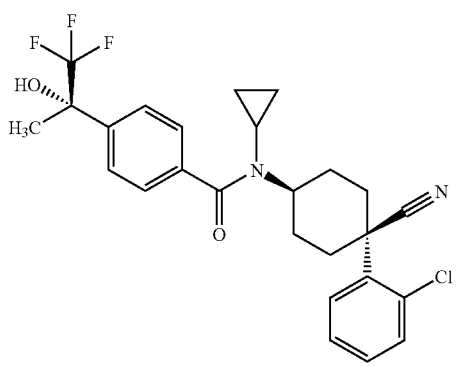
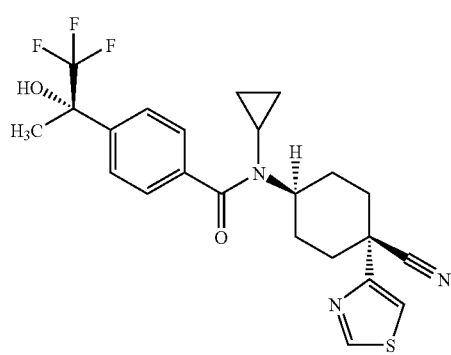
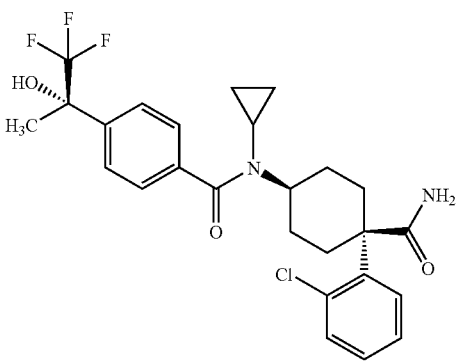
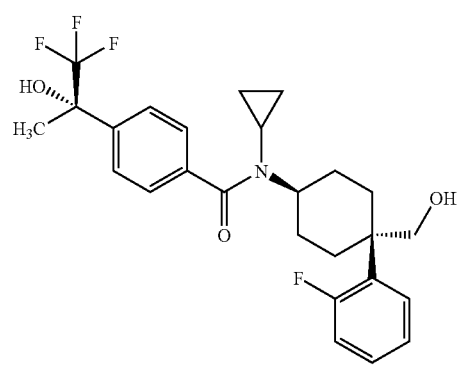
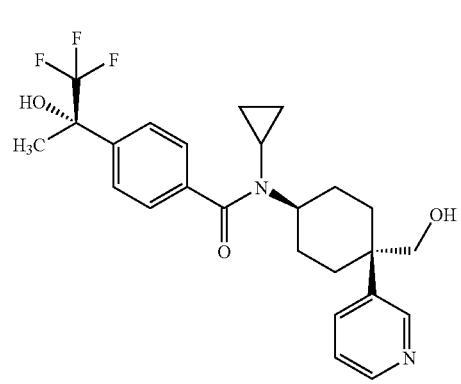
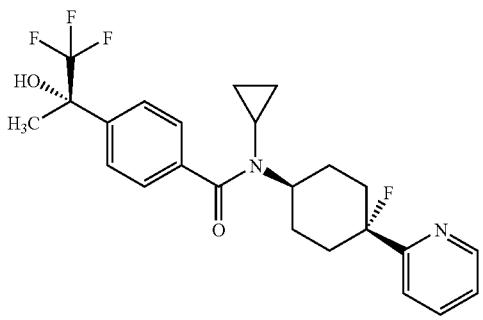
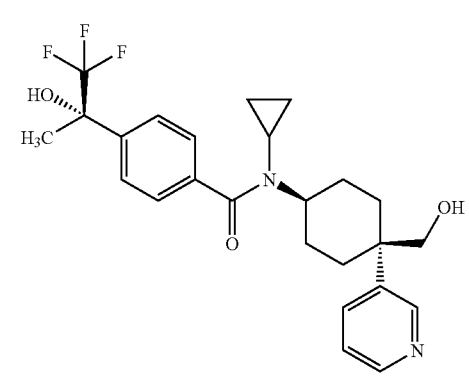

-continued
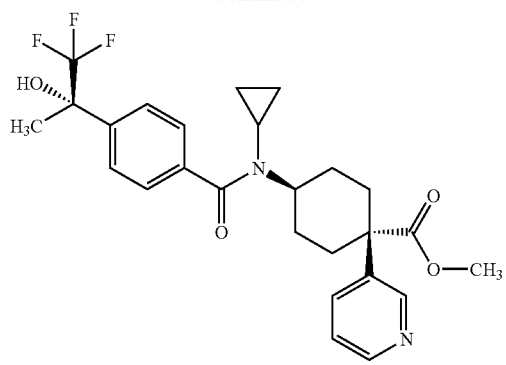
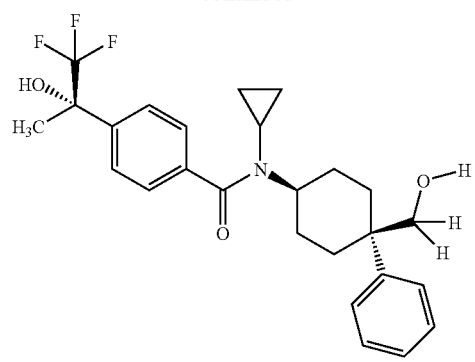
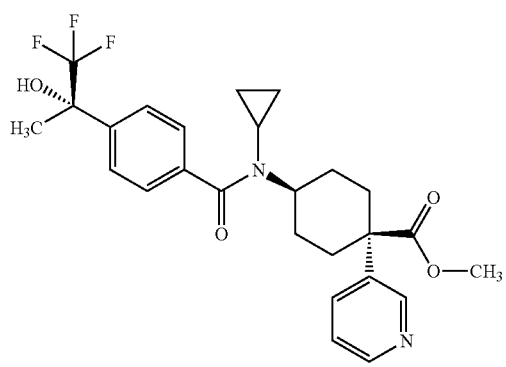
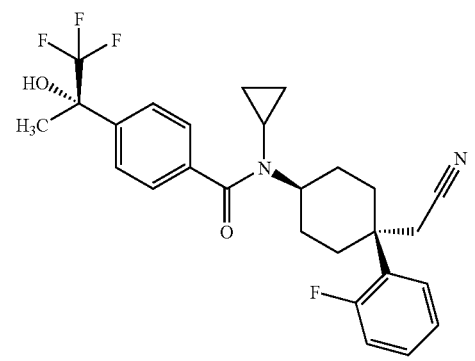
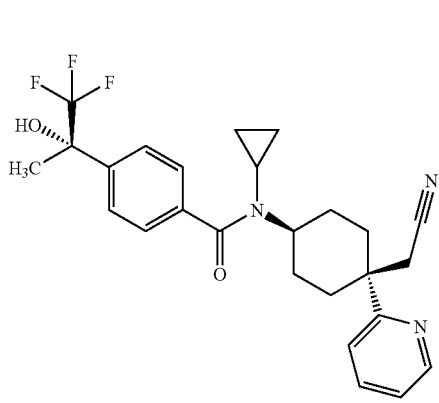
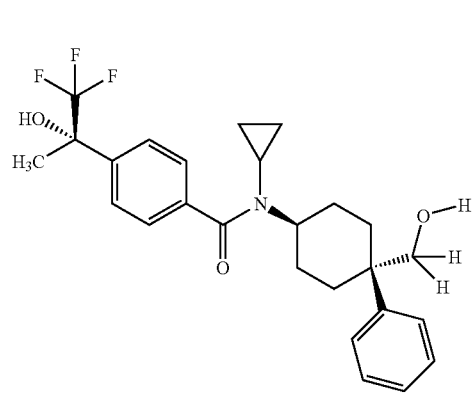
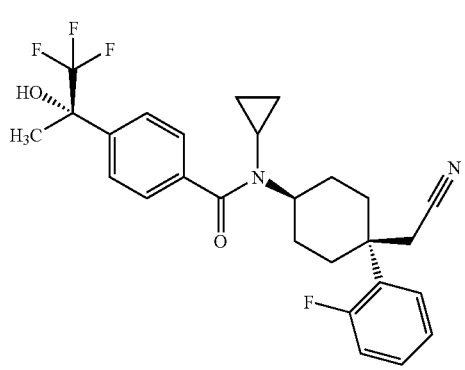
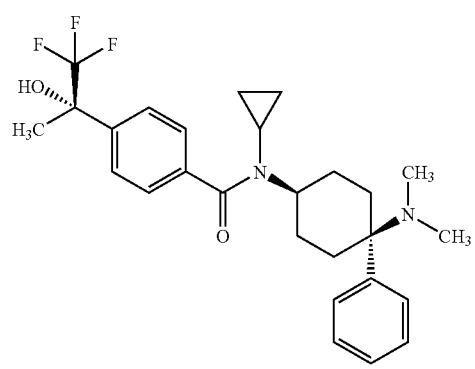

37
-continued
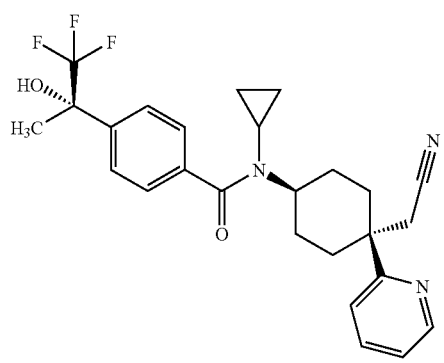
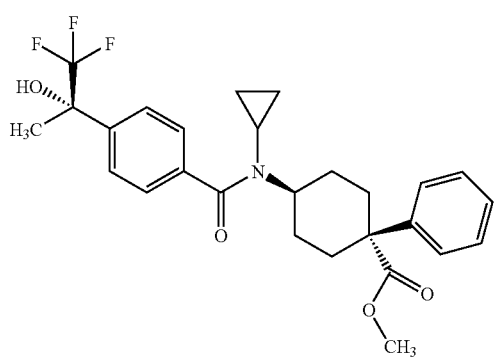
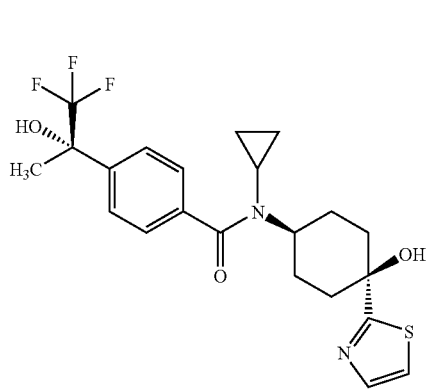
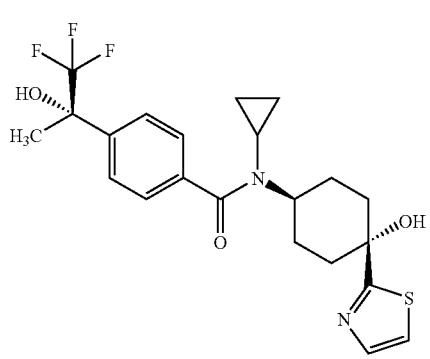
38
-continued
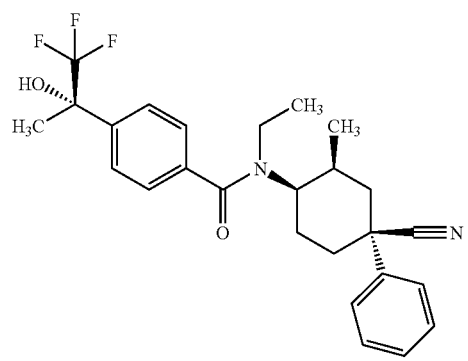
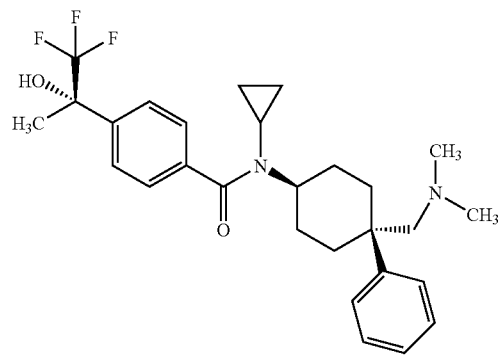
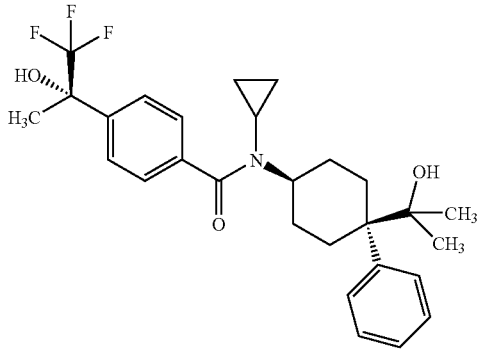
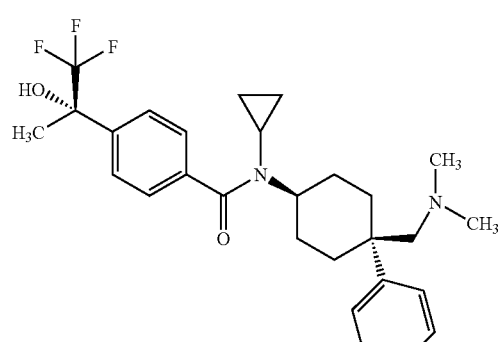

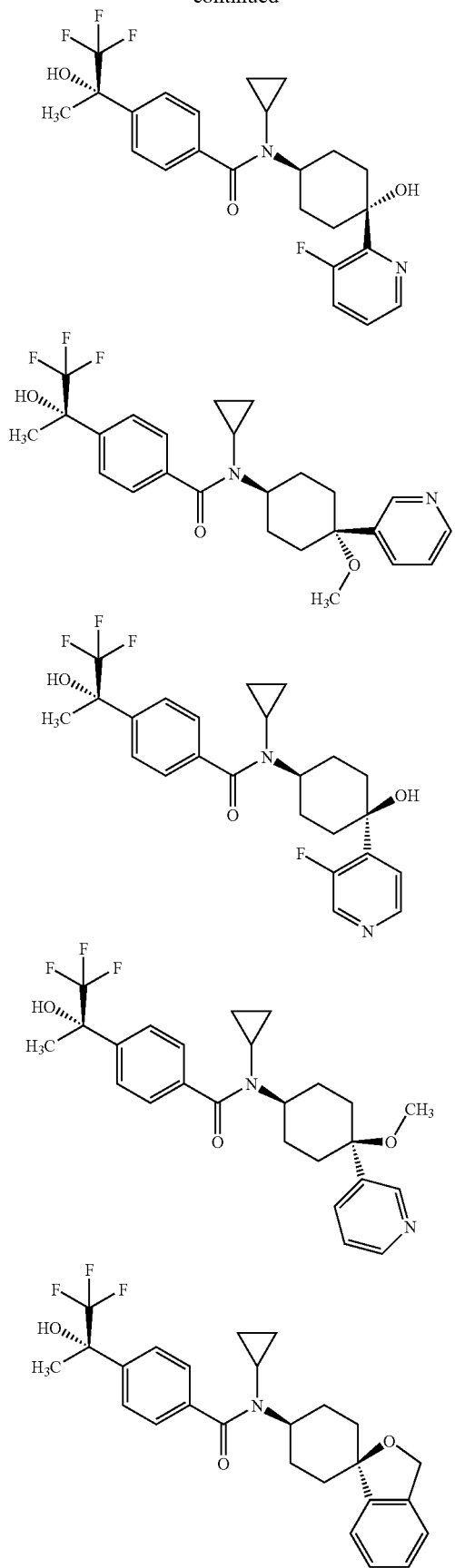
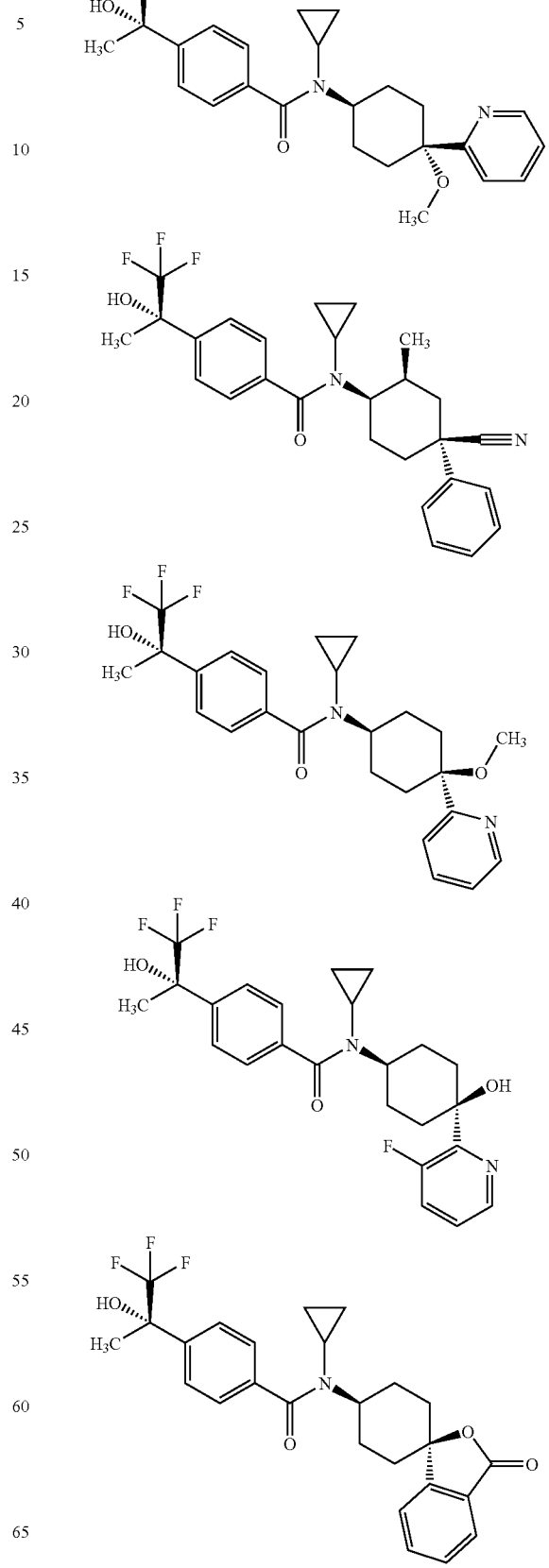

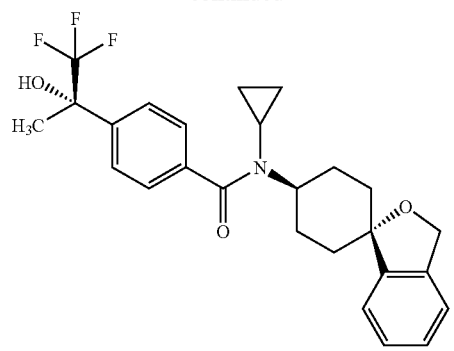
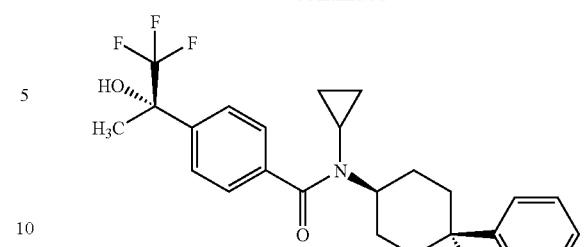
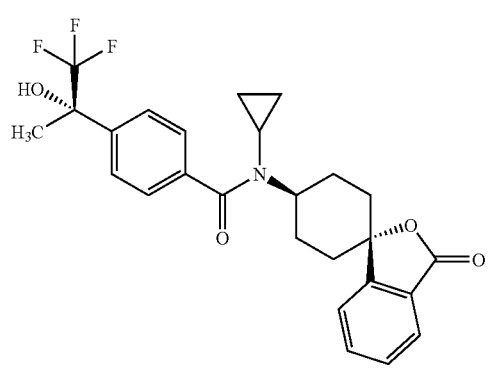
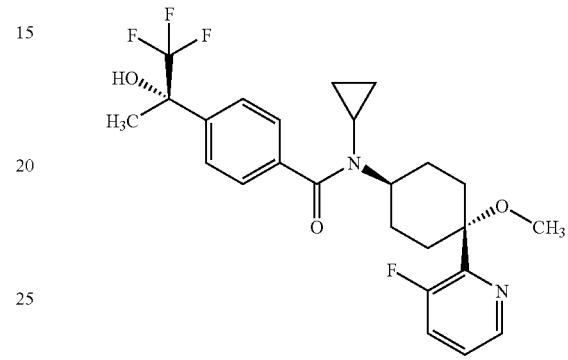
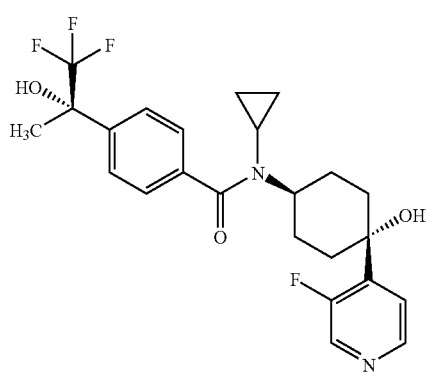
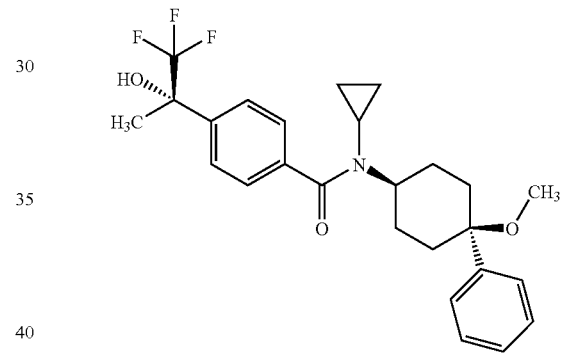
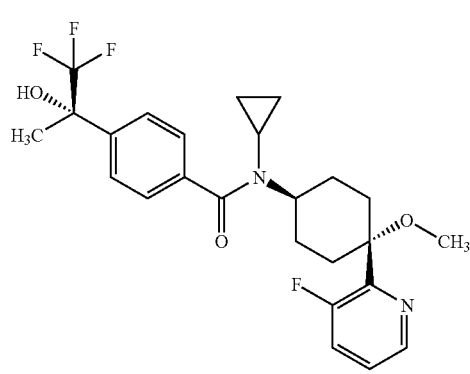
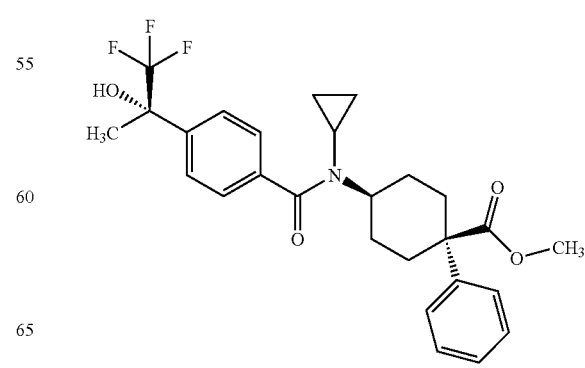

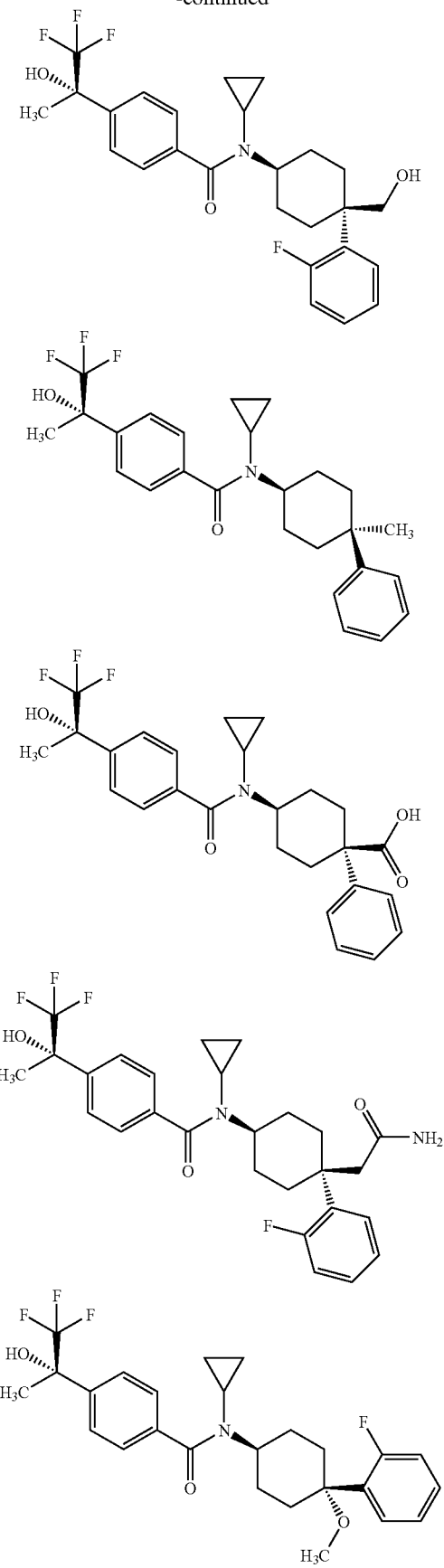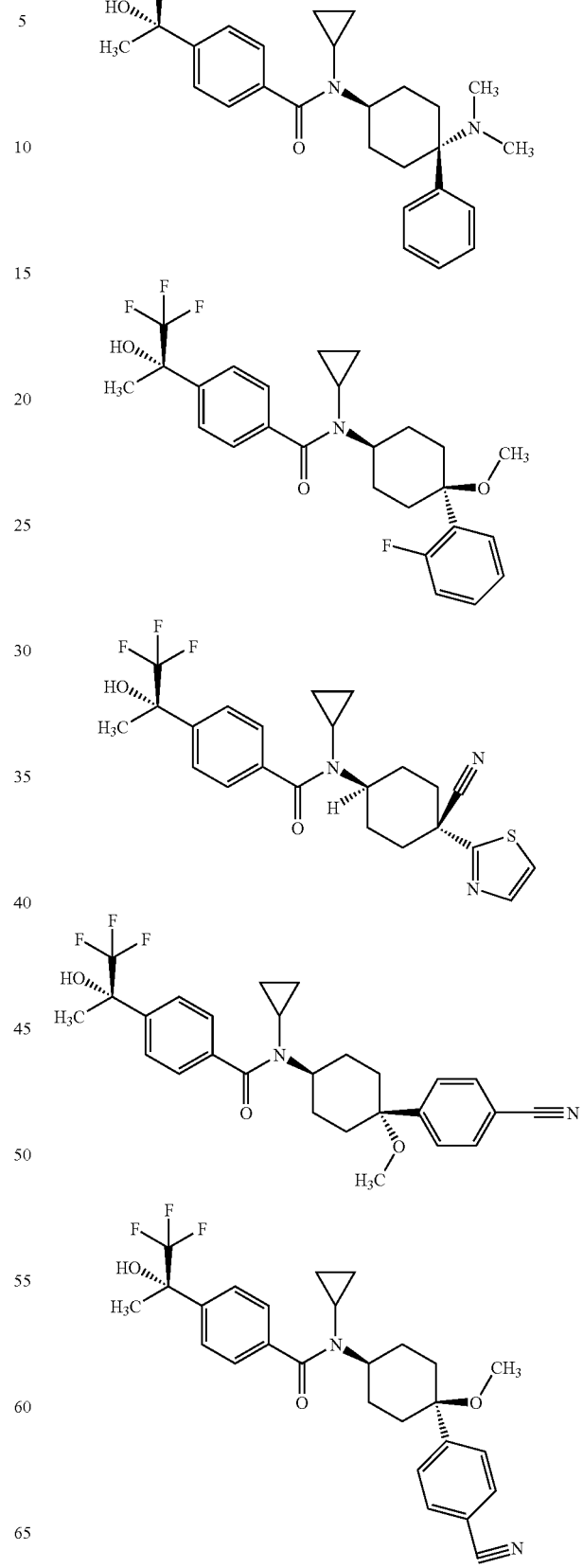

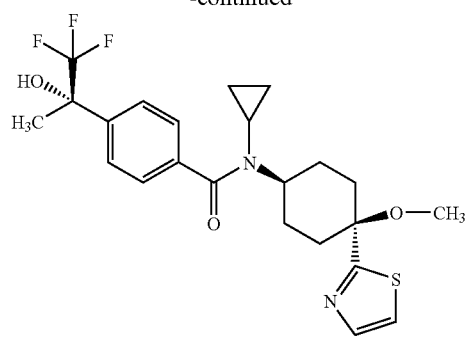
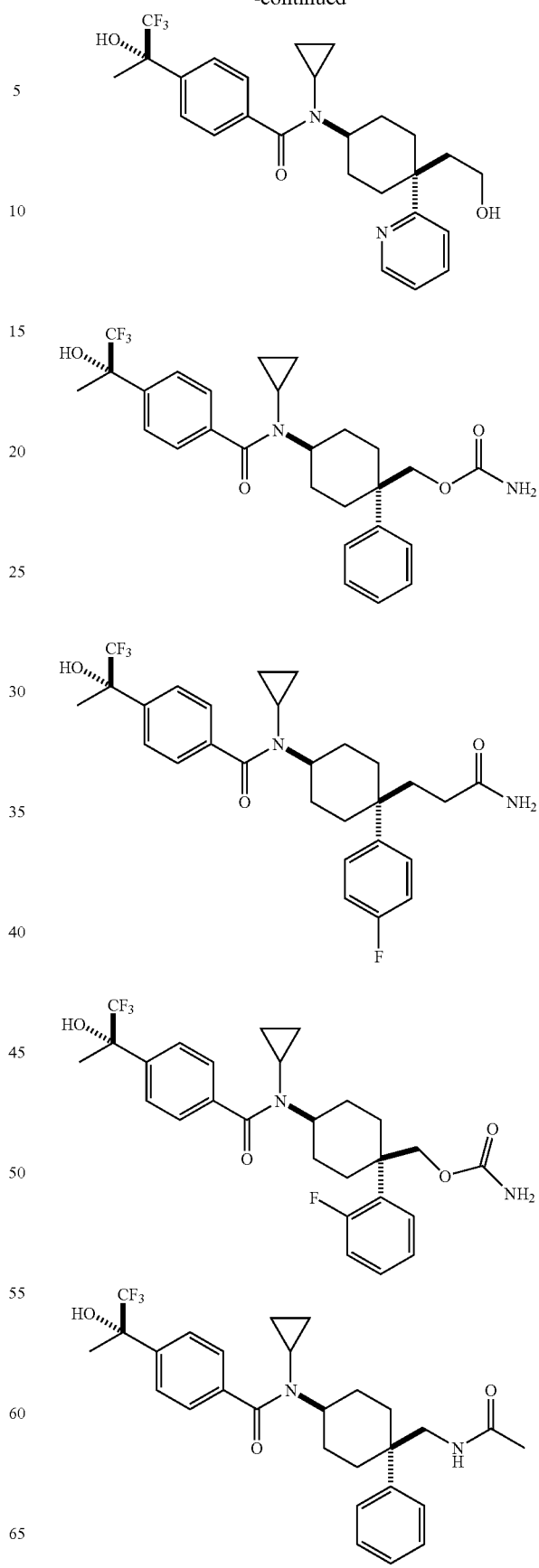

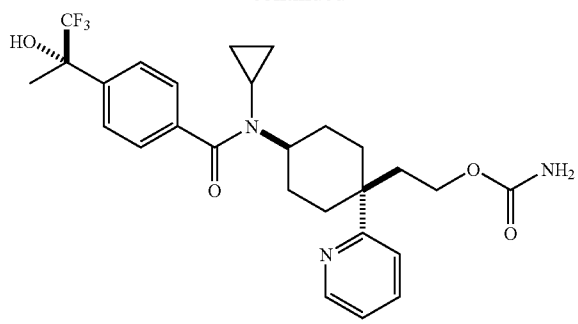
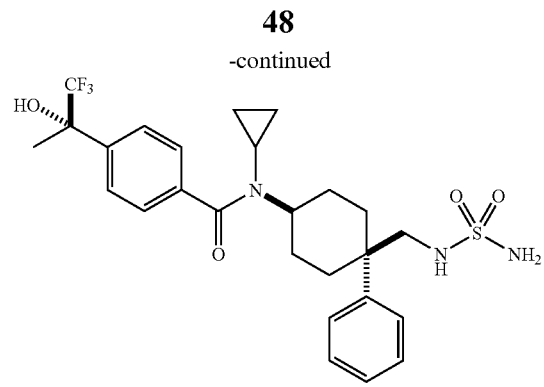
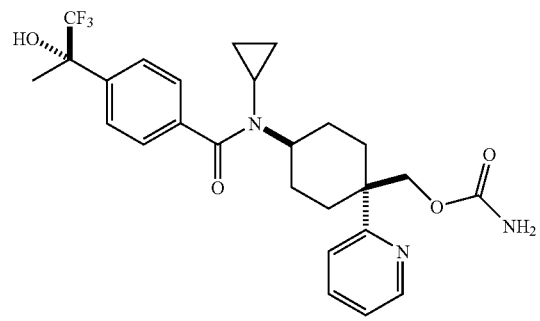
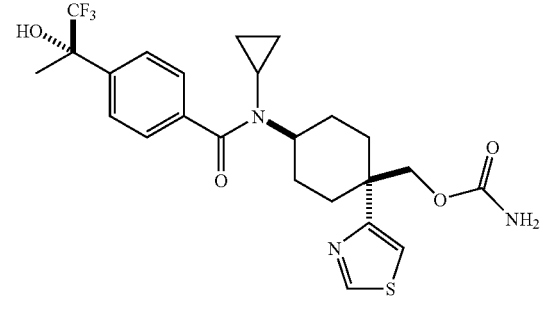
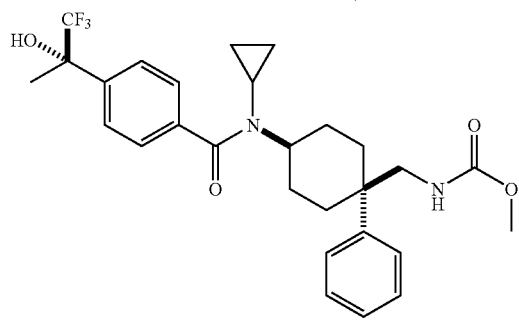
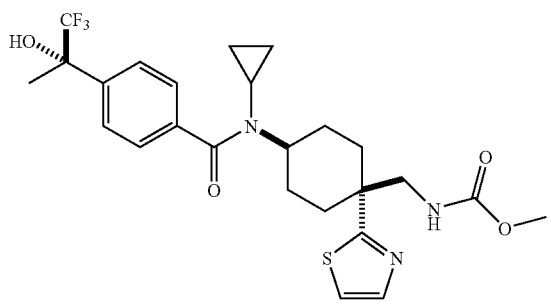
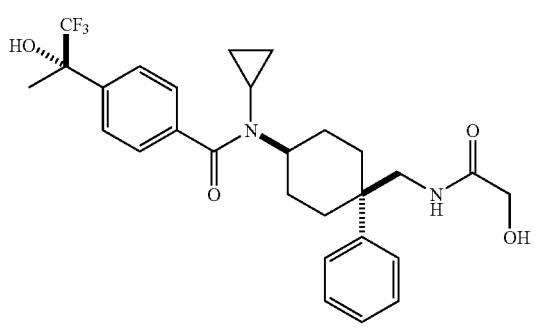
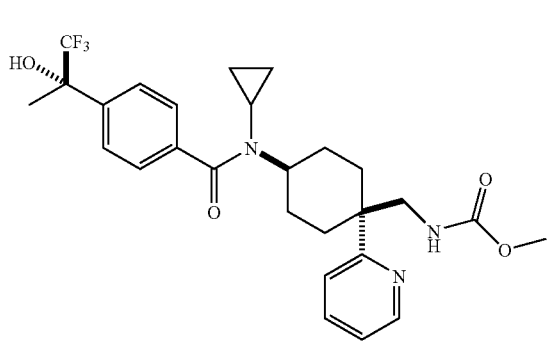
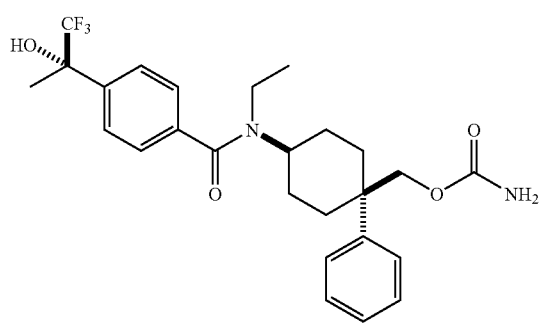
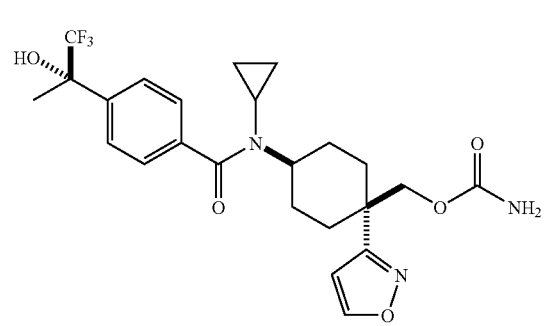

49
-continued
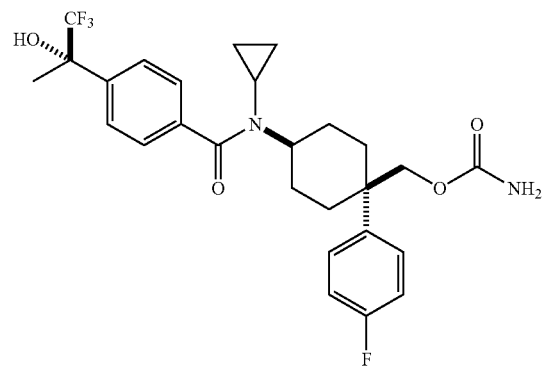
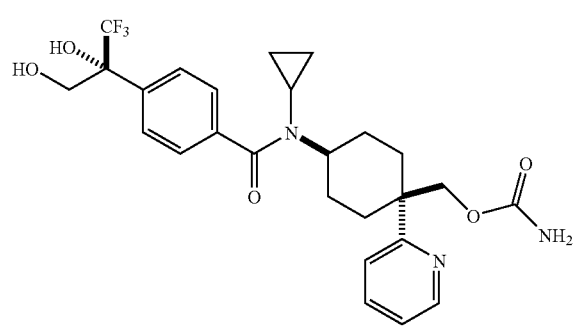
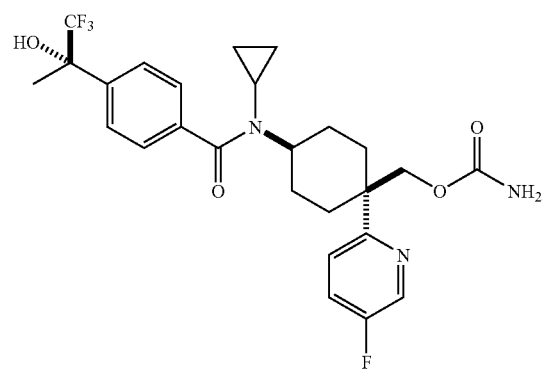
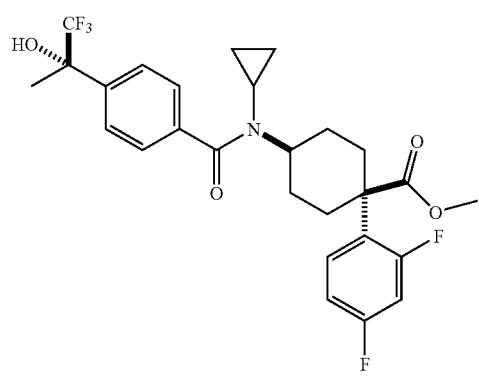
50
-continued
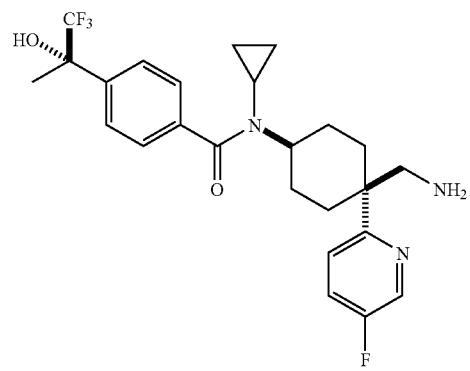
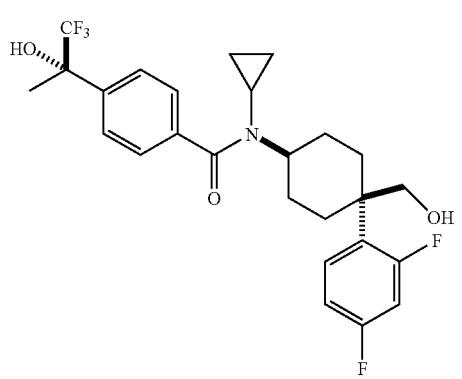
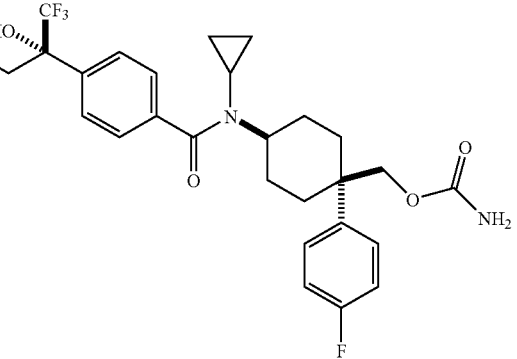
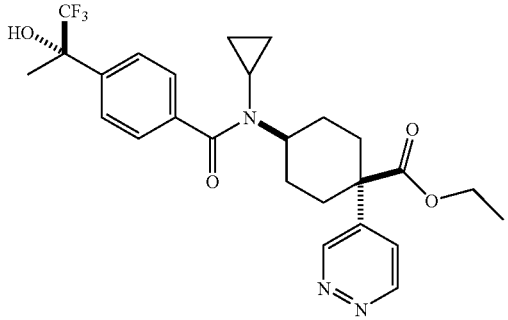

51
-continued
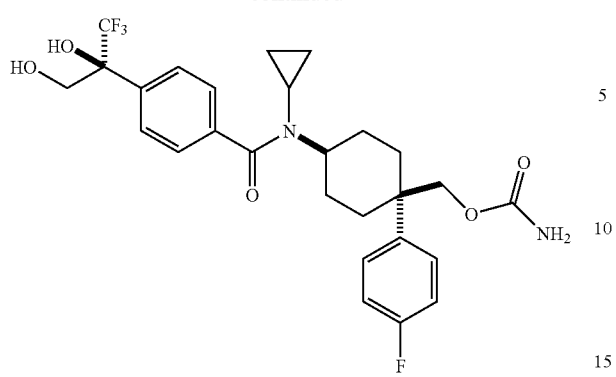
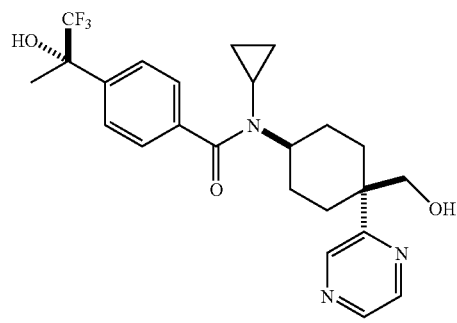
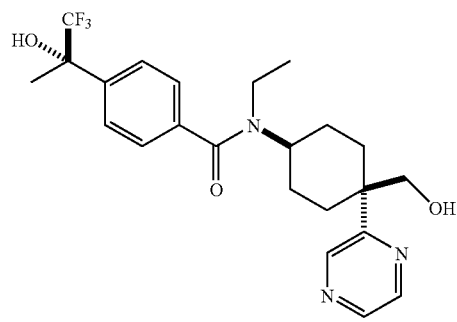
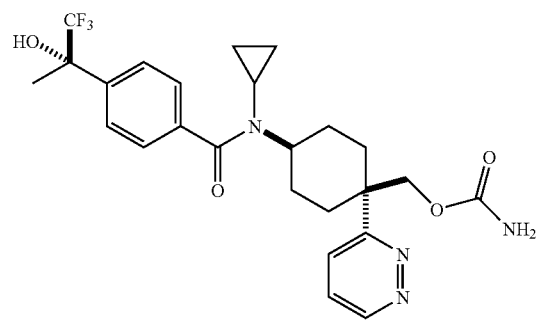
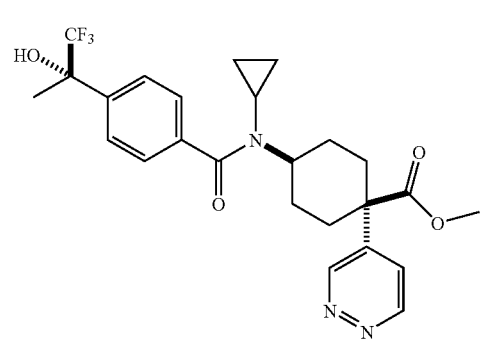
52
-continued
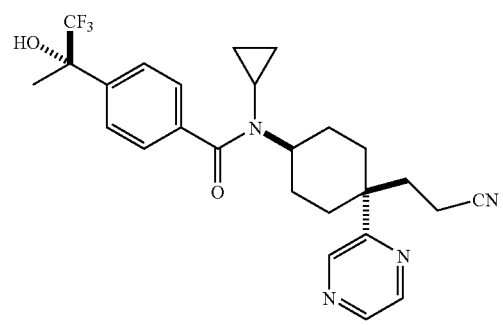
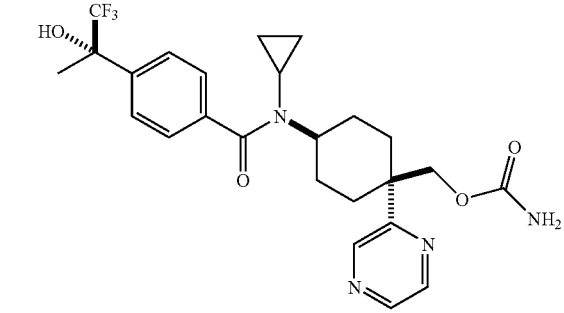
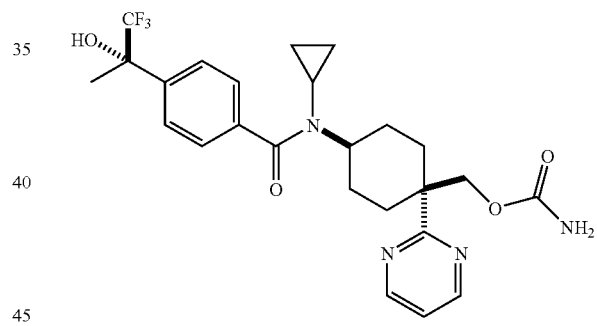
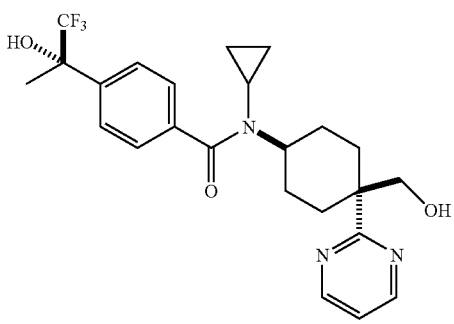
In one embodiment, optionally in combination with any other embodiment herein described, the compound is

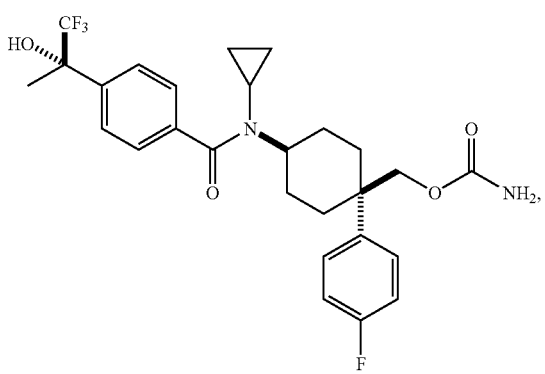

or a pharmaceutically acceptable salt, solvate, stereoisomer or prodrug thereof.

In another embodiment, optionally in combination with any other embodiment herein described, the compound is

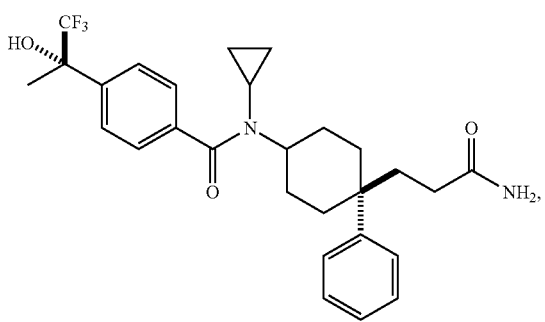

or a pharmaceutically acceptable salt, solvate, stereoisomer or prodrug thereof

In yet another embodiment, optionally in combination with any other embodiment herein described, the compound is

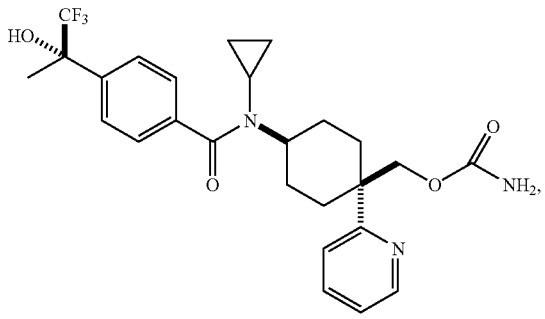

or a pharmaceutically acceptable salt, solvate, stereoisomer or prodrug thereof.

In still another embodiment, optionally in combination with any other embodiment herein described, the compound is

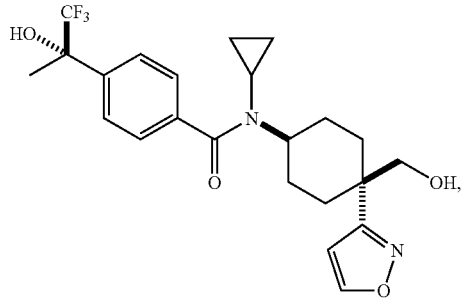

or a pharmaceutically acceptable salt, solvate, stereoisomer or prodrug thereof.

In still another embodiment, optionally in combination with any other embodiment herein described, the compound is

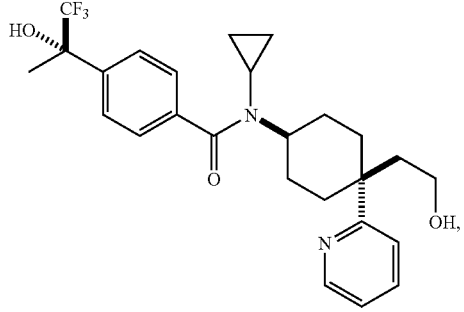

or a pharmaceutically acceptable salt, solvate, stereoisomer or prodrug thereof, The present invention also provides compositions comprising a therapeutically effective amount of a benzamide derivative of Formula (I) and a pharmaceutically acceptable vehicle, carrier, diluent or excipient.

The invention further provides benzamide derivatives of Formula (I) that are in isolated and purified form.

The invention provides methods for treating diabetes comprising administering to a patient in need thereof a therapeutically effective amount of a benzamide derivative as disclosed herein, such as of Formula (I).

The invention also provides methods for treating obesity comprising administering to a patient in need thereof a therapeutically effective amount of a benzamide derivative as disclosed herein, such as of Formula (I).

The invention further provides methods for treating an HSD-mediated condition or disorder comprising administering to a patient in need thereof a therapeutically effective amount of a benzamide derivative as disclosed herein, such as of Formula (I).

The invention further provides methods for treating an 11β-HSD1-mediated condition or disorder comprising administering to a patient in need thereof a therapeutically effective amount of a benzamide derivative as disclosed herein, such as of Formula (I).

The invention further provides methods for treating an 11β-HSD2-mediated condition or disorder comprising administering to a patient in need thereof a therapeutically effective amount of a benzamide derivative as disclosed herein, such as of Formula (I).

The invention further provides methods for treating an 17β-HSD3-mediated condition or disorder comprising administering to a patient in need thereof a therapeutically effective amount of a benzamide derivative as disclosed herein, such as of Formula (I).

The invention further provides methods for treating an HSD-responsive condition or disorder comprising administering to a patient in need thereof a therapeutically effective amount of a benzamide derivative as disclosed herein, such as of Formula (I).

The invention further provides methods for treating an 11β-HSD1-responsive condition or disorder comprising administering to a patient in need thereof a therapeutically effective amount of a benzamide derivative as disclosed herein, such as of Formula (I).

The invention further provides methods for treating an 11β-HSD2-responsive condition or disorder comprising administering to a patient in need thereof a therapeutically effective amount of a benzamide derivative as disclosed herein, such as of Formula (I).

The invention further provides methods for treating an 17β-HSD3-responsive condition or disorder comprising administering to a patient in need thereof a therapeutically effective amount of a benzamide derivative as disclosed herein, such as of Formula (I).

Preparation of the Benzamide Derivatives of Formula I

Those skilled in the art will recognize that there are a variety of methods available to synthesize molecules represented in the claims. In general, useful methods for synthesizing compounds represented in the claims consist of three parts, which may be done in any order: formation of an amide bond, installation of a —$CR^1R^2R^3$ group, and installation or modification of functional groups appended to the —$NR^5R^6$ group and the $R^4$-substituted aryl ring. Retrosynthetic disconnection of the compounds of the invention into fragments a-c useful for construction of the compounds, is shown below:

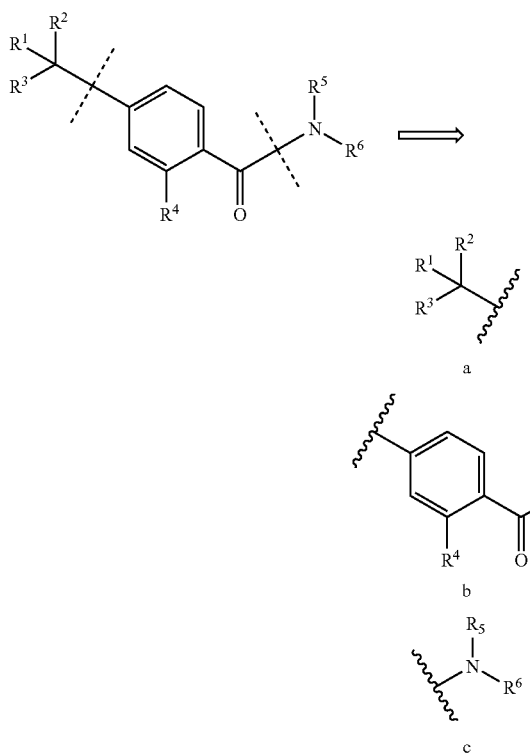

Several methods for the preparation of claimed compounds are exemplary (eq. 1-3). Equation one demonstrates one method of forming the amide linkage. In the case of eq. 1, X may be chosen from an appropriate group such as OH, Cl and F, or from any group capable of activating a carbonyl group for displacement by an amine (e.g., OSu, imidazole, etc.).

eq. 1

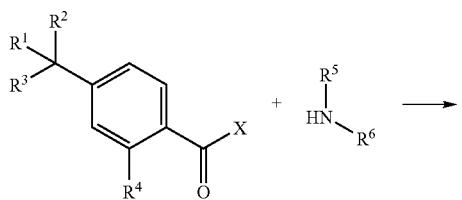

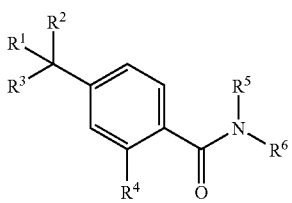

The coupling referred to in eq. 1 may be assisted by the use of organic or inorganic bases, activating agents such as HBTU, and also by catalysts, in particular by those catalysts known in the art which assist in the formation of amide bonds, such as DMAP, HOBT, etc. Suitable coupling partners include a carboxylic acid and an amine, an acyl chloride and an amine, an acyl fluoride and an amine, COOSu and an amine and so forth. Those skilled in the art will recognize that there are other possible combinations which will also result in the desired product.

Installation of the —$CR^1R^2R^3$ group may occur before or after the central coupling reaction, and the group may be further modified at various times during the preparation of the claimed molecules. Equation 2 demonstrates one method, in which the —$CR^1R^2R^3$ group may be installed in the form of a ketone before the central coupling reaction, followed by further modification to reach compounds of the invention. Following the central coupling, addition of a nucleophile ("Nu") such as $CF_3^-$ or $CH_3^-$ via addition of, e.g., $CF_3TMS$, MeLi, MeMgBr or similar reagent completes the installation of the —$CR^1R^2R^3$ group. This may be followed by further modification of substituents to complete the preparation.

eq. 2

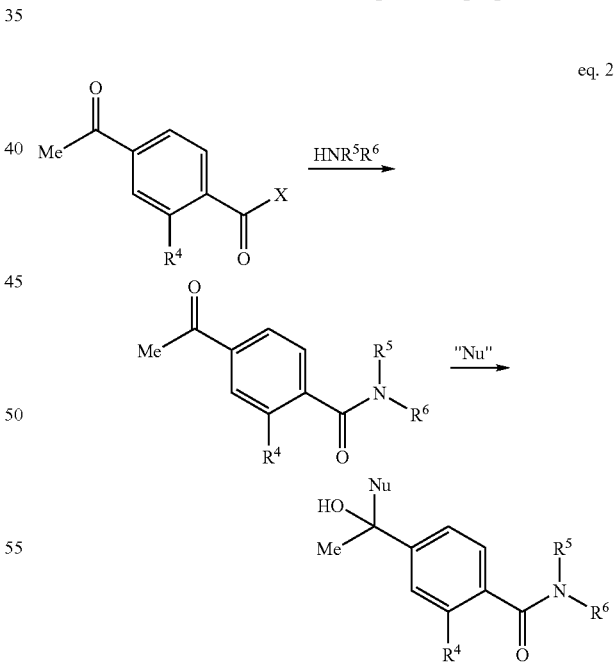

Alternatively, the —$CR^1R^2R^3$ group may be installed following the central coupling via Friedel-Crafts acylation, as shown in eq. 3. Those skilled in the art will understand that this may or may not be advantageous depending on the substituent pattern. Further modification as in eqs. 1 and 2 provides the compounds of the invention.

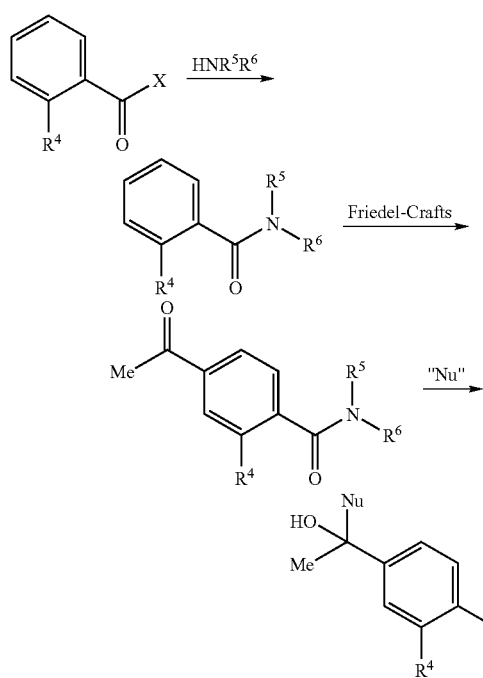

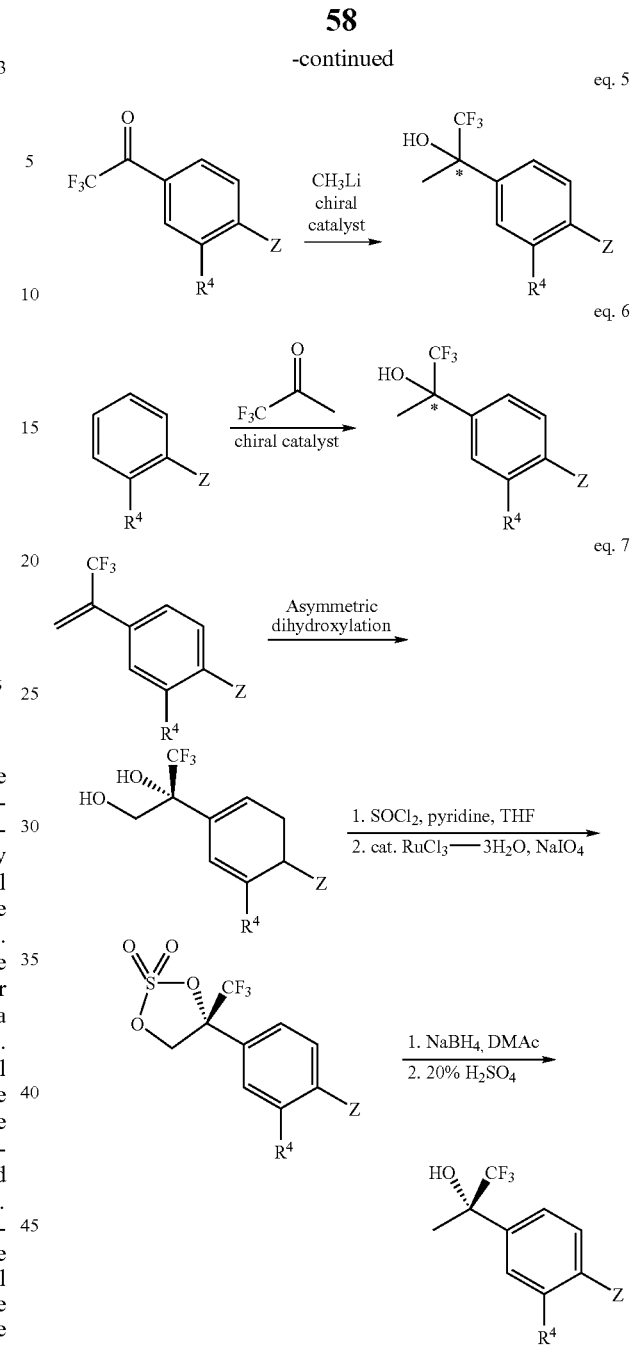

Introduction of a trifluoromethyl carbinol moiety may be achieved via a variety of methods, some of which are exemplified in eq. 4-6. One may introduce the $CF_3$ group by addition to a ketone using $CF_3TMS$ and TBAF, or the quaternary ammonium base of TBAF may be substituted with a chiral quaternary base, such as in eq. 4, to preferentially produce one enantiomer in excess (for an example see Caron et al. (2003) *Synthesis* 1693-1698). Another useful method is the chiral addition of a nucleophile such as MeLi or MeMgBr mediated via an amine or aminoalcohol additive (eq. 5) to a trifluoromethylketone (for an example see Thompson et al. (1995) *Tetrahedron Lett.* 49:8937-8940). Yet another useful method is Friedel-Crafts alkylation (eq. 6), which may be done in a fashion to give optically active products via the use of chiral catalysts such as binaphthol derived titanium catalysts (Ishii et al. (2000) *J. Org. Chem.* 65:1597-1599), and chiral copper catalysts (Zhuang et al. (2001) *J. Org. Chem.* 66:1009-1013). Asymmetric dihydroxylation of trifluoromethyl styrene can be a highly selective method to synthesize this type of chiral carbinol. Sharpless dihydroxylation is well established and usually highly enantioselective. As shown the diol is transferred to the corresponding cyclic sulfate. The sulfate can then be reduced, subsequent hydrolysis gives the desired carbinol (eq. 7). One skilled in the art will understand that a variety of methods are available for this transformation. For the most efficient preparation of any particular compound in the claims, one skilled in the art will recognize that the timing of the introduction of the $—CR^1R^2R^3$ group can vary, and may be the first, last, or intermediate transformation in the preparation of a given compound.

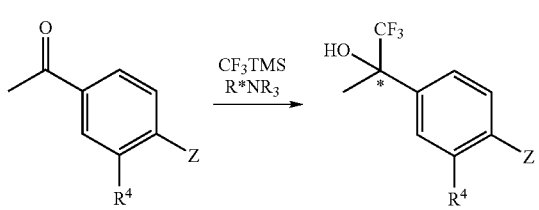

A variety of the methods described above have been used to prepare compounds of the invention, some of which are exemplified in the examples.

Pharmaceutical Compositions

Pharmaceutical compositions and single unit dosage forms comprising a benzamide derivative, or a pharmaceutically acceptable stereoisomer, prodrug, salt, solvate, hydrate, or clathrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or nonaqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous (e.g., <1% water) pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The benzamide derivatives can be administered to a mammal (human, mouse, rat, rabbit, dog, cat, bovine, pig, monkey etc.) as an 11β-HSD1 modulator, a prophylactic or therapeutic drug of diabetes, a prophylactic or therapeutic drug of diabetic complication (retinopathy, nephropathy, neuropathy, cardiac infarction and cerebral infarction based on arteriosclerosis etc.), a prophylactic or therapeutic drug of hyperlipemia, a prophylactic or therapeutic drug of obesity, neurodegenerative disease and the like, or a prophylactic or therapeutic drug of diseases mediated by 11β-HSD1.

The benzamide derivatives can be administered to a mammal concurrently with an additional therapeutic agent for the treatment of a disease, such as diabetes or obesity, with the aim of the prophylaxis or treatment of a disease. As such, the benzamide derivatives of the present invention can be administered in combination with other therapeutic agents for the treatment or prevention of numerous diseases, including, but not limited to, diabetes and obesity.

Depending on the disease to be treated and the patient's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration. The invention also contemplates administration of the compounds of the invention in a depot formulation, in which the active ingredient is released over a defined time period.

In the case of a combined administration, the benzamide derivatives may be administered simultaneously with other another therapeutic agent that is useful for the treatment or prevention of diabetes, obesity or other disease or may be administered at a time prior to or subsequent to another therapeutic agent. In the case of combined administration, a pharmaceutical composition containing the benzamide derivative and an additional therapeutic agent can be administered. Alternatively, a pharmaceutical composition containing the benzamide derivative and a pharmaceutical composition containing an additional therapeutic agent may be administered separately. The administration routes of respective pharmaceutical compositions may be the same or different.

In the case of a combined administration, the benzamide derivatives may be administered at a dose of 50 mg to 800 mg per administration, which is given once to several times a day is contemplated (e.g., once-weekly). In addition, the compound may be administered at a smaller dose. The combined pharmaceutical agent can be administered at a dose generally employed for the prophylaxis or treatment of diabetes or obesity or at a smaller dose than that.

Like the amounts and types of excipients, the amounts and specific types of active ingredients in a dosage form may differ depending on factors such as, but not limited to, the route by which it is to be administered to patients. However, typical dosage forms of the invention comprise a benzamide derivative, or a pharmaceutically acceptable salt, solvate, clathrate, hydrate, polymorph or prodrug thereof. In the treatment or prevention of diabetes, obesity, glaucoma, osteoporosis, cognitive disorders, immune disorders, depression or other conditions or disorders associated with the modulation of an hydroxysteroid dehydrogenase, an appropriate dosage level will generally be from about 0.001 to about 100 mg per kg patient body weight per day which can be administered in single or multiple doses. An exemplary dosage level will be from about 0.01 to about 25 mg/kg per day or about 0.05 to about 10 mg/kg per day. In other embodiments, a suitable dosage level may be from about 0.01 to about 25 mg/kg per day, about 0.05 to about 10 mg/kg per day, or about 0.1 to about 5 mg/kg per day. Within this range the dosage may be from about 0.005 to about 0.05, about 0.05 to about 0.5 or about 0.5 to about 5.0 mg/kg per day lie within the range of from about 0.1 mg to about 2000 mg per day, given as a single once-a-day dose in the morning but typically as divided doses throughout the day taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

For multidrug therapy, the weight ratio of the compound of the invention to the second active ingredient may be varied and will depend upon the effective dose of each ingredient. Generally, an effective dose of each will be used. Thus, for example, when a compound of the invention is combined with an NSAID, the weight ratio of the compound of the invention to the NSAID will generally range from about 1000:1 to about 1:1000, such as about 200:1 to about 1:200. Combinations of a compound of the invention and other active ingredients will generally also be within the aforementioned range, but in each case, an effective dose of each active ingredient should be used.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

For oral administration, the compositions can be provided in the form of tablets containing about 1 to about 1000 milligrams of the active ingredient. In other embodiments, the compositions are provided in provided in the form of tablets containing about 1.0, about 5.0, about 10.0, about 15.0. about 20.0, about 25.0, about 50.0, about 75.0, about 100.0, about 150.0, about 200.0, about 250.0, about 300.0, about 400.0, about 500.0, about 600.0, about 750.0, about 800.0, about 900.0, or about 1000.0 milligrams of the active ingredient for the symptomatic adjustment of the dosage to the patient to be treated. The compounds may be administered on a regimen of 1 to 4 times per day, such as, for example, once or twice per day.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

Controlled-release pharmaceutical products can improve drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intra-arterial. Because their administration typically bypasses patients' natural defenses against contaminants, parenteral dosage forms can be sterile or capable of being sterilized prior to administration to a patient. Examples of parenteral dosage forms include, but are not limited to, solutions ready for injection, dry products ready to-be dissolved or suspended in a pharmaceutically acceptable vehicle for injection, suspensions ready for injection, and emulsions. For example, lyophilized sterile compositions suitable for reconstitution into particulate-free dosage forms suitable for administration to humans.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Parenteral dosage forms are exemplary for the methods of preventing, treating or managing disease in a cancer patient.

Transdermal and Topical Dosage Forms

Transdermal and topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants also can be added to pharmaceutical compositions and dosage forms if desired. Examples of such additional ingredients are well known in the art. See, e.g., Remington's Pharmaceutical Sciences, 18th eds., Mack Publishing, Easton Pa. (1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Mucosal Dosage Forms and Lung Delivery

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

A compound of the invention can also be administered directly to the lung by inhalation (see e.g., Tong et al., International Publication No. WO 97/39745; Clark et al, International Publication No. WO 99/47196, which are herein incorporated by reference). For administration by inhalation, a benzamide derivative can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a benzamide derivative directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a benzamide derivative to the lung (See, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insulator can be formulated containing a powder mix of the compound and a suitable powder base such as lactose or starch for these systems.

Another type of device that can be used to deliver a benzamide derivative to the lung is a liquid spray device supplied, for example, by Aradigm Corporation. Liquid spray systems use extremely small nozzle holes to aerosolize liquid drug formulations that can then be directly inhaled into the lung.

In one embodiment, a nebulizer device is used to deliver a benzamide derivative to the lung. Nebulizers create aerosols from liquid drug formulations by using, for example, ultrasonic energy to form fine particles that can be readily inhaled (See e.g., Verschoyle et al., British J Cancer, 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics. Inhaled compounds, delivered by nebulizer devices, are currently under investigation as treatments for aerodigestive cancer (Engelke et al., Poster 342 at American Association of Cancer Research, San Francisco, Calif., Apr. 1-5, 2000) and lung cancer (Dahl et al., Poster 524 at American Association of Cancer Research, San Francisco, Calif., Apr. 1-5, 2000).

In one embodiment, an electrohydrodynamic ("EHD") aerosol device is used to deliver a benzamide derivative to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No. WO 94/12285; Coffee, International Publication No. WO 94/14543; Coffee, International Publication No. WO 95/26234, Coffee, International Publication No. WO 95/26235, Coffee, International Publication No. WO 95/32807, which are herein incorporated by reference). The electrochemical properties of the compound of the invention formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of a benzamide derivative will be known to the skilled artisan and are within the scope of the invention.

Liquid drug formulations suitable for use with nebulizers and liquid spray devices and EHD aerosol devices will typically include a benzamide derivative with a pharmaceutically acceptable carrier. For instance, the pharmaceutically acceptable carrier is a liquid such as alcohol, water, polyethylene glycol or a perfluorocarbon. Optionally, another material can be added to alter the aerosol properties of the solution or suspension of a benzamide derivative. In some embodiments, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. No. 5,112,598; Biesalski, U.S. Pat. No. 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, a benzamide derivative can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other Delivery Systems

Alternatively, other pharmaceutical delivery systems can be employed. Liposomes and emulsions are well known examples of delivery vehicles that can be used to deliver a benzamide derivative. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med, 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J Macromol. Sci. Rev. Macromol. Chem., 1983, 23, 61; see also Levy et al., Science 1985, 228, 190; During et al., Ann. Neurol., 1989, 25, 351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see e.g., Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to farther adjust the properties of the resulting composition.

Therapeutic Uses of the Benzamide Derivatives

In one embodiment, the invention provides methods of treating or preventing a condition or disorder associated with the modulation of hydroxysteroid dehydrogenases by administering to a patient having such a condition or disorder a therapeutically effective amount of a compound or composition of the invention. In one group of embodiments, conditions and disorders, including chronic diseases of humans or other species, can be treated with modulators, stimulators, or inhibitors of hydroxysteroid dehydrogenases, such as 11β-HSD1.

Treatment or Prevention of Diabetes

Diabetes and diabetic conditions can be treated or prevented by administration of a therapeutically effective amount of a benzamide derivative.

Types of diabetes that can be treated or prevented by administering a therapeutically effective amount of a benzamide derivative include type I diabetes mellitus (juvenile onset diabetes, insulin dependent-diabetes mellitus or IDDM), type II diabetes mellitus (non-insulin-dependent diabetes mellitus or NIDDM), insulinopathies, diabetes associated with pancreatic disorders, diabetes associated with other disorders (such as Cushing's Syndrome, acromegaly, pheochromocytoma, glucagonoma, primary aldosteronism, and somatostatinoma), type A and type B insulin resistance syndromes, lipatrophic diabetes, and diabetes induced by β-cell toxins.

In one embodiment, the type of diabetes being treated is type II diabetes.

Treatment or Prevention of Obesity

Obesity can be treated or prevented by administration of a therapeutically effective amount of a benzamide derivative.

Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Metabolic disorders, such as hyperlidemia and diabetes, and cardiovascular disorders, such as hypertension and coronary artery disease, are commonly associated with obesity.

Complications due to obesity may also be treated or prevented by administering a therapeutically effective amount of a benzamide derivative. Such complications include, but are not limited to, sleep apnea, Pickwickian syndrome, orthopedic disturbances of weight-bearing and non-weight-bearing joints, and skin disorders resulting from increased sweat or skin secretions.

Treatment or Prevention of Other Conditions

Other conditions that can be treated or prevented by administering a therapeutically effective amount of a benzamide derivative include, but are not limited to any condition which is responsive to the modulation, such as inhibition, of hydroxysteroid dehydrogenases or specific isoforms thereof, and thereby benefit from administration of such a modulator. Representative conditions in this regard include, but are not limited to, metabolic disorders and related cardiovascular risk factors such as syndrome X, polycystic ovarian disease, eating disorders (e.g., anorexia and bulimia), craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia and Cushing's syndrome; diseases associated therewith such as hypertension, atherosclerosis, vascular restenosis, retinopathy and nephropathy; neurologic disorders such as neurodegenerative disease, neuropathy and muscle wasting; cognitive disorders, such as age-related learning disorders, dementia, neurodegeneration, as well as for improvement of cognitive function in subjects ranging from the severely impaired (e.g., Parkinsons's or Alzheimer's associated dementia) to mildly impaired (e.g., age-associated memory impairment, drug-induced cognitive impairment) to unimpaired subjects (e.g., cognitive enhancers for the general population) (see, Sandeep, et al., PNAS, electronically available at www.pnas.org/cgi/doi/10.1073/pnas.0306996101); androgen and/or estrogen-related disorders such as prostate cancer, colon cancer, breast cancer, benign prostatic hyperplasia, ovarian cancer, uterine cancer, and male pseudohermaphrodism; endometriosis, dementia, depression, psoriasis, glaucoma, osteoporosis, viral infections, inflammatory disorders, and immune disorders.

Additional Therapeutic Agents

In one embodiment, the present methods for treating or preventing further comprise the administration of a therapeutically effective amount of another therapeutic agent useful for treating or preventing the diseases or disorders disclosed herein. In this embodiment, the time in which the therapeutic effect of the other therapeutic agent is exerted overlaps with the time in which the therapeutic effect of the benzamide derivative is exerted.

The compounds of the invention can be combined or used in combination with other agents useful in the treatment, prevention, suppression or amelioration of the conditions or disorders for which compounds of the invention are useful, including diabetes, obesity, glaucoma, osteoporosis, cognitive disorders, immune disorders, depression and those pathologies noted above.

Such other agents, or drugs, may be administered, by a route and in an amount commonly used therefor, simultaneously or sequentially with a benzamide derivative. In one embodiment, a pharmaceutical composition contains such other drugs in addition to the compound of the invention when a benzamide derivative is used contemporaneously with one or more other drugs. Accordingly, the pharmaceutical compositions of the invention include those that also contain one or more other active ingredients or therapeutic agents, in addition to a benzamide derivative.

In one embodiment, for the treatment or prevention of diabetes, a benzamide derivative can be administered with another therapeutic agent, including, but not limited to, antidiabetic agents such as insulin, inhaled insulin (Exubera®), insulin mimetics, insulin secretogues, sulfonylureas (e.g., glyburide, meglinatide, glimepiride, gliclazide, glipizide, gliquidone, chloropropresponsivemide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide), biguanides (e.g., metformin (Glucophage®)), α-glucosidase inhibitors (e.g., acarbose, voglibose and miglitol), thiazolidinone compounds (e.g., rosiglitazone (Avandia®), troglitazone (Rezulin®), ciglitazone, pioglitazone (Actos®) and englitazone), prandial glucose regulators (e.g., repaglinide and nateglinide) and glucagon receptor antagonists.

In another embodiment, for the treatment or prevention of obesity, a benzamide derivative can be administered with another therapeutic agent, including, but not limited to, β3 adrenergic receptor agonists, leptin or derivatives thereof, neuropeptide Y (e.g., NPY5) antagonists, and mazindol.

Examples of other therapeutic agents that may be combined with a benzamide derivative, either administered separately or in the same pharmaceutical compositions, include, but are not limited to: (i) cholesterol lowering agents such as HMG-CoA reductase inhibitors (e.g., lovastatin, simvastatin (Zocor®), pravastatin, fluvastatin, atorvastatin (Lipitor®) and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acylCoA-cholesterol acyltransferase (ACAT) inhibitors such as melinamide), HMG-CoA synthase inhibitors, squalene epoxidase inhibitors and squalene synthetase inhibitors; (ii) antithrombotic agents, such as thrombolytic agents (e.g., streptokinase, alteplase, anistreplase and reteplase), heparin, hirudin and warfarin derivatives, β-blockers (e.g., atenolol), β adrenergic agonists (e.g., isoproterenol), angiotensin II antagonists, ACE inhibitors and vasodilators (e.g., sodium nitroprusside, nicardipine hydrochloride, nitroglycerin and enaloprilat); (iii) PPAR agonists, e.g., PPARγ and PPAR$_δ$ agonists; (iv) DP antagonists; (v) lubricants or emollients such as petrolatum and lanolin, keratolytic agents, vitamin $D_3$ derivatives (e.g., calcipotriene and calcipotriol (Dovonex®)), PUVA, anthralin (Drithrocreme®), etretinate (Tegison®) and isotretinoin; (vi) glaucoma therapies such as cholinergic agonists (e.g., pilocarpine and carbachol), cholinesterase inhibitors (e.g., physostigmine, neostigmine, demacarium, echothiophate iodide and isofluorophate), carbonic anhydrase inhibitors (e.g., acetazolamide, dichlorphenamide, methazolamide, ethoxzolamide and dorzolamide), non-selective adrenergic agonists (e.g., epinephrine and dipivefrin), $α_2$-selective adrenergic agonists (e.g., apraclonidine and brimonidine), β-blockers (e.g., timolol, betazolol, levobunolol, carteolol and metipranolol), prostaglandin analogs (e.g., latanoprost) and osmotic diuretics (e.g., glycerin, mannitol and isosorbide); corticosteroids, such as beclomethasone, methylprednisolone, betamethasone, prednisone, prenisolone, dexamethasone, fluticasone and hydrocortisone, and corticosteroid analogs such as budesonide; (vii) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (viii) non-steroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, aldlofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetylsalicylic acid and sulfasalazine) and the pyrazolones (e.g., apazone, bezpiperylon, feprazone, mofebutazone, oxyphenbutazone and phenylbutazone); (ix) cyclooxygenase-2 (COX-2) inhibitors such as celecoxib (Celebrex®) and rofecoxib (Vioxx®); (xi) inhibitors of phosphodiesterase type IV (PDE-IV); (xii) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (xiii) a hepatoprotective agent; and (xiv) other compounds such as 5-aminosalicylic acid and prodrugs thereof.

The weight ratio of the compound of the invention to the second active ingredient may be varied and will depend upon the effective dose of each ingredient. Generally, an effective dose of each will be used. Thus, for example, when a benzamide derivative is combined with an NSAID, the weight ratio of the compound of the invention to the NSAID will generally range from about 1000:1 to about 1:1000, such as, for example, about 200:1 to about 1:200. Combinations of a benzamide derivative and other active ingredients will generally also be within the aforementioned range, but in each case, an effective dose of each active ingredient should be used.

Kits

The invention encompasses kits that can simplify the administration of the benzamide derivatives or composition of the invention to a patient.

A typical kit of the invention comprises a unit dosage of a benzamide derivative. In one embodiment, the unit dosage form is in a container, which can be sterile, containing a therapeutically effective amount of a benzamide derivative and a pharmaceutically acceptable vehicle. In another embodiment, the unit dosage form is in a container containing a therapeutically effective amount of a benzamide derivative as a lyophilate or pharmaceutically acceptable salt. In this instance, the kit can further comprise another container that contains a solution useful for the reconstitution of the lyophilate or dissolution of the salt. The kit can also comprise a label or printed instructions for use of the benzamide derivatives.

In a further embodiment, the kit comprises a unit dosage form of a composition of the invention.

Kits; of the invention can further comprise one or more devices that are useful for administering the unit dosage forms of the benzamide derivatives or a composition of the invention. Examples of such devices include, but are not limited to, a syringe, a drip bag, a patch or an enema, which optionally contain the unit dosage forms.

The present invention is not to be limited in scope by the specific embodiments disclosed in the examples which are intended as illustrations of a few embodiments of the invention and any embodiments that are functionally equivalent are within the scope of this invention. Indeed, various modifications of the invention in addition to those shown and described herein will become apparent to those skilled in the art and are intended to fall within the scope of the appended claims. To this end, it should be noted that one or more hydrogen atoms or methyl groups may be omitted from the drawn structures consistent with accepted shorthand notation of such organic compounds, and that one skilled in the art of organic chemistry would readily appreciate their presence.

EXAMPLES

Example 1

Preparation of 4-(1,1,1-Trifluoro-2-hydroxypropan-2-yl)benzoic Acid

Methyl 4-(1,1,1'-trifluoro-2-hydroxypropan-2-yl)benzoate

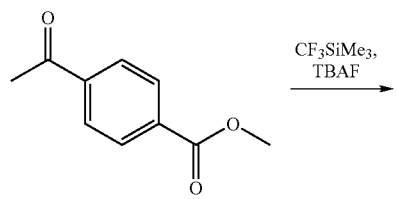

-continued

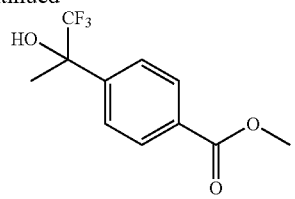

To a mixture of methyl 4-acetylbenzoate (5.0 g, 28.1 mmol) and $CF_3SiMe_3$ (12.5 mL, 84.2 mmol) in THF (150 mL) TBAF (1.0 M, 78.6 mL, 78.6 mmol) was added dropwise at 0° C. The mixture was then stirred for 2.5 h at room temperature, diluted with $Et_2O$ (100 mL). The solution was washed with saturated aqueous $NaHCO_3$ and brine, dried, and concentrated under reduced pressure. Flash chromatography of the residue, using 2:8 EtOAc-hexanes, gave methyl 4-(1,1,1-trifluoro-2-hydroxypropan-2-yl)benzoate: $^1H$ NMR ($CDCl_3$) δ 8.07 (d, J=8.5 Hz, 2H), δ 7.67 (d, J=8.5 Hz, 2H), 3.93 (s, 3H), 2.70 (br, 1H), 1.80 (s, 3H); m/z 249.1 (M+H$^+$).

4-(1,1,1-Trifluoro-2-hydroxypropan-2-yl)benzoic acid

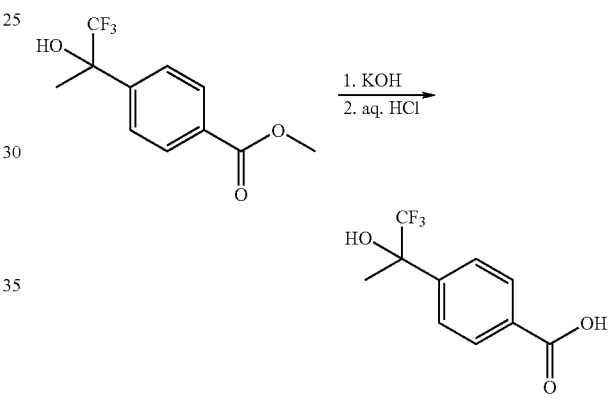

A mixture of methyl 4-(1,1,1-trifluoro-2-hydroxypropan-2-yl)benzoate (6.0 g, 24.2 mmol) and KOH (2.72 g, 48.4 mmol) in 1,4-dioxane (100 mL) and $H_2O$ (50 mL) was refluxed for 2 h. The reaction mixture was cooled to room temperature, and concentrated under reduced pressure to remove the 1,4-dioxane. The aqueous residue was acidified with 2N HCl and extracted with $CH_2Cl_2$. The extracts were washed with brine and dried. Flash chromatography of the residue, using 3:7 EtOAc-Hexane, gave 4-(1,1,1-trifluoro-2-hydroxypropan-2-yl)benzoic acid: $^1H$ NMR ($CDCl_3$) δ 11.0 (br, 1H), 7.95 (d, J=6.8 Hz, 2H), 7.71 (d, J=6.8 Hz, 2H), 6.73 (s, 1H), 1.71 (s, 3H); m/z 235.0 (M+H$^+$).

Synthesis of Optically Active Carboxylic Acid (a) Methyl 4-(1,1,1-trifluoro-2-hydroxypropan-2-yl)benzoate To a 3 L flask containing methyl 4-acetylbenzoate (60 g, 0.34 mol, 1.0 equiv) in 1.0 L THF was added 96.6 g TMS-CF$_3$ (0.68 mol, 2.0 equiv) at 0° C. The solution was allowed to stir for 30 min, followed by the dropwise addition of 680 mL tetrabutylammonium fluoride (1.0M in THF, 0.68 mol, 2.0 equiv) via addition funnel over a period of 3 h. After the addition was complete, the solution was allowed to stir for an additional 30 min and warm to room temperature. The solution was then concentrated down under reduced pressure. Then the mixture was diluted with Sat. $NaHCO_3$ and extracted (4×10% MeOH/$CH_2Cl_2$). The organics were combined, dried (MgSO$_4$), and concentrated under reduced pressure. Purification by flash chromatography (SiO$_2$, 15% EtOAc/Hexanes) gave the product as an orange oil.

(b) Methyl 4-((S)-1,1,1-trifluoro-2-(((S)-1-(naphthalen-1-yl)ethyl)carbamoyloxy)-propan-2-yl)benzoate To a 500 mL flask containing a portion of product obtained above (25 g, 0.1 mol, 1.0 equiv) in 150 mL CH$_2$Cl$_2$ was added 19.7 g DMAP (0.16 mol, 1.6 equiv) at 0° C. 28.5 g 4-Nitrophenyl chloroformate (0.14 mol, 1.4 equiv) was then added in portions. The resulting mixture was allowed to stir for 15 min at 0° C. and 3.0 h at room temperature. The mixture was cooled to 0° C. 34.2 g (S)-1-(1-Naphthalenyl)ethanamine (0.2 mol, 2.0 equiv) was added in portions. After addition, the solution was allowed to stir at room temperature for 1 h. The mixture was then diluted with EtOAc, washed with 6×1 M NaOH, 1 N HCl and brine. The organics were dried and concentrated under reduced pressure. The two diastereomers were purified and separated by flash chromatography (SiO$_2$, 15% methyl-t-butyl ether/hexanes). The first portion of the two close spots was collected and concentrated under reduced pressure to give the pure diastereomer as a colorless oil.

(c) (S)-4-(1,1,1-Trifluoro-2-hydroxypropan-2-yl)benzoic acid

To a 250 mL flask containing product obtained above (13.5 g, 30 mmol, 1.0 equiv) was added 70 mL THF, 30 mL H$_2$O, 30 mL MeOH and 0.73 g LiOH (0.3 mol, 10.0 equiv). The resulting mixture was stirred at 45° C. for overnight. The mixture was extracted with CH$_2$Cl$_2$. The aqueous layer was then acidified with 2 N HCl to pH~4 and extracted (5×10% MeOH/CH$_2$Cl$_2$). The organics were dried (MgSO$_4$) and concentrated under reduced pressure to give the product as white solid.

Example 2

Preparation of N-cyclopropyl-N-(trans-4-cyclopropyl-4-hydroxycyclohexyl)-4-((S)-1,1,1-trifluoro-2-hydroxypropan-2-yl)benzamide

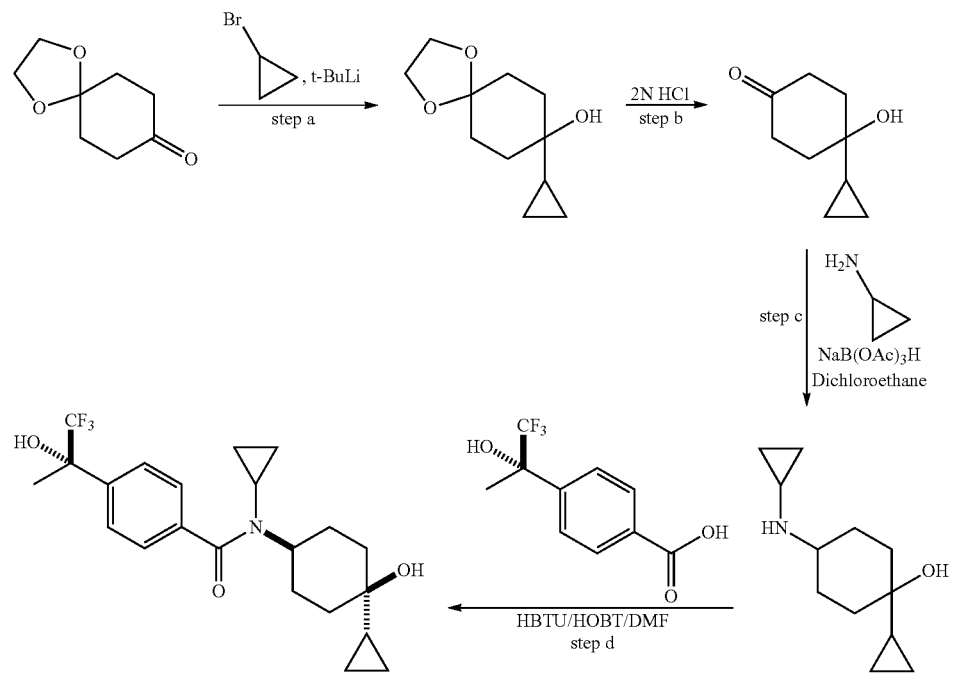

a). To cyclopropyl bromide (0.325 mL, 4.06 mmol) in Et$_2$O (6.5 mL) cooled to −78° C. (dry ice/acetone) was added dropwise t-butyllithium (2.35 mL, 1.7 M in pentane). Additional Et$_2$O (5 mL) was added dropwise to the reaction. After 1 h of stirring at −78° C., a solution of 1,4-cyclohexanedione monoethylene ketal in Et$_2$O (5 mL) was added dropwise. The solution was stirred for 1.25 h then allowed to reach room temperature over 1.5 h. A water quench (5 mL) was followed by separation and drying of the organic layer with MgSO$_4$. TLC (2× elution w/15% ethyl acetate in hexanes, PMA stain) showed product formation with slightly lower R$_f$ (ca. 0.25) relative to starting material. Silica gel chromatography (15, 20, 30% step ethyl acetate in hexanes) afforded the cyclopropyl carbinol. $^1$H NMR (500 MHz, CDCl$_3$): δ 0.37-0.40 (m, 4H), 0.847 (bs, 1H), 0.926-0.97 (m, 1H), 1.55-1.75 (m, 6H), 1.85-1.95 (m, 2H), 3.95-4.0 (m, 4H).

b). To the alcohol prepared above in step a (0.323 g, 1.63 mmol) in THF (3.5 mL) was added 2 N HCl (1.75 mL). The solution was stirred for 6 h. The reaction was diluted with water (10 mL) and extracted with Et$_2$O (2×10 mL). The combined organics were dried with MgSO$_4$ and concentrated in vacuo to yield the ketone. The material was carried on to the next step without purification.

c). To the ketone prepared above in step b (0.200 g, 1.29 mmol) in dichloroethane (4 mL) was added cyclopropylamine (0.0900 mL, 1.29 mmol). The solution was cooled to 0° C. (ice bath), and NaBH(OAc)$_3$ (0.410 g, 1.94 mmol) and AcOH (0.0200 mL, 1.29 mmol) were added. After 5 minutes the ice bath was removed. The reaction was stirred at room temperature for 2 h. The contents were diluted with CH$_2$Cl$_2$ (8 mL) poured in water (10 mL) and brought to pH 2 with 5 N HCl. Following removal of the organic layer, the aqueous layer was brought to pH 12 with 5 N NaOH and extracted with 10% MeOH in CH$_2$Cl$_2$ (3×15 mL). The combined organics were dried with Na$_2$SO$_4$ and removed in vacuo to yield the amine as a viscous clear oil. The crude amine was carried on to the next step without purification.

d). To a solution of (S)-4-(1,1,1-trifluoro-2-hydroxypropan-2-yl)benzoic acid (0.117 g, 0.500 mmol), HBTU (0.228, 0.600 mmol), and HOBt (0.0840 g, 0.625 mmol) in DMF (1.25 mL) was added Hünig's base (0.210 mL, 1.2 mmol). The solution was stirred for 5 minutes prior to the addition of amine prepared in step c (0.17 g, 0.872 mmol). The reaction was stirred at room temperature for 4 h followed by quenching with 3-(dimethylamino)propylamine (0.1 mL). The reaction contents were poured into 1 N HCl (10 mL) and extracted with CH$_2$Cl$_2$ (20 mL). The organic layer was washed with 1 N NaOH (10 mL), dried with Na$_2$SO$_4$, and removed in vacuo. Silica gel chromatography (gradient of 30 to 60% ethyl acetate in hexanes) separated the cis and trans isomers with the trans isomer eluting first. $^1$H NMR (500 MHz, CDCl$_3$, trans isomer): δ 0.37-0.41 (m, 4H), 0.49 (bs, 2H), 0.55-0.62 (m, 2H), 0.91-0.93 (m, 2H), 1.51-1.62 (m, 3H), 1.68-1.75 (m, 2H), 1.76-1.83 (m, 5H), 2.16-2.28 (m, 2H), 2.55-2.63 (m, 1H), 2.71 (s, 1H), 4.15 (bs, 1H), 7.49 (d, J=8.0 Hz, 2H), 7.59 (d, J=8.0 Hz, 2H).

Example 3

Preparation of N-(trans-4-cyano-4-cyclopropylcyclohexyl)-N-cyclopropyl-4-((S)-1,1,1-trifluoro-2-hydroxypropan-2-yl)benzamide mL, 1.9 mmol). The mixture was stirred at 0° C. for 30 min followed by the dropwise addition of a solution of 1,4-cyclohexanedione mono-ethylene ketal (0.32 g, 2.0 mmol) in THF (1 ml). The mixture was allowed to reach room temperature and stirred for 5 h. The reaction was poured into water (25 mL) and extracted with Et$_2$O (3×15 mL). The combined organics were washed with brine, dried with MgSO$_4$, and concentrated in vacuo. Silica gel flash chromatography (gradient elution 5-15% ethyl acetate in hexanes) afforded the benzyl ether. $^1$H NMR (400 Hz, CDCl$_3$): δ 1.65-1.72 (m, 4H), 2.24-2.32 (m, 4H), 2.34-2.39 (m, 2H), 3.48 (t, J=7.1 Hz, 2H), 3.99 (s, 4H), 4.54 (s, 2H), 5.20 (t, J=7.5 Hz, 1H), 7.30-7.33 (m, 1H), 7.36-7.38 (m, 4H).

b). To a solution of benzyl ether prepared above in step a (15.5 g, 53.7 mmol) in EtOH (50 mL), Et$_2$O (225 mL), and NH$_3$ (1000 mL) under an argon atmosphere at −78° C. was added in small pieces sodium metal (total 3.20 g, 139 mmol). The solution was stirred for 30 min at −78° C. then allowed to evaporate overnight after removal of dry ice/acetone bath. The residue was dissolved in water (300 mL) and extracted with Et$_2$O (3×150 mL). The combined organics were washed with brine, dried with MgSO$_4$ and concentrated in vacuo. The crude material was applied to a short plug of silica gel and eluted with 35% ethyl acetate in hexanes to provide the desired alcohol. $^1$H NMR (400 Hz, CDCl$_3$): δ 1.65-1.72 (m, 4H), 2.27-2.35 (m, 6H), 3.64 (t, J=6.3 Hz, 2H), 3.99 (s, 4H), 5.18 (t, J=7.3 Hz, 1H), c). To the alcohol prepared in step b (0.242 g, 1.22 mmol) and s-collidine (0.240 mL, 1.80 mmol) in CH$_2$Cl$_2$ (27 mL) at −78° C. was added dropwise a solution of triflic anhydride (0.316 mL, 1.93 mmol) in CH$_2$Cl$_2$ (3 mL). The resulting solution was stirred for 15 min followed by the dropwise addition of 1 M Et$_2$AlCN in toluene (3.66 mL). The reaction

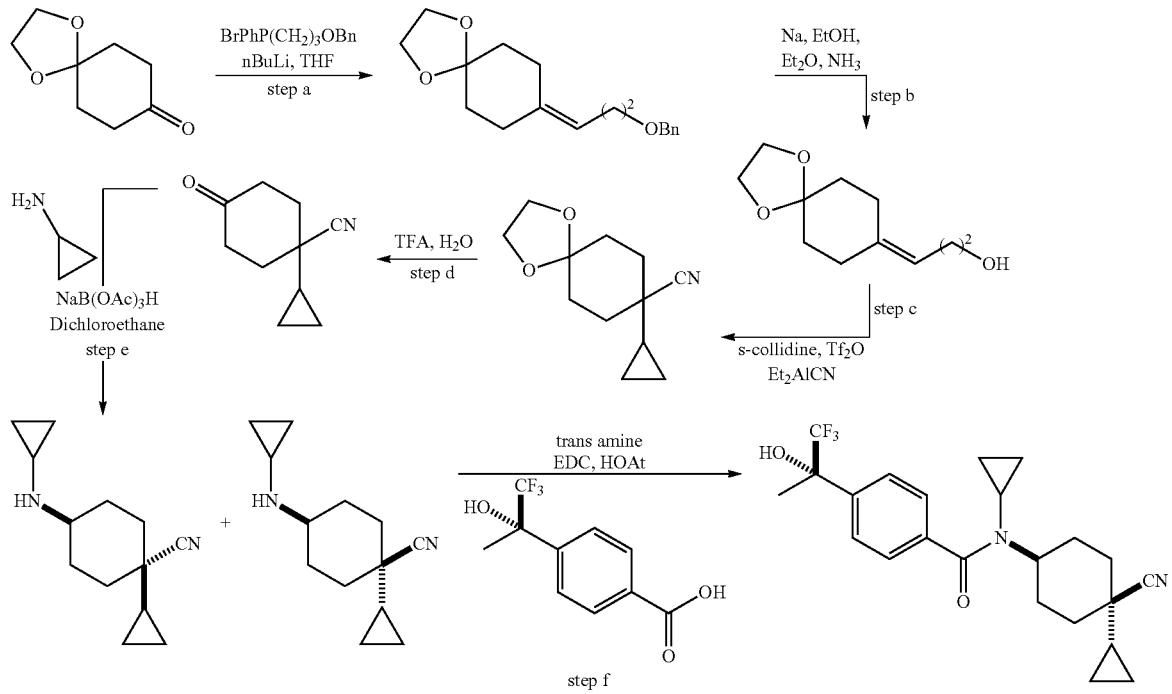

a). To (3-benzyloxypropyl)triphenylphosphonium bromide (1 g, 2.0 mmol) in THF (5 mL) cooled to 0° C. was added dropwise over a period of 30 min 1.6 M nBuLi in THF (1.2 was allowed to reach room temperature over 1 h. The reaction solution was then poured into saturated NaHCO$_3$ (60 mL) and stirred for 5 min. The mixture was filtered through a plug of celite, and the filter agent was washed with $CH_2Cl_2$. The combined organics were washed with 0.2 M HCl (50 mL), washed again with saturated $NaHCO_3$ (60 mL), dried with $Na_2SO_4$, and concentrated in vacuo. Purification via silica gel flash chromatography (gradient elution 5-60% ethyl acetate in hexanes) afforded the product. $^1$H NMR (400 Hz, $CDCl_3$): δ 0.50-0.57 (m, 4H), 0.83-0.90 (m, 1H), 1.73-1.80 (m, 4H), 1.88-1.95 (m, 2H), 2.00-2.09 (m, 2H), 3.93-4.03 (m, 4H).

d). To the cyclopropylcyano acetal prepared above (7.28 g, 35.1 mmol) was added trifluoroacetic acid (100 mL) and water (4 mL). The solution was stirred for 1 h then poured into saturated $NaHCO_3$ (1500 mL). The aqueous was extracted with ethyl acetate (3×300 mL). The combined organics were washed with brine, dried with $MgSO_4$, and concentrated in vacuo to afford the ketone. This material was carried on to the next step without further purification. $^1$H NMR (500 Hz, $CDCl_3$): δ 0.62-0.69 (m, 4H), 0.88-0.94 (m, 1H), 1.88-1.94 (m, 2H), 2.35-2.39 (m, 2H), 2.47-2.51 (m, 2H), 2.68-2.74 (m, 2H).

e). To the ketone prepared in step d (6.0 g, 37 mmol) in dichloroethane (110 mL) was added cyclopropylamine (3.1 mL, 44 mmol). The solution was cooled to 0° C. (ice bath), and $NaBH(OAc)_3$ (12 g, 55 mmol) and AcOH (2.8 mL, 48 mmol) were added. After 5 minutes the ice bath was removed. The reaction was stirred at room temperature for 4 h. The contents were diluted with $CH_2Cl_2$ (100 mL) poured in water (100 mL). The aqueous layer was brought to pH 2 with 5 N HCl. Following removal of the organic layer, the aqueous layer was brought to pH 12 with 5 N NaOH and extracted with 10% MeOH in $CH_2Cl_2$ (3×35 mL). The combined organics were dried with $Na_2SO_4$ and concentrated in vacuo. Silica gel chromatography (gradient of 5 to 10% ethyl acetate in hexanes with 2.5% triethylamine additive) gave the cis amine followed by the trans amine. $^1$H NMR (500 Hz, $CDCl_3$, trans isomer): δ 0.15-0.17 (m, 2H), 0.25-0.29 (m, 2H), 0.34-0.37 (m, 4H), 0.58-0.63 (m, 1H), 1.22-1.31 (m, 4H), 1.84-1.90 (m, 4H), 1.96-2.00 (m, 1H), 2.38-2.40 (m, 1H).

f). To a solution of (S)-4-(1,1,1-trifluoro-2-hydroxypropan-2-yl)benzoic acid (5.7 g, 24 mmol), EDC (5.5, 29 mmol), and HOAt (3.9 g, 29 mmol) in DMF (52 mL) was added $NaHCO_3$ (4.1 g, 49 mmol) and the trans amine prepared in step e (4.5 g, 22 mmol). The solution was stirred for 5 h at 55° C. followed by quenching with 3-(dimethylamino)-propylamine (22 mmol). The reaction contents were poured into 1 N NaOH (500 mL) and extracted with ethyl acetate (500 mL). The organic layer was washed with 1 N HCl (500 mL) then saturated $NaHCO_3$ (500 mL). At this point some precipitation of the desired product initiated and was reversed by addition of $CH_2Cl_2$ (ca. 100 mL). The combined organics were dried with $MgSO_4$ and concentrated in vacuo. Purification by silica gel chromatography (gradient of 2 to 5% MeOH in $CH_2Cl_2$) provided the benzamide product. $^1$H NMR (500 MHz, $CDCl_3$): δ 0.50-0.53 (m, 4H), 0.58-0.62 (m, 4H), 0.95-0.97 (m, 1H), 1.67-1.72 (m, 2H), 1.77 (s, 3H), 2.05-2.15 (m, 4H), 2.20-2.29 (m, 2H), 2.79-2.81 (m, 1H), 4.07-4.17 (m, 1H), 7.55 (d, J=8.5 Hz, 2H), 7.71 (d, J=8.0 Hz, 2H).

Example 4

Preparation of N-(trans-4-(2-cyanoethyl)-4-phenylcyclohexyl)-N-cyclopropyl-4-((S)-1,1,1-trifluoro-2-hydroxypropan-2-yl)benzamide

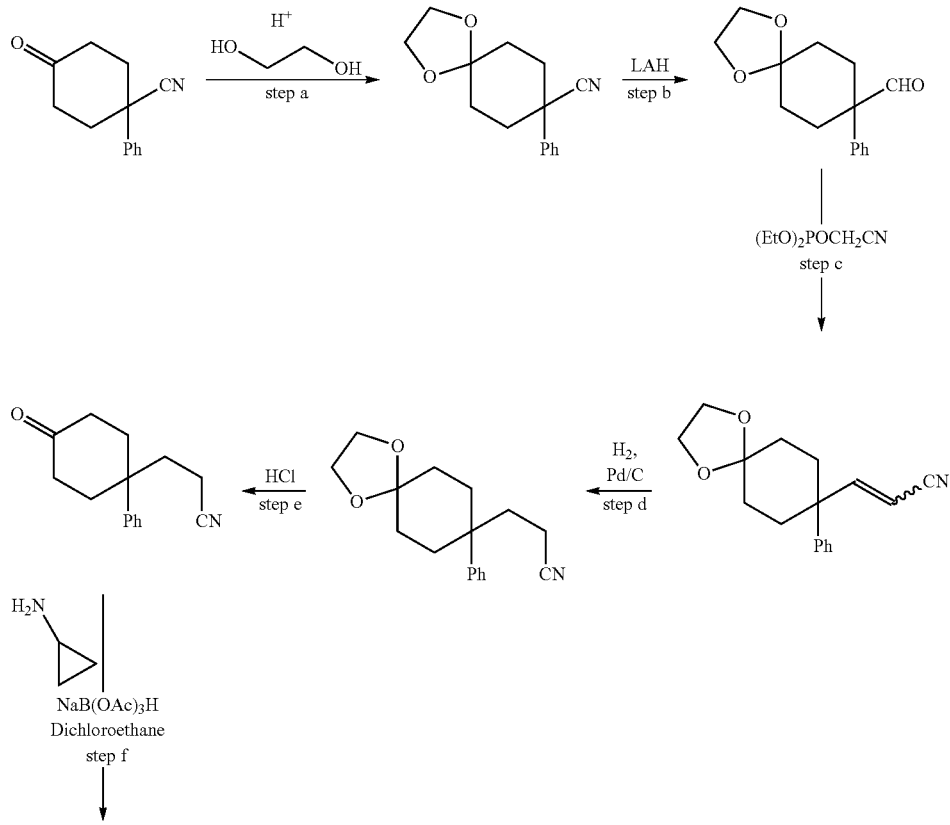

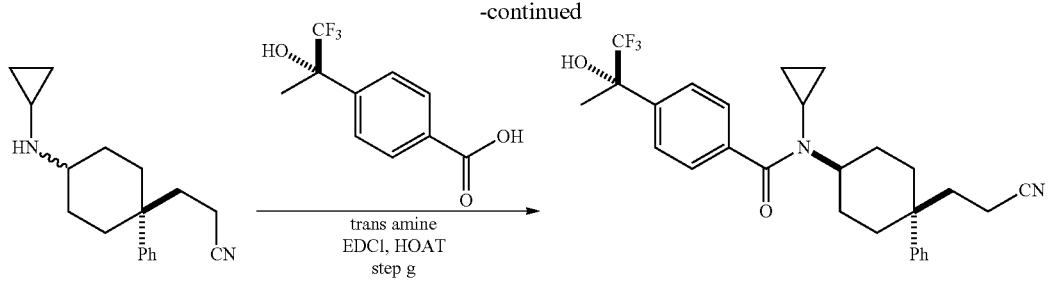

a). 4-Cyano-4-phenylcyclohexanone ethylene ketal: A mixture of 4-cyano-4-phenyl-cyclohexanone (40 g, 200 mmol, 1.0 equiv), 12 g ethylene glycol and 0.8 g p-toluenesulfonic acid in 320 mL of benzene was heated at reflux in a Dean-Stark trap for 3 hours. The solution was then allowed to cool and washed successively with sat. NaHCO$_3$, water, and brine. The organics were dried over Na$_2$SO$_4$ and evaporated to give the product as a white solid.

b). 4-Formyl-4-phenylcyclohexanone ethylene ketal: To a well stirred suspension of LiAlH$_4$ (1.56 g, 41.15 mmol, 0.5 equiv) in 25 mL dry THF, a solution of 4-cyano-4-phenylcyclohexanone ethylene ketal (prepared in step a, 20 g, 82.3 mmol, 1.0 equiv) in 125 mL of THF was added at 10-15° C. over a period of 20 minutes. The mixture was stirred at room temperature for 4 hours, then cooled in an ice bath and treated successively with 5 mL of 2 N NaOH and 10 mL of water. The resulting inorganic gel was collected on a filter and rinsed with ether. The combined filtrates were then evaporated to dryness. A solution of the residue in THF (150 mL) and 3 N HCl (20 mL) was stirred for 20 minutes, treated with 10 g of NaHCO$_3$ and then evaporated to dryness. Dichloromethane was added to the residue, the organic layer was washed with water and brine and concentrated under reduced pressure to yield the desired aldehyde.

c). 4-(2-Cyanovinyl)-4-phenylcyclohexanone ethylene ketal: To a well stirred suspension of NaH (4.52 g, 178.9 mmol, 1.1 equiv) in 100 mL of dry THF, a solution of diethyl (cyanomethyl) phosphonate (30.6 mL, 195.12 mmol, 1.2 equiv) and DMPU (40 mL) in 100 mL THF was added at 0° C. in a period of 20 minutes. The mixture was stirred for 30 minutes, and then treated with a solution of 4-formyl-4-phenylcyclohexanone ethylene ketal prepared in step b (40 g, 162.6 mmol, 1.0 equiv) in 80 mL of THF. After being stirred at 25° C. for 12 h, the reaction was quenched with H$_2$O and extracted with EtOAc. The combined organics were washed with brine, dried over Na$_2$SO$_4$, and concentrated under reduced pressure. Purification of the residue by flash chromatography (SiO$_2$, 30% EtOAc/n-Hexane) afforded the product as a white solid.

d). 4-(2-Cyanoethyl)-4-phenylcyclohexanone ethylene ketal: A solution of cyanovinyl compound prepared above (18 g, 66.9 mmol) in ethyl acetate (300 mL) and ethanol (400 mL) containing 10% Pd/C (2.5 g) was hydrogenated under atmospheric pressure at room temperature for 24 h. After filtration of the catalyst, the solution was concentrated in vacuo to give the product as a colorless liquid. $^1$HNMR (DMSO, 400 MHz) δ 7.38 (m, 4H), 7.25 (m, 1H), 3.88 (m, 4H), 2.29 (m, 2H), 2.03 (m, 2H), 1.83 (m, 2H), 1.72 (m, 2H), 1.60 (m, 2H), 1.35 (m, 2H).

e). 3-(4-Oxo-1-phenylcyclohexyl)propanenitrile: 3 N HCl (45 mL) was added to a solution of the ketal prepared above (18 g) in THF (100 mL). The mixture was stirred at room temperature for 12 h and then diluted with sat. NaHCO$_3$ (100 mL). The resulting solution was extracted with EtOAc (100 mL×2), dried, and concentrated under reduced pressure. The residue was purified by flash chromatography (SiO$_2$, 40% EtOAc/Hexane) to give the product ketone as a white solid.

f). 3-(4-(Cyclopropylamino)-1-phenylcyclohexyl)propanenitrile: A solution of 3-(4-oxo-1-phenylcyclohexyl)propanenitrile prepared in step e (11.5 g, 50.67 mmol, 1.0 equiv) in 1,2-dichloroethane (100 mL) was treated at 0° C. with cyclopropylamine (7.1 mL, 101.3 mmol, 2 equiv), acetic acid (0.9 mL, 1.0 equiv) and NaBH(OAc)$_3$ (21.5 g, 2.0 equiv) successively. After being stirred at 25° C. for 12 h, the reaction mixture was carefully diluted (sat.NaHCO$_3$), extracted (10% MeOH/CH$_2$Cl$_2$), washed (brine), dried (Na$_2$SO$_4$) and concentrated under reduced pressure. Flash chromatography (SiO$_2$, 40% EtOAc/hexane containing 2.5% triethylamine) gave the cis-amine followed by the trans-amine.

g). N-(trans-4-(2-cyanoethyl)-4-phenylcyclohexyl)-N-cyclopropyl-4-((S)-1,1,1-trifluoro-2-hydroxypropan-2-yl)benzamide: A solution of trans amine prepared as in step f (4.8 g, 17.98 mmol, 1.0 equiv) and of (S)-4-(1,1,1-trifluoro-2-hydroxypropan-2-yl)benzoic acid (4.21 g, 1.0 equiv) in DMF (60 mL) was treated at 0° C. with EDCl (4.58 g, 1.3 equiv), HOAt (3.18 g, 1.3 equiv) and NaHCO$_3$ (3.02 g, 2.0 equiv) successively. After being stirred at 25° C. for 12 h, the reaction was diluted (EtOAc), washed (1 N NaOH and brine), dried (Na$_2$SO$_4$) and concentrated under reduced pressure. Purification of the residue by flash chromatography (SiO$_2$, 50% EtOAc/n-Hexane) afforded the product as a white solid. $^1$H NMR (CDCl$_3$, 400 MHz) δ 7.61 (d, J=7.9 Hz, 2H), 7.51 (d, J=7.9 Hz, 2H), 7.40-7.27 (m, 5H), 4.08 (m, 1H), 2.76 (m, 1H), 2.68 (s, 1H), 2.31-2.07 (m, 6H), 1.96 (m, 4H), 1.82 (s, 3H), 1.79 (m, 2H), 0.58 (m, 4H).

Example 5

Preparation of N-(trans-4-(3-amino-3-oxopropyl)-4-phenylcyclohexyl)-N-cyclopropyl-4-((S)-1,1,1-trifluoro-2-hydroxypropan-2-yl)benzamide

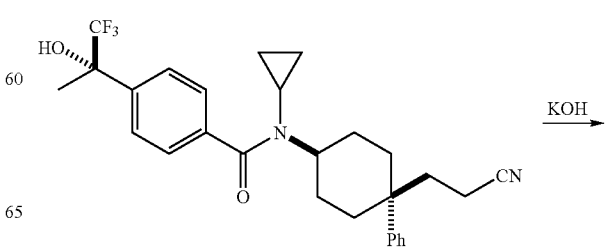

-continued

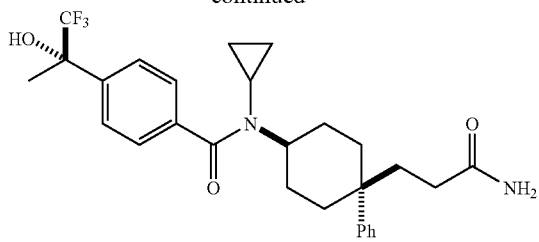

2 g of potassium hydroxide was added to a solution of 2 g N-(trans-4-(2-cyanoethyl)-4-phenylcyclohexyl)-N-cyclopropyl-4-((S)-1,1,1-trifluoro-2-hydroxypropan-2-yl)benzamide in 20 mL tert-BuOH. The mixture was heated at 90° C. for 1.5 h and then diluted with 10% MeOH/CH$_2$Cl$_2$. The resulting solution was washed (1× brine), dried (Na$_2$SO$_4$) and concentrated under reduced pressure. Purification by flash chromatography (SiO$_2$, 5% MeOH/CH$_2$Cl$_2$) gave the product as a white solid. $^1$H NMR (CDCl$_3$, 400 MHz) δ 7.58 (d, J=7.9 Hz, 2H), 7.46 (d, J=7.9 Hz, 2H), 7.35 (m, 4H), 7.23 (m, 1H), 5.31 (s, 1H), 5.23 (s, 1H), 4.07 (m, 1H), 2.66 (m, 1H), 2.40-2.17 (m, 6H), 2.00-1.71 (m, 6H), 1.75 (s, 3H), 0.58 (m, 4H).

Example 6

Preparation of N-cyclopropyl-N-(trans-4-(2-hydroxyethyl)-4-(pyridin-2-yl)cyclohexyl)-4-((S)-1,1,1-trifluoro-2-hydroxypropan-2-yl)benzamide

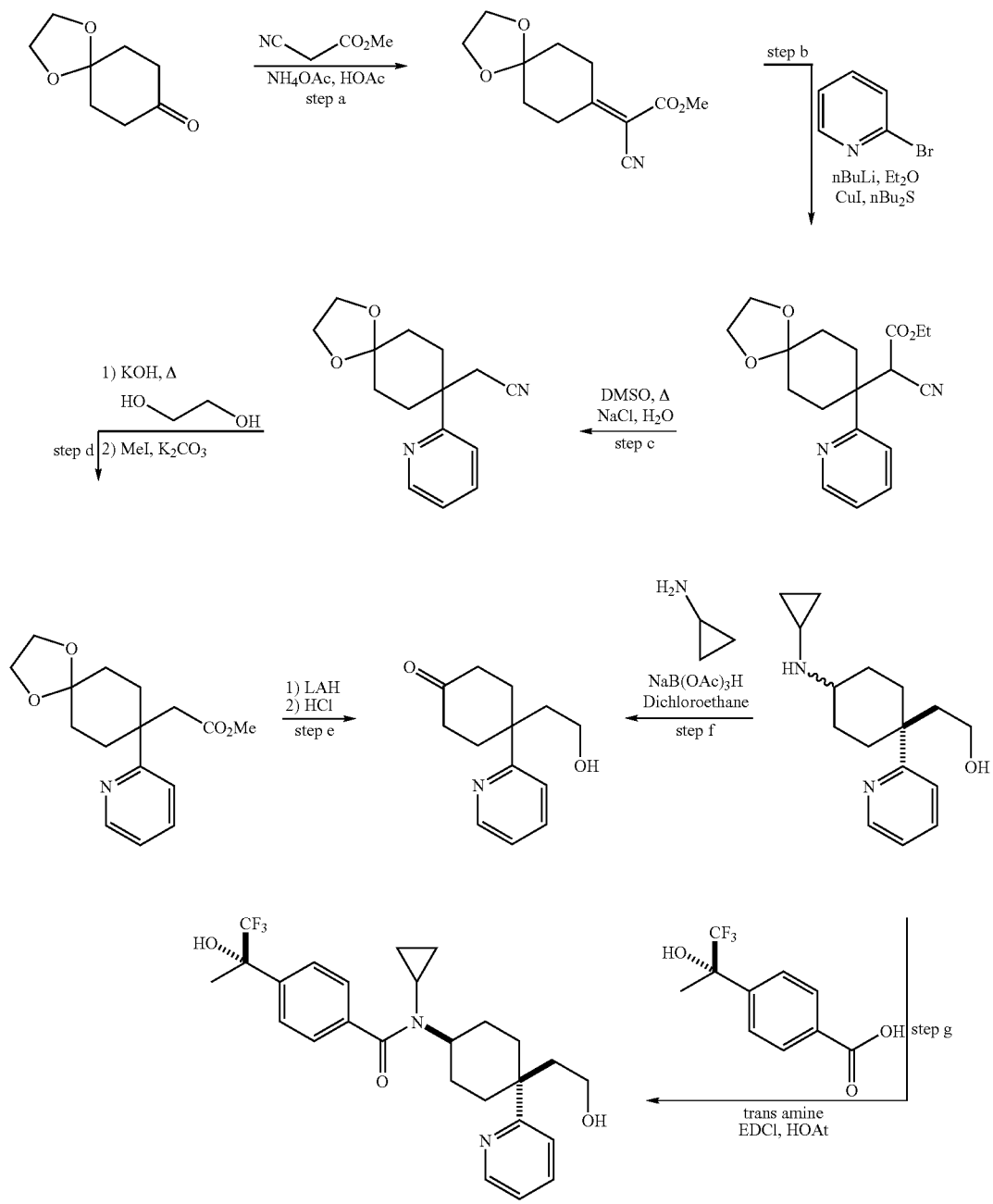

a). To a mixture of 1,4-cyclohexanedione monoethylene ketal (100.0 g, 640 mmol) and ethyl cyanoacetate (76.0 mL, 706 mmol) in toluene (400 mL) was added acetic acid (5.8 mL, 102 mmol) and ammonium acetate (2.4 g, 32 mmol). A Dean-Stark trap and reflux condenser were attached to the reaction flask and the mixture was heated to reflux. After being stirred at 120° C. for 15 hrs, the reaction was cooled to 23° C. and quenched with saturated aqueous $NaHCO_3$ (400 mL). The aqueous layer was extracted with EtOAc (250 mL) and the combined organic layers were dried with $MgSO_4$, filtered, and concentrated in vacuo. The crude yellow solid was recrystallized with ~20% EtOAc in hexanes to afford the product enoate as a light yellow solid.

b). CuI (91.0 g, 478 mmol) was charged into a 3 L flask and $nBu_2S$ (145 mL, 829 mmol) was added. The resulting viscous solution was diluted with $Et_2O$ (750 mL) and cooled to 0° C. In a separate flask, a solution of nBuLi (2.5 M in hexanes, 382 mL, 956 mmol) in $Et_2O$ (250 mL) was cooled to −78° C., and 2-bromopyridine (91.0 mL, 956 mmol) was added neat. After being stirred for 10 min, the resulting dark red mixture was cannulated into the 3 L reaction flask. The mixture was stirred for 20 min at 0° C. prior to the addition of enoate 2 (80.0 g, 319 mmol) in $Et_2O$ (400 mL) via cannula and the resulting olive green reaction mixture was stirred for 20 h, while slowly warming to 23° C. After this time, the mixture was cooled to 0° C., quenched with saturated aqueous $NH_4Cl$, diluted with EtOAc, and air was bubbled through the mixture for 6 h. The aqueous layer was extracted with EtOAc (250 mL) and $CH_2Cl_2$ (250 mL) and the combined organic layers were washed with $H_2O$ (2×400 mL) and brine (400 mL), dried with $MgSO_4$, filtered, and concentrated in vacuo to afford a brown oil. The crude material was filtered through a plug of silica gel eluting with 10%-50% EtOAc in hexanes to afford the pyridine addition product as a brown oil.

c). A mixture of the pyridyl compound prepared in step b (51.0 g, 154 mmol), NaCl (2.7 g, 46 mmol), $H_2O$ (3.0 mL), and DMSO (300 mL) was heated to 160° C. for 3 h. The reaction was then cooled to 23° C. and diluted with $H_2O$ (500 mL) and EtOAc (300 mL). The aqueous layer was extracted with EtOAc (3×300 mL) and the combined organic layers were washed with brine (400 mL), dried with $MgSO_4$, filtered, and concentrated in vacuo. The crude material was filtered through a plug of silica gel eluting with 10%→50% EtOAc in hexanes to afford the decarboxylated acetonitrile as a yellow oil.

d). A mixture of the decarboxylated acetonitrile prepared above (~44.0 g, 170 mmol), pulverized KOH (38.0 g, 680 mmol), and ethylene glycol (250 mL) was heated to 170° C. After being stirred for 18 h, the reaction mixture was cooled to 23° C. and diluted with $H_2O$ (300 mL) and $CH_2Cl_2$ (200 mL). The organic layer was separated from the aqueous layer and discarded. The aqueous layer was acidified to pH 2-3 with 3 N HCl and extracted with 10% MeOH/$CH_2Cl_2$ (7×200 mL). The combined organic layers were dried with $MgSO_4$, filtered, and concentrated in vacuo to afford the acid (40 g) as a white solid. To a solution of the crude acid (40.0 g, 144 mmol) in DMF (300 mL) at 0° C. was added $K_2CO_3$ (60.0 g, 432 mmol), and iodomethane (14.0 mL, 217 mmol). After being stirred for 1.5 h, the reaction was quenched with saturated aqueous $NaHCO_3$ (500 mL) and diluted with EtOAc (300 mL). The aqueous layer was extracted with EtOAc (300 mL) and the combined organic layers were washed with $H_2O$ (2×500 mL) and brine (500 mL), dried with $MgSO_4$, filtered, and concentrated in vacuo to afford the ester as a yellow oil. The crude material was used in the subsequent reaction without further purification.

e). To a mixture of LAH (11.5 g, 302 mmol) in THF (600 mL) at 0° C. was added a solution of the methyl ester prepared above (40.0 g, 137 mmol) in THF (200 mL) via cannula over a period of 30 min. After being stirred for 35 min, the reaction mixture was carefully quenched with MeOH and $H_2O$, and diluted with $Et_2O$ (200 mL) and EtOAc (200 mL). Saturated aqueous Rochelle's salt (50 mL) was added to the mixture and stirred for an additional 30 min, while warming to 23° C. The aqueous layer was extracted with EtOAc (2×200 mL) and the combined organic layers were washed with brine (400 mL), dried with $MgSO_4$, filtered, and concentrated in vacuo to afford the alcohol as a yellow oil. The crude alcohol was dissolved in THF (400 mL) and 2 N HCl (200 mL). After being stirred for 15 h at 23° C., the reaction mixture was carefully quenched with saturated aqueous $NaHCO_3$ and diluted with EtOAc (300 mL). The aqueous layer was extracted with EtOAc (200 mL) and $CH_2Cl_2$ (2×200 mL) and the combined organic layers were washed with brine (300 mL), dried with $MgSO_4$, filtered, and concentrated in vacuo to afford the ketone. The crude material was used in the subsequent reaction without further purification.

f). Cyclopropyl amine (12.4 mL, 185 mmol) was added to a solution of the ketone prepared above (27.0 g, 123 mmol) in dichloroethane (600 mL) and acetic acid (14.0 mL, 246 mmol). The reaction mixture was cooled to 0° C. and NaBH(OAc)$_3$ (52 g, 246 mmol) was added protionwise. After being stirred for 2.75 h at 23° C., the reaction was re-cooled to 0° C. and quenched with 1 M NaOH (200 mL). The aqueous layer was extracted with $CH_2Cl_2$ (2×200 mL) and the combined organic layers were washed with brine (300 mL), dried with $MgSO_4$, filtered, and concentrated in vacuo. The crude mixture of cis and trans amines was purified by flash column chromatography 75% EtOAc/hexanes (2.5% TEA)→100% EtOAc (2.5% TEA)→10% MeOH/$CH_2Cl_2$ (1% $NH_4OH$) to provide the trans amine as an off-white solid.

g). The trans amine prepared above (5.5 g, 21.4 mmol), (S)-4-(1,1,1-trifluoro-2-hydroxypropan-2-yl)benzoic acid (5.0 g, 21.4 mmol), EDCl (5.3 g, 27.8 mmol), HOAt (3.8 g, 27.8 mmol), and $NaHCO_3$ (3.6 g, 42.8 mmol) were combined and dissolved in DMF (70 mL). After being stirred for 15 h at 23° C., the reaction was quenched with 1 M NaOH (150 mL) and diluted with EtOAc (300 mL). The aqueous layer was extracted with EtOAc (100 mL) and the combined organic layers were washed with $H_2O$ (400 mL) and brine (400 mL), dried with $MgSO_4$, filtered, and concentrated in vacuo to give a mixture of the desired amide and bisacylated (N,O) ester-amide. The crude material was purified by flash column chromatography (2%→10% MeOH/$CH_2Cl_2$) to afford 3.5 g of the desired amide and 5.0 g of bisacylated (N,O) ester-amide. The bisacylated (N,O) ester-amide was dissolved in MeOH (50 mL) and 1 M NaOH (20 mL) and stirred for 2 h at 23° C. The reaction mixture was concentrated and diluted with $CH_2Cl_2$ (200 mL) and $H_2O$ (50 mL). The aqueous layer was extracted with $CH_2Cl_2$ (2×200 mL) and the combined organic layers were washed with brine (200 mL), dried with $MgSO_4$, filtered, and concentrated in vacuo. The crude material was combined with the desired benzamide isolated directly from the reaction, and purified by flash column chromatography (2%→10% MeOH/$CH_2Cl_2$) to afford the desired benzamide as a white solid: $^1$H NMR (500 MHz, MeOD) δ 8.51 (dd, J=4.8, 1.34 Hz, 1H), 7.77 (td, J=7.8, 1.7 Hz, 1H), 7.70 (d, J=8.3 Hz, 2H), 7.53 (d, J=8.3 Hz, 2H), 7.46 (d, J=8.1 Hz, 1H), 7.23 (dd, J=6.7, 4.8 Hz, 1H), 4.03 (m, 1H), 3.24 (t, J=10.0 Hz, 2H), 2.83 (m, 1H), 2.41 (m, 2H), 2.28 (m, 4H), 1.93 (m, 2H), 1.76 (s, 3H), 1.69 (m, 2H), 0.63 (m, 2H), 0.54 (m, 2H).

Example 7

Preparation of 2-(trans-4-(N-cyclopropyl-4-((S)-1,1,1-trifluoro-2-hydroxypropan-2-yl)benzamido)-1-(pyridin-2-yl)cyclohexyl)ethyl carbamate

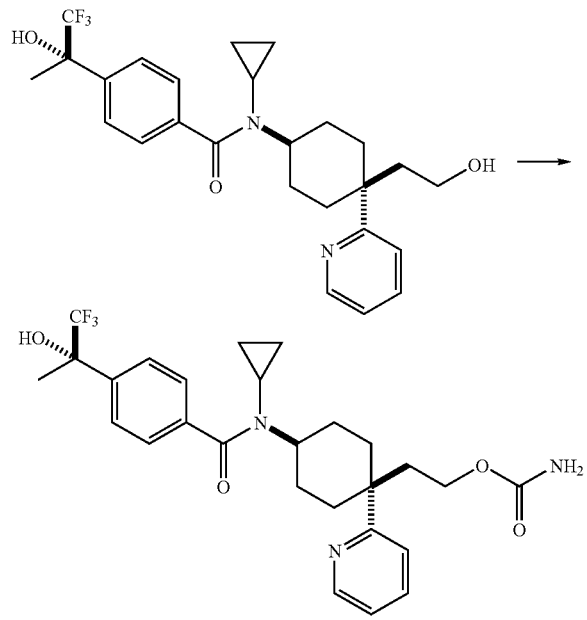

a). To a solution of N-cyclopropyl-N-(trans-4-(2-hydroxyethyl)-4-(pyridin-2-yl)cyclohexyl)-4-((S)-1,1,1-trifluoro-2-hydroxypropan-2-yl)benzamide prepared in example E (48 mg, 0.1 mmol) in $CH_2Cl_2$ (1.5 mL) was added trichloroacetyl isocyanate (14 μL, 0.12 mmol) After being stirred for 20 min at 23° C., activated neutral alumina was added to the reaction and allowed to stand for an additional 2 h. The alumina was washed with 1.0% $MeOH/CH_2Cl_2$ and the filtrate concentrated in vacuo. The crude material was purified by flash column chromatography (gradient elution, 3%→10% $MeOH/CH_2Cl_2$) to afford the carbamate product as an off-white solid. $^1$H NMR (400 MHz, MeOD) δ 8.53 (d, J=4.0 Hz, 1H), 7.78 (t, J=7.5 Hz, 1H), 7.70 (d, J=8.1 Hz, 2H), 7.53 (d, J=8.3 Hz, 2H), 7.48 (d, J=8.0 Hz, 1H), 7.24 (dd, J=7.3, 4.9 Hz, 1H), 4.04 (m, 1H), 3.73 (t, J=7.2 Hz, 2H) 2.84 (m, 1H), 2.37 (m, 6H), 1.95 (d br, J=10.7 Hz, 2H), 1.76 (s, 3H), 1.72 (m, 2H), 0.63 (m, 2H), 0.54 (m, 2H).

Example 8

Preparation of N-(trans-4-cyano-4-(2-fluorophenyl)cyclohexyl)-N-cyclopropyl-4-((S)-1,1,1-trifluoro-2-hydroxypropan-2-yl)benzamide

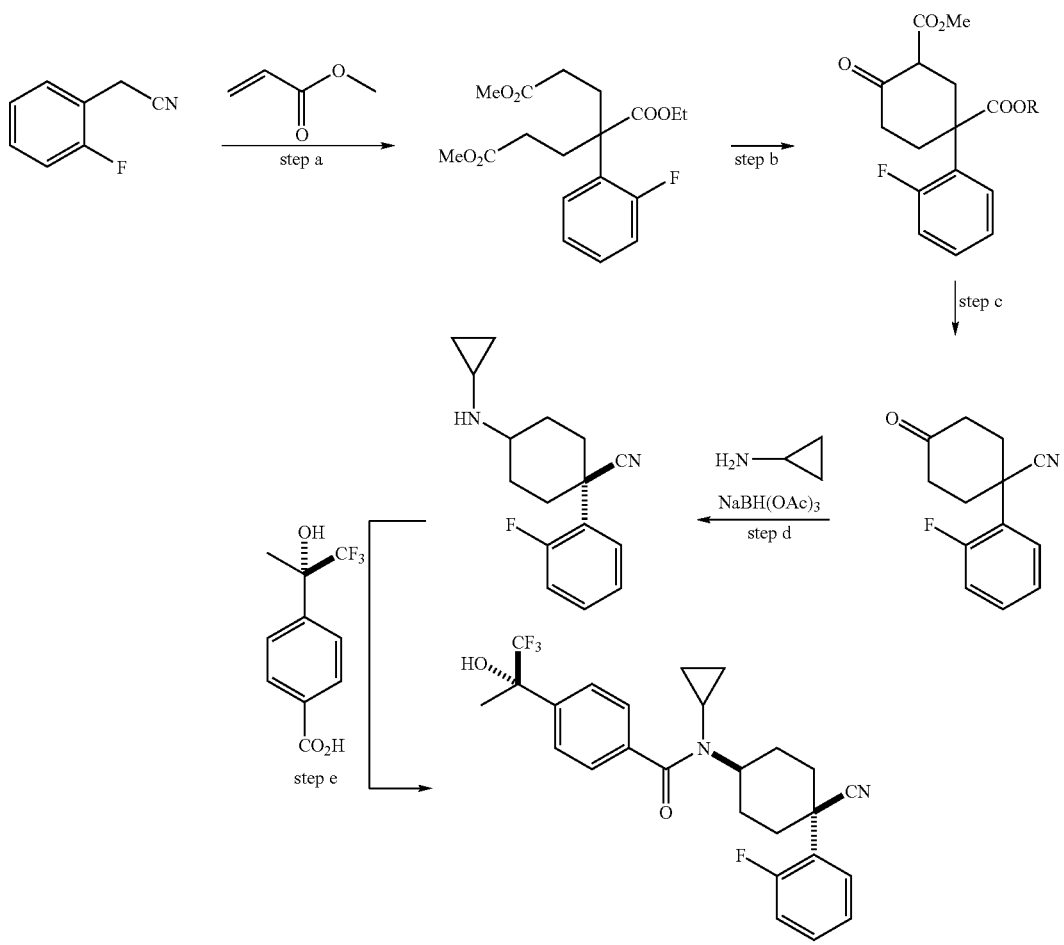

a). 9.5 g 2-(2-fluorophenyl)acetonitrile (0.07 mol) was combined with 33 mL methyl acrylate in 35 mL t-butyl alcohol. The resulting mixture was heated to reflux. The heat was removed and 11 mL 40% methanolic Triton B (tetramethylammonium hydroxide) in 16 mL t-butyl alcohol was added. After 4 hours of heating at reflux, the mixture was cooled to room temperature and concentrated under reduced pressure. The residue was diluted with 200 mL $CH_2Cl_2$. The organics were washed successively with 2.5 N hydrochloric acid, water and brine. Then the organics were dried ($MgSO_4$) and concentrated under reduced pressure. Purification by flash chromatography ($SiO_2$, 20% EA/Hexanes) gave the product as light-brown oil.

b). To a 2 L flask containing the diester obtained above (21.0 g, 68.4 mmol, 1.0 equiv) and 400 mL toluene was added 4.92 g sodium hydride (205.1 mmol, 3.0 equiv). After 5 hours of heating at reflux, the mixture was cooled in ice. 2.5 N Acetic acid was slowly added until a clear two-phase solution resulted. The organic layer was separated, washed successively with water, sat. $NaHCO_3$ and brine. Then the organics were dried ($MgSO_4$) and concentrated under reduced pressure to give the ketoester product as a yellow solid.

c). 10.0 g Of the ketoester obtained above was combined with 250 mL acetic acid and 125 mL 10% sulfuric acid. After 24 hours of heating at 105° C., the mixture was cooled to room temperature, diluted with water and extracted (4×50% EA/Hexanes). Then the organics were dried ($MgSO_4$) and concentrated under reduced pressure. Purification by flash chromatography ($SiO_2$, 30% EA/hexanes, 35% EA/hexanes) gave the ketone product as white solid. $^1$H NMR (DMSO-$d_6$, 500 MHz) δ7.53 (m, 1H), 7.48 (m, 1H), 7.35-7.29 (m, 2H), 2.74-2.67 (m, 2H), 2.51-2.40 (m, 6H).

d). A solution of trans-4-(cyclopropylamino)-1-(2-fluorophenyl)cyclohexanecarbonitrile (4.4 g, 20.2 mmol, 1.0 equiv.) in 1,2-dichloroethane (40 mL) was treated at 0° C. with cyclopropylamine (2.31 g, 40.4 mmol, 2.0 equiv.) and $NaBH(OAc)_3$ (8.56 g, 40.4 mmol, 2.0 equiv.) successively. After being stirred at 25° C. for 12 h, the reaction mixture was diluted (EtOAc), washed (1×1 N NaOH and 2× brine), dried ($Na_2SO_4$) and concentrated under reduced pressure. Purification by flash chromatography ($SiO_2$, 20% EtOAc/n-Hexane containing 2.5% of TEA) gave the trans amine as a colorless oil.

e). A solution of amine obtained above (210 mg, 0.82 mmol, 1.0 equiv.) and (S)-4-(1,1,1-trifluoro-2-hydroxypropan-2-yl)benzoic acid (190 mg, 0.82 mmol, 1.0 equiv.) in DMAF (5.0 mL) was treated with EDCl (205 mg, 1.06 mmol, 1.3 equiv.), HOAt (145 mg, 1.06 mmol, 1.3 equiv.), and $NaHCO_3$ (138 mg, 1.64 mmol, 2.0 equiv.) successively. After being stirred at 25° C. for 12 h, the reaction was diluted (EtOAc), washed (2×1 N HCl, 2×1 N NaOH, and 1× brine), dried ($Na_2SO_4$), and concentrated under reduced pressure. Purification by flash chromatography ($SiO_2$, 30-35% EtOAc/n-Hexane) gave the product as white solid. $^1$H NMR (DMSO, 500 MHz) δ 7.63 (d, J=8.1 Hz, 2H), 7.56-7.53 (m, 3H), 7.48 (m, 1H), 7.35-7.29 (m, 2H), 6.67 (s, 1H), 4.12 (m, 1H), 2.82 (m, 1H), 2.38-2.27 (m, 4H), 2.11-2.03 (m, 4H), 1.72 (s, 3H), 0.53-0.52 (m, 2H), 0.43 (m, 2H), m/z (ESI) 475.2 $[M+H]^+$.

Example 9

Preparation of N-(trans-4-carbamoyl-4-(2-fluorophenyl)cyclohexyl)-N-cyclopropyl-4-((S)-1,1,1-trifluoro-2-hydroxypropan-2-yl)benzamide

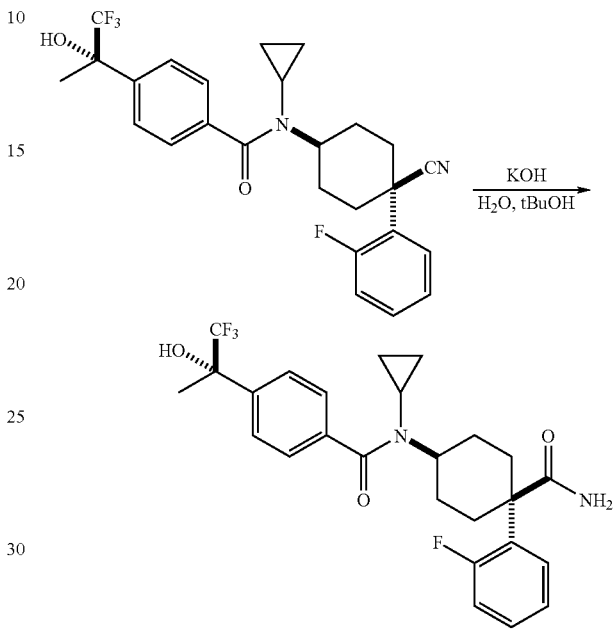

N-(trans-4-cyano-4-(2-fluorophenyl)cyclohexyl)-N-cyclopropyl-4-((S)-1,1,1-trifluoro-2-hydroxypropan-2-yl)benzamide prepared in the previous example (50 mg, 0.11 mmol, 1.0 equiv) was hydrolyzed in 1 mL tert-butanol in the presence of KOH (100 mg) at 100° C. overnight. The mixture was allowed to cool to ambient temperature, diluted with water, extracted (3×10% MeOH/$CH_2Cl_2$), dried ($Na_2SO_4$), filtered and concentrated. Purification by flash chromatography ($SiO_2$, 50-55% EtOAc/n-Hexane) gave the product as white solid. $^1$H NMR (DMSO-$d_6$, 500 MHz) δ 7.61 (d, J=8.1 Hz, 2H), 7.49 (d, J=8.2 Hz, 2H), 7.44 (m, 1H), 7.30 (m, 1H), 7.19 (m, 1H), 7.12 (dd, J=8.1, 12.5 Hz, 1H), 7.01 (m, 2H), 6.66 (s, 1H), 4.07 (m, 1H), 2.69 (m, 1H), 2.56 (m, 2H), 2.20 (m, 2H), 1.82 (m, 2H), 1.72 (m, 5H), 0.46-0.45 (m, 2H), 0.35 (m, 2H); m/z (ESI) 493.2 $[M+H]^+$.

Example 10

Preparation of (trans-4-(N-cyclopropyl-4-((S)-1,1,1-trifluoro-2-hydroxypropan-2-yl)benzamido)-1-phenylcyclohexyl)methyl carbamate

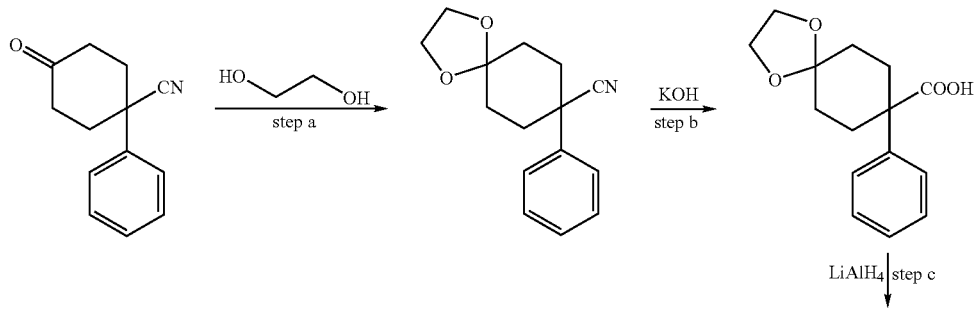

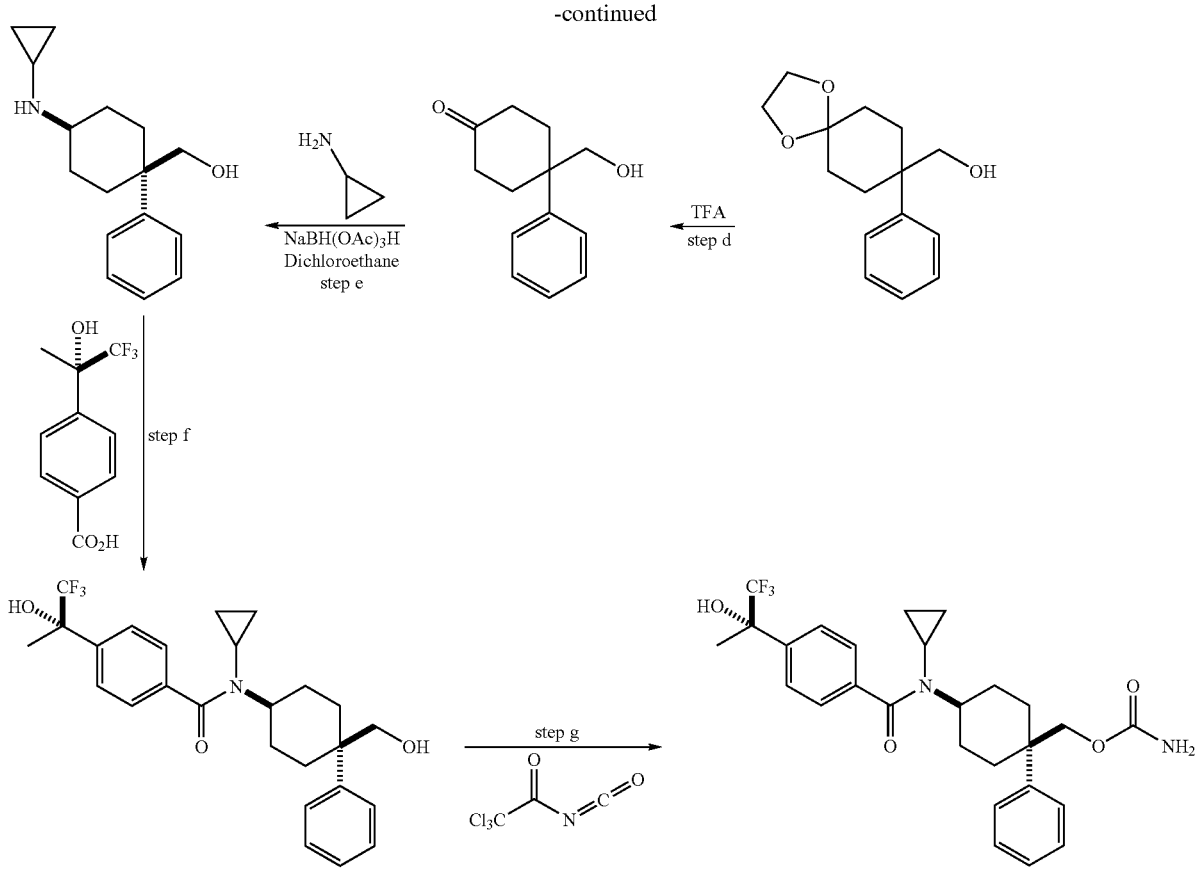

a). A mixture of 20.0 g 4-cyano-4-phenylcyclohexanone (0.1 mol), 5.5 mL ethylene glycol (6.2 g, 0.1 mol, 1.0 equiv) and 0.24 g of p-toluenesulfonic acid in 180 mL of benzene was heated at reflux under a Dean-Stark trap for 6 hours. The solution was cooled to room temperature and washed successively with sat. NaHCO$_3$, water and brine. Then the organics were dried (MgSO$_4$) and concentrated under reduced pressure. The residue was recrystallized from cyclohexane to give the product as white solid.

b). A mixture of 21.0 g 4-cyano-4-phenylcyclohexanone, ethylene ketal prepared in step a and 21.0 g of KOH in 180 mL ethylene glycol was heated at 170° C. for 16 hours. The solution was then cooled to room temperature, diluted with water and washed with ether. Then the aqueous layer was acidified to pH~4. The aqueous layer was extracted (2× ether), dried (Na$_2$SO$_4$), filtered and concentrated under reduced pressure to give the crude product as white solid. The product was used for next step without further purification.

c). A solution of 12.0 g of 4-carboxy-4-phenylcyclohexanone ethylene ketal prepared in step 1, (45.8 mol, 1.0 equiv) in 200 mL THF was added to 4.35 g of lithium aluminum hydride in 50 mL THF. Following 6 hours of heating at reflux, the mixture was cooled in ice and treated successively with 3.5 mL water, 3.5 mL of 15% NaOH solution and 10.5 mL water. The resulting inorganic gel is collected on a filter and rinsed with ether. The combined filtrates were dried (MgSO$_4$) and concentrated under reduced pressure to give the crude alcohol product as white solid. The product was used for the next step without further purification.

d). A solution of 9.5 g of 4-(hydroxymethyl)-4-phenylcyclohexanone, ethylene ketal prepared in step c in 20 mL trifluoroacetic acid and 1 mL H$_2$O was stirred at room temperature for 0.5 h. Then the mixture was diluted with sat. NaHCO$_3$. The resulting solution was extracted (10% MeOH/CH$_2$Cl$_2$), dried (Na$_2$SO$_4$) and concentrated under reduced pressure. The ketone product was used for next step without further purification.

e). A solution of 4-(hydroxymethyl)-4-phenylcyclohexanone (5.0 g, 24.5 mmol, 1.0 equiv.) in 1,2-dichloroethane (50 mL) was treated at 0° C. with cyclopropylamine (4.2 g, 74.0 mmol, 3.0 equiv.), 1 mL acetic acid and NaBH(OAc)$_3$ (15.6 g, 74.0 mmol, 3.0 equiv.) successively. After being stirred at 25° C. for 12 h, the reaction mixture was diluted (EtOAc), washed (1×1 N aqueous NaOH and 2× brine), dried (Na$_2$SO$_4$) and concentrated under reduced pressure. Purification by flash chromatography (SiO$_2$, 50% EtOAc/n-Hexane with 5% TEA) gave the trans amine isomer (the bottom spot on the TLC).

f). A solution of trans amine obtained above (440 mg, 1.8 mmol, 1.0 equiv.) and (S)-4-(1,1,1-trifluoro-2-hydroxypropan-2-yl)benzoic acid (420 mg, 1.8 mmol, 1.0 equiv.) in DMF (6.0 mL) was treated with EDCl (449 mg, 2.3 mmol, 1.3 equiv.), HOAt (319 mg, 2.3 mmol, 1.3 equiv.), and NaHCO$_3$ (302 mg, 3.6 mmol, 2.0 equiv.) successively. After being stirred at 25° C. for 12 h, the reaction was diluted (EtOAc), washed (2×1 N aqueous HCl, 2×1 N NaOH, and 1× brine), dried (Na$_2$SO$_4$), and concentrated under reduced pressure.

The mixture was purified by HPLC 50-70% acetonitrile/water with 0.1% TFA 20 min. $^1$H NMR (DMSO, 500 MHz) δ 7.62 (d, J=8.1 Hz, 2H), 7.50 (d, J=7.6 Hz, 2H), 7.41 (d, J=8.1 Hz, 2H), 7.29 (t, J=7.3 Hz, 2H), 7.16 (t, J=7.2 Hz, 1H), 6.67 (s, 1H), 4.46 (t, J=4.9 Hz, 1H), 3.92 (m, 1H), 3.77 (d, J=4.9 Hz, 2H), 2.77 (m, 1H), 2.23-2.15 (m, 4H), 1.82-1.75 (m, 2H), 1.72 (s, 3H), 1.58-1.47 (m, 2H), 0.54-0.48 (m, 2H), 0.43 (m, 2H), m/z (ESI) 462.2 [M+H]$^+$.

g). A solution of product obtained above (50.0 mg, 0.1 mmol, 1.0 equiv.) in chloroform (1.5 mL) was treated with 23.0 mg tricholoacetyl isocyanate (0.12 mmol, 1.2 equiv.) in 1 mL benzene. After being stirred at 25° C. for 0.5 h, the reaction mixture was soaked into a pad of neutral aluminum oxide (activity II) for 10 mins. The pad was then washed with 10% MeOH/DCM. The organics were diluted with sat. NaHCO$_3$, extracted (2×10% MeOH/DCM), dried (Na$_2$SO$_4$) and concentrated under reduced pressure. The mixture was purified by HPLC 50-70% acetonitrile/water with 0.1% TFA 20 min. to give the product. $^1$H NMR (DMSO, 500 MHz) δ 7.67 (d, J=8.3 Hz, 2H), 7.56 (d, J=8.6 Hz, 2H), 7.49 (d, J=7.6 Hz, 2H), 7.37 (t, J=7.7 Hz, 2H), 7.25 (t, J=7.2 Hz, 1H), 6.72 (s, 1H), 4.41 (s, 2H), 4.01 (m, 1H), 2.84 (m, 1H), 2.30-2.20 (m, 4H), 1.92-1.85 (m, 2H), 1.77 (s, 3H), 1.75-1.65 (m, 2H), 0.60-0.54 (m, 2H), 0.47 (m, 2H), m/z (ESI) 505.2 [M+H]$^+$.

Example 11

Preparation of N-(trans-4-cyano-4-phenylcyclohexyl)-N-cyclopropyl-4-[(S)-1,1,1-trifluoro-2-hydroxypropan-2-yl]benzamide a). A solution of 4-cyano-4-phenylcyclohexanone (572 mg, 2.87 mmol) in 1,2-dichloroethane (16 mL) was treated at 0° C. with cyclopropylamine (298 □L, 4.31 mmol, 1.5 equiv.), acetic acid (329 □L, 5.74 mmol, 2.0 equiv.), and NaBH(OAc)$_3$ (1.22 g, 5.74 mmol, 2.0 equiv) successively. After being stirred at 25° C. for 12 h, the reaction mixture was diluted (EtOAc) and washed (1×1 N aqueous NaOH and 2× brine). The organics were dried (Na$_2$SO$_4$) and concentrated under reduced pressure to provide the crude product (3:1 mixture of trans and cis amines) as a colorless liquid. The product was used for next step without further purification.

b). A solution of N-cyclopropyl-4-cyano-4-phenylcyclohexanamine prepared above in step a (608 mg, 2.53 mmol, 1.0 equiv.) and (S)-4-(1,1,1-trifluoro-2-hydroxypropan-2-yl)benzoic acid (592 mg, 2.53 mmol, 1.0 equiv.) in DMF (8.5 mL) was treated at 0° C. with EDCl (630 mg, 3.29 mmol, 1.3 equiv.), HOAt (448 mg, 3.29 mmol, 1.3 equiv), and NaHCO$_3$ (425 mg, 5.06 mmol, 2.0 equiv.) successively. After being stirred at 25° C. for 12 h, the reaction was diluted (EtOAc) and washed (1×10% aqueous citric acid, 1× saturated aqueous NaHCO$_3$, and 1× brine). The organics were dried (Na$_2$SO$_4$), and concentrated under reduced pressure. Flash chromatography (SiO$_2$, 30-40% EtOAc/Hexanes, gradient elution) gave the desired product as a white solid: $^1$H NMR (CDCl$_3$, 400 MHz) δ 7.60 (d, J=8.1 Hz, 2H), 7.52-7.49 (m, 2H), 7.50 (d, J=8.2 Hz, 2H), 7.43-7.39 (m, 2H), 7.35-7.33 (m, 1H), 4.50-4.40 (m, 1H), 2.64-2.60 (m, 1H), 2.58 (s, 1H), 2.45-2.25 (m, 4H), 2.18-2.12 (m, 2H), 2.08-2.00 (m, 2H), 1.80 (s, 3H), 0.68-0.64 (m, 2H), 0.56-0.52 (m, 2H); m/z (ESI) 457 [M+H]$^+$.

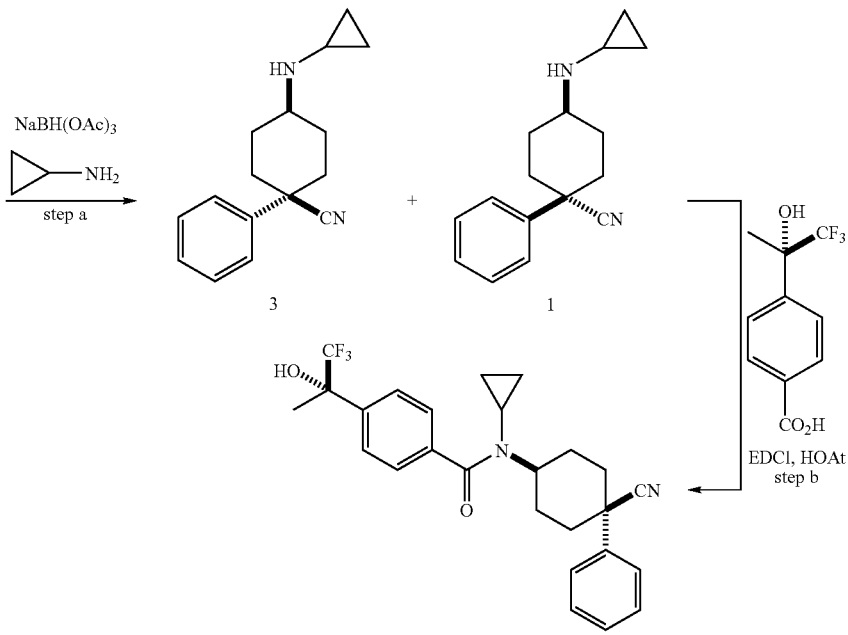

Example 12

Preparation of N-(trans-4-(acetamidomethyl)-4-phenylcyclohexyl)-N-cyclopropyl-4-((S)-1,1,1-trifluoro-2-hydroxypropan-2-yl)benzamide

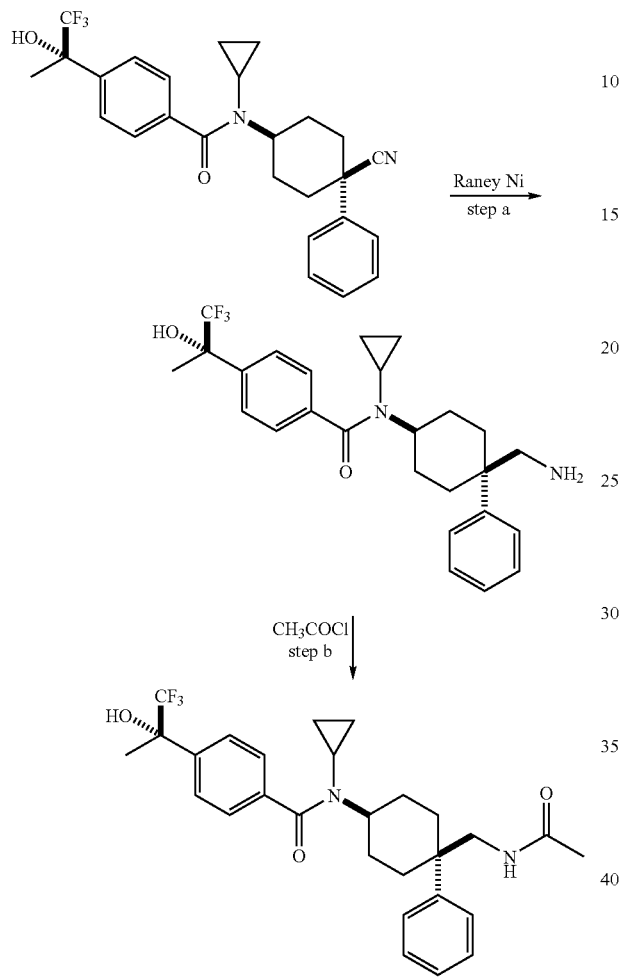

a). To N-(trans-4-cyano-4-phenylcyclohexyl)-N-cyclopropyl-4-((S)-1,1,1-trifluoro-2-hydroxypropan-2-yl)benzamide (1.0 g, 2.2 mmol, prepared as in example J) in MeOH (70 mL) under nitrogen atmosphere was added 28% $NH_4OH$ (0.56 mL) and an aqueous suspension of Raney Ni (Raney 2800 Ni active catalyst, 2.8 mL). The reaction vessel was evacuated and purged to $H_2$ three times. The reaction was then stirred for 12 h under $H_2$ (1 atm). Following replacement of $H_2$ with $N_2$, the solution was decanted. The nickel residue was washed with MeOH and decanted (4×10 mL). The combined methanolic solution was reduced to 20 mL in vacuo, diluted with water (100 mL), acidified to pH 2 with 5 N HCl, and washed with $CH_2Cl_2$ (10 mL). The aqueous layer was brought to pH 12 with 5 N NaOH and was extracted with 10% MeOH in $CH_2Cl_2$ (5×70 mL). The combined organics were dried over $Na_2SO_4$ and removed in vacuo to provide N-(trans-4-(aminomethyl)-4-phenylcyclohexyl)-N-cyclopropyl-4-((S)-1,1,1-trifluoro-2-hydroxypropan-2-yl)benzamide.

b). To a solution of N-(trans-4-(aminomethyl)-4-phenylcyclohexyl)-N-cyclopropyl-4-((S)-1,1,1-trifluoro-2-hydroxypropan-2-yl)benzamide (0.10 g, 0.22 mmol) in DMF (1.5 mL) and Hünig's base (0.30 mL, 1.7 mmol) was added acetyl chloride (0.020 mL, 0.26 mmol). After stirring overnight at room temperature, the reaction solution was poured into water (15 mL). The resulting mixture was acidified to pH 2 with 5 N HCl and extracted with $CH_2Cl_2$ (3×5 mL). The combined organics were dried over $Na_2SO_4$ and removed in vacuo. Silica gel chromatography (gradient of 2 to 5% MeOH in $CH_2Cl_2$) afforded N-(trans-4-(acetamidomethyl)-4-phenylcyclohexyl)-N-cyclopropyl-4-((S)-1,1,1-trifluoro-2-hydroxypropan-2-yl)benzamide. $^1$H NMR (500 MHz, $CD_3OD$): δ 0.57 (bs, 2H), 0.68 (bs, 2H), 1.68-1.75 (m, 2H), 1.77 (s, 3H), 1.83 (s, 3H), 1.88-1.98 (m, 2H), 2.27-2.34 (m, 2H), 2.37-2.50 (m, 2H), 2.83 (bs, 1H), 3.77 (s, 2H), 7.23 (t, J=7.5 Hz, 1H), 7.36 (t, J=7.5 Hz, 2H), 7.43 (d, J=7.5 Hz, 2H), 7.55 (d, J=10 Hz, 2H), 7.71 (d, J=10 Hz, 2H).

Example 13

Preparation of N-cyclopropyl-N-(trans-4-((2-hydroxyacetamido)methyl)-4-phenylcyclohexyl)-4-((S)-1,1,1-trifluoro-2-hydroxypropan-2-yl)benzamide

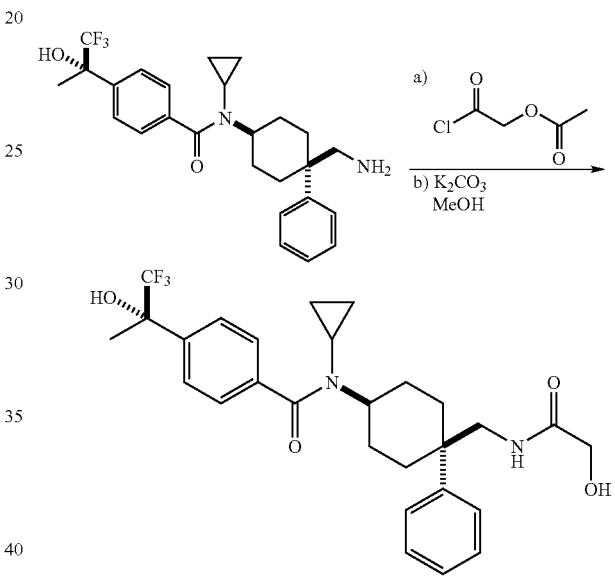

a). To a solution of N-(trans-4-(aminomethyl)-4-phenylcyclohexyl)-N-cyclopropyl-4-((S)-1,1,1-trifluoro-2-hydroxypropan-2-yl)benzamide (85 mg, 0.184 mmol, prepared as in example K) in DMF (3 mL) and N,N-diisopropylethylamine (0.30 mL, 1.7 mmol) was added acetoxyacetyl chloride (0.024 ml, 0.221 mmol). The reaction was stirred 18 h at room temperature, then poured into ethyl acetate (60 ml). The resulting mixture was washed with water (2×40 mL) and saturated NaCl (40 ml), dried with $MgSO_4$, and evaporated to give a white solid. Chromatography over silica gel (hexane/0-100% ethyl acetate) yielded 2-((trans-4-(N-cyclopropyl-4-((S)-1,1,1-trifluoro-2-hydroxypropan-2-yl)benzamido)-1-phenylcyclohexyl)methylamino)-2-oxoethyl acetate as a white solid.

b). To a solution of 2-((trans-4-(N-cyclopropyl-4-((S)-1,1,1-trifluoro-2-hydroxypropan-2-yl)benzamido)-1-phenylcyclohexyl)methylamino)-2-oxoethyl acetate (79 mg, 0.144 mmol) in methanol (5 mL) was added potassium carbonate (300 mg, 2.2 mmol). After stirring at room temperature for 1.5 h, the reaction solution was poured into water (50 mL). The resulting mixture was extracted with ethyl acetate (3×50 mL), the combined organics were dried over $MgSO_4$ and then reduced in vacuo. Silica gel chromatography (hexane/0-100% ethyl acetate) afforded N-cyclopropyl-N-(trans-4-((2-hydroxyacetamido)methyl)-4-phenylcyclohexyl)-4-((S)-1,1,1-trifluoro-2-hydroxypropan-2-yl)benzamide. $^1$H NMR (500 MHz, $CD_3OD$): δ 0.58 (bs, 2H), 0.65 (bs, 2H), 1.67-1.73 (m, 2H), 1.75 (s, 3H), 1.88-1.98 (m, 2H), 2.24-2.30 (m, 2H), 2.37-2.50 (m, 2H), 2.80 (bs, 1H), 3.80 (s, 2H), 3.86 (s, 3H), 7.24 (t, J=7.3 Hz, 1H), 7.37 (t, J=7.8 Hz, 2H), 7.44 (d, J=7.5 Hz, 2H), 7.52 (d, J=8.6 Hz, 2H), 7.69 (d, J=8.1 Hz, 2H).

Example 14

Preparation of Methyl (trans-4-(N-cyclopropyl-4-((S)-1,1,1-trifluoro-2-hydroxypropan-2-yl)benzamido)-1-phenylcyclohexyl)methylcarbamate

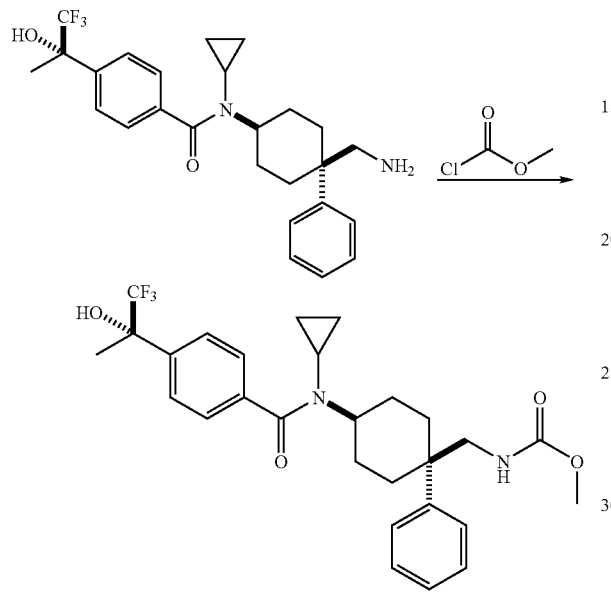

To a solution of N-(trans-4-(aminomethyl)-4-phenylcyclohexyl)-N-cyclopropyl-4-((S)-1,1,1-trifluoro-2-hydroxypropan-2-yl)benzamide (85 mg, 0.184 mmol, prepared as in example K) in DMF (2.5 mL) and N,N-diisopropylethylamine (0.25 mL, 1.4 mmol) was added methyl chloroformate (0.017 ml, 0.221 mmol). The reaction was stirred 19 h at room temperature, then poured into ethyl acetate (40 ml). The resulting mixture was washed with water (2×40 mL) and saturated NaCl (40 ml), dried with MgSO₄, and evaporated to give a pale yellow oil. Chromatography over silica gel (hexane/0-70% ethyl acetate) yielded methyl (trans-4-(N-cyclopropyl-4-((S)-1,1,1-trifluoro-2-hydroxypropan-2-yl)benzamido)-1-phenylcyclohexyl)methylcarbamate as a white solid.

¹H NMR (500 MHz, CD₃OD): δ 0.55 (bs, 2H), 0.64 (bs, 2H), 1.69-1.72 (m, 2H), 1.75 (s, 3H), 1.83 (s, 3H), 1.88-1.95 (m, 2H), 2.26-2.30 (m, 2H), 2.36-2.43 (m, 2H), 2.80 (bs, 1H), 3.54 (s, 3H) 3.65 (s, 2H), 7.20 (t, J=7.2 Hz, 1H), 7.32 (t, J=7.8 Hz, 2H), 7.38 (d, J=7.5 Hz, 2H), 7.52 (d, J=8.6 Hz, 2H), 7.69 (d, J=8.0 Hz, 2H).

Example 15

Preparation of N-(trans-4-(sulfamidomethyl)-4-phenylcyclohexyl)-N-cyclopropyl-4-((S)-1,1,1-trifluoro-2-hydroxypropan-2-yl)benzamide

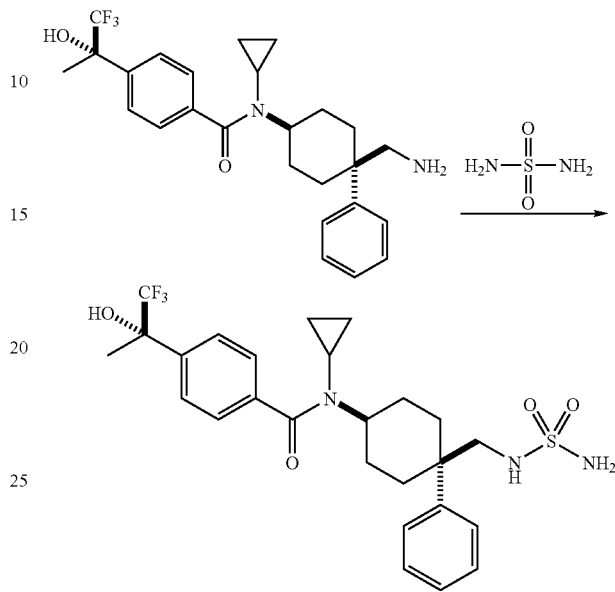

N-(trans-4-(aminomethyl)-4-phenylcyclohexyl)-N-cyclopropyl-4-((S)-1,1,1-trifluoro-2-hydroxypropan-2-yl)benzamide (135 mg, 0.293 mmol, prepared as in example K) and sulfamide (169 mg, 1.8 mmol) were dissolved in water (1.5 mL) and methanol (1.5 mL). The solution was heated at reflux for 16 h, then another 80 mg sulfamide added, followed by 6 h more at reflux. The resulting solution was added to water (60 mL) and extracted with ethyl acetate (3×60 mL). The combined organics were dried (MgSO₄) and reduced in vacuo to give a white solid. Chromatography over silica gel (hexane/0-100% ethyl acetate) yielded N-(trans-4-(sulfamidomethyl)-4-phenylcyclohexyl)-N-cyclopropyl-4-((S)-1,1,1-trifluoro-2-hydroxypropan-2-yl)benzamide as a white solid. ¹H NMR (500 MHz, CD₃OD): δ 0.53 (bs, 2H), 0.62 (bs, 2H), 1.69-1.72 (m, 2H), 1.75 (s, 3H), 1.91-1.93 (m, 2H), 2.33-2.40 (m, 2H), 2.37-2.50 (m, 2H), 2.80 (bs, 1H), 3.51 (s, 2H), 7.22 (t, J=7.2 Hz, 1H), 7.35 (t, J=7.6 Hz, 2H), 7.43 (d, J=7.5 Hz, 2H), 7.52 (d, J=8.1 Hz, 2H), 7.69 (d, J=8.1 Hz, 2H).

Example 16

Preparation of N-(trans-4-(3-amino-3-oxopropyl)-4-(4-fluorophenyl)cyclohexyl)-N-cyclopropyl-4-((S)-1,1,1-trifluoro-2-hydroxypropan-2-yl)benzamide

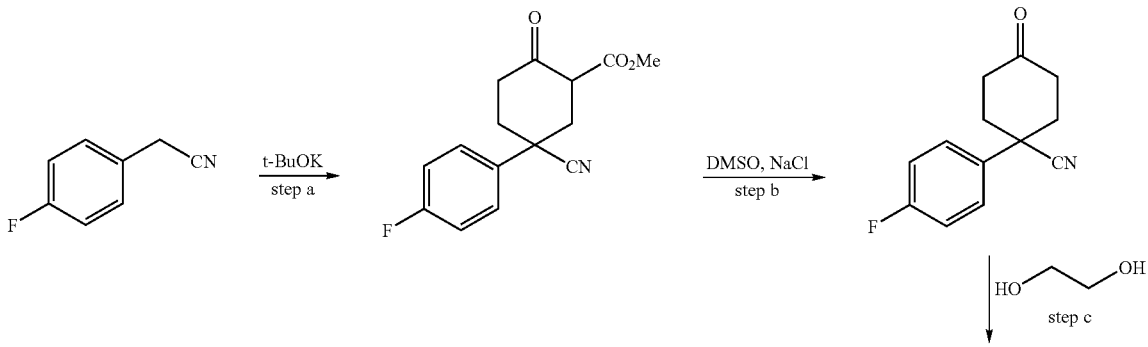

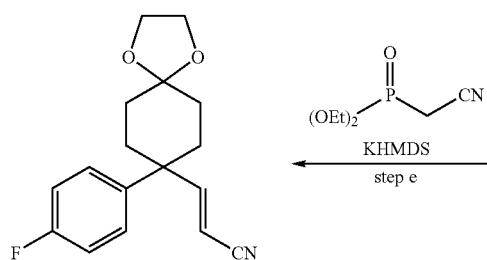 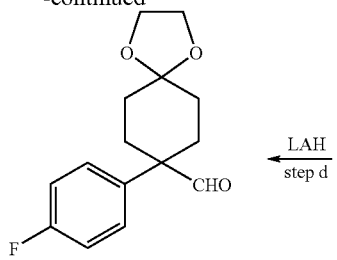 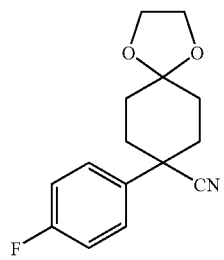

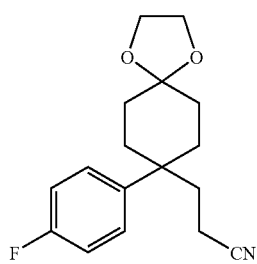 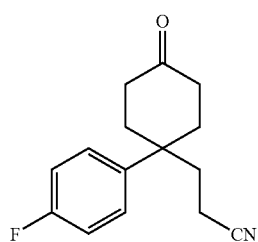 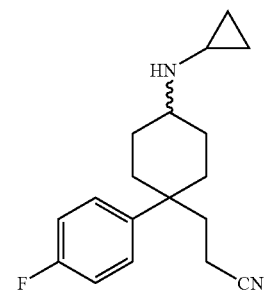

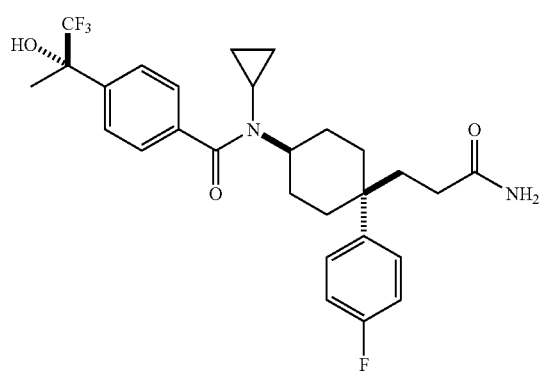

a). To a stirred solution of 4-fluorophenylacetonitrile (50 g, 370 mmol, 1 equiv.) and methyl acrylate (66 mL, 740 mmol, 2 equiv.) in 1000 mL dry THF cooled to 0° C. in an ice bath was added solid t-BuOK (50 g, 446 mmol, 1.2 equiv.). Upon addition the mixture changed to an orange color and warmed slightly. After 15 minutes the reaction was diluted with 1.5 L 3 N HCl, extracted 3×10% MeOH in CH$_2$Cl$_2$, washed 1× brine, dried over Na$_2$SO$_4$, filtered and concentrated to yield the product as an orange solid.

b). To a stirred solution of the ketoester product of step a (122 g, 443 mmol, 1 equiv.) in 600 mL DMSO was added H$_2$O (32 mL) and NaCl (32 g, 542 mmol, 1.3 equiv.), and the mixture heated to 160° C. for 7 hours. The mixture was allowed to cool to ambient temperature overnight, was diluted 1 L brine, extracted 10× ether and concentrated. The resulting residues were taken up in ether, washed 3×H$_2$O, 1× brine, dried over Na$_2$SO$_4$, filtered and concentrated. The material was purified over 1500 mL silica with 100% CH$_2$Cl$_2$ to yield the product as a yellow solid.

c). The ketone product of step b (35 g, 161 mmol, 1 equiv.) was refluxed in benzene in the presence of ethylene glycol (13.3 mL, 241 mmol, 1.5 equiv.) and a catalytic amount of p-TsOH under a Dean-Stark trap overnight. The reaction mixture was allowed to cool to ambient temperature, was diluted with H$_2$O, and extracted 3×EtOAc. The organics were pooled and dried over Na$_2$SO$_4$, filtered and concentrated to yield the product as a yellow oil.

d). To a stirred solution of ketal product of step c (43 g, 165 mmol, 1 equiv.) in 200 mL dry THF at 0° C. in an ice bath under N$_2$ was added LAH (82.5 mL, 1 M in THF, 0.5 equiv.)

and the reaction stirred 3 hours. The mixture was carefully quenched NH₄Cl, extracted 3×EtOAc, dried over Na₂SO₄, filtered and concentrated. The mixture was purified over 500 mL silica with 100% DCM to yield the expected aldehyde as an orange oil.

e). To a stirred solution of diethylcyanomethylphosphonate (3.08 g, 17.4 mmol. 2 equiv.) in 30 mL dry toluene was added KHMDS (35 mL, 17.4 mmol, 0.5 M in toluene, 2 equiv.) at 0 C in an ice bath. The mixture was allowed to warm to ambient temperature and stirred 1 hour, followed by the addition of the aldehyde product of step d (2.3 g, 8.71 mmol, 1 equiv.) in 10 mL dry toluene. The reaction was allowed to stir overnight, and was then diluted with NH₄Cl, extracted 3×100 mL Et₂O, washed 1×bicarb, 1× brine, dried over Na₂SO₄, filtered, concentrated, and flushed through a plug of silica with 100% CH₂Cl₂. The recovered organics were concentrated to yield the product as a yellow oil.

f). The alkene product of step e (2.49 g, 8.71 mmol, 1 equiv.) was reduced under an atmosphere of H₂ in the presence of an excess of 10% Pd/C (~100 mg) in 20 ml EtOH overnight. The mixture was filtered through celite to remove Pd/C, concentrated and purified over 100 ml silica with 100% CH₂Cl₂ to yield the product as a yellow oil.

g). The ketal product of step f (2.3 g, 7.72 mmol, 1 equiv.) was deprotected in 10 mL 1:1 THF: 3 N HCl at 80° C. for 2 hours. The mixture was cooled to 0° C., diluted with saturated bicarbonate solution, and extracted 3×5% MeOH/CH₂Cl₂, the organics were pooled and dried over Na₂SO₄, filtered and concentrated to yield the desired ketone.

h). The ketone product of step g (1 g, 394 mmol, 1 equiv.) was reacted with cyclopropylamine (246 mg, 4.33 mmol, 1.1 equiv.) and sodium triacetoxyborohydride (1.58 g, 5.99 mmol, 1.5 equiv.) in 10 mL THF/dichloroethane. The reaction was stirred overnight, and was then quenched with H₂O, extracted 3×CH₂Cl₂, washed 1× brine, dried over Na₂SO₄, concentrated and purified over 100 mL silica with 10% MeOH in CH₂Cl₂ to yield the cyclopropylamine product as a racemic mixture.

i). A solution of (S)-4-(1,1,1-trifluoro-2-hydroxypropan-2-yl)benzoic acid (580 mg, 2.35 mmol, 1.2 equiv.), HOAt (400 mg, 2.94 mmol, 1.5 equiv.), EDCl (565 mg, 2.94 mmol, 1.5 equiv.), NaHCO₃ (494 mg, 5.88 mmol, 3 equiv.) and the cyclopropylamine product of step h (578 mg, 1.96 mmol, 1 equiv.) in 10 mL dry DMF was heated at 40° C. under N₂ overnight. The reaction was cooled to ambient temperature, diluted with 10 mL sodium bicarbonate solution, extracted 3×50 mL CH₂Cl₂, concentrated under reduced pressure, and purified over silica with 10% MeOH: CH₂Cl₂ to yield the product as a mixture of cis and trans geometric isomers.

j). The nitrile product of step i (250 mg, 0.480 mmol, 1 equiv.) was hydrolyzed to the carboxyamide in 3 mL t-butanol with KOH at 80° C. for 1 hour. The mixture was cooled to ambient temperature, diluted with 3 mL H₂O, extracted 3×10% MeOH in CH₂Cl₂, concentrated under reduced pressure, and purified by preparative normal phase HPLC (50-70% acetonitrile: water, 35 minutes, 20 mL/min) to yield the final product as a white solid. ¹H NMR (MeOD, 400 MHz) δ 7.63 (d, J=8.4 Hz, 2H), 7.46 (d, J=8.4 Hz, 2H), 7.32 (dd, J=8.8 Hz, 5.6 Hz, 2H), 6.98 (dd, J=8.4 Hz, 8.4 Hz, 2H), 4.05-3.92 (m, 1H), 2.757 (m, 1H), 2.40-2.20 (m, 2H), 2.20-2.05 (m, 4H), 1.86-1.83 (m, 2H), 1.77-1.1.74 (m, 2H), 1.68 (s, 3H), 1.68-1.61 (m, 2H), 0.562 (m, 2H), 0.472 (m, 2H); m/z (ESI) 521 [M+H]⁺.

Example 17

Preparation of (trans-4-(N-cyclopropyl-4-((S)-1,1,1-trifluoro-2-hydroxypropan-2-yl)benzamido)-1-(2-fluorophenyl)cyclohexyl)methyl carbamate

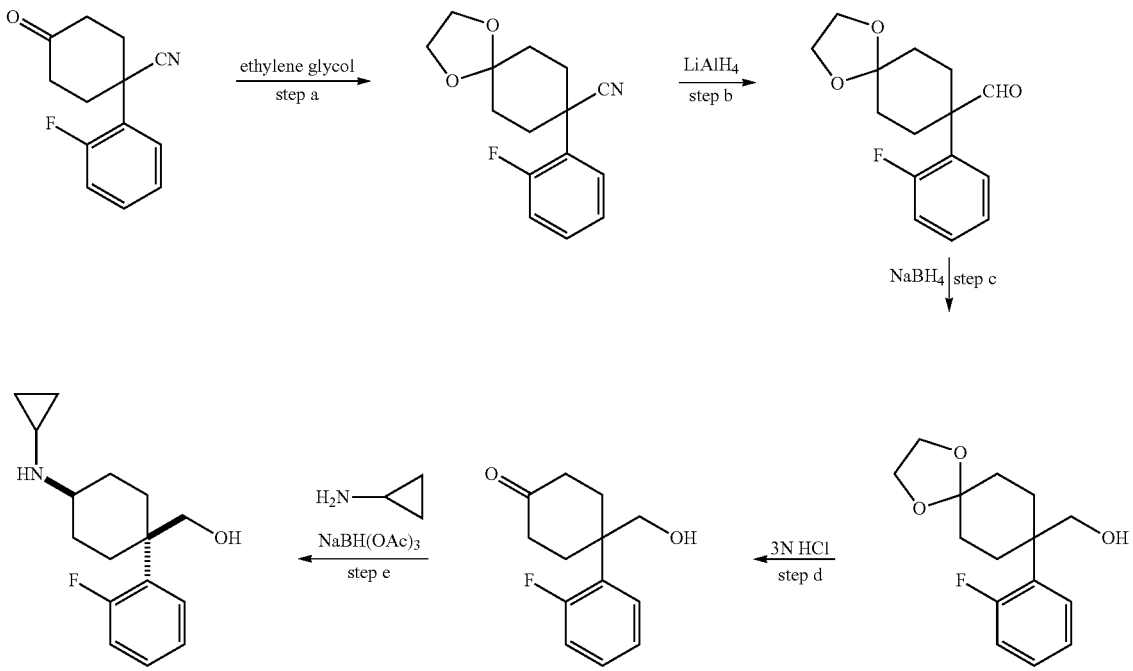

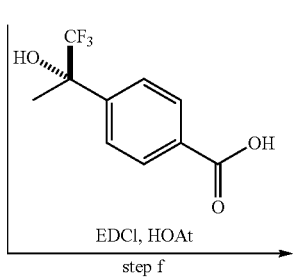 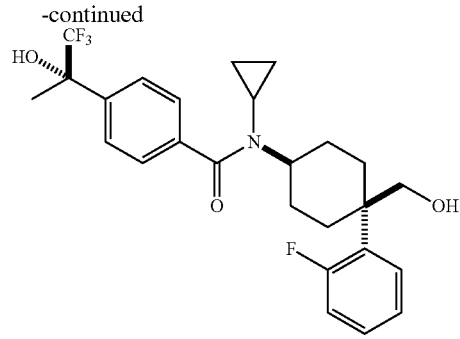

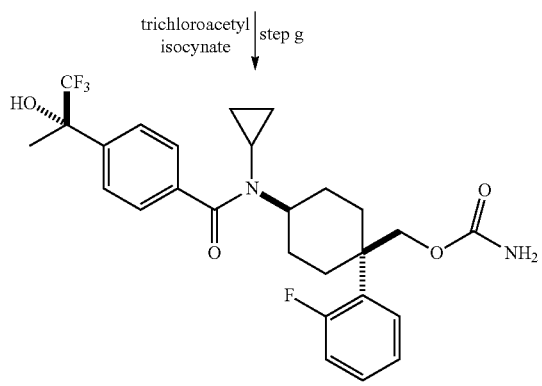

a). A mixture of 1-(2-fluorophenyl)-4-oxocyclohexanecarbonitrile (20 g, 100 mmol, 1.0 equiv, prepared as in example G), 6.2 g ethylene glycol and 0.6 g p-toluenesulfonic acid in benzene (150 mL) was heated at reflux under a Dean-Stark trap for 3 hours. The solution was cooled and washed successively with sat. NaHCO$_3$, water, and brine. The organics were dried over Na$_2$SO$_4$ and evaporated to give the ketal as a white solid.

b). To a well stirred suspension of LiAlH$_4$ (1.75 g, 46 mmol, 0.5 equiv) in dry THF (25 mL) was added a solution of 4-cyano-4-(2-fluorophenyl)cyclohexanone ethylene ketal (24 g, 92 mmol, 1.0 equiv) in THF (125 mL) at 10-15° C. over a period of 20 minutes. The mixture was stirred at room temperature for 4 hours, then cooled in an ice bath and treated successively with 2 N NaOH (5 mL) and water (10 mL). The resulting inorganic gel was collected on a filter and rinsed with ether. The combined filtrates were evaporated to dryness. A solution of the residue in THF (150 mL) and 3 N HCl (20 mL) was stirred for 20 minutes, treated with 10 g of NaHCO$_3$ and then evaporated to dryness. Dichloromethane was added to the residue, the organic layer was washed with water, brine and evaporated to yield the desired product.

c). To a solution of 4-(2-fluorophenyl)-4-formyl-cyclohexanone ethylene ketal (21.3 g, 80.7 mmol) in methanol (150 mL) was added NaBH$_4$ (5.4 g, 142 mmol, 1.8 equiv) at 0° C. in a period of 15 min. After being stirred at 25° C. for 2 h, the reaction solution was concentrated and diluted (EtOAc). The organics were washed (brine), dried (Na$_2$SO$_4$), and concentrated under reduced pressure. Purification of the residue by flash chromatography (SiO$_2$, 40% EtOAc/hexanes) afforded the alcohol as a white solid.

d). 3 N HCl (75 mL) was added to a solution of 4-(2-fluorophenyl)-4-(hydroxymethyl)-cyclohexanone ethylene ketal (24 g) in THF (150 mL). The mixture was stirred at room temperature for 12 h and then diluted with sat. NaHCO$_3$ (100 mL). The resulting solution was extracted (EtOAc) and the organics were dried and concentrated to give the ketone as a white solid.

e). A solution of 4-(2-fluorophenyl)-4-(hydroxymethyl)cyclohexanone (19 g, 85.5 mmol, 1.0 equiv) in 1,2-dichloroethane (150 mL) was treated at 0° C. with cyclopropylamine (12 mL, 171 mmol, 2.0 equiv), acetic acid (1.2 mL) and NaBH(OAc)$_3$ (36.2 g, 2.0 equiv) successively. After being stirred at 25° C. for 12 h, the reaction mixture was carefully diluted (sat.NaHCO$_3$), extracted (10% MeOH/CH$_2$Cl$_2$), washed (brine), dried (Na$_2$SO$_4$) and concentrated under reduced pressure. Purification of the residue by flash chromatography (SiO$_2$, 50% EtOAc/hexanes containing 2.5% triethylamine) gave the cis amine and then further elution afforded the trans amine.

f). A solution of the trans amine prepared above (5.3 g, 20.15 mmol, 1.0 equiv) and (S)-4-(1,1,1-trifluoro-2-hydroxypropan-2-yl)benzoic acid (4.72 g, 1.0 equiv) in DMF (70 mL) was treated at 0° C. with EDCl (4.74 g, 1.2 equiv), HOAt (3.29 g, 1.2 equiv) and NaHCO$_3$ (3.39 g, 2.0 equiv) successively. After being stirred at 25° C. for 12 h, the reaction was diluted (EtOAc), washed (1 N NaOH and brine), dried (Na$_2$SO$_4$), and concentrated under reduced pressure. Purification of the residue by flash chromatography (SiO$_2$, from 60% EtOAc/n-hexane to 10% MeOH/CH$_2$Cl$_2$) afforded the product as a white solid. $^1$HNM (DMSO, 400 MHz) δ 7.63 (d, J=8.0 Hz, 2H), 7.51 (d, J=8.0 Hz, 2H), 7.39 (m, 1H), 7.26 (m, 1H), 7.16-7.07 (m, 2H), 6.69 (s, 1H), 4.56 (m, 1H), 4.04 (s, 2H), 4.03 (m, 1H), 2.77 (m, 1H), 2.34-2.11 (m, 4H), 1.81-1.62 (m, 4H), 1.73 (s, 3H), 0.47 (m, 4H).

g). A solution of trichloroacetyl isocynate (147 uL, 1.2 mmol, 1.2 equiv) in benzene (5 mL) was added to another solution of N-cyclopropyl-N-(trans-4-(2-fluorophenyl)-4-(hydroxymethyl)cyclohexyl)-4-((S)-1,1,1-trifluoro-2-hydroxypropan-2-yl)benzamide (479 mg, 1.0 equiv) in CHCl$_3$ (15 mL) and DMF (1.5 mL) at room temperature. After being stirred for 0.5 h, the reaction mixture was treated with excess activated, neutral Al₂O₃ (keep adding Al₂O₃ till the stirrer stops stirring). The Al₂O₃ was filtered off and washed with 10% MeOH/CH₂Cl₂. The filtrate was washed (brine), dried (Na₂SO₄), and concentrated under reduced pressure. Purification of the residue by flash chromatography (SiO₂, 70% EA/hexanes) gave the product as a white solid. ¹H NMR (DMSO, 400 MHz) δ 7.63 (d, J=8.1 Hz, 2H), 7.51 (d, J=8.1 Hz, 2H), 7.39 (m, 1H), 7.26 (m, 1H), 7.16-7.07 (m, 2H), 6.69 (s, 1H), 6.34 (s, 2H), 4.53 (s, 2H), 4.03 (m, 1H), 2.78 (m, 1H), 2.34-2.01 (m, 4H), 1.86-1.73 (m, 4H), 1.73 (s, 3H), 0.47 (m, 4H).

Example 19

Preparation of (trans-4-(N-cyclopropyl-4-((S)-1,1,1-trifluoro-2-hydroxypropan-2-yl)benzamido)-1-(pyridin-2-yl)cyclohexyl)methyl carbamate

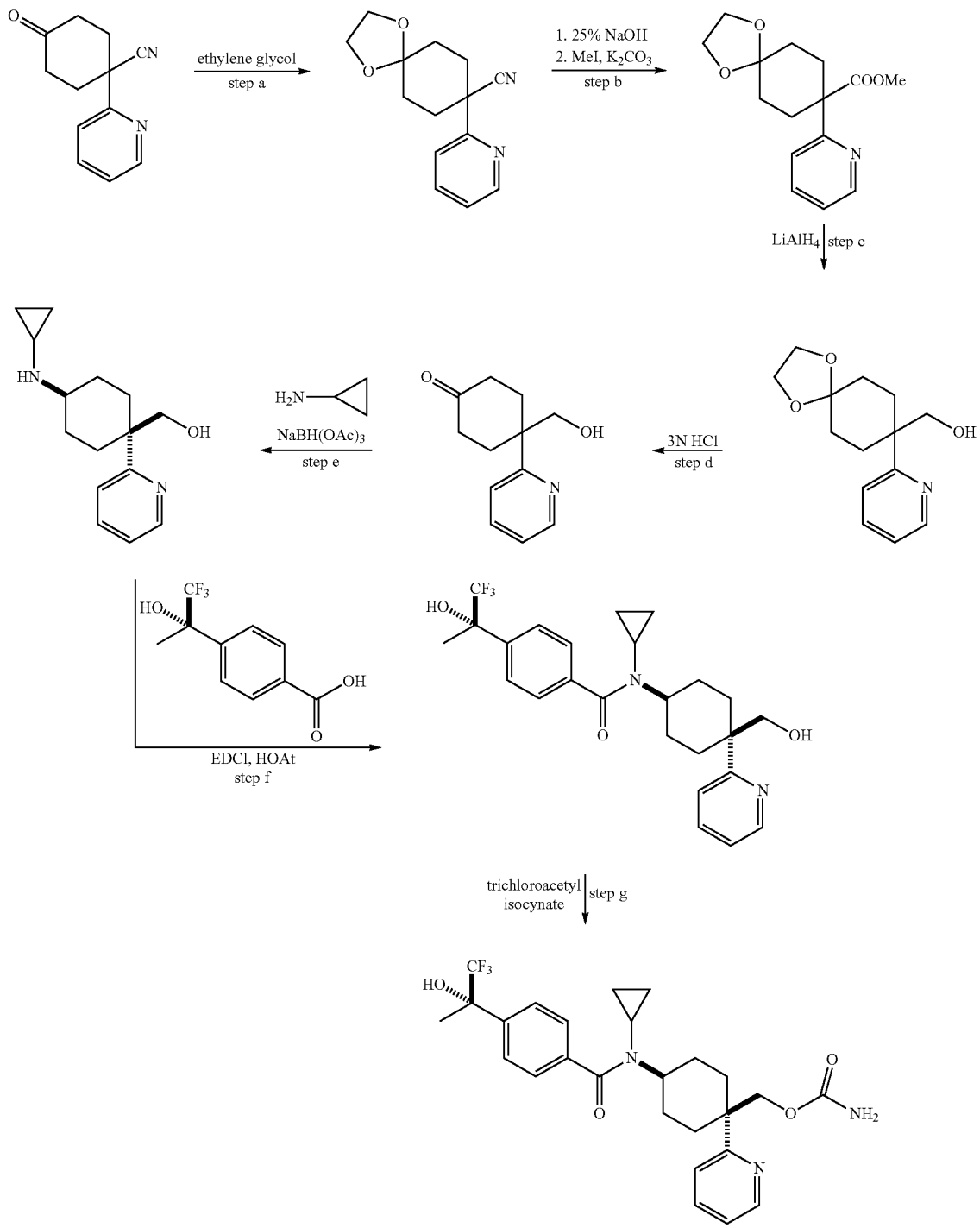

a). A mixture of 4-oxo-1-(pyridin-2-yl)cyclohexanecarbonitrile (5.0 g, 25 mmol, 1.0 equiv, prepared as in example G but substituting pyridin-2-ylacetonitrile for (2-fluorophenyl) acetonitrile), 1.8 g ethylene glycol and 120 mg p-toluenesulfonic acid in 50 mL of benzene was heated at reflux under a Dean-Stark trap for 3 hours. The solution was cooled and washed successively with sat. NaHCO$_3$, water and brine. The organics were dried over Na$_2$SO$_4$ and evaporated to give the product as a white solid.

b). A 100 mL flask was charged with 4-cyano-4-(pyridin-2-yl)cyclohexanone ethylene ketal (2.44 g, 10 mmol, 1 equiv), 25% NaOH aqueous solution (15 mL) and methanol (15 mL). The flask was equipped with a reflux condenser, and then placed into a preheated 100° C. bath. After stirring for 12 h, the reaction mixture was cooled, adjusted to pH 7 with con. HCl, and then concentrated under reduced pressure. The dry residue was then treated with DMF (60 mL), potassium carbonate (2.76 g, 20 mmol, 2 equiv) and methyl iodide (0.89 mL, 6 mmol, 1.5 equiv) successively. After being stirred at 25° C. for 2 h, the reaction mixture was quenched (sat. NaHCO$_3$) and extracted (EtOAc). The organics were washed (brine), dried (Na$_2$SO$_4$) and concentrated under reduced pressure. Purification of the residue by flash chromatography (SiO$_2$, 60% EtOAc/hexanes) gave the desired ester as a white solid.

c). To a solution of methyl carboxylate prepared above in step b (1.28 g, 4.6 mmol, 1 equiv)) in dry THF (50 mL) was slowly added LiAlH$_4$ (1.0 M in diethyl ether, 9.2 mL, 2 equiv) at 0° C. After being stirred for 2 h at 0° C., the reaction mixture was quenched (H$_2$O), extracted (10% MeOH/CH$_2$Cl$_2$), dried (Na$_2$SO$_4$), and concentrated in vacuo. The crude material was purified by flash column chromatography (SiO$_2$, 5% MeOH/CH$_2$Cl$_2$) to provide the product as a white solid.

d). 3 N HCl (5 mL) was added to a solution of 4-(hydroxymethyl)-4-(pyridin-2-yl)cyclohexanone ethylene ketal (600 mg, 2.4 mmol) in THF (10 mL). The mixture was stirred at room temperature for 12 h and then diluted with sat. NaHCO$_3$. The resulting solution was extracted (10% MeOH/CH$_2$Cl$_2$) and the organics were dried and concentrated to give the product as a white solid, which was used in the next step without further purification.

e). A solution of 4-(hydroxymethyl)-4-(pyridin-2-yl)cyclohexanone (410 mg, 2.0 mmol, 1.0 equiv) in 1,2-dichloroethane (15 mL) was treated at 0° C. with cyclopropylamine (280 uL, 4.0 mmol, 2 equiv), acetic acid (0.1 mL) and NaBH(OAc)$_3$ (848 mg, 2.0 equiv) successively. After being stirred at 25° C. for 12 h, the reaction mixture was carefully diluted (sat.NaHCO$_3$) and extracted (10% MeOH/CH$_2$Cl$_2$). The organics were washed (brine), dried (Na$_2$SO$_4$) and concentrated under reduced pressure. The crude material was purified by flash column chromatography (SiO$_2$, 5% MeOH/CH$_2$Cl$_2$ containing 2.5% NH$_4$OH) to provide the trans amine. Further elution afforded the cis amine.

f). A solution of trans amine prepared above in step d (170 mg, 0.69 mmol, 1.0 equiv) and (S)-4-(1,1,1-trifluoro-2-hydroxypropan-2-yl)benzoic acid (162 mg, 1.0 mmol) in DMF (10 mL) was treated at 0° C. with EDCl (176 mg, 1.3 equiv), HOAt (122 mg, 1.3 equiv) and NaHCO$_3$ (168 mg, 2.0 equiv) successively. After being stirred at 25° C. for 12 h, the reaction was diluted (EtOAc), washed (1 N NaOH and brine), dried (Na$_2$SO$_4$) and concentrated under reduced pressure. Purification of the residue by flash chromatography (SiO$_2$, 5% MeOH/CH$_2$Cl$_2$) afforded the product. $^1$H NMR (DMSO, 400 MHz) δ 8.53 (d, J=3.7 Hz, 1H), 7.77 (m, 1H), 7.63 (d, J=8.1 Hz, 2H), 7.51 (d, J=8.1 Hz, 2H), 7.44 (d, J=7.9 Hz, 1H), 7.20 (m, 1H), 6.69 (s, 1H), 4.58 (t, J=5.0 Hz, 1H), 4.00 (m, 1H), 3.90 (d, J=5.0 Hz, 2H), 2.79 (m, 1H), 2.18 (m, 4H), 1.86-1.63 (m, 4H), 1.73 (s, 3H), 0.47 (m, 4H).

g). A solution of trichloroacetyl isocynate (14 uL, 0.12 mmol, 1.2 equiv) in benzene (1 mL) was added to another solution of N-cyclopropyl-N-(trans-4-(hydroxymethyl)-4-(pyridin-2-yl)cyclohexyl)-4-((S)-1,1,1-trifluoro-2-hydroxypropan-2-yl)benzamide (46 mg, 1.0 equiv) in 2 mL of CHCl$_3$ at room temperature. After being stirred for 0.5 h, the reaction mixture was treated with excess activated, neutral Al$_2$O$_3$ (keep adding Al$_2$O$_3$ till the stirrer stops stirring). The Al$_2$O$_3$ was filtered off and washed with 10% MeOH/CH$_2$Cl$_2$. The filtrates were washed with brine, dried over Na$_2$SO$_4$ and concentrated under reduced pressure. Purification of the residue by flash chromatography (SiO$_2$ 5% MeOH/CH$_2$Cl$_2$) gave the product as a white solid. $^1$H NMR (DMSO, 400 MHz) δ 8.56 (s, 1H), 7.77 (m, 1H), 7.63 (d, J=8.1 Hz, 2H), 7.51 (d, J=8.1 Hz, 2H). 7.46 (d, J=7.9 Hz, 1H), 7.24 (m, 1H), 6.69 (s, 1H), 6.35 (s, 2H), 4.51 (s, 2H), 3.98 (m, 1H), 2.79 (m, 1H), 2.17 (m, 4H), 1.86-1.73 (m, 4H), 1.73 (s, 3H), 0.48 (m, 4H).

Example 20

Preparation of (trans-4-(N-cyclopropyl-4-((S)-1,1,1-trifluoro-2-hydroxypropan-2-yl)benzamido)-1-(thiazol-4-yl)cyclohexyl)methyl carbamate

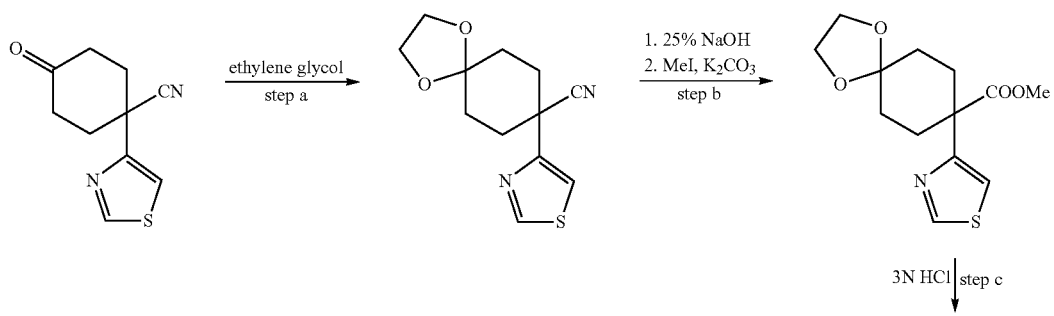

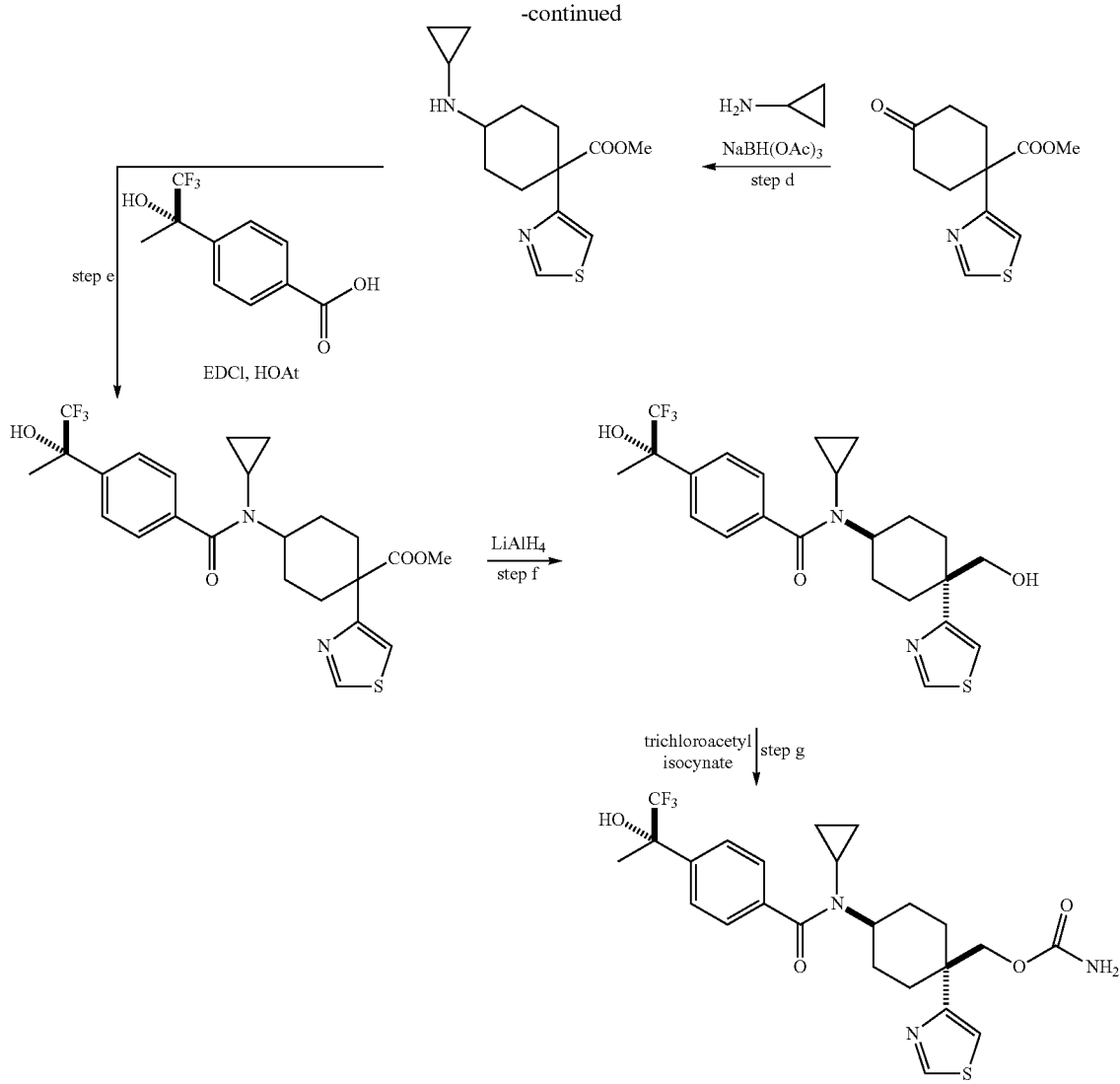

a). A mixture of 4-oxo-1-(thiazol-4-yl)cyclohexanecarbonitrile (4.2 g, 20.4 mmol, 1.0 equiv, prepared as in example G but substituting thiazol-2-ylacetonitrile for (2-fluorophenyl)acetonitrile), 1.6 g ethylene glycol and 120 mg p-toluenesulfonic acid in 50 mL of benzene was heated at reflux under a Dean-Stark trap for 3 hours. The solution was cooled and washed successively with sat. $NaHCO_3$, water and brine. The organics were dried over $Na_2SO_4$ and evaporated to give the product as a white solid.

b). A 100, mL flask was charged with 4-cyano-4-(thiazol-4-yl)cyclohexanone ethylene ketal (1 g, 4 mmol, 1 equiv), 25% NaOH aqueous solution (6 mL) and methanol (6 mL). The flask was equipped with a reflux condenser, and then placed into a preheated 100° C. bath. After stirring for 12 h, the reaction mixture was cooled, adjusted to pH 7 with con. HCl, and concentrated under reduced pressure. The dry residue was then treated with DMF (15 mL), potassium carbonate (1.1 g, 8 mmol, 2 equiv) and methyl iodide (852 mg, 6 mmol, 1.5 equiv) successively. After being stirred at 25° C. for 2 h, the reaction mixture was quenched (sat. $NaHCO_3$), and extracted (EtOAc). The organics were washed (brine), dried ($Na_2SO_4$) and concentrated under reduced pressure. Purification of the residue by flash chromatography ($SiO_2$, 60% EtOAc/hexane) gave the product as a white solid.

c). 3 N HCl (75 mL) was added to a solution of methyl carboxylate prepared above in step b (450 mg, 1.6 mmol) in THF (150 mL). The mixture was stirred at room temperature for 12 h and then diluted with sat.$NaHCO_3$. The resulting solution was extracted (EtOAc) and organics were dried and concentrated under reduced pressure to give the product as a white solid, which was used in the next step without further purification.

d). A solution of methyl 4-oxo-1-(thiazol-4-yl)cyclohexanecarboxylate (382 mg, 1.6 mmol, 1.0 equiv) in 1,2-dichloroethane (10 mL) was treated at 0° C. with cyclopropylamine (224 uL, 3.2 mmol, 2 equiv), acetic acid (0.1 mL) and NaBH$(OAc)_3$ (678.4 mg, 2.0 equiv) successively. After being stirred at 25° C. for 12 h, the reaction mixture was carefully diluted (sat. $NaHCO_3$) and extracted (10% MeOH/$CH_2Cl_2$). The organics were washed (brine), dried ($Na_2SO_4$), and concentrated under reduced pressure to give the crude mixture of cis and trans amines, which was used in the next step without further isolation.

e). A solution of cis/trans amines prepared above in step d (420 mg, 1.5 mmol, 1.0 equiv) and (S)-4-(1,1,1-trifluoro-2-hydroxypropan-2-yl)benzoic acid (351 mg, 1.5 mmol) in DMF (15 mL) was treated at 0° C. with EDCl (382 mg, 1.3 equiv), HOAt (265 mg, 1.3 equiv) and NaHCO$_3$ (252 mg, 2.0 equiv) successively. After being stirred at 25° C. for 12 h, the reaction was diluted (EtOAc), washed (1N NaOH and brine), dried (Na$_2$SO$_4$), and concentrated under reduced pressure. Purification of the residue by flash chromatography (SiO$_2$, 70% EtOAc/n-Hexane) afforded the product as a mixture of two isomers.

f). To a solution of amine prepared above in step e (122 mg, 0.245 mmol) in dry THF (5 mL) was slowly added LiAlH$_4$ (1.0 M in diethyl ether, 0.49 mL, 2 equiv) at 0° C. After being stirred for 2 h at 0° C., the reaction mixture was quenched with water, extracted (10% MeOH/CH$_2$Cl$_2$), dried (Na$_2$SO$_4$), and concentrated in vacuo. The crude material was purified by flash column chromatography (5% MeOH/CH$_2$) to provide the trans product. Further elution afforded the cis product.

g). A solution of trichloroacetyl isocynate (20 uL, 0.22 mmol, 1.2 equiv) in benzene (2 mL) was added to another solution of N-cyclopropyl-N-(trans-4-(hydroxymethyl)-4-(thiazol-4-yl)cyclohexyl)-4-((S)-1,1,1-trifluoro-2-hydroxypropan-2-yl)benzamide (trans isomer prepared above in step f, 66 mg, 1.0 equiv) in 4 mL of CHCl$_3$ at room temperature. After being stirred for 0.5 h, the reaction mixture was treated with excess activated neutral Al$_2$O$_3$ (keep adding Al$_2$O$_3$ till the stirrer stops stirring). The Al$_2$O$_3$ was filtered off and washed with 10% MeOH/CH$_2$Cl$_2$. The filtrates were washed with brine, dried over Na$_2$SO$_4$ and concentrated under reduced pressure. Flash chromatography (SiO$_2$, 80% EA/hexane) gave the product as a white solid. $^1$H NMR (DMSO, 400 MHz) δ 9.04 (s, 1H), 7.63 (d, J=8.0 Hz, 2H), 7.52 (d, J=8.0 Hz, 2H), 7.41 (s, 1H), 6.67 (s, 1H), 6.37 (s, 2H), 4.48 (s, 2H), 4.01 (m, 1H), 2.78 (m, 1H), 2.17 (m, 4H), 1.83-1.73 (m, 4H), 1.73 (s, 3H), 0.47 (m, 4H).

Example 21

Preparation of ((trans)-4-(N-cyclopropyl-4-((S)-1,1,1-trifluoro-2-hydroxypropan-2-yl)benzamido)-1-(isoxazol-3-yl)cyclohexyl)methyl carbamate

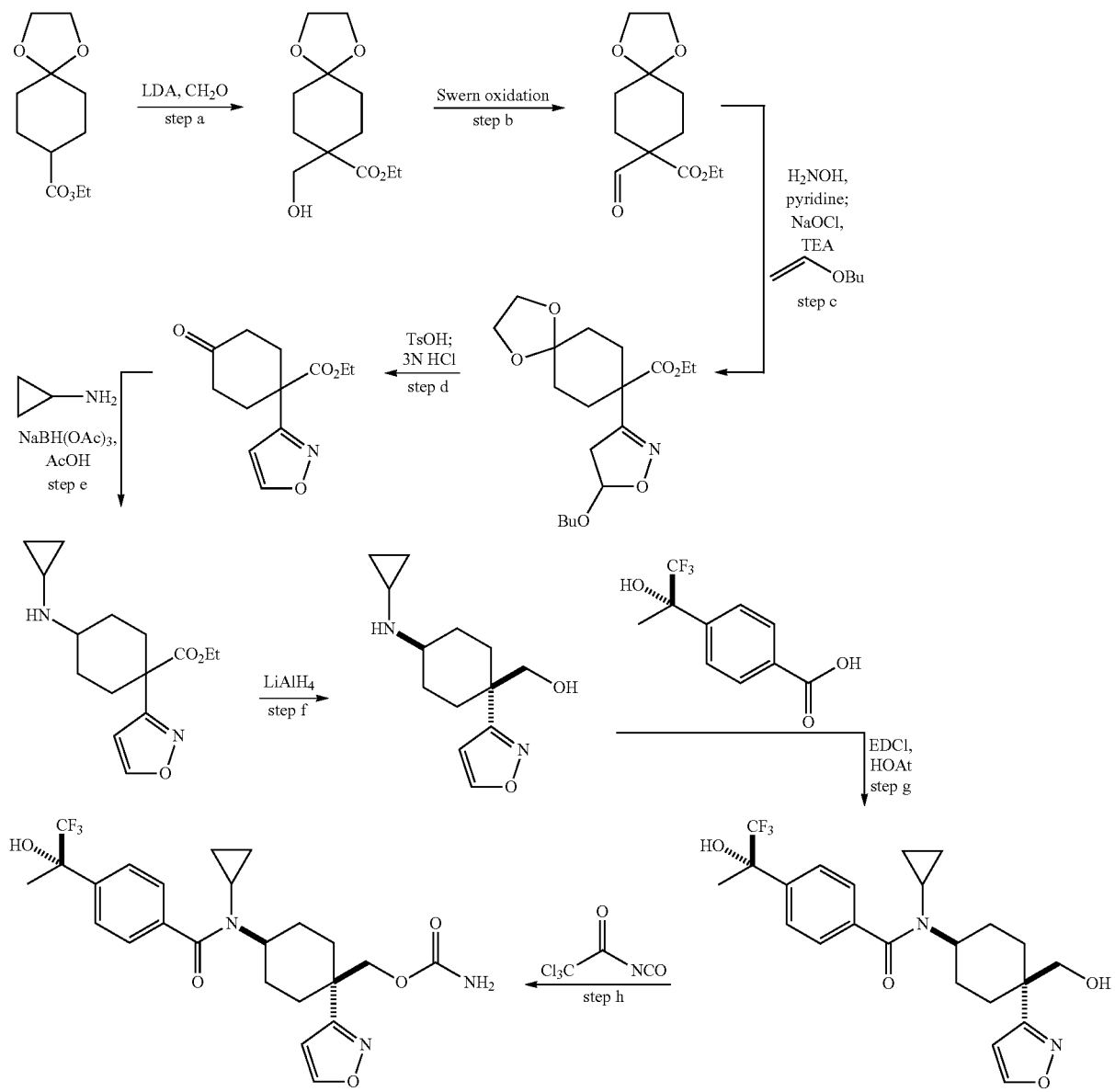

a). A solution of LDA (280 mmol) was prepared by addition of n-BuLi (1.6 M in THF, 175 mL, 280 mmol) to a solution of diisopropylamine (39.3 mL, 280 mmol) in THF (400 mL) at −40° C. and stirring the resulting solution at −15° C. for 30 min. Subsequently the solution was cooled down to −78° C. and a solution of the starting material (50.0 g, 233 mmol) in THF (400 mL) was added dropwisely. After 1 h, gaseous formaldehyde (1.05 mol), which was prepared by heating paraformaldehyde (31.5 g, 1.05 mol) in a separate flask connected by a polyethylene tube to the reaction flask, was passed at −78° C. through this solution over a period of 1 h. After being stirred at −78° C. for additional 30 min and allowed to reach 25° C. over 3 h, the reaction was quenched (saturated aqueous $NH_4Cl$) and extracted (3×EtOAc). The combined organic layers were washed (brine), dried ($Na_2SO_4$), and concentrated under reduced pressure. Flash chromatography ($SiO_2$, 30-60% EtOAc/hexanes, gradient elution) gave the product as a pale yellow oil.

b). A solution of DMSO (60.6 g, 776 mmol) in $CH_2Cl_2$ (100 mL) was added dropwise at −78° C. to a solution of oxalyl chloride (33.8 mL, 387 mmol) in $CH_2Cl_2$ (500 mL) over a period of 45 min. After being stirred −78° C. for 5 min, the reaction was treated with a solution of the alcohol prepared above in step a (79.0 g, 323 mmol) in $CH_2Cl_2$ (200 mL) at −78° C. over a period of 15 min. The resulting solution was stirred at −78° C. for 15 min and allowed to reach to room temperature over 1 h. The reaction was quenched (saturated aqueous $NH_4Cl$) and extracted (3×$CH_2Cl_2$). The combined organic layers were washed (brine), dried ($Na_2SO_4$), and concentrated under reduced pressure. Flash chromatography ($SiO_2$, 20-30% EtOAc/hexanes, gradient elution) gave the product as a pale yellow oil.

c). A solution of the aldehyde prepared above in step b (54.6 g, 225 mmol) in pyridine (230 mL) was treated with hydroxylamine hydrochloride (17.2 g, 248 mmol) at 0° C. After being stirred at 0° C. for 1 h and at 25° C. for 12 h, pyridine was removed under reduced pressure. The residue was poured into 10% aqueous citric acid and extracted (4×$CH_2Cl_2$). The combined organics were washed (brine), dried ($MgSO_4$), and concentrated under reduced pressure to provide the crude oxime as a pale brown liquid. To a solution of this crude oxime, n-butyl vinyl ether (57.9 mL, 450 mmol), and TEA (3.14 mL, 22.5 mmol) in $CH_2Cl_2$ (646 mL) was added NaOCl (6% in $H_2O$, 646 mL) at 0° C. over a period of 15 min. After being stirred at 0° C. for 30 min and 25° C. for 2 h, the reaction was extracted (3×$CH_2Cl_2$), washed (brine), dried ($Na_2SO_4$), and concentrated under reduced pressure. Flash chromatography ($SiO_2$, 10-30% EtOAc/hexanes, gradient elution) gave the product as a pale yellow viscous oil.

d). A solution of the isoxazoline prepared above in step c (51.9 g, 146 mmol) in toluene (300 mL) was treated with TsOH.$H_2O$ (2.78 g, 14.6 mmol). After being refluxed for 1 h, toluene was removed under reduced pressure and the residue was dissolved in THF (320 mL). To a solution of the crude isoxazole in THF was added 3 N aqueous HCl (320 mL) and the resulting solution was stirred at 25° C. for 20 h. After THF was removed under reduced pressure, the reaction was neutralized with aqueous saturated $NaHCO_3$ and extracted (3×$CH_2Cl_2$). The combined organic layers were washed (brine), dried ($Na_2SO_4$), and concentrated under reduced pressure to yield the crude ketone as a pale yellow viscous oil. The product was used for the next step without further purification.

e). A solution of the crude ketone prepared above in step d (146 mmol) in $CH_3CN$ (730 mL) was treated at 0° C. with cyclopropylamine (20.2 mL, 292 mmol), acetic acid (16.7 mL, 292 mmol), and $NaBH(OAc)_3$ (46.4 g, 219 mmol), successively. The reaction was stirred at 25° C. for 12 h and $CH_3CN$ was removed under reduced pressure. The resulting residue was poured into water and brought to pH 2 with ice-cold 3 N aqueous HCl. Following the removal of organic impurity by extraction (2×$Et_2O$), the aqueous layer was brought to pH 12 with ice-cold 3 N aqueous NaOH and extracted (4×$CH_2Cl_2$). The combined organic layers were dried ($Na_2SO_4$) and concentrated under reduced pressure to provide the crude amine as a pale brown oil. The product was used for the next step without further purification.

f). A solution of the amine prepared above in step e (35.5 g, 128 mmol) in THF (320 mL) was treated at −40° C. with $LiAlH_4$ (1 M in THF, 128 mL, 128 mmol). After being stirred at −40° C. for 10 min and at −20° C. for 30 min, the reaction was quenched by adding $H_2O$ (5.0 mL), 15% aqueous NaOH (5.0 mL), and $H_2O$ (15 mL), successively. The resulting inorganic gel was collected on a filter and rinsed with EtOAc. The filtrate was dried ($Na_2SO_4$) and concentrated under reduced pressure. Flash chromatography ($SiO_2$, 80% EtOAc/hexanes containing 2.5% $Et_3N$) gave 14.6 g of the cis-amine. Further elution with more polar solvent (7% MeOH/$CH_2Cl_2$ containing 1% $NH_4OH$) afforded 10.1 g of the desired trans-amine as a pale yellow solid.

g). A solution of the trans-amine prepared above in step f (9.40 g, 40.0 mmol) and (S)-4-(1,1,1-trifluoro-2-hydroxypropan-2-yl)benzoic acid (9.13 g, 39.0 mol) in DMF (80 mL) was treated at 0° C. with EDCl (9.97 g, 52.0 mmol), HOAt (7.08 g, 52.0 mmol), and $NaHCO_3$ (6.72 g, 80.0 mmol), successively. After being stirred at 25° C. for 12 h, DMF was removed under reduced pressure. The residue was poured into 10% aqueous citric acid and extracted (2×EtOAc). The combined organic layers were washed (saturated aqueous $NaHCO_3$ and brine), dried ($Na_2SO_4$), and concentrated under reduced pressure. Flash chromatography ($SiO_2$, 80% EtOAc/hexanes) gave the product as a white solid.

h). A solution of the amide prepared above in step g (9.39 g, 20.8 mmol) in 10% DMF/$CH_2Cl_2$ (200 mL) was treated at 0° C. with trichloroacetyl isocyante (2.98 mL, 25.0 mmol). After being stirred at 0° C. for 30 min and 25° C. for 30 min, the reaction mixture was treated with neutral alumina (activity II) and allowed to stand at 25° C. for an additional 1 h. The alumina was filtered off and washed (10% MeOH/$CH_2Cl_2$) and the filtrates were concentrated under reduced pressure. Flash chromatography ($SiO_2$, 0-5% MeOH/$CH_2Cl_2$, gradient elution) gave the title compound as a white solid: $^1$H NMR (500 MHz, DMSO-$d_6$) δ 8.78 (d, J=1.6 Hz, 1H), 7.60 (d, J=8.1 Hz, 2H), 7.48 (d, J=8.4 Hz, 2H), 6.66 (d, J=1.6 Hz, 1H), 6.65 (s, 1H), 6.50 (s, br, 1H), 6.50 (s, br, 1H), 4.34 (s, 2H), 3.98-3.92 (m, 1H), 2.78-2.74 (m, 1H), 2.24-2.16 (m, 4H), 1.85-1.70 (m, 4H), 1.71 (s, 3H), 0.51-0.47 (m, 2H), 0.42-0.38 (m, 2H); MS (ESI) 496 $[M+H]^+$.

Example 22
Preparation of (((trans)-4-(N-cyclopropyl-4-((S)-1,1,1-trifluoro-2-hydroxypropan-2-yl)benzamido)-1-(4-fluorophenyl)cyclohexyl)methyl carbamate
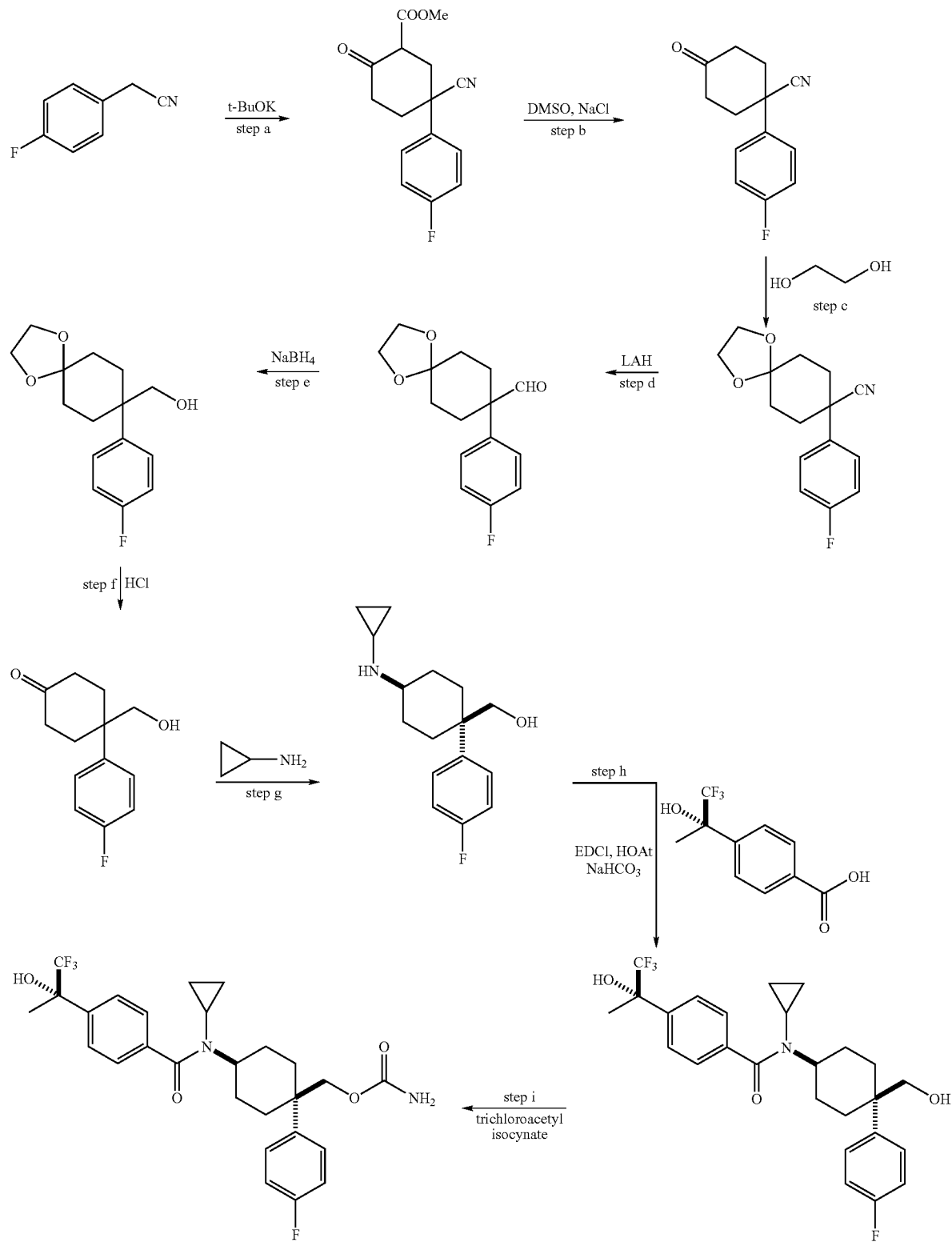

a). To a stirred solution of 4-fluorophenylacetonitrile (50 g, 370 mmol, 1 equiv.) and methyl acrylate (66 mL, 740 mmol, 2 equiv.) in 1000 mL dry THF cooled to 0° C. in an ice bath was added solid t-BuOK (50 g, 446 mmol, 1.2 equiv.). Upon addition the mixture changed to an orange color and warmed slightly. After 15 minutes the reaction was diluted with 1.5 L 3 N HCl, extracted 3×10% MeOH in $CH_2Cl_2$, washed 1× brine, dried over $Na_2SO_4$, filtered and concentrated to yield the product as an orange solid.

b). To a stirred solution of the ketoester product of step a (122 g, 443 mmol, 1 equiv.) in 600 mL DMSO was added $H_2O$ (32 mL) and NaCl (32 g, 542 mmol, 1.3 equiv.), and the mixture heated to 160° C. for 7 hours. The mixture was allowed to cool to ambient temperature overnight, and was then diluted (1 L brine), extracted (10× ether) and concentrated. The resulting residues were taken up in ether, washed 3×$H_2O$, 1× brine, dried over $Na_2SO_4$, filtered and concentrated. The material was purified over 1500 mL silica with 100% $CH_2Cl_2$ to yield the product as a yellow solid.

c). The product obtained above in step b (48 g, 220 mmol, 1 equiv.) was refluxed in benzene in the presence of ethylene glycol (13.6 mL, 220 mmol, 1.0 equiv.) and a catalytic amount of p-TsOH under a Dean-Stark trap overnight. The reaction mixture was allowed to cool to ambient temperature, diluted with $H_2O$, and extracted (3×EtOAc). The organics were dried ($Na_2SO_4$), filtered and concentrated under reduced pressure. The crude mixture was purified by crystallization (10% EtOAc/Hexanes) to give the product as a light-yellow solid.

d). To a stirred solution of the product obtained above (43 g, 165 mmol, 1 equiv.) in 200 mL dry THF at 0° C. in an ice bath under $N_2$ was added LAH (82.5 mL, 1 M in THF, 0.5 equiv.) and the reaction stirred 3 hours. The mixture was carefully quenched (10 mL $H_2O$, 5 mL 1N NaOH). The solid was filtered out and washed with 10% MeOH/DCM. The organics were washed (brine), dried ($Na_2SO_4$) and concentrated under reduced pressure.

e). To a solution of crude product obtained above (165 mmol) in methanol (300 mL) was added $NaBH_4$ (15.6 g, 412 mmol, 2.5 equiv) at 0° C. in a period of 15 min. After being stirred at 25° C. for 2 h, the reaction mixture was quenched (sat.$NaHCO_3$) and extracted (10% MeOH/DCM). The organics were washed (brine), dried ($Na_2SO_4$) and concentrated under reduced pressure.

f). The crude product obtained above was dissolved in 3 N HCl (100 mL) and THF (300 mL). The mixture was stirred at room temperature for 12 h and then was added 50% aq.NaOH till pH~7. The resulting solution was extracted (10% MeOH/DCM) and organics were dried and concentrated under reduced pressure. The crude material was purified by flash column chromatography (25~45% EtOAc/Hexanes) to provide the product as a colorless oil.

g). A solution of product obtained above (20 g, 89.7 mmol, 1.0 equiv.) in $CH_3CN$ (200 mL) was treated at 0° C. with cyclopropylamine (10.24 g, 179.4 mmol, 2.0 equiv), acetic acid (2 mL) and $NaBH(OAc)_3$ (38 g, 179.4 mmol, 2.0 equiv) successively. After being stirred at 25° C. for 12 h, the reaction mixture was carefully diluted (sat.$NaHCO_3$) and extracted (10% MeOH/$CH_2Cl_2$). The organics were washed (brine), dried ($Na_2SO_4$) and concentrated under reduced pressure to give the crude mixture of cis and trans amines. The mixture was separated by flash chromatography ($SiO_2$) using 60% EtOAc/hexanes with 2.5% TEA to get rid of the undesired isomer (top spot). Further elution using 5% MeOH/DCM with 2.5% TEA gave 12.5 g of the trans amine as white solid.

h). A solution of trans amines (9.6 g, 36.5 mmol, 1.0 equiv) and (S)-4-(1,1,1-trifluoro-2-hydroxypropan-2-yl)benzoic acid (8.5 g, 36.5 mmol, 1.0 equiv) in DMF (100 mL) was treated at 0° C. with EDCl (9.1 g, 47.4 mmol, 1.3 equiv), HOAt (6.45 g, 47.4 mmol, 1.3 equiv) and $NaHCO_3$ (7.05 g, 84.0 mmol, 2.3 equiv) successively. After being stirred at 25° C. for 12 h, the reaction was diluted (10% MeOH/DCM), washed (1N NaOH, sat. $NaHCO_3$ and brine), dried ($Na_2SO_4$) and concentrated under reduced pressure. The crude product was purified by crystallization (EtOAc, MeOH with Hexanes) to provide 7.6 g of the product as a white solid.

i). To a solution of the product prepared above in step a (6.6 g, 13.5 mmol, 1.0 equiv) in 100 mL of $CHCl_3$ and 40 mL DMF was added a solution of trichloroacetyl isocynate (3.05 g, 16.2 mmol, 1.2 equiv) in benzene (50 mL) at room temperature. After being stirred for 0.5 h, the reaction mixture was treated with 100 g activated (II), neutral $Al_2O_3$. After stirring for 2 hours the $Al_2O_3$ was filtered and washed with 10% MeOH/$CH_2Cl$, The filtrates were washed with sat.$NaHCO_3$, brine, dried ($Na_2SO_4$) and concentrated under reduced pressure. The crude product was purified by crystallization (EtOAc, MeOH with Hexanes) to provide the product as a white solid. $^1$H NMR (DMSO-$d_6$, 400 MHz) δ 7.61 (d, J=8.0 Hz, 2H), 7.46 (m, 4H), 7.11 (t, J=8.7 Hz, 2H), 6.66 (s, 1H), 6.35 (br., 2H), 4.32 (s, 2H), 3.95 (m, 1H), 2.77 (m, 1H), 2.18 (m, 4H), 1.82 (m, 2H), 1.71 (s, 3H), 1.60 (m, 2H), 0.49 (m, 2H), 0.40 (m, 2H), MS (ESI) 523 [M+H]$^+$. Anal. cacld for $C_{27}H_{30}F_4N_2O_4$: C, 62.06; H, 5.79; N, 5.36. Found: C, 61.95; H, 5.78; N, 5.28.

Example 23

Preparation of ((trans)-4-(N-cyclopropyl-4-((S)-1,1,1-trifluoro-2-hydroxypropan-2-yl)benzamido)-1-(5-fluoropyridin-2-yl)cyclohexyl)methyl carbamate

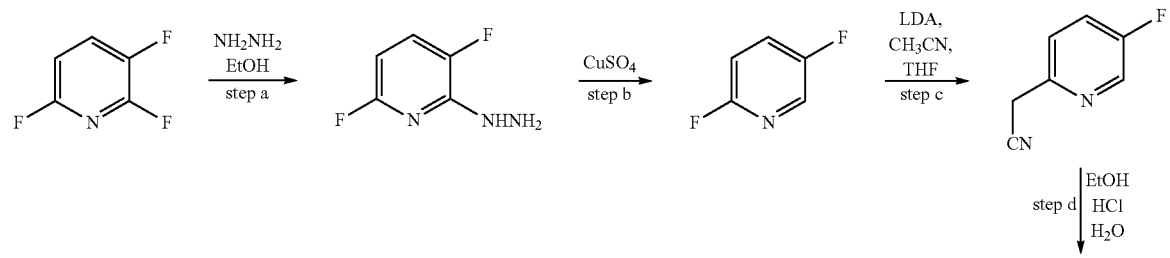

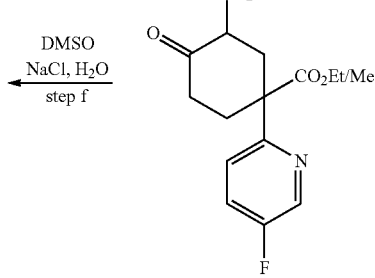
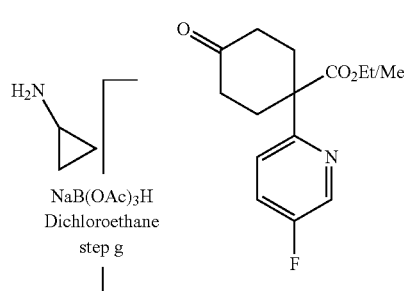
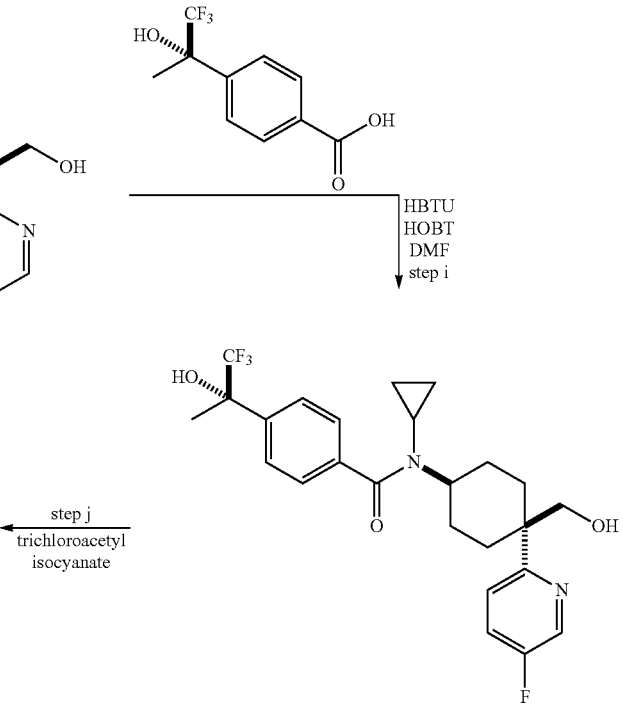
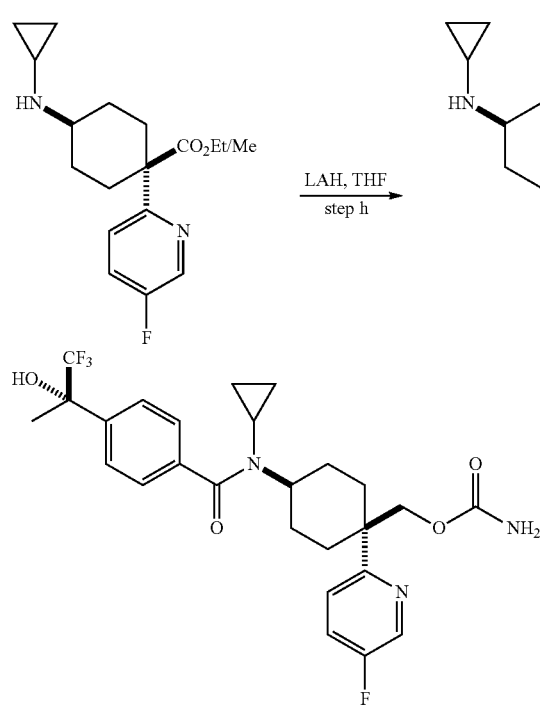

(a) To 2,3,6-trifluoropyridine (12.5 g, 94.0 mmol) in EtOH (35 mL) at 0° C., was added hydrazine hydrate (9.14 mL, 188 mmol). The reaction was warmed to room temperature and then refluxed for 2 h. After cooling, the reaction was diluted with water (5×) and extracted against CH$_2$Cl$_2$. The organics were dried with Na$_2$SO$_4$ and removed in vacuo. The residue was recrystallized from 15 mL of EtOH to obtain the product. $^1$H NMR (500 Hz, CDCl$_3$): δ 3.40-4.10 (bs, 2H), 5.85-6.12 (bs, 1H), 6.13-6.22 (m, 1H), 7.22-7.31 (m, 1H).

(b) To a solution of CuSO$_4$ (20 g, 120 mmol) in water (120 mL) was added the product of step a (8.9 g, 61 mmol). The mixture was held at reflux until roughly 60 mmol of gas were collected by water displacement (ca. 1 h). The product was steam distilled using a simple short path and collected in 3 fractions. $^1$H NMR (400 Hz, CDCl$_3$): δ 6.93 (dt, J=9.0, 3.5 Hz, 1H), 7.5 (symm. m 1H) 8.05 (bt [dd], 1H).

(c) To diisopropylamine (0.60 mL, 4.3 mmol) in THF (0.75 mL) at −20° C. was added dropwise 2.5 M n-BuLi (1.7 mL, 4.2 mmol). The solution was stirred for 15 min and was then warmed to 0° C. After 15 minutes the solution was cooled to −78° C. To the LDA solution was added dropwise a solution of CH$_3$CN in THF (0.75 mL). The mixture was stirred for 15 min and was then cannulated into a −78° C. solution of the product of step b in THF (0.75 mL). The reaction was stirred for 30 min and then warmed to 0° C. and stirred for 1 h. The reaction was quenched with saturated NH$_4$Cl (10 mL) and the organics were sequestered. The aqueous was extracted with Et$_2$O (5×20 mL). The combined organics were washed with brine, dried with MgSO$_4$, and removed in vacuo. Silica gel chromatography (gradient elution of 20-80% Et$_2$O in hexanes) afforded 0.15 g of the product as the first eluting UV absorbing species. $^1$H NMR (400 Hz, CDCl$_3$): δ 3.93 (s, 2H) 7.42-7.47 (m, 2H) 8.42 (bs, 1H).

(d) To a saturated solution of ethanolic HCl (330 mL) was added the product of step c (335 mmol). After the material was dissolved, water (7.44 mL) was added. The reaction was heated to 80° C. and stirred for 3 h. After cooling to room temperature, the reaction was diluted with 350 mL, neutralized with saturated aq. sodium bicarbonate, and extracted with CH$_2$Cl$_2$ (2× total volume). The combined organics were dried with Na$_2$SO$_4$ and removed in vacuo to provide the product, which was carried on to the next step without further purification.

(e) To a solution of the product of step d (25 g, 136 mmol) in THF (425 mL) was added methyl acrylate (24.4 mL, 272 mmol) followed by portionwise addition of KOtBu (45.9 g, 409 mmol) over 2 min. After 10 min, the reaction was quenched with saturated NH$_4$Cl, and extracted CH$_2$Cl$_2$. The combined organics were dried over Na₂SO₄ and removed in vacuo to provide the product. The material was carried on to the next step without further purification.

(f) To the product of step e (136 mmol) was added DMSO (320 mL), water (3.2 mL), NaCl (2.7 g), and broken glass. The solution was heated to 160° C. and stirred for 3 h. After cooling to room temperature, the solution was poured into water (10× volume) and extracted with 1:1; ethyl acetate: hexane (5×500 mL). The combined organics were washed with water, brine, dried over MgSO₄ and removed in vacuo. Silica gel chromatography (gradient of 5 tp 50% ethyl acetate in hexanes) provided the product.

(g) To the product of step g (14.4 g, ca 55 mmol) in dichloroethane (167 mL) was added cyclopropylamine (4.55 mL, 65.1 mmol). The solution was cooled to 0° C. (ice bath), and NaBH(OAc)₃ (16.7 g, 81.1 mmol) and AcOH (4.00 mL, 70.3 mmol) were added. After 5 minutes the ice bath was removed. The reaction was stirred at room temperature for 3 h. The contents were poured into water (750 mL) and brought to pH 1.9 with 3 N HCl. Following removal of the organic layer, the aqueous layer was brought to pH 9.6 with 5 N NaOH and extracted with 10% MeOH in CH₂Cl₂ (4×250 mL). The combined organics were dried with MgSO₄ and removed in vacuo to yield the product. The crude amine was carried on to the next step without purification.

(h) To a solution of the product of step g (13 g, ca 43 mmol) in THF (325 mL) cooled to −15° C. was dropwise added 2 M LiAlH₄ in THF (43 mL, 86 mmol). Upon complete addition, the reaction was stirred at 0° C. for 1 h. To the reaction were added sequentially at 10 min intervals water (3.3 mL), 10% NaOH (3.3 mL), and once more water (10 mL). After stirring for 10 min, the water was absorbed by addition of MgSO₄. The suspension was filtered and organics were removed in vacuo. Silica gel chromatography (gradient of 50 to 100% ethyl acetate in hexanes, 2.5% triethylamine additive) provided the slower eluting trans product.

(i) To a solution of (S)-4-(1,1,1-trifluoro-2-hydroxypropan-2-yl)benzoic acid (4.3 g, 18 mmol), EDC (4.2 g, 22 mmol), and HOAt (3.0 g, 22 mmol) in DMF (40 mL) was added NaHCO₃ (3.4 g, 40 mmol) and the trans amine prepared in step h (4.8 g, 18 mmol). The solution was stirred for 18 h at 55° C. followed by quenching with 3-(dimethylamino)-propylamine (22 mmol). The reaction contents were poured into water (300 mL) and acidified to pH 3 with 5 N HCl, and extracted with CH₂Cl₂ (1×200 mL, 1×100 mL). The combined organics were washed with 1 N NaOH (300 mL), water (3×300 mL), dried over Na₂SO₄, and removed in vacuo to yield the product, which was carried on to the next step without purification.

(j) To a suspension of the product of step i (7.5 g, 16 mmol), CHCl₃ (230 mL), and DMF (23 mL) was added dropwise a solution of trichloroacetyl isocyanate (5 mL, 42 mmol) in benzene (75 mL). After stirring for 2 h, the solution was adsorbed onto activity II neutral alumina and left for 16 h. The crude product was eluted with 20% MeOH in CH₂Cl₂ and the organics were removed in vacuo. Silica gel chromatography (gradient of 0 to 10% methanol in CH₂Cl₂) provided the product. ¹H NMR (500 MHz, DMSO-d₆): δ 0.35-0.58 (m, 4H), 1.61-1.95 (m, 7H), 2.12-2.32 (m, 4H), 2.78 (bs, 1H), 3.91-4.02 (m, 1H), 4.47 (s, 2H), 6.32 (bs, 2H), 6.65 (s, 1H), 7.45-7.69 (m, 6H), 8.51 (d, J=5.0 Hz, 1H).

Example 24

Preparation of ((1s,4s)-4-(N-cyclopropyl-4-((S)-1,1,1-trifluoro-2-hydroxypropan-2-yl)benzamido)-1-(5-fluoropyridin-2-yl)cyclohexyl)methyl carbamate

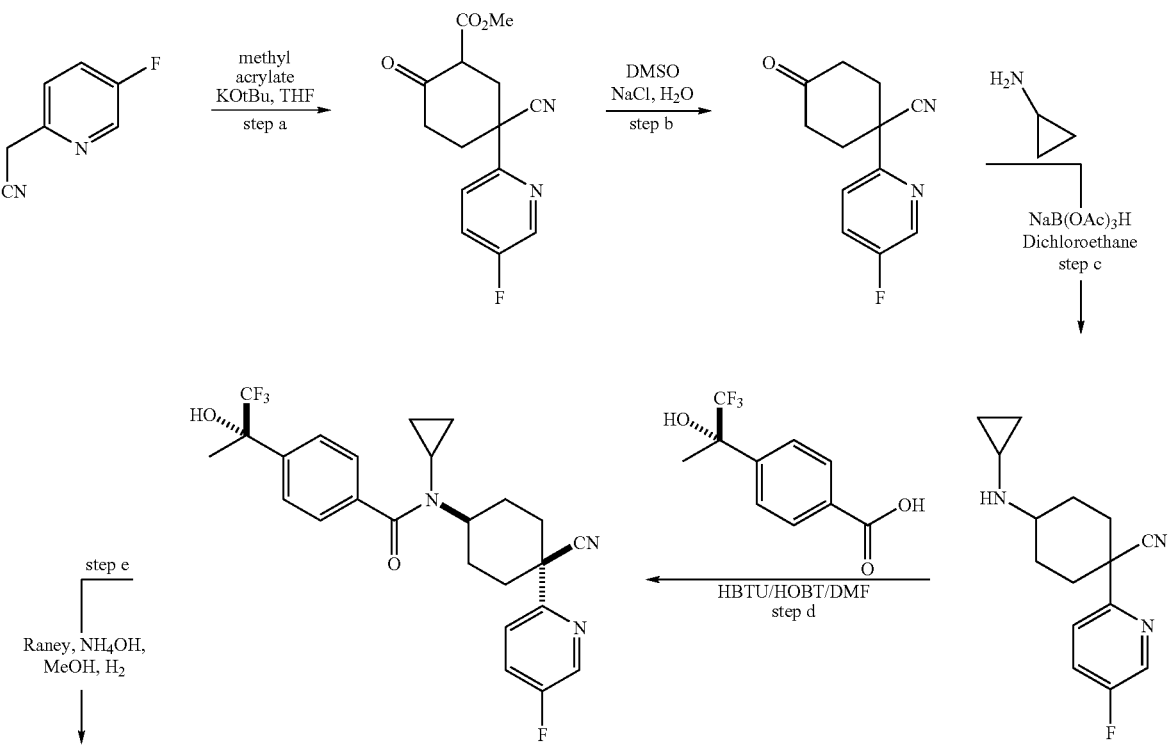

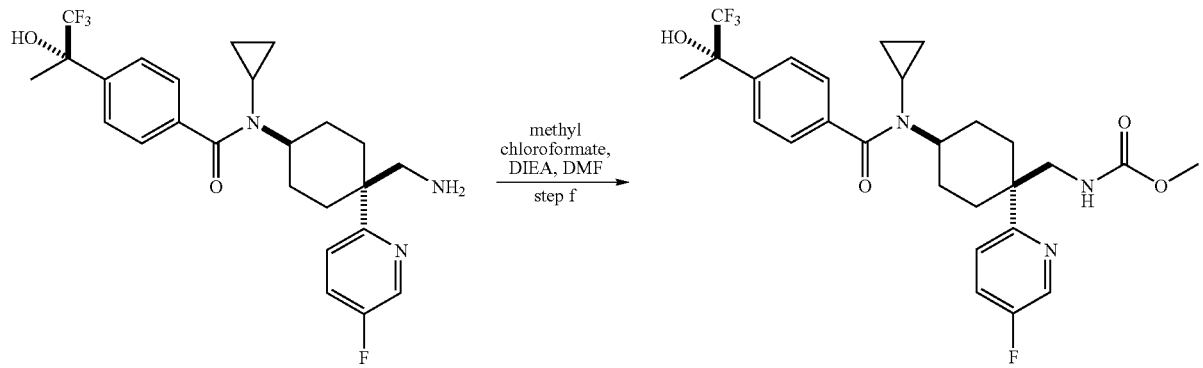

(a) To 2-(5-fluoropyridin-2-yl)acetonitrile (prepared as above, 41 g, 300 mmol) in THF (820 mL) was added methyl acrylate (54 mL, 600 mmol) followed by portionwise addition of KOtBu (100 g, 900 mmol) over a period of 5 min. The reaction was stirred for 10 min and was then poured into 2 L of 0.5 M HCl. After sequestration of organics, the aqueous was extracted with $CH_2Cl_2$ (1×1 L, 1×0.4 L). The combined organics were dried over $Na_2SO_4$ and removed in vacuo. Silica gel chromatography (gradient elution of 5-60% EtOAc in hexanes) afforded the desired ketoester. $^1$H NMR (500 Hz, $CDCl_3$): δ 2.25-2.3 (m, 1H), 2.37-2.47 (m, 1H), 2.52-2.60 (m 1H), 2.77-2.90 (m, 1H), 2.91-3.02 (m, 2H), 3.80 (s, 3H), 7.47-7.53 (m, 1H), 7.67-7.71 (m, 1H) 8.48-8.50 (m, 1H).

(b) To a solution of ketoester prepared above (3.6 g, 13 mmol) in DMSO (45 mL) containing boiling chips, was added NaCl (0.25 g, 4.3 mmol) and $H_2O$ (0.45 mL). The reaction was heated to 160° C. with a reflux condenser in place and stirred for 1 h. The reaction was diluted with $H_2O$ (10×) and extracted with $Et_2O$ (3×50 mL). The combined organic, were washed with brine, dried over $MgSO_4$, and removed in vacuo. Silica gel chromatography (gradient elution 15-85% EtOAc in hexanes) afforded the ketone. $^1$H NMR (400 Hz, $CDCl_3$): δ 2.4-2.65 (m, 6H), 2.80-2.89 (m, 2H), 7.45-7.51 (m, 1H), 7.70 (dd, J=12, 4 Hz, 1H), 8.46 (d, J=2.7 Hz, 1H).

(c) To the product of step b (20.0 g, 91.7 mmol) in dichloroethane (275 mL) was added cyclopropylamine (7.72 mL, 110 mmol). The solution was cooled to 0° C. (ice bath), and NaBH(OAc)$_3$ (29.2 g, 138 mmol) and AcOH (6.80 mL, 119 mmol) were added. After 5 minutes the ice bath was removed. The reaction was stirred at room temperature for 18 h. The contents were poured in water (200 mL) and brought to pH 1 with 5 N HCl. Following removal of the organic layer, the aqueous layer washed with $CH_2Cl_2$ (200 mL). The aqueous was brought to pH 12 with 5 N NaOH and extracted with 10% MeOH in $CH_2Cl_2$ (3×150 mL). The combined organics were dried with $Na_2SO_4$ and removed in vacuo. Silica gel chromatography (30% ethyl acetate in hexanes, 2.5% TEA additive) afforded the slower eluting desired product.

(d) To a solution of (S)-4-(1,1,1-trifluoro-2-hydroxypropan-2-yl)benzoic acid (5.30 g, 22.6 mmol), EDC (5.20 g, 27.1 mmol), and HOAt (3.70 g, 27.1 mmol) in DMF (50 mL) was added NaHCO$_3$ (4.18 g, 49.7 mmol) and the trans amine prepared in step c above (5.85 g, 22.6 mmol). The solution was stirred for 7 h at 55° C. The reaction contents were poured into water (500 mL) and the suspension was brought to pH 12 with 5 N NaOH. The aqueous suspension was extracted with ethyl acetate (3×100 mL). The combined organics were washed with brine, dried over $MgSO_4$, and removed in vacuo. Silica gel chromatography (gradient elution of 20% to 60% ethyl acetate in hexanes) afforded the product.

(e) The product of step d (0.900 g, 1.89 mmol), MeOH (60.0 mL), Raney nickel (2800 slurry in $H_2O$, 2.40 mL), aq. NH$_4$OH (0.500 mL) were combined and stirred overnight under 1 atm $H_2$. Following purging to $N_2$, the solution was decanted. The nickel was washed with MeOH (2×25 mL) and decanted. The combined organics were reduced to 10 mL by rotary evaporation. After dilution with $CH_2Cl_2$ (90 mL), the organics were extracted against 1 N HCl (70 mL). The separated aqueous was brought to basic pH with 5 N NaOH and extracted with 10% MeOH in $CH_2Cl_2$ (3×50 mL). The combined organics were dried over $Na_2SO_4$ and removed in vacuo to provide the product.

(f) To a solution of the product of step e (0.20 g, 0.42 mmol) in DMF (2 mL) was added Hünig's base (0.36 mL, 2 mmol) and methylchloroformate (0.036 mL, 0.46 mmol). The reaction was stirred at room temperature for 48 h and was then poured into water (20 mL) and extracted with ethyl acetate (2×10 mL). The combined organics were washed with brine, dried over MgSO$_4$ and removed in vacuo. Silica gel chromatography (gradient elution of 20% to 60% ethyl acetate in hexanes) afforded the product. $^1$H NMR (500 MHz, DMSO-d$_6$): δ 0.35-0.58 (m, 4H), 1.54-1.68 (m, 2H), 1.72 (s, 3H), 1.75-1.86 (m, 2H), 2.10-2.32 (m, 4H), 2.76 (bs, 1H), 3.45 (s, 3H), 3.95 (bs, 1H), 6.54-6.62 (m, 1H), 6.66 (s, 1H), 7.43-7.50 (m, 1H), 7.5 (d, J=10 Hz, 2, H), 7.58-7.67 (m, 3H), 8.50 (d, J=5.0 Hz, 1H).

Example 25

((1s,4s)-4-(N-cyclopropyl-4-(1,1,1-trifluoro-2,3-dihydroxypropan-2-yl)benzamido)-1-(4-fluorophenyl)cyclohexyl)methyl carbamate

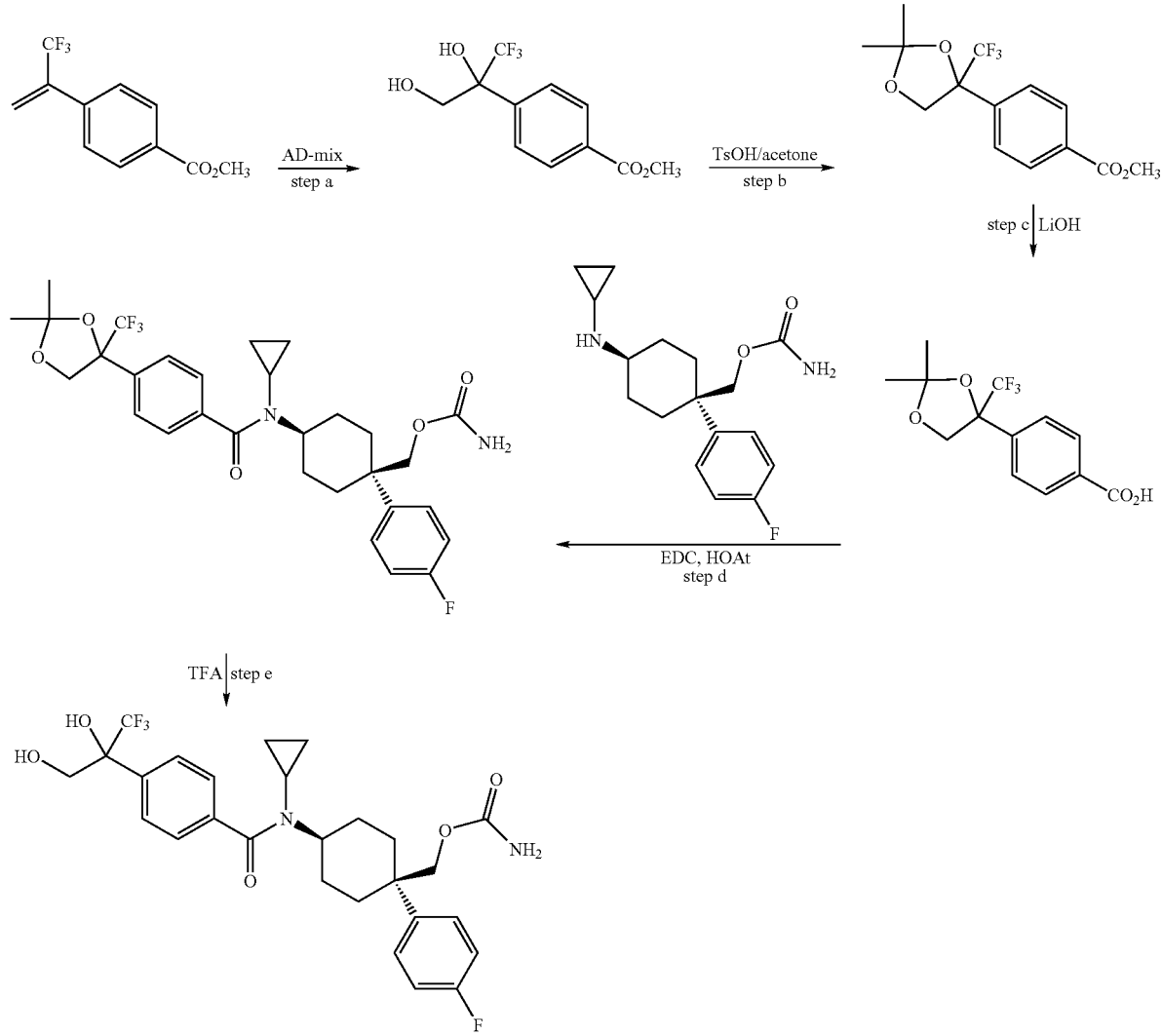

a). Methyl 4-(1,1,1-trifluoroprop-2-en-2-yl)benzoate (2.8 g, 12.2 mmol) was dissolved in tert-butanol:water (10 mL:10 mL) and treated with AD-mix-alpha (3.0 g). The resulting reaction was stirred at room temperature for 36 hours and at 40° C. for 16 hours. The solvent was then removed under reduced pressure and the residue diluted with water (100 mL) and ethyl acetate (300 mL). The separated organic layer was dried (MgSO$_4$), filtered and evaporated under reduced pressure. The residue was purified by flash chromatography (silica gel, 25% ethyl acetate in hexanes eluant) to give the product as a white solid (1.8 g, 56%). LC-MS ESI (pos.) m/e: 265 (M+H); $^1$H NMR (400 MHz, MeOD) δ 6.53 (dt, J=8.6 Hz, 2.0 Hz, 2H); 6.24 (d, J=8.2 Hz, 2H); 2.56 (d, J=11.7 Hz, 1H); 2.48 (d, J=11.7 Hz, 1H); 2.40 (s, 3H). The reaction was repeated under the same reaction conditions using AD-mix-beta instead of AD-mix-alpha. The product of both reactions were combined in a 1:1 ratio and used in the next reaction step.

b). The methyl 4-(1,1,1-trifluoro-2,3-dihydroxypropan-2-yl)benzoate prepared in the above step (1.8 g, 6.8 mmol) was dissolved in acetone (25 mL) and p-toluenesulfonic acid (320 mg, 1.7 mmol) was added in one portion. The reaction was then heated to 75° C. and stirred at this temperature for 24 hours. The reaction was then cooled to room temperature and the solvent was evaporated in vacuo. The residue was purified by flash chromatography (silica gel, 5% ethyl acetate in hexanes eluant) to give the product as a white solid (1.3 g, 63%). LC-MS ESI (pos.) m/e: 305 (M+H); $^1$H-NMR (400 MHz, CDCl$_3$) δ 8.06 (d, J=9.0 Hz, 2H); 7.55 (d, J=8.2 Hz, 2H); 4.74 (d, J=9.4 Hz, 1H); 4.23 (dd, J=9.4 Hz, 1.6 Hz, 1H); 3.92 (s, 3H); 1.61 (s, 3H); 1.32 (s, 3H).

c). The methyl 4-(2,2-dimethyl-4-(trifluoromethyl)-1,3-dioxolan-4-yl)benzoate prepared in the above step (400 mg, 1.31 mmol) was dissolved in a 1:1 mixture of methanol and tetrahydrofuran (7.5 ml of methanol and 7.5 ml of tetrahydrofuran) and a 1.0 M aqueous solution of LiOH (1.3 mL, 1.3 mmol) was added in one portion. The reaction was stirred at room temperature for 2 hours and then further treated with a 1.0 M aqueous solution of LiOH (0.8 mL, 0.8 mmol) in one portion. The reaction was stirred for 3 hours and then treated with ethyl acetate (100 mL) and water (200 mL). The separated organic layer was discarded and the aqueous layer was acidified to pH 2 with 1.0 M aqueous HCl (5 mL). The aqueous layer was then extracted with ethyl acetate (2×150 mL) and the combined organic layers were dried (MgSO$_4$), filtered and evaporated under reduced pressure to give the product as a white solid (350 mg, 92%). LC-MS ESI (pos.) m/e: 291 (M+H); $^1$H-NMR (400 MHz, CDCl$_3$) δ 8.07 (d, J=8.6 Hz, 2H); 7.53 (d, J=8.2 Hz, 2H); 4.69 (d, J=9.4 Hz, 1H); 4.17 (dd, J=9.4 Hz, 1.6 Hz, 1H); 1.55 (s, 3H); 1.27 (s, 3H).

d). The 4-(2,2-dimethyl-4-(trifluoromethyl)-1,3-dioxolan-4-yl)benzoic acid prepared in the above step (208 mg, 0.72 mmol) and ((1S,4S)-4-(cyclopropylamino)-1-(4-fluorophenyl)cyclohexyl)methyl carbamate (220 mg, 0.72 mmol) were dissolved in DMF (8 mL) and treated with EDC (179 mg, 0.93 mmol), hoat (127 mg, 0.93 mmol) and NaHCO$_3$ (139 mg, 1.65 mmol). The resulting reaction was stirred at room temperature for 14 hours and then treated with ethyl acetate (100 mL) and a 1.0 M aqueous solution of LiCl (50 mL). The separated organic layer was dried (MgSO$_4$), filtered and evaporated under reduced pressure. The residue was purified by flash chromatography (silica gel, 30% ethyl acetate in hexanes eluant) to give the product as a white solid (120 mg, 29%). LC-MS ESI (pos.) m/e: 579 (M+H); $^1$H-NMR (400 MHz, CDCl$_3$) δ 7.50-7.45 (m, 4H); 7.36-7.31 (m, 2H); 7.02-6.97 (m, 2H); 4.73-4.71 (m, 3H); 4.43 (s, 2H); 4.22 (d, J=9.4 Hz, 1H); 4.16 (s, 1H); 2.66-2.59 (m, 1H); 2.30-2.20 (m, 4H); 1.92-1.90 (m, 2H); 1.80-1.76 (m, 2H); 1.60 (s, 3H); 1.31 (s, 3H); 0.60-0.48 (m, 4H).

Preparation of ((1s,4s)-4-(cyclopropylamino)-1-(4-fluorophenyl)cyclohexyl)methyl carbamate

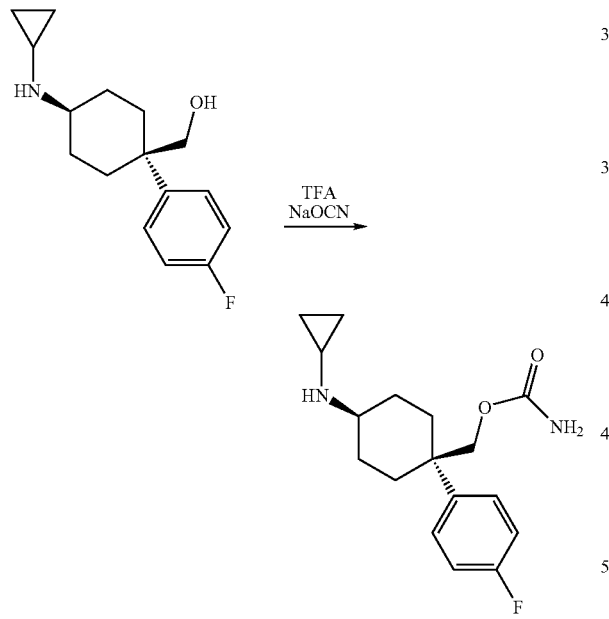

To a stirred solution of ((1S,4S)-4-(cyclopropylamino)-1-(4-fluorophenyl)cyclohexyl)methanol (400 mg, 1519 μmol) in trifluoroacetic acid (20 mL) at room temperature was added sodium cyanate (306 μl, 9113 μmol) portionwise over 1 minute. The reaction was stirred for 5 hours at room temperature and then the trifluoroacetic acid was removed under reduced pressure. Dichloromethane (80 mL) was added to the residue and the solution treated with NaHCO$_3$ (40 mL, saturated aqueous solution). The aqueous layer was extracted with dichloromethane (3×70 mL), dried (MgSO$_4$), filtered and evaporated under reduced pressure. The resulting residue was purified by flash chromatography (silica gel, 40% ethyl acetate in hexanes containing 2.5% triethylamine as eluant) to give the product as a white solid (130 mg, 27.9% yield). LC-MS ESI (pos.) m/e: 307 (M+H); $^1$H-NMR (400 MHz, MeOD): 7.45-7.40 (m, 2H); 7.03 (m, 2H); 3.36 (s, 2H); 2.76-2.72 (m, 1H); 2.28-2.12 (m, 3H); 1.94-1.90 (m, 2H), 1.75-1.50 (m, 4H); 0.58-0.43 (m, 4H).

e). The ((1s,4s)-4-(N-cyclopropyl-4-(2,2-dimethyl-4-(trifluoromethyl)-1,3-dioxolan-4-yl)benzamido)-1-(4-fluorophenyl)cyclohexyl)methyl carbamate prepared in the above step (100 mg, 0.17 mmol) was treated with trifluoroacetic acid (5 mL) and stirred at room temperature for 5 hours. The trifluoroacetic acid was then removed under reduced pressure and the resulting residue was subjected to preparative chiral HPLC (Chiralpak ADH column (ADHOCJ-EB004)) by injecting in methanol and running at 20 ml/min a program that runs at 25% A-75% B for 60 minutes. Eluent A is isopropyl alcohol, and eluent B is hexanes. The fractions between 20-25 minutes were collected to give the first eluted isomer of ((1s,4s)-4-(N-cyclopropyl-4-(1,1,1-trifluoro-2,3-dihydroxypropan-2-yl)benzamido)-1-(4-fluorophenyl)cyclohexyl)methyl carbamate as a colorless film (30 mg, 32%): LC-MS ESI (pos.) m/e: 539 (M+H); $^1$H-NMR (400 MHz, CDCl$_3$) δ 7.47 (d, J=8.2 Hz, 2H); 7.38 (d, J=8.2 Hz, 2H); 7.26 (dd, J=8.8, 5.3 Hz, 2H); 6.94 (t, J=8.6 Hz, 2H); 4.53 (s, 2H); 4.36 (s, 2H); 4.17-4.12 (m, 2H); 4.08-3.95 (m, 1H); 3.62 (d, J=11.7 Hz, 1H); 3.00-2.90 (s, 1H); 2.58-2.52 (s, 1H); 2.24-2.12 (m, 4H); 1.84-1.82 (<m, 2H); 1.73-1.62 (m, 2H); 0.58-0.42 (m, 4H). The fractions between 40-45 minutes were collected to give the second eluted isomer of ((1s,4s)-4-(N-cyclopropyl-4-(1,1,1-trifluoro-2,3-dihydroxypropan-2-yl)benzamido)-1-(4-fluorophenyl)cyclohexyl)methyl carbamate as a white solid (15 mg, 16%): LC-MS ESI (pos.) m/e: 539 (M+H); $^1$H-NMR (400 MHz, CDCl$_3$) δ 7.49 (d, J=8.2 Hz, 2H); 7.40 (d, J=8.6 Hz, 2H); 7.26 (dd, J=9.0 Hz, 5.1 Hz, 2H); 6.94 (t, J=8.8 Hz, 2H); 4.51 (s, 2H); 4.37 (s, 2H); 4.19 (d, J=12.1 Hz, 1H); 4.10-3.95 (m, 2H); 3.69 (d, J=11.3 Hz, 1H); 2.58-2.53 (m, 1H); 2.25-2.15 (m, 4H); 1.87-1.80 (m, 2H); 1.73-1.65 (m, 2H); 0.54-0.41 (m, 4H).

Example 26

Preparation of ((1S,4S)-4-(N-cyclopropyl-4-(1,1,1-trifluoro-2,3-dihydroxypropan-2-yl)benzamido)-1-(pyridin-2-yl)cyclohexyl)methyl carbamate

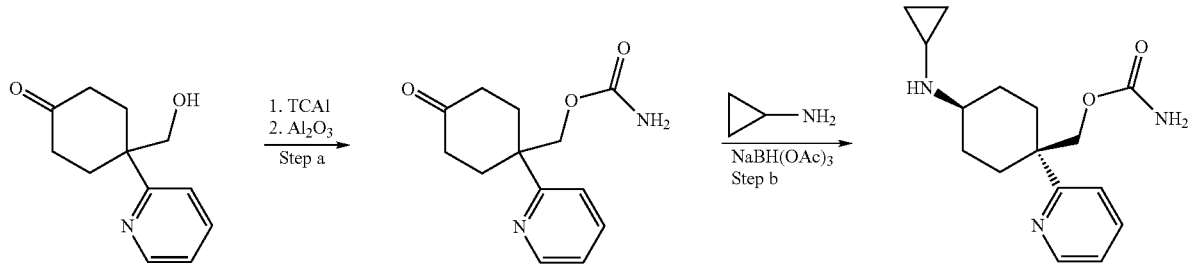

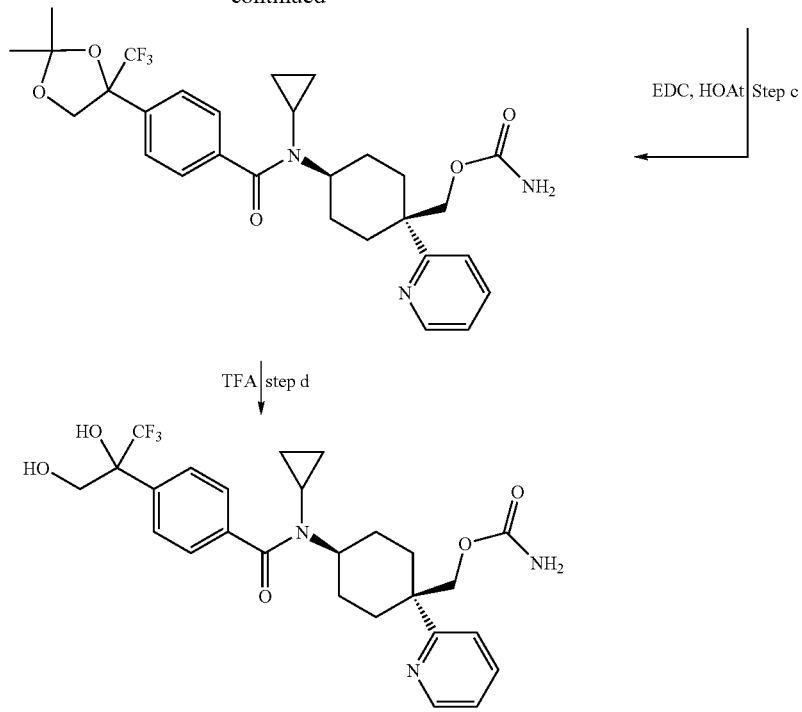

a). To a stirred solution of 4-(hydroxymethyl)-4-(pyridin-2-yl)cyclohexanone (2.2 g, 10.7 mmol) in anhydrous chloroform (50 mL) was added trichloroacetyl isocyanate (1.53 mL, 12.9 mmol). The resulting mixture was stirred for 30 minutes and then treated with activated aluminum oxide (20 g, activated with 10% water). The mixture was stirred at room temperature for 1 hour and then filtered, washing the aluminum oxide with dichloromethane:methanol (90 mL: 10 mL). The organic extracts were combined, washed with $NaHCO_3$ (60 mL) and then dried ($MgSO_4$), filtered and evaporated under reduced pressure to give the product as a white solid (2.0 g, 75%).

b). The (4-oxo-1-(pyridin-2-yl)cyclohexyl)methyl carbamate (2.0 g, 8.1 mmol) prepared in the above step in anhydrous acetonitrile (40 mL) at 0° C. was treated with cyclopropanamine (914 mg, 16.0 mmol) and $NaBH(OAc)_3$ (3.39 g, 16 mmol). The reaction was stirred for 4 hour at room temperature and then treated with dichloromethane:methanol (9:1, 200 ml). The separated organic layer was washed with $NaHCO_3$ (50 mL) and then dried ($MgSO_4$), filtered and evaporated under reduced pressure. The resulting residue was purified by column chromatography (silica gel, 10% methanol in dichloromethane containing 2 mM of triethylamine) to give the product as a mixture of cis and trans isomers. This mixture was further purified by preparative HPLC (Gemini, C18 column) by injecting in methanol and running at 20 ml/min a program that runs 75% A-25% B, for 40 minutes. Eluent A is water with 20 mM of triehylamine, and eluent B is acetonitrile with 20 mM of triehylamine. The fractions between 15-20 minutes were collected and evaporated under reduced pressure to give the product as a white solid (800 mg, 35%). LC-MS ESI (pos.) m/e: 290 (M+H); $^1$H-NMR (400 MHz, d6-DMSO) δ 8.53 (d, J=3.7 Hz, 1H); 7.71 (td, J=7.7 Hz, 3.0 Hz, 1H); 7.41 (d, J=8.0 Hz, 1H); 7.18 (dd, J=7.2 Hz, 7.4 Hz, 1H); 6.28 (s, 2H); 4.20 (s, 2H); 2.50 (s, 2H); 2.07-2.03 (m, 1H); 1.96-1.92 (m, 2H); 1.82-1.74 (m, 2H); 1.78-1.65 (m, 2H); 1.43-1.35 (m, 2H); 0.37-0.32 (m, 2H); 0.21-0.18 (m, 2H).

c). The ((1S,4S)-4-(cyclopropylamino)-1-(pyridin-2-yl)cyclohexyl)methyl carbamate prepared in the above step (150 mg, 0.52 mmol) and 4-(2,2-dimethyl-4-(trifluoromethyl)-1,3-dioxolan-4-yl)benzoic acid (150 mg, 0.52 mmol) were dissolved in DMF (5 mL) and treated with EDC (129 mg, 0.67 mmol), hoat (91 mg, 0.67 mmol) and $NaHCO_3$ (100 mg, 1.19 mmol). The resulting reaction was stirred at room temperature for 14 hours and then treated with ethyl acetate (100 mL) and a 1.0 M aqueous solution of LiCl (50 mL). The separated organic layer was dried ($MgSO_4$), filtered and evaporated under reduced pressure to give the product as a white solid (200 mg, 69%). LC-MS ESI (pos.) m/e: 562 (M+H); $^1$H-NMR (400 MHz, MeOD) δ 8.50 (dt, J=4.7 Hz, 1.0 Hz, 1H); 7.74 (td, J=8.0 Hz, 2.0 Hz, 1H); 7.57 (s, 4H); 7.48 (d, J=8.0 Hz, 1H); 7.22 (ddd, J=7.4 Hz, 4.89 Hz, 1.0 Hz, 1H); 4.79 (d, J=9.6 Hz, 1H); 4.61 (s, 2H); 4.32 (dd, J=9.7 Hz, 1.1 Hz, 1H); 4.11 (s, 1H); 2.83-2.78 (m, 1H); 2.37-2.27 (m, 4H); 1.99-1.93 (m, 2H); 1.85-1.75 (m, 2H); 1.57 (s, 3H); 1.30 (s, 3H); 0.62-0.52 (m, 4H).

d). The ((1S,4S)-4-(N-cyclopropyl-4-(2,2-dimethyl-4-(trifluoromethyl)-1,3-dioxolan-4-yl)benzamido)-1-(pyridin-2-yl)cyclohexyl)methyl carbamate prepared in the above step (100 mg, 0.18 mmol) was treated with trifluoroacetic acid (5 mL) and stirred at room temperature for 5 hours. The trifluoroacetic acid was then removed under reduced pressure and the resulting residue was subjected to preparative chiral HPLC (Chiralpak ADH column (ADH0CJ-EB004)) by injecting in methanol and running at 20 ml/min a program that runs at 25% A-75% B for 60 minutes. Eluent A is isopropyl alcohol, and eluent B is hexanes. The fractions coming between 40 to 45 minutes were collected and evaporated in vacuo to give the product as a white solid (18 mg, 19%). LC-MS ESI (pos.) m/e: 522 (M+H); $^1$H-NMR (400 MHz, d6-DMSO): 8.60 (dd, J=4.7 Hz, 1.5 Hz, 1H); 7.79 (td, J=7.8 Hz, 2.0 Hz, 1H); 7.68 (d, J=8.2 Hz, 2H); 7.54 (d, J=8.2 Hz, 2H); 7.49 (d, J=8.2 Hz, 1H); 7.28-7.25 (m, 1H); 6.57 (s, 1H); 6.38 (s, 2H); 5.27 (t, J=5.5 Hz, 1H); 4.55 (s, 2H); 4.02 (s, 1H);

3.98 (d, J=5.5 Hz, 2H); 2.85-2.80 (m, 1H); 2.26-2.20 (m, 4H); 1.90-1.80 (m, 4H); 0.58-0.46 (m, 4H).

Example 27

Preparation of (1s,4s)-methyl 4-(N-cyclopropyl-4-((S)-1,1,1-trifluoro-2-hydroxypropan-2-yl)benzamido)-1-(2,4-difluorophenyl)cyclohexanecarboxylate

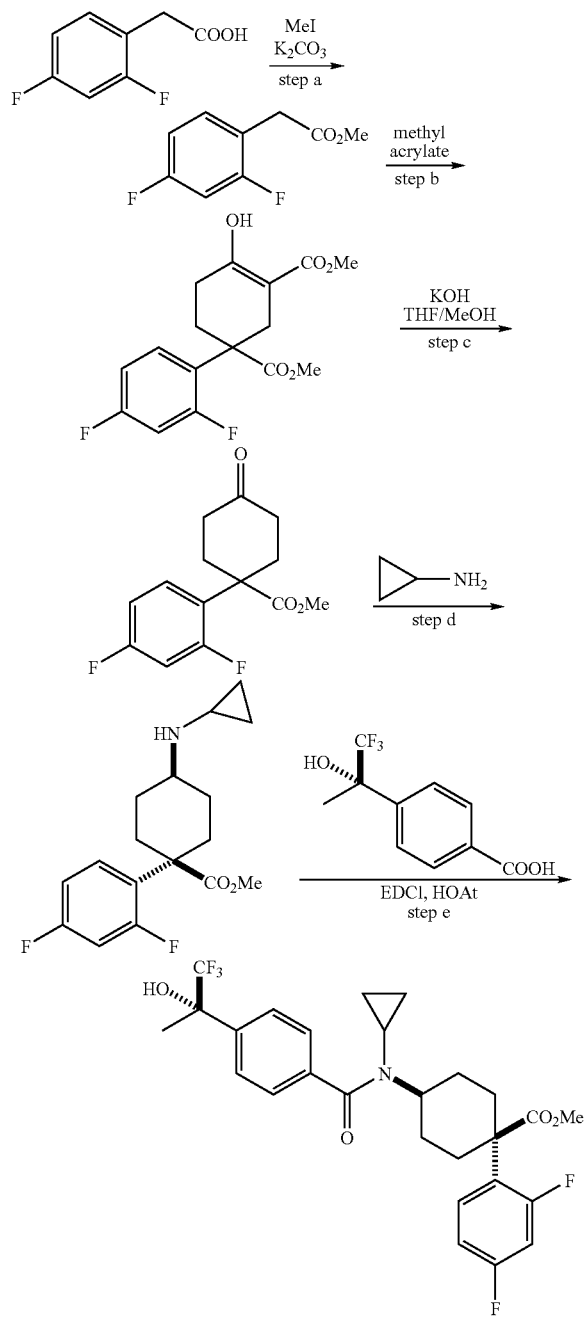

a). To a stirred solution 2,4-difluorophenylacetic acid (5.0 g, 29 mmol) and potassium carbonate (5.3 mL, 87.1 mmol) in 60 mL DMF was added methyl iodide (2.7 mL, 43.6 mmol) and the reaction stirred overnight. The reaction was diluted 100 mL H$_2$O, extracted 3×MeOH in DCM, washed 1×H$_2$O, 1× brine, dried over sodium sulfate, filtered and concentrated to yield the product as a clear oil (4.06 g, 75%).

b). To a stirred solution methyl 2-(2,4-difluorophenyl)acetate (4.06 g, 21.8 mmol) and methyl acrylate (3.94 ml, 43.6 mmol) in 40 mL dry THF was added potassium t-butoxide (2.69 g, 24.0 mmol) and the mixture was allowed to stir for 0.5 hr. Upon complete solvation of the base, the reaction mixture had changed to a golden color. The reaction was quenched 3 N HCl, extracted 3×EtOAc, organics combined and washed 1× brine, dried over sodium sulfate, filtered and concentrated. The resulting pale yellow solid was triturated from MeOH, filtered to yield a white solid (3.95 g) and the filtrate was concentrated to yield a yellow oil. The oil was purified over 200 mL silica 10% EtOAc/Hexane, to yield 500 mg additional material. Combined recovery of pure product was 4.45 g, 62.5%.

c). To a stirred solution dimethyl 1-(2,4-difluorophenyl)-4-oxocyclohexane-1,3-dicarboxylate (4.45 g, 13.6 mmol) in 25 mL H$_2$O, 10 mL THF and 10 mL MeOH was added potassium hydroxide (460 mg, 8.2 mmol) and the reaction was heated to reflux. The reaction was maintained at reflux overnight, was cooled to ambient temperature, low boiling organics stripped via rotary evaporation, and the aqueous layer extracted 3×10% MeOH in DCM. The organics were dried over sodium sulfate, filtered, and concentrated to yield the product as a clear oil, which solidified to a white solid (1.88 g, 51%).

d). To a stirred solution methyl 1-(2,4-difluorophenyl)-4-oxocyclohexanecarboxylate (1.87 g, 7.0 mmol), acetic acid, 99.5% 0.60 mL, 10.5 mmol), and cyclopropylamine (0.60 mL 10.5 mmol) in 15 mL ACN was added sodium triacetoxyborohydride (2.97 g, 14 mmol) and the reaction stirred overnight at ambient temperature. The reaction was quenched with 15 mL 1 N NaOH and the mixture extracted 3×10% MeOH in DCM. The organics were concentrated and purified over silica to yield two isomers, top spot A (650 mg, 30%) and bottom spot B (630 mg, 29%). The bottom spot was assigned to as the -trans isomer based on the chemical shift of the cyclopropyl protons (0.5 ppm vs 0.1 ppm).

e). To a stirred solution sodium bicarbonate (285 mg, 3.3 mmol), 3H-[1,2,3]triazolo[4,5-b]pyridin-3-ol (185 mg, 1.35 mmol), N1-((ethylimino)methylene)-N3,N3-dimethylpropane-1,3-diamine hydrochloride (260 mg, 1.35 mmol), (S)-4-(1,1,1-trifluoro-2-hydroxypropan-2-yl)benzoic acid (318 mg, 1.35 mmol) in 2 mL DMF, was added (1r,4r)-methyl 4-(cyclopropylamino)-1-(2,4-difluorophenyl)cyclohexanecarboxylate (350 mg, 1.13 mmol) and the reaction stirred overnight at ambient temperature. TLC indicated the reaction was complete, and the reaction was quenched with 5 mL H$_2$O. The product crashed as a white solid and was filtered and washed 1×H$_2$O and 1×Et$_2$O (recovery 430 mg, 72%): $^1$H NMR (400 MHz, DMSO-d6): δ 0.16 (d, J=2.36 Hz, 2H), 0.28 (d, J=6.64 Hz, 2H), 1.52 (s, 3H), 1.69 (m, 4H), 1.94 (m, 2H), 2.21 (d, J=12.5 Hz, 2H), 2.536 (m, 1H), 3.14 (s, 1H), 3.47 (s, 3H), 3.91 (m, 1H), 6.91 (ddd, J=2, 8.1, 8.2 Hz, 1H), 7.021 (ddd, J=2.4, 9, 12.5 Hz, 1H), 7.31 (d, J=8.6 Hz, 2H), 7.350 (m, 1H), 7.423 (d, J=8.6 Hz, 2H).

Example 28

Preparation of N-cyclopropyl-N-((1s,4s)-4-(2,4-difluorophenyl)-4-(hydroxymethyl)cyclohexyl)-4-((S)-1,1,1-trifluoro-2-hydroxypropan-2-yl)benzamide

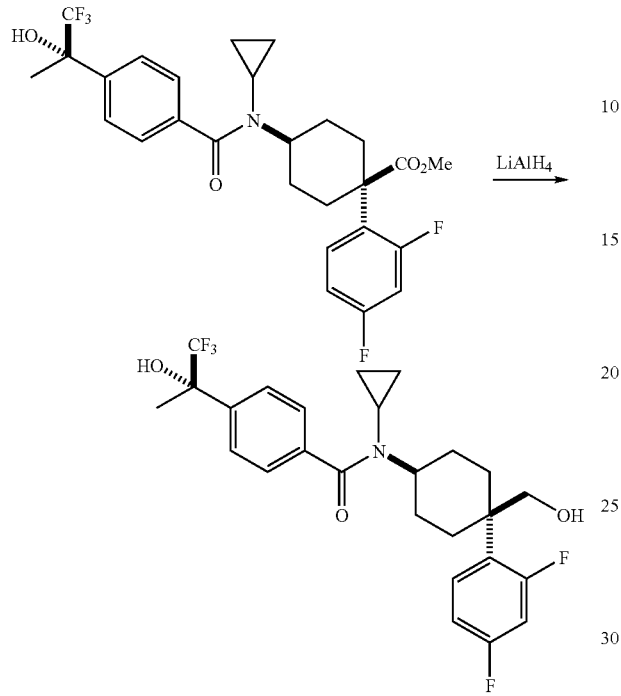

To a stirred solution (1s,4s)-methyl 4-(N-cyclopropyl-4-((S)-1,1,1-trifluoro-2-hydroxypropan-2-yl)benzamido)-1-(2,4-difluorophenyl)cyclohexanecarboxylate (367 mg, 698 μmol) in 2 mL dry THF at 0° C. in an ice bath was added lithium aluminum hydride (698 μl, 698 μmol) dropwise and the mixture stirred for 1 hour. The reaction was quenched with 2 mL saturated ammonium chloride solution and extracted 3×10% MeOH in DCM. The organics were concentrated and purified by HPLC (Phenomenex Gemini C18 Column, 250× 21.20 mm, 55-75% acetonitrile:water) to give the product as a white solid (247 mg, 71%): $^1$H NMR (400 MHz, DMSO-d6): δ 0.19 (m, 2H), 0.30 (d, J=6.2 Hz, 2H), 1.41 (m, 2H), 1.50 (s, 3H), 1.58 (m, 2H), 1.97 (m, 2H), 2.10 (m, 2H), 2.56 (m, 1H), 3.68 (d, J=5.1 Hz, 2H), 4.36 (dd, J=5.3, 5.3 Hz, 1H), 6.46 (s, 1H), 6.80 (ddd, J=2.8, 8.2, 8.4 Hz, 1H), 6.90 (ddd, J=2.7, 9.2, 13.3 Hz, 1H), 7.18 (ddd, J=7.0, 9.0, 9.2 Hz, 1H), 7.280 (d, J=8.6 Hz, 2H), 7.41 (d, J=8.6 Hz, 2H).

Example 29

Preparation of ((1s,4s)-4-(N-cyclopropyl-4-((S)-1,1,1-trifluoro-2-hydroxypropan-2-yl)benzamido)-1-(pyrazin-2-yl)cyclohexyl)methyl carbamate

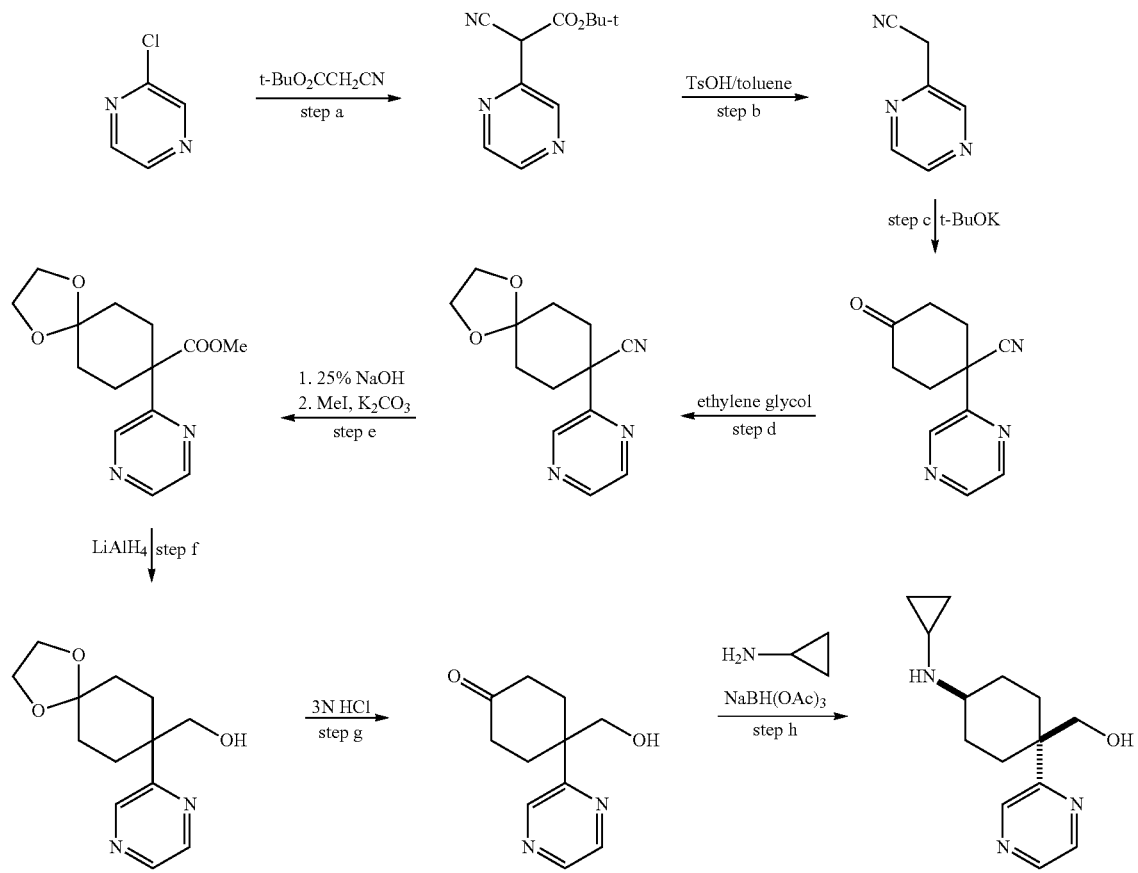

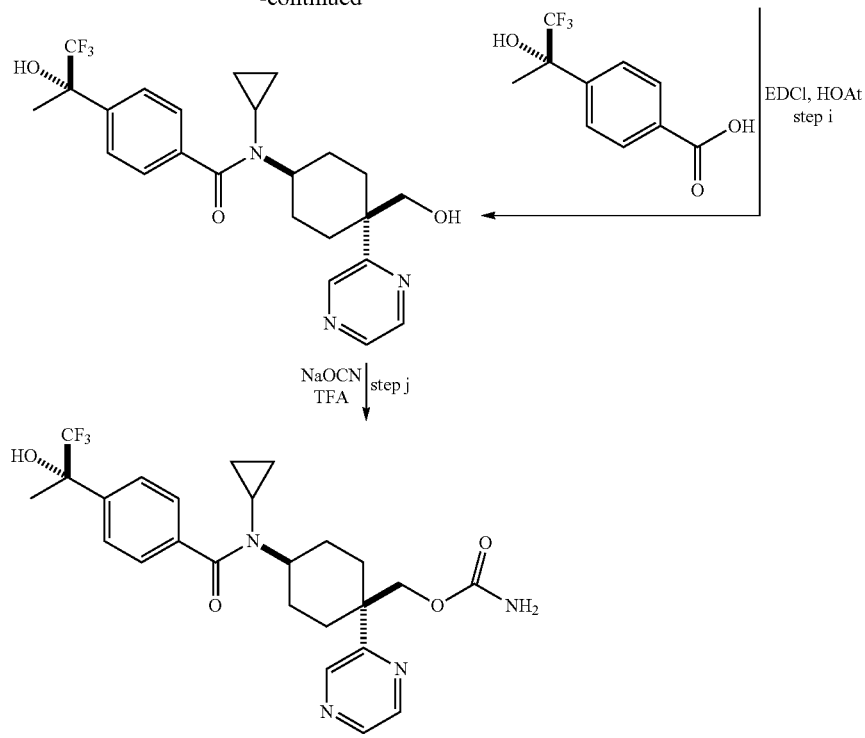

a). To a stirred solution of tert-butyl cyanoacetate (20.7 mL, 140 mmol, 2.0 equiv.) in dry THF (150 mL) at 0° C. was added solid t-BuOK (19.6 g, 175 mmol, 2.5 equiv.). The ice-bath was removed. After being stirred at 25° C. for 10 minutes, 2-chloropyrazine (8.0 g, 69.8 mmol, 1.0 equiv.) was added to the solution. Then the flask was equipped with a reflux condenser, and placed into a preheated 90° C. bath. After being stirred at 90° C. for 12 h, the reaction mixture was cooled to 25° C. and the THF was evaporated. The residue was partitioned between water (100 mL) and $CH_2Cl_2$ (100 mL), and acidified with 3N HCl to PH 1. The organic layer was separated, dried with $Na_2SO_4$, filtered and concentrated under reduced pressure to give the crude product as a black solid, which was used in the next step without further purification.

b). The product prepared above in step a was combined with TsOH (1.0 g) in Toluene (200 mL). After being stirred at refluxing for 12 h, the reaction was cooled to 25° C., diluted (sat. $NaHCO_3$), extracted (3×10% $MeOH/CH_2Cl_2$), washed with brine, dried with $Na_2SO_4$, filtered and concentrated under reduced pressure. Purification of the crude material by flash chromatography ($SiO_2$, 40-45% EtOAc/Hexanes) gave 4.46 g of the product (37.4 mmol, 54% for two steps) as light yellow oil.

c). To a stirred solution of 2-(pyrazin-2-yl)acetonitrile (4.46 g, 37 mmol, 1.0 equiv.) prepared above in step b and methyl acrylate (6.8 mL, 75 mmol, 2.0 equiv.) in dry THF (60 mL) at 25° C. was added solid t-BuOK (6.3 g, 56 mmol, 1.5 equiv.). Upon addition the mixture changed to an orange color and warmed slightly. After being stirred at 25° C. for 30 minutes, the reaction was diluted with water (300 mL). Then the flask was equipped with a reflux condenser, and placed into a preheated 85° C. bath. After being stirred at 85° C. for 12 h, the reaction was cooled to 25° C., extracted (3×10% $MeOH/CH_2Cl_2$), washed with brine, dried with $Na_2SO_4$, filtered and concentrated under reduced pressure to give 5.0 g of crude product, which was used in the next step without further purification.

d). A mixture of 4-oxo-1-(pyrazin-2-yl)cyclohexanecarbonitrile (5.0 g, 25 mmol, 1.0 equiv.) prepared above in step c, ethylene glycol (1.5 g, 25 mmol, 1.0 equiv.) and p-toluenesulfonic acid (500 mg) in benzene (100 mL) was heated at reflux under a Dean-Stark trap for 6 hours. The solution was cooled to 25° C. and washed successively with sat. $NaHCO_3$, water and brine. The organics were dried with $Na_2SO_4$ and evaporated to give 5.7 g of crude product, which was used in the next step without further purification.

e). A 250 mL flask was charged with 4-cyano-4-(pyrazin-2-yl)cyclohexanone ethylene ketal (5.7 g, 23 mmol, 1.0 equiv), 25% NaOH aqueous solution (50 mL) and methanol (50 mL). The flask was equipped with a reflux condenser, and then placed into a preheated 100° C. bath. After being stirred at 100° C. for 8 h, the reaction mixture was cooled to 25° C., adjusted to pH 7 with con. HCl, extracted (3×10% MeOH/$CH_2Cl_2$), washed (brine), dried ($Na_2SO_4$), filtered and concentrated under reduced pressure with a cold bath. The dry residue was then treated with DMF (40 mL), potassium carbonate (9.54 g, 69 mmol, 3.0 equiv) and methyl iodide (1.72 mL, 27.6 mmol, 1.2 equiv) successively. After being stirred at 25° C. for 2 h, the reaction mixture was quenched (sat-.$NaHCO_3$) and extracted (10% MeOH/$CH_2Cl_2$). The organics were washed with brine, dried with $Na_2SO_4$ and concentrated under reduced pressure. Purification of the crude material by flash chromatography ($SiO_2$, 40-50% EtOAc/hexanes) gave 4.60 g of the product as a colorless oil (16.5 mmol, 72% for two steps).

f). To a solution of methyl carboxylate prepared above in step e (4.6 g, 17.0 mmol, 1.0 equiv.) in dry THF (40 mL) was slowly added $LiAlH_4$ (1.0 M in diethyl ether, 17.0 mL, 1.0 equiv) at −40° C. After being stirred at −40° C. for 0.5 h, the reaction mixture was quenched (0.2 mL $H_2O$, 3 mL 1N NaOH). After being stirred for 0.5 h, the solid was filtered. The solution was extracted (10% MeOH/CH$_2$Cl$_2$), dried with Na$_2$SO$_4$, and concentrated under reduced pressure. The crude material was purified by flash column chromatography (SiO$_2$, 85-100% EtOAc/Hexanes) to provide 2.3 g of the product as a white solid (9.2 mmol, 56%).

g). 3 N HCl (10 mL) was added to a solution of the product prepared above in step f (1.0 g, 4.0 mmol) in THF (50 mL). The mixture was stirred at 25° C. for 12 h and then diluted with sat.NaHCO$_3$. The resulting solution was extracted (10% MeOH/CH$_2$Cl$_2$) and the organics were dried with Na$_2$SO$_4$ and concentrated under reduced pressure. The crude material was purified by flash column chromatography (SiO$_2$, EtOAc) to provide 0.72 g of the product as a colorless oil (3.5 mmol, 87%).

h). A solution of 4-(hydroxymethyl)-4-(pyrazin-2-yl)cyclohexanone (360 mg, 2.0 mmol, 1.0 equiv) in acetonitrile (4 mL) was treated with cyclopropylamine (280 μL, 4.0 mmol, 2.0 equiv), acetic acid (0.1 mL) and NaBH(OAc)$_3$ (848 mg, 4.0 mmol, 2.0 equiv) successively. After being stirred at 25° C. for 12 h, the reaction mixture was carefully diluted (sat. NaHCO$_3$) and extracted (10% MeOH/CH$_2$Cl$_2$). The organics were washed with brine, dried with Na$_2$SO$_4$ and concentrated under reduced pressure. The crude material was purified by flash column chromatography (SiO$_2$, EtOAc containing 2.5% NH$_4$OH then EtOAc/5% MeOH containing 2.5% NH$_4$OH, the second spot was collected) to provide 180 mg of trans amine as a white solid (0.70 mmol, 42%).

(m, 1H), 8.44 (d, J=2.4 Hz, 1H), 7.60 ((, J=8.2 Hz, 2H), 7.49 (d, J=8.6 Hz, 2H), 6.65 (s, 1H), 4.65 (t, J=5.0 Hz, 1H), 3.89 (m, 3H), 2.77 (m, 1H), 2.27-2.11 (m, 4H), 1.84-1.74 (m, 2H), 1.73-1.63 (m, 5H), 0.50 (m, 2H), 0.39 (m, 2H). Anal. cacld for C$_{24}$H$_{28}$F$_3$N$_3$O$_3$+⅓CH$_3$CN+⅓MeOH: C, 61.70; H, 6.22; N, 9.45. Found: C, 61.55; H, 6.15; N, 9.45.

j). Trifluoroacetic acid (1.0 mL) was added slowly to a stirred mixture of the product prepared above in step i (65 mg, 0.14 mmol, 1.0 equiv) and sodium cyanate (68 mg, 0.84 mmol, 6.0 equiv) at 25° C. After being stirred at 25° C. for 30 minutes, the reaction was quenched (sat. NaHCO$_3$) and the solution was extracted (10% MeOH/CH$_2$Cl$_2$), washed with brine, dried with Na$_2$SO$_4$ and concentrated under reduced pressure. Purification of the crude material by HPLC gave 38 mg of the product as a white solid (0.075 mmol, 53%). $^1$H NMR (DMSO-d$_6$, 400 MHz) δ 8.75 (d, J=1.6 Hz, 1H), 8.62 (m, 1H), 8.50 (d, J=2.4 Hz, 1H), 7.61 (d, J=8.2 Hz, 2H), 7.50 (d, J=8.6 Hz, 2H), 6.66 (s, 1H), 4.49 (s, 2H), 3.96 (m, 1H), 2.78 (m, 1H), 2.26-2.15 (m, 4H), 1.88-1.75 (m, 4H), 1.71 (s, 3H), 0.50 (m, 2H), 0.40 (m, 2H).

Example 30

Preparation of N-ethyl-N-((1s,4s)-4-(hydroxymethyl)-4-(pyrazin-2-yl)cyclohexyl)-4-((S)-1,1,1-trifluoro-2-hydroxypropan-2-yl)benzamide and N-ethyl-N-((1s,4r)-4-(hydroxymethyl)-4-(pyrazin-2-yl)cyclohexyl)-4-((S)-1,1,1-trifluoro-2-hydroxypropan-2-yl)benzamide

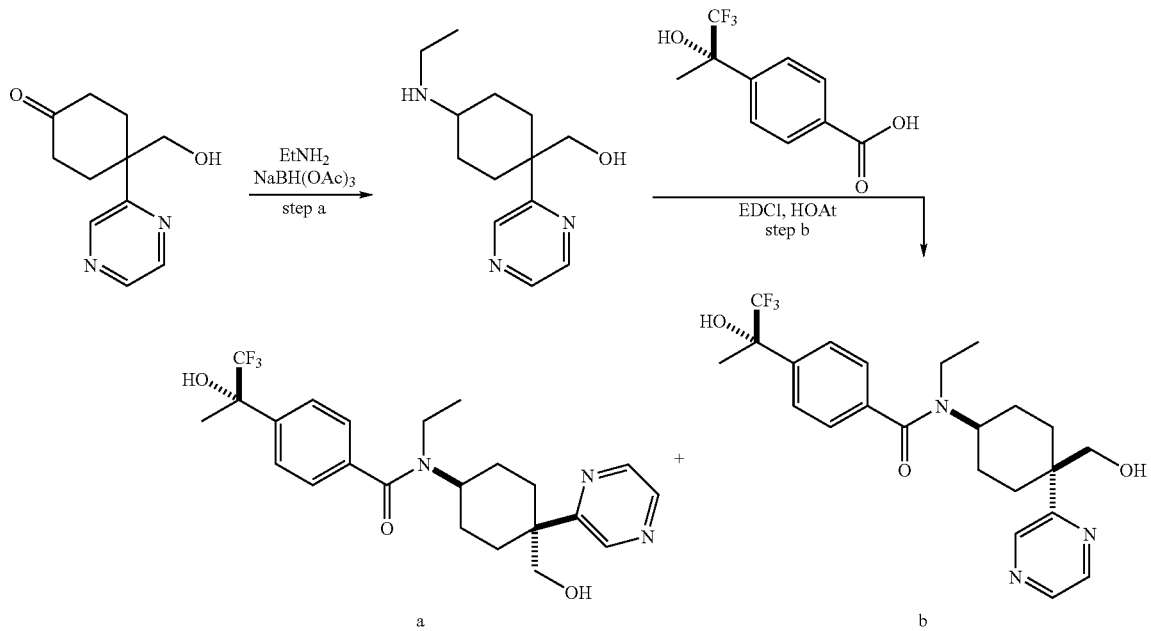

i). A solution of trans amine prepared above in step h (180 mg, 0.69 mmol, 1.0 equiv) and (S)-4-(1,1,1-trifluoro-2-hydroxypropan-2-yl)benzoic acid (162 mg, 0.69 mmol, 1.0 equiv) in DMF (2.5 mL) was treated with EDCl (176 mg, 1.3 equiv), HOAt (122 mg, 1.3 equiv) and NaHCO$_3$ (140 mg, 2.3 equiv) successively. After being stirred at 25° C. for 12 h, the reaction was diluted (EtOAc), washed with 1 N NaOH and brine, dried with Na$_2$SO$_4$ and concentrated under reduced pressure. Purification of the crude material by HPLC gave 190 mg of the product as a white solid (0.41 mmol, 56%). $^1$H NMR (DMSO-d$_6$, 400 MHz) δ 8.69 (d, J=1.6 Hz, 1H), 8.58 a). A solution of 4-(hydroxymethyl)-4-(pyrazin-2-yl)cyclohexanone prepared as in the above example (360 mg, 1.7 mmol, 1.0 equiv) in acetonitrile (4 mL) was treated with ethanamine hydrochloride (280 mg, 3.5 mmol, 2.0 equiv), acetic acid (0.1 mL) and NaBH(OAc)$_3$ (740 mg, 3.5 mmol, 2.0 equiv) successively. After being stirred at 25° C. for 12 h, the reaction mixture was carefully diluted (sat.NaHCO$_3$) and extracted (10% MeOH/CH$_2$Cl$_2$). The organics were washed with brine, dried with Na$_2$SO$_4$ and concentrated under reduced pressure to give 130 mg of the crude product, which was used in the next step without further purification.

b). A solution of amine prepared above in step a (130 mg, 0.60 mmol, 1.0 equiv) and (S)-4-(1,1,1-trifluoro-2-hydroxypropan-2-yl)benzoic acid (130 mg, 0.60 mmol, 1.0 equiv) in DMF (2.0 mL) was treated with EDCl (156 mg, 1.3 equiv), HOAt (111 mg, 1.3 equiv) and NaHCO₃ (100 mg, 2.3 equiv) successively. After being stirred at 25° C. for 12 h, the reaction was diluted (EtOAc), washed with 1 N NaOH and brine, dried with Na₂SO₄ and concentrated under reduced pressure. Purification of the crude material by HPLC gave 7.0 mg of the cis isomer a (0.017 mmol, 3%) and 10.0 mg of the trans isomer b (0.021 mmol, 4%) as a white solid. a: ¹H NMR (CDCl₃, 400 MHz) δ 8.73-8.63 (m, 2H), 8.50 (m, 1H), 7.61 (m, 2H), 7.35 (m, 2H), 3.65-3.46 (m, 3H), 3.15 (m, 1H), 2.65 (m, 1H), 1.88-1.45 (m, 12H), 1.13 (m, 2H). b: ¹H NMR (CDCl₃, 400 MHz) δ 8.73-8.47 (m, 3H), 7.61 (d, J=8.2 Hz, 2H), 7.38 (d, J=8.6 Hz, 2H), 4.10-3.05 (m, 5H), 2.21-1.50 (m, 12H), 1.13 (m, 2H).

Example 31

Preparation of N-((1r,4r)-4-(3-amino-3-oxopropyl)-4-(pyrazin-2-yl)cyclohexyl)-N-cyclopropyl-4-((S)-1,1,1-trifluoro-2-hydroxypropan-2-yl)benzamide

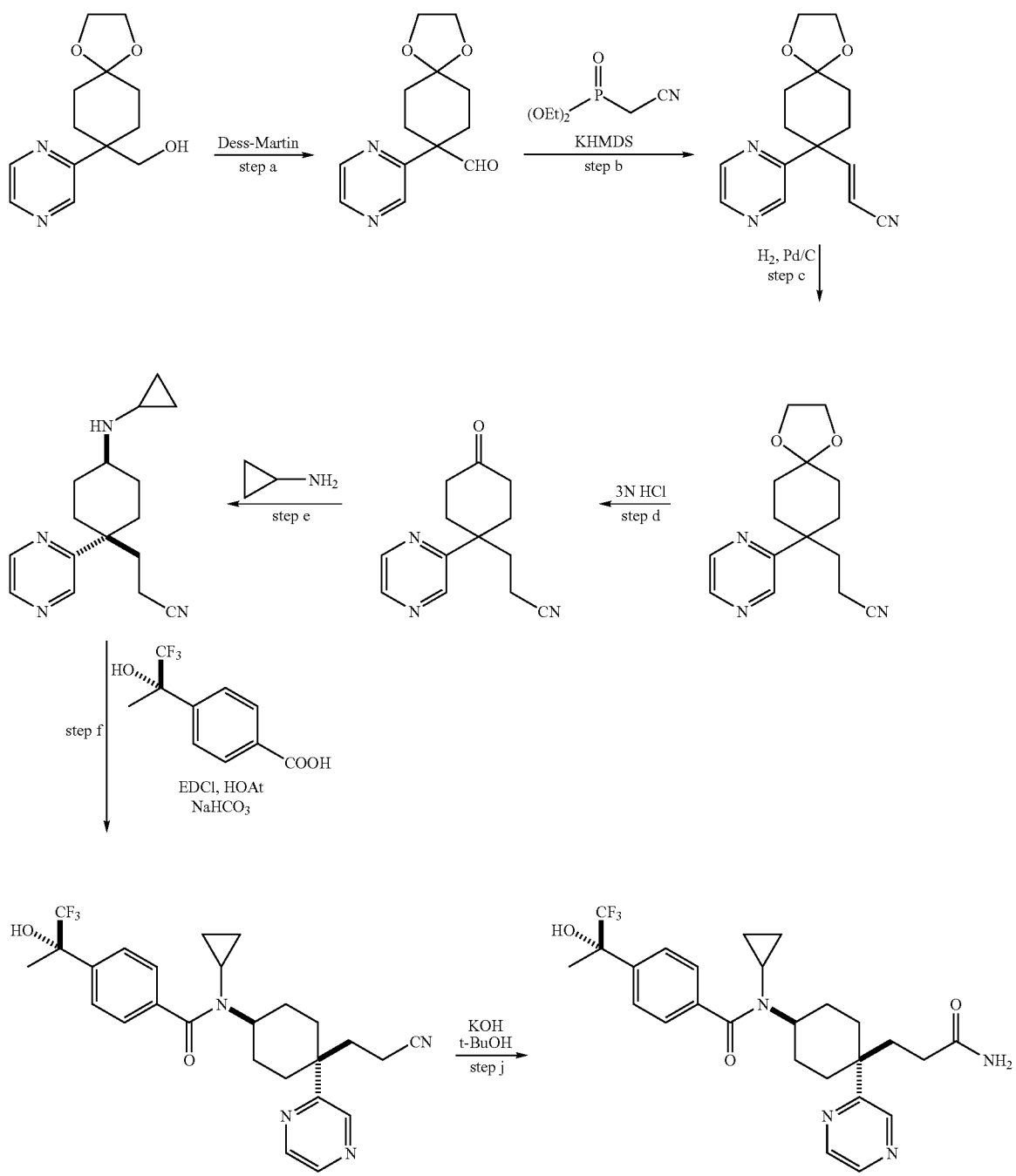

a). To a stirred solution of 4-(hydroxymethyl)-4-(pyrazin-2-yl)-cyclohexanone ethylene ketal prepared as in the above example (1.05 g, 4.2 mmol, 1.0 equiv.) in dry DCM (10 mL) was added Dess-Martin periodinane (3.55 g, 8.4 mmol, 2.0 equiv.). After being stirred at 25° C. for 1 h, the reaction mixture was diluted with sat.NaHCO$_3$ (20 ml) and 0.5 M Na$_2$S$_2$O$_3$ (20 ml). Let it stir for 15 minutes. The resulting solution was extracted (10% MeOH/CH$_2$Cl$_2$). The organics were washed with brine, dried with Na$_2$SO$_4$ and concentrated under reduced pressure to give 0.90 g of the crude product, which was used in the next step without further purification.

b). To a stirred suspension of NaH (60% in mineral oil, 0.16 g, 4.0 mmol, 1.1 equiv.) in THF (10 mL) was added a solution of diethylcyanomethylphosphonate (0.77 g, 4.3 mmol. 1.2 equiv.) and DMNP (1.0 mL) in dry THF (10 mL). After being stirred at 25° C. for 0.5 hour, a solution of the aldehyde product prepared above in step a (0.90 g, 3.6 mmol, 1.0 equiv.) in dry THF (5 mL) was added to the mixture. After being stirred at 25° C. for 2 h, the reaction mixture was diluted (water), extracted (3×10% MeOH/DCM), washed with brine, dried with Na$_2$SO$_4$, filtered and concentrated under reduced pressure. Purification of the crude material by flash chromatography (SiO$_2$, 40-55% EtOAc/hexanes) gave 0.76 g of the product as a white solid (2.8 mmol, 67% for two steps).

c). A solution of alkene product prepared above in step b (0.76 g, 2.8 mmol, 1.0 equiv.) in EtOH: (5 mL) and EA (10 mL), containing 10% Pd/C (~100 mg), was hydrogenated under atmospheric pressure for 12 h. The mixture was filtered through celite to remove Pd/C, concentrated under reduced pressure to give the crude product, which was used in the next step without further purification.

d). To a stirred solution of the ketal product prepared above in step c in THF (20 mL) was added 3 N HCl (10 mL). After being stirred at 25° C. for 12 h, the reaction mixture was diluted with sat.NaHCO$_3$, extracted (3×10% MeOH/CH$_2$Cl$_2$), washed with brine, dried with Na$_2$SO$_4$ and concentrated under reduced pressure to give 0.61 g of the crude product, which was used in the next step without further purification e). A solution of 3-(4-oxo-1-(pyrazin-2-yl)cyclohexyl)propanenitrile (610 mg, 2.7 mmol, 1.0 equiv) in acetonitrile (10 mL) was treated with cyclopropylamine (380 μL, 5.3 mmol, 2.0 equiv), acetic acid (0.1 mL) and NaBH(OAc)$_3$ (1.1 g, 5.3 mmol, 2.0 equiv) successively. After being stirred at 25° C. for 12 h, the reaction mixture was carefully diluted (sat.NaHCO$_3$) and extracted (10% MeOH/CH$_2$Cl$_2$). The organics were washed with brine, dried with Na$_2$SO$_4$ and concentrated under reduced pressure. Purification of the crude material by flash chromatography (SiO$_2$, 70-80% EtOAc/hexanes containing 2.5% triethylamine) gave 0.24 g of the trans amine (0.89 mmol, 33%) and then further elution afforded 0.24 g of the cis amine (0.89 mmol, 33%).

f). A solution of trans amine prepared above in step e (130 mg, 0.48 mmol, 1.0 equiv) and (S)-4-(1,1,1-trifluoro-2-hydroxypropan-2-yl)benzoic acid (113 mg, 0.48 mmol, 1.0 mmol) in DMF (2.0 mL) was treated with EDCl (120 mg, 0.63 mmol, 1.3 equiv), HOAt (85 mg, 0.63 mmol, 1.3 equiv) and NaHCO$_3$ (93 mg, 1.1 mmol 2.3 equiv) successively. After being stirred at 25° C. for 12 h, the reaction was diluted (EtOAc), washed with 1 N NaOH and brine, dried with Na$_2$SO$_4$ and concentrated under reduced pressure. Purification of the crude material by HPLC gave 170 mg of the product as a white solid (0.34 mmol, 73%). $^1$H NMR (DMSO-d$_6$, 400 MHz) δ 8.76 (d, J=1.6 Hz, 1H), 8.61 (m, 1H), 8.52 (d, J=2.4 Hz, 1H), 7.61 (d, J=8.6 Hz, 2H), 7.49 (d, J=8.6 Hz, 2H), 6.65 (s, 1H), 3.89 (m, 1H), 2.81 (m, 1H), 2.32-2.16 (m, 8H), 1.84-1.70 (m, 7H), 0.51 (m, 2H), 0.42 (m, 2H). Anal. cacld for C$_{26}$H$_{29}$F$_3$N$_4$O$_2$: C, 64.18; H, 6.01; N, 11.52. Found: C, 64.22; H, 6.24; N, 11.24.

g). Combined the product prepared above in step f (104 mg, 0.210 mmol, 1.0 equiv.) and KOH (60 mg, 1.1 mmol, 5.0 equiv.) in t-butanol (4 mL). Then the flask was equipped with a reflux condenser, and placed into a preheated 90° C. bath. After being stirred at 90° C. for 1 hour, the mixture was cooled to 25° C., diluted with H$_2$O (3 mL), extracted (3×10% MeOH/CH$_2$Cl$_2$), dried with Na$_2$SO$_4$ and concentrated under reduced pressure. Purification of the crude material by HPLC gave 75 mg of the product as a white solid (0.15 mmol, 70%). $^1$H NMR (DMSO-d$_6$, 400 MHz) δ 8.72 (d, J=1.6 Hz, 1H), 8.61 (m, 1H), 8.49 (d, J=2.4 Hz, 1H), 7.61 (d, J=8.2 Hz, 2H), 7.49 (d, J=8.2 Hz, 2H), 7.15 (br, 1H), 6.65 (s, 1H), 6.63 (br, 1H), 3.89 (m, 1H), 2.78 (m, 1H), 2.26-2.14 (m, 6H), 1.82 (m, 2H), 1.71-1.63 (m, 7H), 0.51 (m, 2H), 0.42 (m, 2H). Anal. cacld for C$_{26}$H$_{31}$F$_3$N$_4$O$_3$+⅓ MeOH: C, 61.39; H, 6.33; N, 10.87. Found: C, 61.52; H, 6.42; N, 10.68.

Example 32

Preparation of (S)-ethyl 4-(N-cyclopropyl-4-(1,1,1-trifluoro-2-hydroxypropan-2-yl)benzamido)-1-(pyridazin-4-yl)cyclohexanecarboxylate and (S)-methyl 4-(N-cyclopropyl-4-(1,1,1-trifluoro-2-hydroxypropan-2-yl)benzamido)-1-(pyridazin-4-yl)cyclohexanecarboxylate

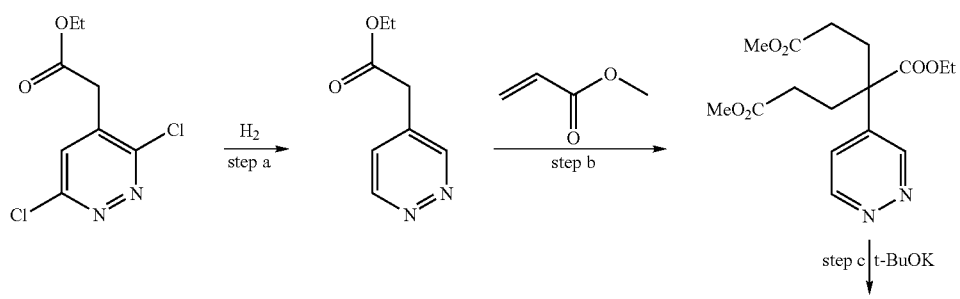

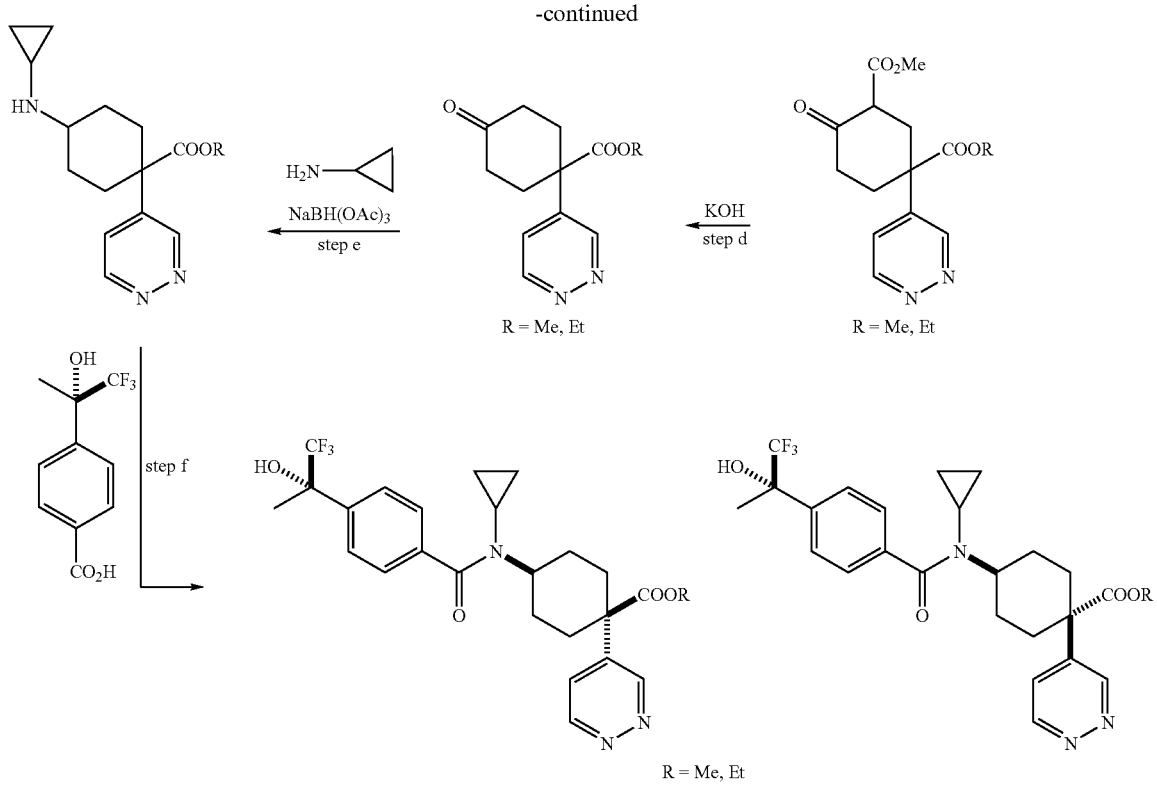

R = Me, Et a). A solution of ethyl 2-(3,6-dichloropyridazin-4-yl)acetate (1.1 g, 4.7 mmol, 1.0 equiv.) in MeOH (10 mL), containing 10% Pd/C (~200 mg) and triethylamine (1.3 mL, 9.4 mmol, 2.0 equiv.), was hydrogenated under atmospheric pressure for 3.5 h. Then the reaction mixture was filtered through celite to remove Pd/C, and concentrated under reduced pressure. Purification of the crude material by flash chromatography (SiO$_2$, EtOAc) gave 0.61 g of the product (3.7 mmol, 78%).

b). Ethyl 2-(pyridazin-4-yl)acetate (0.61 g, 3.67 mmol, 1.0 equiv.) was combined with methyl acrylate (1.0 mL, 11.0 mmol, 3.0 equiv.) in t-butyl alcohol (4.5 mL). N,N,N-trimethyl (benzylammonium hydroxide) was added (0.25 mL, 1.3 mmol). After being stirred for 1 h at reflux, the mixture was cooled to 25° C. and diluted with water and CH$_2$Cl$_2$. The organics were washed with brine, dried with MgSO$_4$ and concentrated under reduced pressure. Purification of the crude material by flash chromatography (SiO$_2$, EtOAc) gave 1.02 g of the product (3.0 mmol, 82%).

c). To a solution of the product prepared above in step b (4.5 mL, 1.4 mmol, 1.0 equiv.) in THF (10 mL) was added solid t-BuOK (158 mg, 1.4 mmol, 1.0 equiv.). After being stirred at 25° C. for 0.5 h, the reaction mixture was neutralized (2N HCl), extracted (3×CH$_2$Cl$_2$), washed with brine, dried with Na$_2$SO$_4$, filtered and concentrated under reduced pressure. Purification of the crude material by flash chromatography (SiO$_2$, EtOAc) gave 302 mg of the product (72%) as a 1.1:1 mixture of ethyl and methyl ester.

d). To a solution of the product prepared above in step c (597 mg, 1.95 mmol, 1.0 equiv.) in water (2 mL), MeOH (2 mL) and THF (2 mL) was added KOH (55 mg, 0.97 mmol, 0.5 equiv.). After being stirred at 75° C. for 12 h, the mixture was cooled to 25° C., diluted with water, extracted (3×CH$_2$Cl$_2$), dried with Na$_2$SO$_4$, and concentrated under reduced pressure. Purification of the crude material by flash chromatography (SiO$_2$, 80% EtOAc/Hexanes→EtOAc containing 2.5% TEA) gave 146 mg of the product (0.58 mmol, 30%.)

e). A solution of product obtained above in step d (65 mg, 0.26 mmol, 1.0 equiv) in DCE (1.5 mL) was treated with cyclopropylamine (27 µL, 0.39 mmol, 1.5 equiv), acetic acid (30 µL, 0.52 mmol, 2.0 equiv) and NaBH(OAc)$_3$ (83 mg, 0.39 mmol, 1.5 equiv) successively. After being stirred at 25° C. for 12 h, the reaction mixture was diluted with 1M NaOH and extracted (2×CH$_2$Cl$_2$). The organics were washed with brine, dried with Na$_2$SO$_4$ and concentrated under reduced pressure to give 75 mg of the crude product, which was used in the next step without further purification.

f). A solution of amine prepared above in step e (74 mg, 0.26 mmol, 1.0 equiv) and (S)-4-(1,1,1-trifluoro-2-hydroxypropan-2-yl)benzoic acid (61 mg, 0.26 mmol, 1.0 equiv) in DMF (1.0 mL) was treated with EDCl (64 mg, 0.33 mmol, 1.3 equiv), HOAt (45 mg, 0.33 mmol, 1.3 equiv) and NaHCO$_3$ (43 mg, 0.51 mmol, 2.3 equiv) successively. After being stirred at 25° C. for 12 h, the reaction was diluted with EtOAc, washed with 1 N NaOH and brine, dried with Na$_2$SO$_4$ and concentrated under reduced pressure. Purification of the crude material by HPLC gave 4.8 mg of trans methyl ester compound (0.0097 mmol, 3.8%), 13.0 mg of cis ethyl ester compound (0.026 mmol, 10%), and 24.0 mg of trans ethyl ester compound (0.048 mmol, 19%).

Methyl ester compound (trans): $^1$H NMR (400 MHz. MeOD) δ 9.28 (dd, J=3.5, 1.2 Hz, 1H), 9.16 (dd, J=5.9, 1.2 Hz, 1H), 7.76 (dd, J=5.9, 2.7 Hz, 1H), 7.70 (d, J=8.2 Hz, 2H), 7.54 (dd, J=8.6, 2.0 Hz, 2H), 4.13 (m, 1H), 3.80 (s, 3H), 2.79 (m, 3H), 2.24 (ddd, J=12.9, 12.9, 2.7 Hz, 2H), 2.08 (m, 2H), 1.87 (dt, J=13.3, 1.9 Hz, 2H), 1.77 (s, 3H), 0.58 (m, 2H), 0.47 (m, 2H).

Ethyl ester compound (cis): $^1$H NMR (400 MHz. MeOD) δ 9.42 (dd, J=2.6, 1.1 Hz, 1H), 9.22 (dd, J=5.5, 1.0 Hz, 1H), 7.94 (dd, J=5.7, 2.8 Hz, 1H), 7.67 (d, J=8.2 Hz, 2H), 7.47 (dd, J=8.8, 1.8 Hz, 2H), 4.12 (m, 1H), 4.10 (q, J=7.0 Hz, 2H), 2.88

(dd, J=14.6, 2.7 Hz, 2H), 2.67 (m, 1H), 2.17 (dd, J=13.3, 4.9 Hz, 2H), 1.94 (m, 4H), 1.74 (s, 3H), 1.16 (t, J=7.2 Hz, 3H), 0.39 (m, 2H), 0.27 (m, 2H).
Ethyl ester compound (trans): $^1$H NMR (400 MHz. MeOD) δ 9.17 (dd, J=2.6, 1.2 Hz, 1H), 9.04 (dd, J=5.5, 1.2 Hz, 1H), 7.65 (dd, J=5.7, 2.7 Hz, 1H), 7.59 (d, J=8.2 Hz, 2H), 7.42 (dd, J=8.8, 1.8 Hz, 2H), 4.16 (q, J=7.0 Hz, 2H), 4.02 (m, 1H), 2.65 (m, 3H), 2.14 (ddd, J=12.9, 12.9, 3.0 Hz, 2H), 1.97 (m, 2H), 1.73 (dd, J=13.1, 2.9 Hz, 2H), 1.65 (s, 3H), 1.16 (t, J=7.0 Hz, 3H), 0.46 (m, 2H), 0.36 (m, 2H).
Example 33
Preparation of N-cyclopropyl-N-((1s,4s)-4-(hydroxymethyl)-4-(pyrimidin-2-yl)cyclohexyl)-4-((S)-1,1,1-trifluoro-2-hydroxypropan-2-yl)benzamide (A)
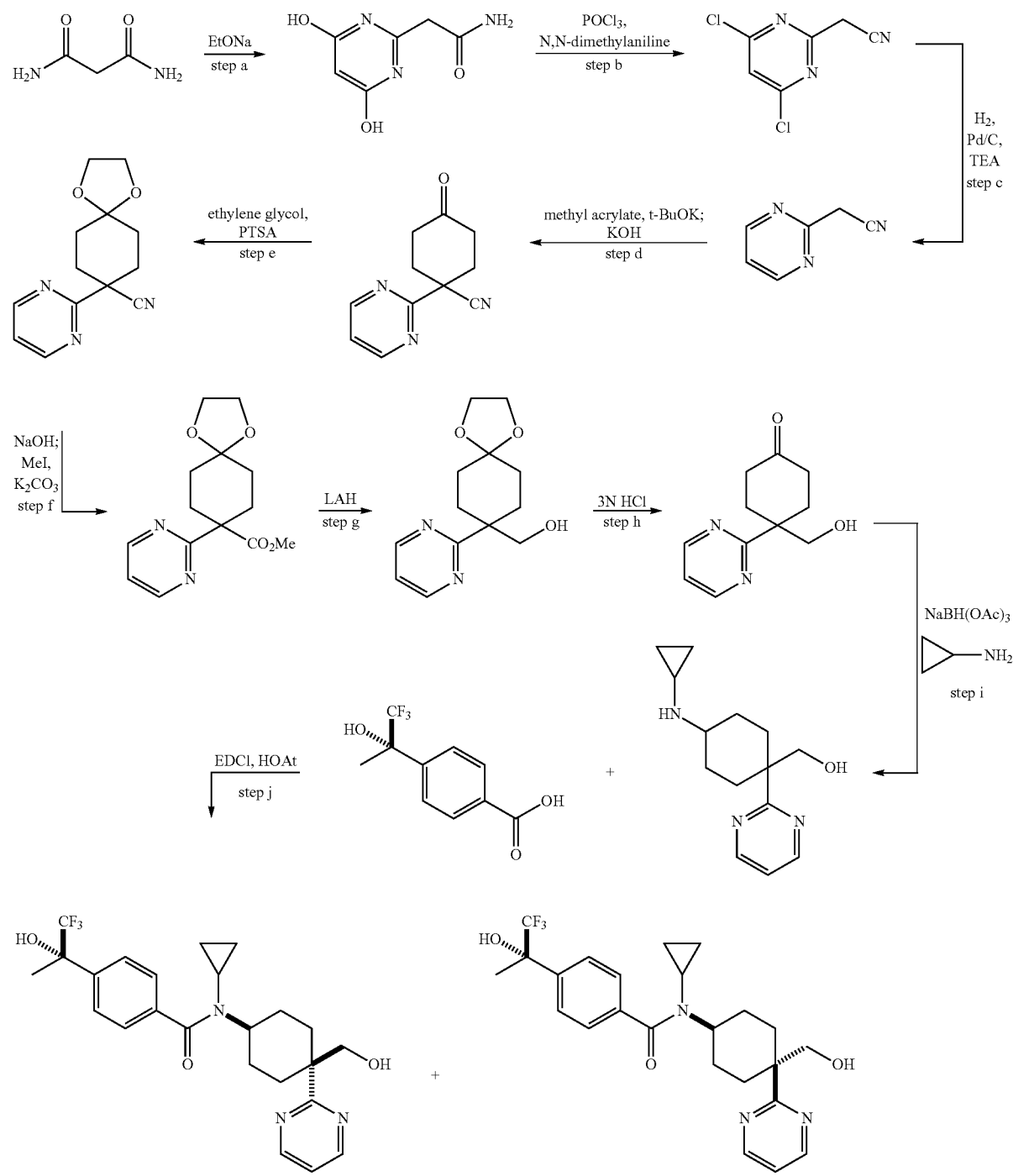

a). To a solution of NaOEt (21% in EtOH, 167 ml, 450 mmol) in EtOH (170 ml) was added malonamide (22.9 g, 224 mmol). After being refluxed for 2 h, half of EtOH was removed under reduced pressure and the precipitated solid was filtered and dried under high vacuum for overnight. The dried solid sodium salt (24 g) was dissolved in ice-cold $H_2O$ (70 mL) and brought to pH 2-3 using 3 N aqueous HCl (50 mL). Recrystallization from water (0° C., 6 h) gave 2-(4,6-dihydroxypyrimidin-2-yl)acetamide (6.28 g, 37.1 mmol, 33%) as a pale yellow solid.

b). A solution of 2-(4,6-dihydroxypyrimidin-2-yl)acetamide (6.28 g, 37.1 mmol) in phosphorous oxychloride (19 ml, 204 mmol) was placed in a flask which was then attached to a reflux condenser. Through the condenser was added N,N-dimethylaniline (10 ml, 79 mmol). The mixture was warmed cautiously in an oil bath which is quickly removed when the reaction began. After the initial vigorous reaction had subsided the reaction was refluxed for ten minutes longer. The hot material was poured over 100 g ice and the resulting suspension was extracted ($3\times CH_2Cl_2$). The combined organic layers were dried ($Na_2SO_4$) and concentrated under reduced pressure. The product was purified by column chromatography ($SiO_2$, 15-20% EtOAc/hexanes) to provide 2-(4,6-dichloropyrimidin-2-yl)acetonitrile (5.10 g, 27.1 mmol, 73%) as a yellow solid.

c). To a solution of 2-(4,6-dichloropyrimidin-2-yl)acetonitrile (4.10 g, 21.8 mmol) and TEA (6.07 ml, 43.6 mmol) in EtOAc/MeOH (1/1, 80 mL) was added 10% Pd/C (800 mg) and the solution was vigorously stirred for 2.5 h under $H_2$ atmosphere (1 atm). The reaction was filtered through celite and washed the celite with MeOH. The combined filtrates were concentrated under reduced pressure and purified by flash chromatography ($SiO_2$, 40-6% EtOAc/flexanes, gradient elution) to provide 2-(pyrimidin-2-yl)acetonitrile (1.56 g, 13.1 mmol, 60%) as a pale red liquid.

d). To a solution of 2-(pyrimidin-2-yl)acetonitrile (290 mg, 2.43 mmol) and methyl acrylate (462 μl, 5.11 mmol) in THF (10 mL) was added t-BuOK (1.0 M in THF, 2.92 ml, 2.92 mmol) at 0° C. After being stirred at 0° C. for 10 min and 25° C. for 50 min, the reaction mixture was quenched with ice-cold $H_2O$, adjusted pH=4 with aqueous 10% citric acid (6 mL), and extracted (3×EtOAc). The combined organic layers were dried over $Na_2SO_4$ and concentrated under reduced pressure to provide crude methyl 5-cyano-2-oxo-5-(pyrimidin-2-yl)cyclohexanecarboxylate as a dark brown solid.

The crude methyl 5-cyano-2-oxo-5-(pyrimidin-2-yl)cyclohexanecarboxylate was completely dissolved in THF/MeOH (1/1, 8 mL) and the clear solution was treated with 1 M aqueous KOH (3.0 mL, 1.2 equiv.) and $H_2O$ (2.5 mL). After being refluxed for 24 h, The organic solvent was removed under reduced pressure. The concentrated reaction was diluted ($H_2O$), neutralized (10% citric acid) and extracted (3×DCM). The combined organics were dried ($Na_2SO_4$) and concentrated under reduced pressure to provide 4-oxo-1-(pyrimidin-2-yl)cyclohexanecarbonitrile (333 mg, 1.66 mmol, 68% yield) as a yellow solid.

e). A solution of 4-oxo-1-(pyrimidin-2-yl)cyclohexanecarbonitrile (333 mg, 1.66 mmol), ethylene glycol (96.9 μl, 1.74 mmol), and p-toluenesulfonic acid monohydrate (15.7 mg, 82.7 μmol) in benzene (10 mL) was refluxed for 1.5 h while the water formed during the reaction was removed azeotropically using a Dean-Stark apparatus. After being cooled down to room temperature, the reaction was diluted ($Et_2O$) and washed ($2\times H_2O$, 2×sat aqueous $NaHCO_3$, and 2× brine). The organic layer was dried ($Na_2SO_4$) and concentrated under reduced pressure. Purification of the residue by flash chromatography ($SiO_2$, 40-50% EtOAc/Hexanes, gradient elution) gave 8-pyrimidin-2-yl-1,4-dioxa-spiro[4,5]decane-8-carbonitrile (325 mg, 1.33 mmol, 80%) as a white solid.

f). To a solution of 8-pyrimidin-2-yl-1,4-dioxa-spiro[4,5]decane-8-carbonitrile (220 mg, 0.897 mmol) in THF (1.3 mL) was added 25% aqueous NaOH (2.3 mL) and MeOH (1.3 mL). After being refluxed for 5.5 h, the reaction was cooled, adjusted to pH 7 (3 N aqueous HCl, ~5 mL), and extracted (3×EtOAc). The combined organics were dried ($Na_2SO_4$) and concentrated under reduced pressure to provide crude 8-pyrimidin-2-yl-1,4-dioxa-spiro[4,5]decane-8-carboxylic acid as a white solid.

To a solution of crude 8-pyrimidin-2-yl-1,4-dioxa-spiro[4,5]decane-8-carboxylic acid and $K_2CO_3$ (227 mg, 1.64 mmol) in DMF (5 mL) was added MeI (76.7 μl, 1.23 mmol) at 25° C. After being stirred at 25° C. for 15 h, DMF was removed under reduced pressure and the residue was diluted ($H_2O$), extracted (2×EtOAc), and washed (2× brine). The combined organic layers were dried ($Na_2SO_4$) and concentrated under reduced pressure. Purification of the residue by flash chromatography ($SiO_2$, 40-50% EtOAc/Hexanes, gradient elution) gave 8-pyrimidin-2-yl-1,4-dioxa-spiro[4,5]decane-8-carboxylic acid methyl ester (170 mg, 0.611 mmol, 74%) as a colorless liquid.

g). To a solution of 8-pyrimidin-2-yl-1,4-dioxa-spiro[4,5]decane-8-carboxylic acid methyl ester (1.02 g, 3.67 mmol) in THF (15 mL) was added LAH (1.0 M in $Et_2O$, 3.67 ml, 3.67 mmol) dropwisely at −45° C. for 10 min. After being stirred at −45° C. for 3 h, the reaction was quenched by adding $H_2O$ (150 μL), 15% aqueous NaOH (150 μL), and $H_2O$ (450 μL) successively and stirred at 25° C. for 1 h. The resulting inorganic gel was removed by filtration and the filter cake was rinsed with EtOAc. The combined filtrates were then concentrated under reduced pressure and purification of the residue by flash chromatography ($SiO_2$, 90-100% EtOAc/Hexanes, gradient elution) gave (8-pyrimidin-2-yl-1,4-dioxa-spiro[4,5]dec-8-yl)-methanol (518 mg, 2.07 mmol, 56%) as a colorless liquid.

h). To a solution of (8-pyrimidin-2-yl-1,4-dioxa-spiro[4,5]dec-8-yl)-methanol (295 mg, 1.18 mmol) in THF (10 mL) was added 3 N aqueous HCl (10 mL) at 25° C. After being stirred at 25° C. for 24 h, THF was removed under reduced pressure and the reaction was neutralized (saturate aqueous $NaHCO_3$) and extracted (4×10% MeOH/DCM). The combined organic layers were dried ($Na_2SO_4$) and concentrated under reduced pressure to provide 4-(hydroxymethyl)-4-(pyrimidin-2-yl)cyclohexanone (238 mg, 1.15 mmol, 98%) as a pale yellow solid.

i). A solution of 4-(hydroxymethyl)-4-(pyrimidin-2-yl)cyclohexanone (238 mg, 1.15 μmol), cyclopropylamine (106 μl, 1.50 mmol), and acetic acid (87 μl, 1.50 mmol) in acetonitrile (6 mL) was treated at 0° C. with $NaBH(OAc)_3$ (367 mg, 1.73 mmol). After being stirred at 25° C. for 20 h, the reaction was then basified (1 M aqueous NaOH, pH~12), extracted (5×10% MeOH/DCM), and washed (1× brine). The combined organic layers were dried ($Na_2SO_4$) and concentrated under reduced pressure to provide (4-(cyclopropylamino)-1-(pyrimidin-2-yl)cyclohexyl)methanol (281 mg, 1.14 mmol, quantitatively) as a pale yellow film.

j). A solution of (4-(cyclopropylamino)-1-(pyrimidin-2-yl)cyclohexyl)methanol (281 mg, 114 mmol) and (S)-4-(1,1,1-trifluoro-2-hydroxypropan-2-yl)benzoic acid (253 mg, 108 mmol) in DMF (2.8 mL) was treated at 0° C. with EDC (327 mg, 1.70 mmol), HOAt (232 mg, 1.70 mmol), and $NaHCO_3$ (286 mg, 3.41 mmol) successively. After being stirred at 25° C. for 20 h, the reaction was diluted (10% aqueous citric acid), extracted (2×EtOAc) and washed (1× brine, 1× saturated $NaHCO_3$, and 1× brine). The combined organic layers were dried ($Na_2SO_4$) and concentrated under reduced pressure. Purification of the crude product using RP HPLC (C18, 35-70% MeCN/$H_2O$ with 0.1% TFA in 30 min) provided the cis isomer (112 mg, 0.24 mmol, 21%) and the title compound A (trans isomer, 127 mg, 0.27 mmol, 24%) as a white solid.

N-cyclopropyl-N-((1r,4r)-4-(hydroxymethyl)-4-(pyrimidin-2-yl)cyclohexyl)-4-((S)-1,1,1-trifluoro-2-hydroxypropan-2-yl)benzamide (cis): $^1$H NMR (400 MHz, DMSO-$d_6$) δ 8.81 (2H, d, J=4.7 Hz), 7.57 (2H, d, J=8.2 Hz), 7.42 (2H, d, J=8.6 Hz), 7.32 (1H, t, J=4.9 Hz), 6.63 (1H, s), 4.00 (1H, s), 3.37-3.69 (3H, m), 2.61 (2H, d, J=12.1 Hz), 1.66-1.79 (7H, m), 1.42-1.58 (2H, m), 0.22 (2H, d, J=5.9 Hz), 0.09 (2H, s); MS (ESI) 464.2 [M+H]$^+$.

N-cyclopropyl-N-((1s,4s)-4-(hydroxymethyl)-4-(pyrimidin-2-yl)cyclohexyl)-4-((S)-1,1,1-trifluoro-2-hydroxypropan-2-yl)benzamide (trans): $^1$H NMR (400 MHz, DMSO-$d_6$) δ 8.75 (2H, d, J=4.7 Hz), 7.61 (2H, d, J=8.2 Hz), 7.48 (2H, d, J=8.6 Hz), 7.31 (1H, t, J=4.9 Hz), 6.65 (1H, s), 4.39 (1H, t, J=5.7 Hz), 3.99 (2H, d, J=5.5 Hz), 3.89 (1H, d), 2.76 (1H, s), 2.16 (4H, t, J=12.5 Hz), 1.72-1.87 (4H, m), 1.71 (3H, s), 0.51 (2H, d, J=5.9 Hz), 0.40 (2H, d, J=2.7 Hz); MS (ESI) 464.2 [M+H]$^+$.

Example 34

Preparation of ((1s,4s)-4-(N-cyclopropyl-4-((S)-1,1,1-trifluoro-2-hydroxypropan-2-yl)benzamido)-1-(pyrimidin-2-yl)cyclohexyl)methyl carbamate

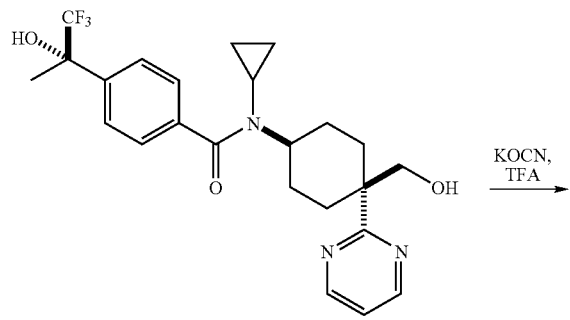

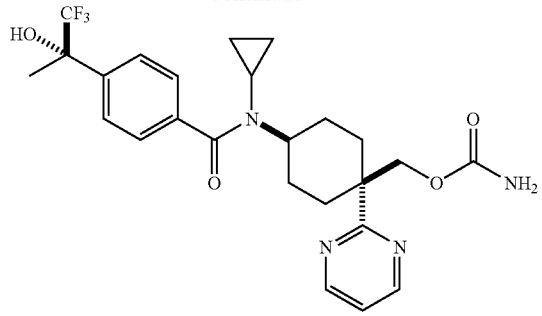

To a mixture of N-cyclopropyl-N-((1s,4s)-4-(hydroxymethyl)-4-(pyrimidin-2-yl)cyclohexyl)-4-((S)-1,1,1-trifluoro-2-hydroxypropan-2-yl)benzamide (118 mg, 0.255 mmol) and potassium cyanate (124 mg, 1.53 mmol) was added TFA (2 mL) at 0° C. After being stirred at 25° C. for 30 min, the reaction was basified (saturated aqueous NaHCO$_3$) and extracted (3×10% MeOH/DCM). The combined organic layers were dried (Na$_2$SO$_4$) and concentrated under reduced pressure. Purification of the residue by flash chromatography (SiO$_2$, 0-10% MeOH/DCM, gradient elution) gave ((1s,4s)-4-(N-cyclopropyl-4-((S)-1,1,1-trifluoro-2-hydroxypropan-2-yl)benzamido)-1-(pyrimidin-2-yl)cyclohexyl)methyl carbamate (30.4 mg, 0.060 mmol, 24%) as a white solid: $^1$H NMR (400 MHz, DMSO-$d_6$) δ 8.78 (2H, d, J=4.7 Hz), 7.61 (2H, d, J=8.2 Hz), 7.49 (2H, d, J=8.6 Hz), 7.34 (1H, t, J=4.9 Hz), 6.66 (1H, s), 6.28 (2H, s), 4.60 (2H, s), 3.95 (1H, s), 2.03-2.30 (4H, m), 1.77-1.95 (4H, m), 1.71 (3H, s), 0.51 (2H, d, J=6.3 Hz), 0.41 (2H, d, J=3.1 Hz); MS (ESI) 507.1 [M+H]$^+$.

Example 35

Preparation of ((1s,4s)-4-(N-cyclopropyl-4-((S)-1,1,1-trifluoro-2-hydroxypropan-2-yl)benzamido)-1-(pyridazin-3-yl)cyclohexyl)methyl carbamate

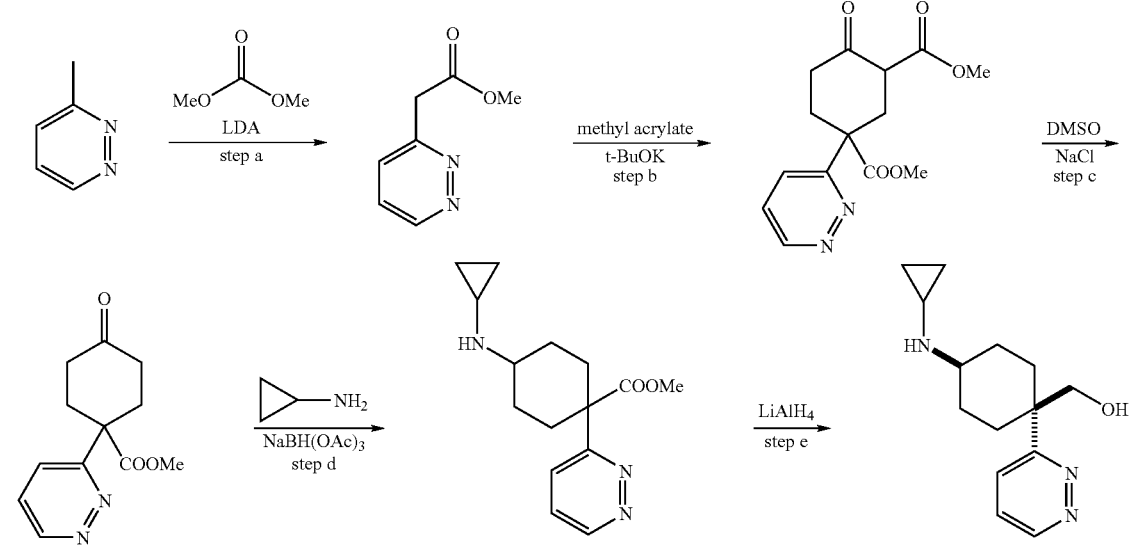

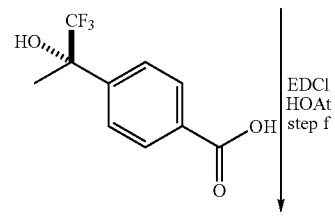

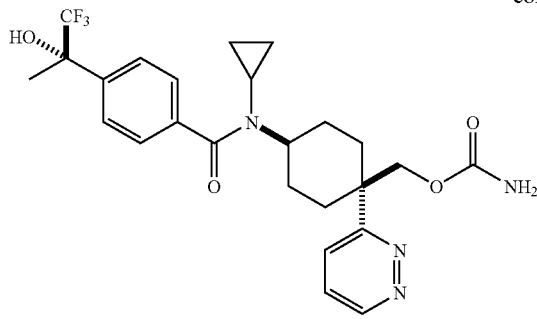 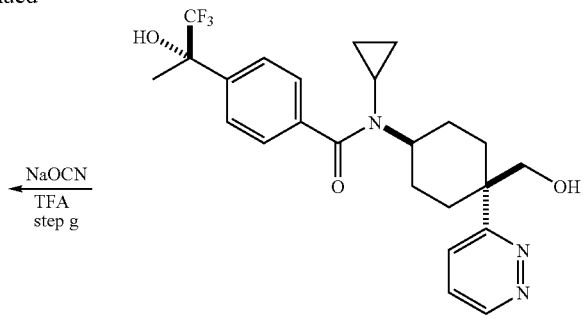

NaOCN
TFA
step g

-continued a). To a solution of diisopropylamine (19 ml, 130 mmol, 1.3 equiv) in dry THF (100 mL) at 0° C. under a N₂, was added n-butyllithium (81 ml, 130 mmol, 1.3 equiv) slowly. The mixture was stirred at 0° C. for 30 min and then cooled to −78° C. A solution of 3-methylpyridazine (9 ml, 100 mmol, 1.0 equiv) in THF (50 mL) was added dropwise over a period of 1:5 min. The resulting mixture was stirred at −78° C. for 1 h, and a solution of dimethyl carbonate (17 ml, 200 mmol, 2 equiv) in THF (50 mL) was added dropwise. The mixture was allowed to warm slowly to 25° C. and stirred for 2 days. Sat.NH₄Cl was added and the resulting solution was extracted with 10% MeOH/DCM. The combined organics were washed with water and brine, dried over Na₂SO₄ and concentrated. The residue was purified by flash chromatography (2.5% MeOH/DCM) to give 1.6 g of methyl 2-(pyridazin-3-yl)acetate as a brown liquid (11 mmol, 11%).

b). To a stirred solution of methyl 2-(pyridazin-3-yl)acetate (304 mg, 2.0 mmol, 1.0 equiv) and methyl acrylate (400 uL, 4.4 mmol, 2.2 equiv) in THF (15 mL) at 25° C., was added solid t-BuOK (336 mg, 3.0 mmol, 1.5 equiv) over 10 minutes. After being stirred at 25° C. for 30 min, the solution was concentrated under reduced pressure and the resulting mixture was quenched (sat. NH₄Cl) and the aqueous solution was extracted (EtOAc). The organics were washed (H₂O and brine), dried (Na₂SO₄) and concentrated under reduced pressure to give 525 mg of the crude product, which was used in the next reaction without further purification.

c). The ketoester (2.32 g, 8 mmol, 1.0 equiv) prepared above was combined with NaCl (467 mg. 8 mmol 1.0 equiv), DMSO (25 mL) and H₂O (2.5 mL). After heating at 150° C. for 24 h the mixture was cooled to r.t, quenched (H₂O), and extracted (EtOAc). The organics were washed (H₂O and brine), dried (Na₂SO₄) and concentrated under reduced pressure. Purification of the residue by flash chromatography (SiO₂, 5% MeOH/DCM) gave 0.8 g of the product as white solid (3.4 mmol, 43%).

d). A solution of ketone (600 mg, 2.56 mmol, 1.0 equiv) prepared step c in acetonitrile (25 mL) was treated with cyclopropylamine (360 ul mg, 5.12 mmol, 2 equiv), acetic acid (145 uL, 2.56 mmol, 1.0 equiv) and NaBH(OAc)₃ (1.09 g, 2.0 equiv) at 0° C. After being stirred at 25° C. for 3 h, the solution was concentrated under reduced pressure and the resulting mixture was quenched (2 N NaOH) and the aqueous solution was extracted (10% MeOH/CH₂Cl₂). The organics were washed (H₂O and brine), dried (Na₂SO₄) and concentrated under reduced pressure to give 0.7 g of the product as a colorless liquid (2.54 mmol, 100%), which was used in the next reaction without further purification.

e). To a solution of the ester prepared in step d (600 mg, 2.2 mmol, 1.0 equiv) in dry THF (15 mL) was slowly added LiAlH₄ (2.2 mL, 1.0 M in THF, 1.0 equiv) at 0° C. After being stirred for 1 h at 0° C., the reaction mixture was quenched (water and 2N NaOH), extracted (10% MeOH/CH₂Cl₂), dried (Na₂SO₄) and concentrated under reduced pressure.

The crude product was purified by flash chromatography (10% MeOH/DCM+2.5% TEA) to provide 220 mg of trans amine (0.89 mmol, 41%).

f). A solution of trans amine (220 mg, 0.89 mmol, 1.0 equiv) prepared in step e and (S)-4-(1,1,1-trifluoro-2-hydroxypropan-2-yl)benzoic acid (208 mg, 0.89 mmol, 1.0 mmol) in DMF (6 mL) was treated at 0° C. with EDCl (222 mg, 1.3 mmol, 1.3 equiv), HOAt (202 mg, 0.89 mmol, 1.0 equiv) and NaHCO₃ (149 mg, 1.8 mmol, 2.0 equiv) successively. After being stirred at 25° C. for 12 h, the reaction was diluted (EtOAc), washed (1N NaOH, sat.NaHCO₃ and brine), dried (Na₂SO₄) and concentrated under reduced pressure. The crude product was purified by the flash chromatography (5% MeOH/DCM) to provide 170 mg of N-cyclopropyl-N-((1s,4s)-4-(hydroxymethyl)-4-(pyridazin-3-yl)cyclohexyl)-4-((S)-1,1,1-trifluoro-2-hydroxypropan-2-yl)benzamide as a white solid (0.37 mmol, 41%). ¹H NMR (DMSO, 500 MHz) δ 9.07 (d, J=5.0 Hz, 1H), 7.72 (d, J=10.0 Hz, 1H), 7.61 (dd, J=10.0, 5.0 Hz, 1H), 7.61 (d, J=10.0 Hz, 2H), 7.50 (d, J=10.0 Hz, 2H), 6.65 (s, 1H), 4.65 (t, J=5.0 Hz, 1H), 3.94 (s, 2H), 3.94 (m, 1H), 2.79 (m, 1H), 2.32-2.20 (m, 4H), 1.84-1.72 (m, 4H), 1.72 (s, 3H), 0.47 (m, 4H).

g). Trifluoroacetic acid (1.2 mL) was added slowly to a stirred mixture of N-cyclopropyl-N-((1s,4s)-4-(hydroxymethyl)-4-(pyridazin-3-yl)cyclohexyl)-4-((S)-1,1,1-trifluoro-2-hydroxypropan-2-yl)benzamide (100 mg, 0.22 mmol, 1.0 equiv) and sodium cyanate (105 mg, 1.3 mmol, 6.0 equiv) at 25° C. After being stirred at 25° C. for 15 minutes, the reaction was quenched (saturated NaHCO₃) and the solution was extracted (EtOAc), washed (brine), dried (Na₂SO₄) and concentrated under reduced pressure. The residue was purified by the flash chromatography (8% MeOH/DCM) to afford 60 mg of ((1s,4s)-4-(N-cyclopropyl-4-((S)-1,1,1-trifluoro-2-hydroxypropan-2-yl)benzamido)-1-(pyridazin-3-yl)cyclohexyl)methyl carbamate as a white solid (0.12 mmol, 55% yield). ¹H NMR (DMSO, 500 MHz) δ 9.10 (d, J=5.0 Hz, 1H), 7.78 (d, J=10.0 Hz, 1H), 7.66 (dd, J=10.0, 5.0 Hz, 1H), 7.63 (d, J=10.0 Hz, 2H), 7.51 (d, J=10.0 Hz, 2H), 6.65 (s, 1H), 6.35 (s, 2H), 4.55 (s, 2H), 3.95 (m, 1H), 2.80 (m, 1H), 2.25 (m, 4H), 2.52 (m, 2H), 1.87 (m, 4H), 1.72 (s, 3H), 0.48 (m, 4H).

Biological Examples

Procedures Useful for the Biological Evaluation of the Benzamide Derivatives

In addition to the extensive literature disclosing the role of HSDs in various diseases and disorders, described herein are assays useful for testing the Benzamide Derivatives of the present invention.

Assays

In Vitro 11β-HSD1 (Hydroxysteroid Dehydrogenase 1) Activity Inhibitory Action The 11β-HSD1 inhibitory activity was examined by quantitative determination by an SPA (scintillation proximity assay) system of the suppressive action on the conversion from cortisone to cortisol using human 11β-HSD1 (hereinafter recombinant 11β-HSD1) expressed using a baculo-virus system as an enzyme source. For the reaction, a reagent was added to a 96 well plate (96 well Opti-plates™-96 (Packard)) to the following final concentration and a volume of 100 µl was reacted at room temperature for 90 min. The reaction solution used was 0.1 µg/ml recombinant 11β-HSD1, 500 µM NADPH, 16 nM $^3$H cortisone (Amersham Biosciences, 1.78 Tbq/mol) dissolved in 0.1% BSA (Sigma)-containing PBS and the test drug was 2 µl of a compound solution (dissolved in DMSO). After 90 min, the reaction was stopped by adding PBS (410 µl, containing 0.1% BSA (Sigma)) containing 0.08 µg of anti-cortisol mouse monoclonal antibody (East Coast Biologics), 365 µg SPA PVT mouse antibody-binding beads (Amersham Biosciences) and 175 µM carbenoxolone (Sigma) to the reaction solution. After the completion of the reaction, the plate was incubated overnight at room temperature and the radioactivity was measured by Topcount (Packard). For control, the value (0% inhibition) of the well containing 2 µl of DMSO instead of the test drug was used, and for positive control, the value (100% inhibition) of the well containing carbenoxolone instead of the test drug at the final concentration of 50 µM was used. The inhibition (%) of the test drug was calculated by ((value of control−value of test drug)/(value of control−value of positive control))×100(%). The $IC_{50}$ value was analyzed using a computer-based curve fitting software.

This example provides assays that are useful in evaluating and selecting a compound that modulates 11β-HSD1.

Biochemical 11β-HSD1 Assay by SPA

Recombinant human, mouse and rat 11-HSD1 were expressed in baculovirus expression system, isolated by affinity purification and used as the enzyme sources for cortisone to cortisol conversion in vitro. $^3$H-Cortisone (Amersham Bioscience, 1.78 Tbq/mol. 49 Ci/mmol) was used as the substrate, and a monoclonal anti-cortisol antibody and the scintillation proximity assay (SPA) system were used to detect the product of the 11β-HSD1-catalyzed reaction, 3H-cortisol. Reactions took place at room temperature for 90 min. in 96-well Opti-plates™-96 (Packard) in 100 µL volume with 2 µL test compounds or control in DMSO, 0.1 µg/mL 11β-HSD1 protein, 500 µM NADPH and 16 nM radioactive cortisone, in PBS buffer supplemented with 0.1% BSA (Sigma). Reaction was stopped with the addition of 40 µL buffer containing 0.08 fig anti-cortisol monoclonal antibody (East Coast Biologics), 365 µg SPA PVT antibody-binding beads (Amersham Biosciences) and 175 µM carbenoxolone (Sigma).

Plates were incubated at room temperature overnight before being read on a Topcount (Packard). The point of 50% inhibition of 11β-HSD1 enzyme activity ($IC_{50}$) was determined by computer-based curve fitting.

Cell-Based 11β-HSD1 Assay by SPA

This cell-based assay measures the conversion of $^3$H-cortisone to $^3$H-cortisol in a HEK-293 cell line stably overexpressing human recombinant 11β-HSD1. HEK-293 cells were grown in DMEM/F12 supplemented with 10% fetal bovine serum, and plated onto poly-D-lysine-coated 96-well assay plates (Costar 3903), 100,000 cells per well in 50 µL assay media (phenol free DMEM/F12 (Invitrogen)+0.2% BSA+1% antibiotic-antimycotic solutions). The solution was incubated at 37° C. for 24 h, and the reaction was initiated by the addition of 25 µL of assay media containing compounds of desired concentration and 25 µL of assay media containing 40 nM of $^3$H-cortisone to each well. The reaction mixture was incubated at 37° C. for 90 min. and the reaction terminated by the addition of 25 µL of assay media containing 0.2 µg of anti-cortisol monoclonal antibody (East Coast Biologics), 500 µg SPA PVT antibody-binding beads (Amersham Biosciences) and 500 µM carbenoxolone (Sigma).

Plates were incubated at room temperature for at least 2 h before being read on Topcount (Packard). The point of 50% inhibition of 11β-HSD1 enzyme activity ($IC_{50}$) was determined by computer-based curve fitting.

Scintillation Proximity Assay

[1,2(n)-$^3$H]-cortisone was purchased from Amersham Pharmacia Biotech. Anti-cortisol monoclonal mouse antibody, clone 6D6.7 was obtained from Immunotech and Scintillation proximity assay (SPA) beads coated with monoclonal antimouse antibodies were from Amersham Pharmacia Biotech. NADPH, tetrasodium salt was from Calbiochem and glucose-6-phosphate (G-6-P) was supplied by Sigma. The human 11-β-hydroxysteroid dehydrogenase type-1 enzyme (11-β-HSD$_1$) was expressed in *Pichia pastoris*. 18-β-glycyrrhetinic acid (GA) was obtained from Sigma. The serial dilutions of the compounds were performed on a Tecan Genesis RSP 150. Compounds to be tested were dissolved in DMSO (1 mM) and diluted in 50 mM Tris-HCl, pH 7.2 containing 1 mM EDTA.

The multiplication of plates was done on a WallacQuadra. The amount of the product [$^3$H]-cortisol, bound to the beads was determined in a Packard, Top Count microplate liquid scintillation counter.

The 11-β-HSD$_1$ enzyme assay was carried out in 96 well microtiter plates (Packard, Optiplate) in a total well volume of 220 µL and contained 30 mM Tris-HCl, pH 7.2 with 1 mM EDTA, a substrate mixture tritiated Cortisone/NADPH (175 nM/181 µM), G-6-P (1 mM) and inhibitors in serial dilutions (9 to 0.15 µM). Reactions were initiated by the addition of human 11-β-HSD1, either as *Pichia pastoris* cell homogenate or microsomes prepared from *Pichia pastoris* (the final amount of enzyme used was varied between 0.057 to 0.11 mg/mL). Following mixing, the plates were shaken for 30 to 45 minutes at room temperature. The reactions were terminated with 10 µL 1 mM GA stop solution. Monoclonal mouse antibody was then added (10 µL of 4 µM) followed by 100 µL of SPA beads (suspended according to the manufacturers instructions). Appropriate controls were set up by omitting the 11β-HSD$_1$ to obtain the non-specific binding (NSB) value.

The plates were covered with plastic film and incubated on a shaker for 30 minutes, at room temperature, before counting. The amount of [$^3$H]-cortisol, bound to the beads was determined in a microplate liquid scintillation counter. The calculation of the $K_i$ values for the inhibitors was performed by use of Activity Base. The $K_i$ value is calculated from $IC_{50}$ and the $K_m$ value is calculated using the Cheng Prushoff equation (with reversible inhibition that follows the Michaelis-Menten equation): $K_i=IC_{50}(1+[S]/K_m)$ [Cheng, Y. C.; Prushoff, W. H. Biochem. Pharmacol. 1973, 22, 3099-3108]. The $IC_{50}$ is measured experimentally in an assay wherein the decrease of the turnover of cortisone to cortisol is dependent on the inhibition potential of each substance.

Cloning, Expression and Purification of 11β-HSD1

The expression and purification of the murine enzyme is described by J. Zhang, et al. Biochemistry, 44, 2005, pp 6948-57. The expression and purification of the human enzyme is similar to that of the murine sequence.

Enzyme Assay:

The IC50 and Ki of the compounds are determined by the following method:
1. Prepare an Assay Buffer, (pH 7.2, 50 mM Tris-HCL, 1 mM EDTA) fresh each week.
2. Prepare the following solutions:
NADPH (Sigma, 200 µM)
$^3$H-Cortisone (Amersham Biosciences, 45 Ci/mmol, 200 nM)
Enzyme Prep (20 nM for human, 10 nM for mouse)
Cortisol Antibody (East Coast Biologicals, (1:50 dilution)
Anti-mouse SPA beads (Amersham Biosciences, 15 mg/ml)
18β-Glycyrrhetinic acid ("GA")(Aldrich, 1 µM)
Compound Stock Solution (10 mM in DMSO), serially diluted in assay buffer. Each compound is tested at six different concentrations usually (10 µM to 0.1 nM). All of the solutions and dilutions are made in the Assay Buffer.
3. Assay is run using white/white, 96-well assay plates (Corning) in a total volume of 100 µL.
4. Into each well of a 96-well plate is added Assay Buffer (30 µL), compound (10 µL) NADPH (10 µL), and $^3$H-cortisone (10 µL).
5. Initiate reaction by adding 40 µL of HSD-1 enzyme prep to the wells.
6. The plate is covered with tape and incubated on an orbital shaker for 1 h at RT.
7. After 1 h, the tape is removed and anti-cortisol antibody (10 µL), GA solution (10 µL), and SPA bead preparation (100 µL) is added.
8. The plate is incubated (30 min) on an orbital shaker at RT.
9. The counts are read on a TopCount NXT reader.
10. A dose-response curve is first plotted using the Graphpad Prism software, to generate the IC50 values.

With this IC50 value and the known Km value for the substrate and HSD1 enzyme, an estimated Ki can be calculated with the Chen and Prusoff equation {Ki=IC50/[1+(substrate/Km)]}.

The compounds of the present invention all show 11β-HSD1 enzyme activity (IC$_{50}$) in the assays ranging from 1000 nM to <1 nM.

What is claimed is:

1. A compound having the formula (I):

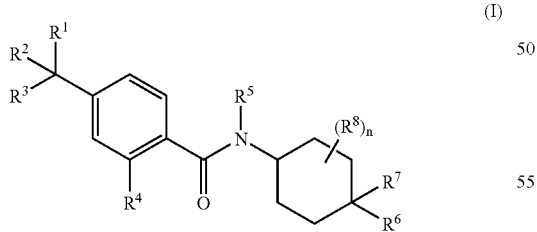

(I)

or pharmaceutically acceptable salts, solvates, stereoisomers or prodrugs thereof,
wherein:
n is 0;
$R^1$ is a member selected from the group consisting of —OH, halogen and $(C_1-C_8)$haloalkyl;
$R^2$ and $R^3$ are members independently selected from the group consisting of halogen, $(C_1-C_8)$alkyl, $(C_2-C_8)$alkenyl, $(C_2-C_8)$alkynyl, $(C_1-C_8)$alkoxy, $(C_1-C_8)$haloalkyl, $(C_2-C_8)$hydroxyalkyl and $(C_3-C_8)$cycloalkyl, wherein no more than two of $R^1$, $R^2$ and $R^3$ are halogen;
$R^4$ is a member selected from the group consisting of hydrogen, halogen, $(C_1-C_8)$alkyl and $(C_3-C_8)$cycloalkyl;
$R^5$ is selected from the group consisting of $(C_1-C_8)$alkyl, $(C_1-C_8)$haloalkyl, $(C_2-C_8)$hydroxyalkyl, $(C_3-C_8)$cycloalkyl, and $(C_3-C_8)$heterocycloalkyl;
$R^6$ is selected from the group consisting of $(C_2-C_8)$alkenyl, $(C_1-C_8)$haloalkyl, aryl$(C_1-C_6)$alkyl, $(C_3-C_8)$cycloalkyl, $(C_3-C_8)$heterocycloalkyl, heteroaryl, and aryl;
wherein each aryl and heteroaryl group is optionally substituted by substituents numbering from one to the number of open valences on the aryl or heteroaryl group selected from the group consisting of -halo, —OR', —OC(O)R', —NR'R", —SR', —R', —CN, —NO$_2$, —CO$_2$R', —C(O)NR'R", —C(O)R', —OC(O)NR'R", —NR"C(O)R', —NR"CO$_2$R', —NR'"C(O)NR'R", —NR'"SO$_2$NR'R", —NHC(NH$_2$)=NH, —NR'C(NH$_2$)=NH, —NH—C(NH$_2$)=NR', —S(O)R', —SO$_2$R', —SO$_2$NR'R", —NR"SO$_2$R', —N$_3$, —CH(Ph)$_2$, perfluoroalkoxy and perfluoro(C$_1$-C$_4$)alkyl;
wherein $R^5$ or $R^6$ is optionally substituted with from one to two members selected from the group consisting of halogen, —CN, —NO$_2$, (C$_1$-C$_4$)alkyl, (C$_2$-C$_8$)alkenyl, (C$_2$-C$_8$)alkynyl, (C$_1$-C$_4$)alkoxy, (C$_1$-C$_4$)haloalkyl, (C$_2$-C$_4$)hydroxyalkyl, —C(O)R', —C(O)OR', —NR'C(O)OR', —OR', —SR', —OC(O)R', —C(O)N(R')$_2$, —S(O)R', —SO$_2$R', —SO$_2$N(R')$_2$, —N(R')$_2$, —NR'C(O)R' and —NR' SO$_2$R';
$R^7$ is selected from the group consisting of —CN, (C$_2$-C$_8$)alkyl, (C$_2$-C$_8$)alkenyl, (C$_2$-C$_8$)alkynyl, (C$_1$-C$_8$)haloalkyl, (C$_1$-C$_8$)hydroxyalkyl, —C(O)R', —C(O)OR', —NR'C(O)OR', —OR', —OC(O)R', —C(O)N(R')$_2$, —S(O)R', —SO$_2$R', —SO$_2$N(R')$_2$, —N(R')$_2$, —NR'C(O)R', —NR'SO$_2$R', —X—CN, —X—C(O)R', —X—C(O)OR', —X—NR'C(O)OR', —X—OR', —X—OC(O)R', —X—C(O)N(R')$_2$, —X—S(O)R', —X—SO$_2$R', —X—SO$_2$N(R')$_2$, —X—N(R')$_2$, —X—NR'C(O)R',
wherein each alkyl, alkenyl, and alkynyl can be substituted by one to three substitutents selected from the group consisting of —OR', =O, =NR', =N—OR', —NR'R", —SR', -halo, —SiR'R"R'", —OC(O)R', —C(O)R', —CO$_2$R', —CONR'R", —OC(O)NR'R", —NR"C(O)R', —NR'"C(O)NR'R", —NR'"SO$_2$NR'R", —NR"CO$_2$R', —NHC(NH$_2$)=NH, —NR'C(NH$_2$)=NH, —NHC(NH$_2$)=NR', —S(O)R', —SO$_2$R', —SO$_2$NR'R", —NR"SO$_2$R', —CN and —NO$_2$;
$R^6$ and $R^7$ may be combined to form a (C$_3$-C$_8$)cycloalkyl or (C$_3$-C$_8$)heterocycloalkyl;
$R^8$ is selected from the group consisting of halogen, —CN, (C$_1$-C$_6$)alkyl, (C$_1$-C$_6$)alkyloxy, and —OH;
X is a branched or straight chain (C$_1$-C$_8$)alkylene group;
each occurrence of R', R", and R'" is independently hydrogen or an unsubstituted member selected from the group consisting of (C$_1$-C$_8$)alkyl, (C$_2$-C$_8$)alkenyl, (C$_2$-C$_8$)alkynyl, (C$_1$-C$_4$)alkoxy(C$_1$-C$_4$)alkyl, (C$_1$-C$_8$)haloalkyl, (C$_2$-C$_8$)hydroxyalkyl, (C$_3$-C$_8$)cycloalkyl, (C$_3$-C$_8$)heterocycloalkyl, heteroaryl, aryl, (C$_3$-C$_8$)cycloalkyl(C$_1$-C$_6$)alkyl, (C$_3$-C$_8$)heterocycloalkyl(C$_1$-C$_6$)alkyl, heteroaryl(C$_1$-C$_6$)alkyl, aryl(C$_1$-C$_6$)alkyl, or two R' groups, when attached to the same nitrogen atom, can be combined with the nitrogen atom to which they are attached to form a heterocycle or heteroaryl group; and with the proviso that when R¹ is —OH, then R² and R³ are not both CF₃.

2. The compound of claim 1, or a pharmaceutically acceptable salt, solvate, stereoisomer, or prodrug thereof, wherein:
n is 0;
R¹ is —OH; R² is (C₁-C₃)alkyl; and R³ is (C₁-C₃)haloalkyl;
R⁵ is selected from the group consisting of (C₁-C₄)alkyl, (C₃-C₆)cycloalkyl, (C₁-C₃)haloalkyl; and
R⁶ is selected from the group consisting of (C₃-C₈)cycloalkyl, aryl, and heteroaryl.

3. The compound of claim 2, wherein R⁶ is optionally substituted phenyl or pyridinyl.

4. The compound of claim 2, wherein R⁶ is cyclopropyl.

5. The compound of claim 1, wherein R¹ is —OH, R² is methyl, and R³ is trifluoromethyl.

6. The compound according to claim 5, wherein R¹, R², and R³, together with the carbon atom to which they are attached, are an (S)-trifluoromethyl carbinol group of the formula:

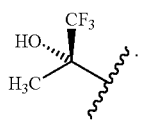

7. The compound according to claim 5, wherein R¹, R², and R³, together with the carbon atom to which they are attached, are an (R)-trifluoromethyl carbinol group of the formula:

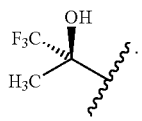

8. A pharmaceutical composition comprising the compound of claim 1, and a pharmaceutically acceptable carrier.

9. A pharmaceutical composition comprising the compound of claim 1, and an additional therapeutic agent.

10. A pharmaceutical composition of claim 9, wherein the additional therapeutic agent is useful for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, cognitive disorders, dementia, depression, psoriasis, glaucoma, osteoporosis, a viral infection, an inflammatory disorder and an immune disorder.

11. A method for treating a condition or disorder selected from the group consisting of diabetes, syndrome X, obesity, Cushing's syndrome, and atherosclerosis, comprising administering to a patient in need thereof a therapeutically effective amount of a compound of claim 1.

12. The method of claim 11, wherein the condition or disorder is diabetes or obesity.

13. A compound selected from the group consisting of:

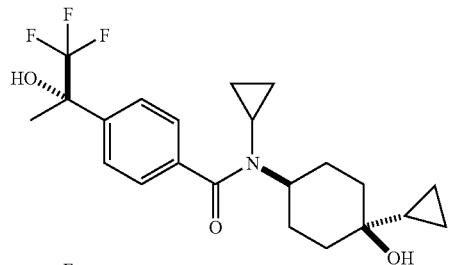

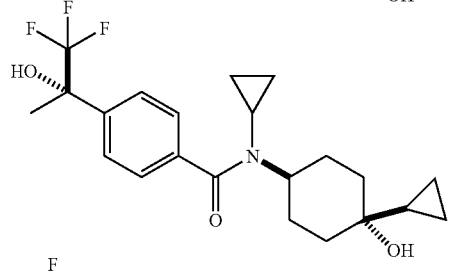

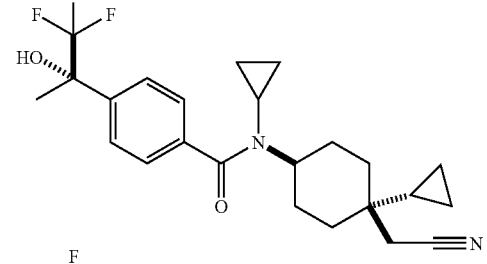

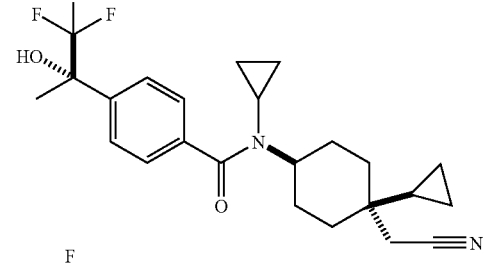

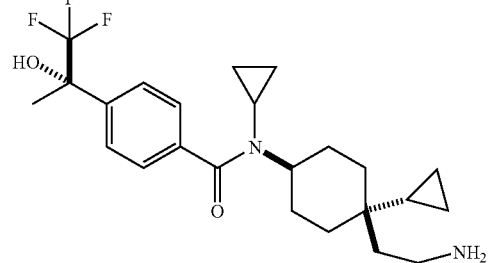

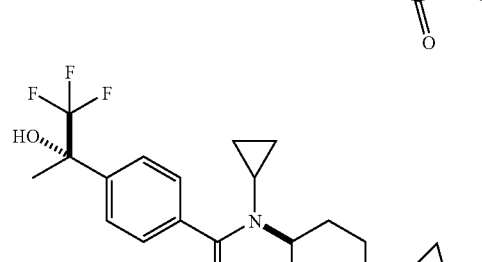

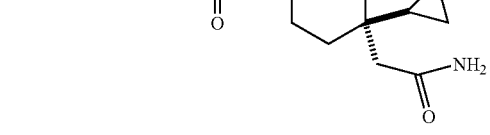

157
-continued
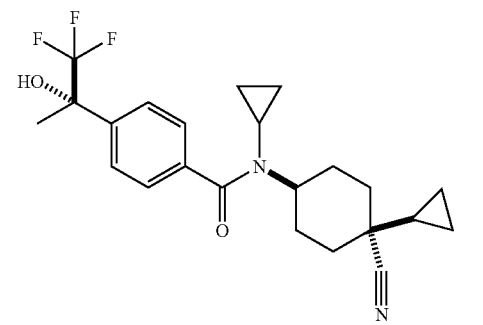
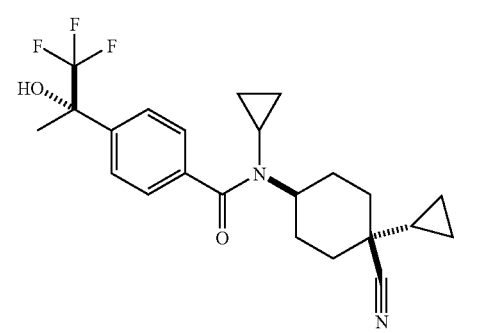
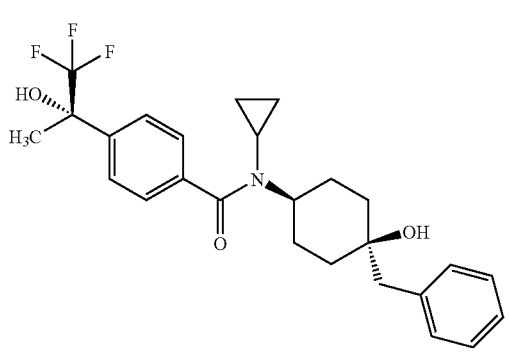
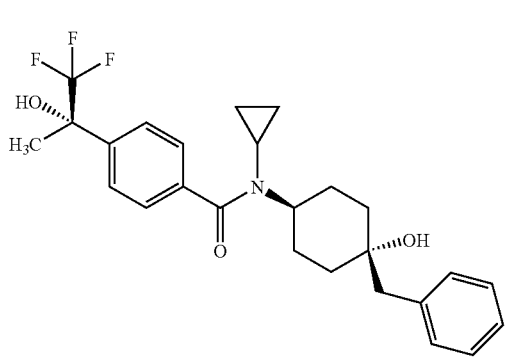
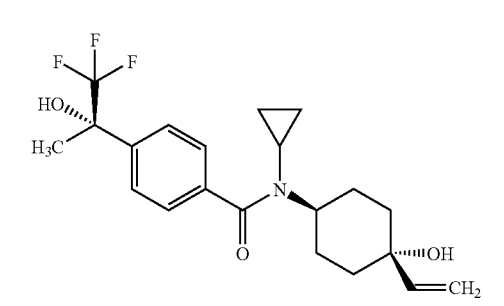
158
-continued
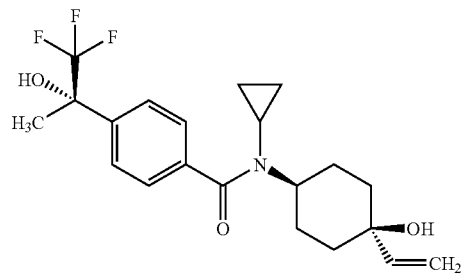
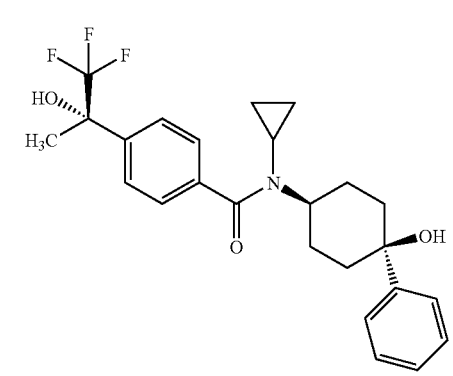
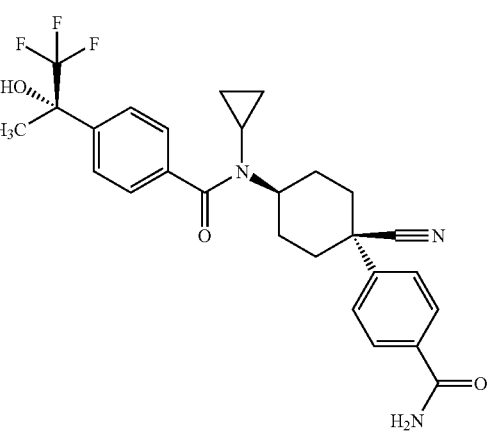
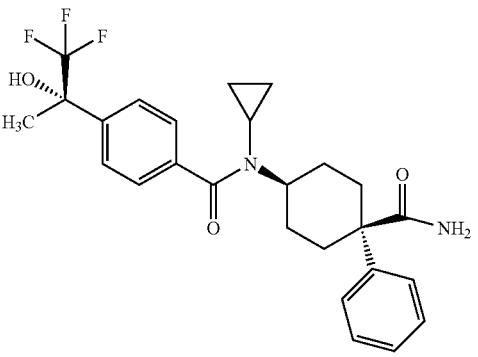

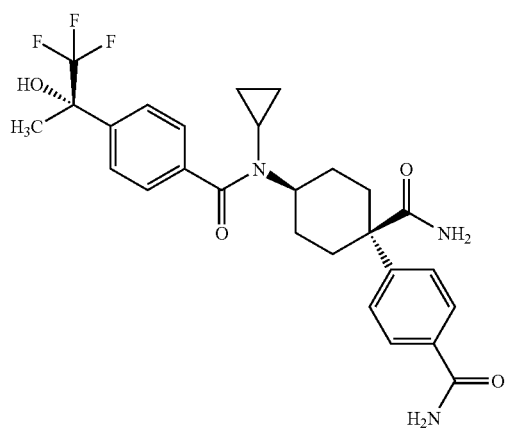
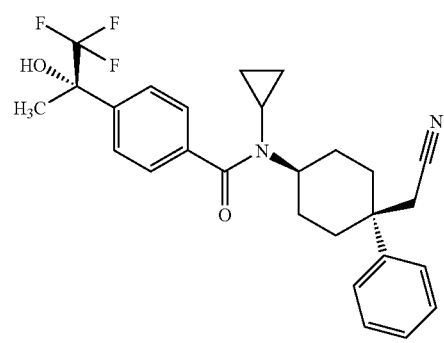
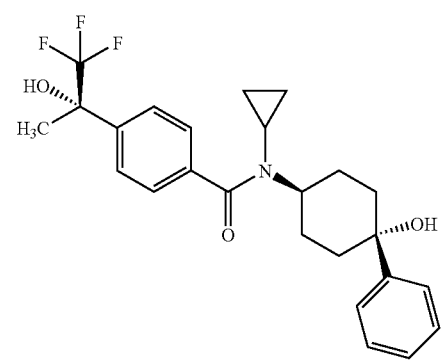
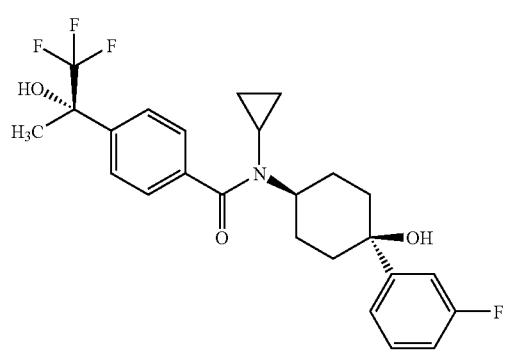
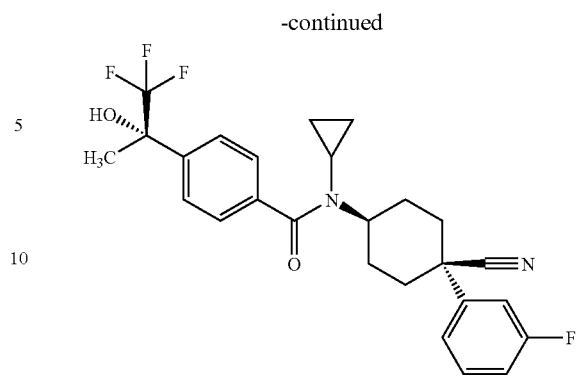
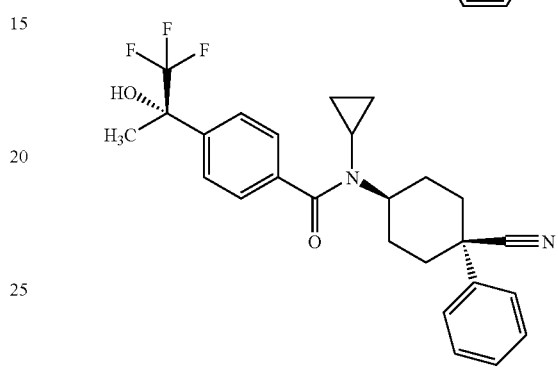
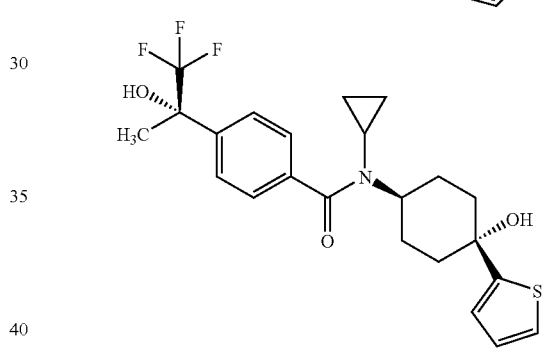
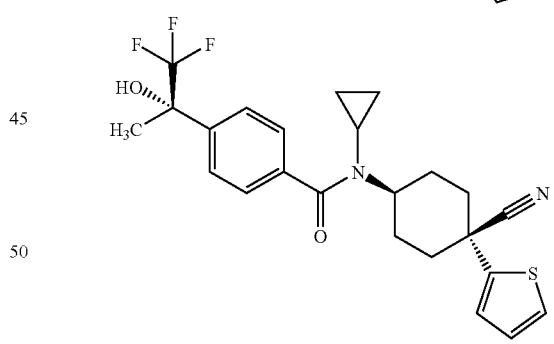
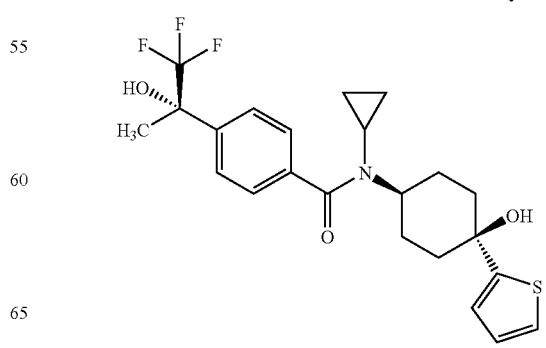

161
-continued
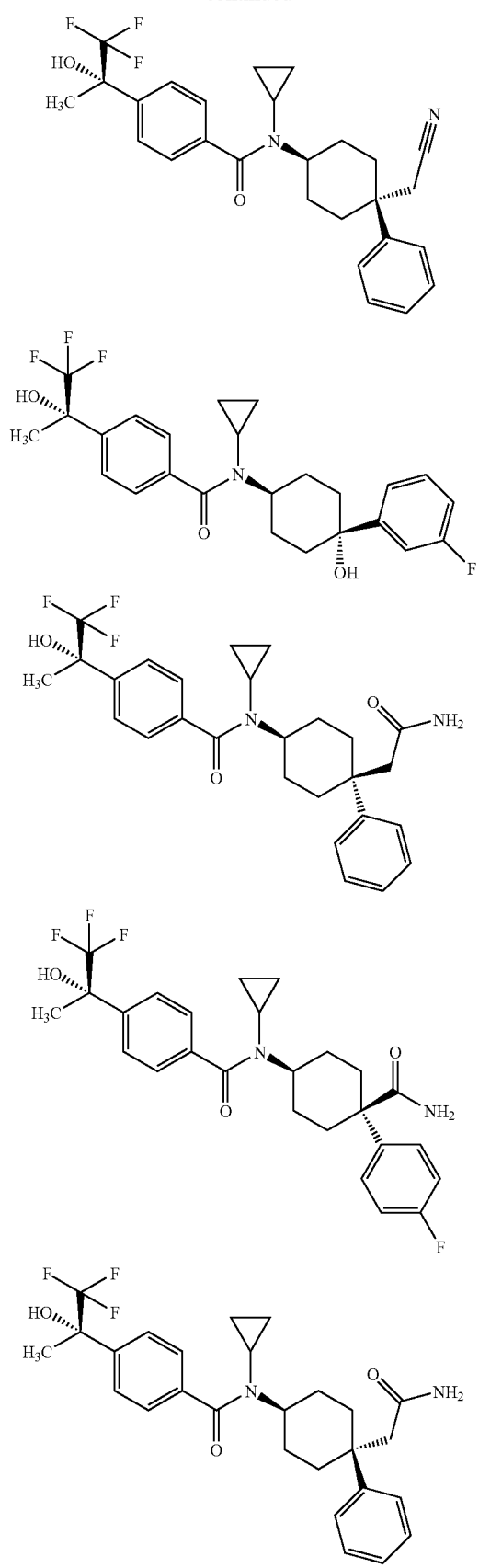
162
-continued
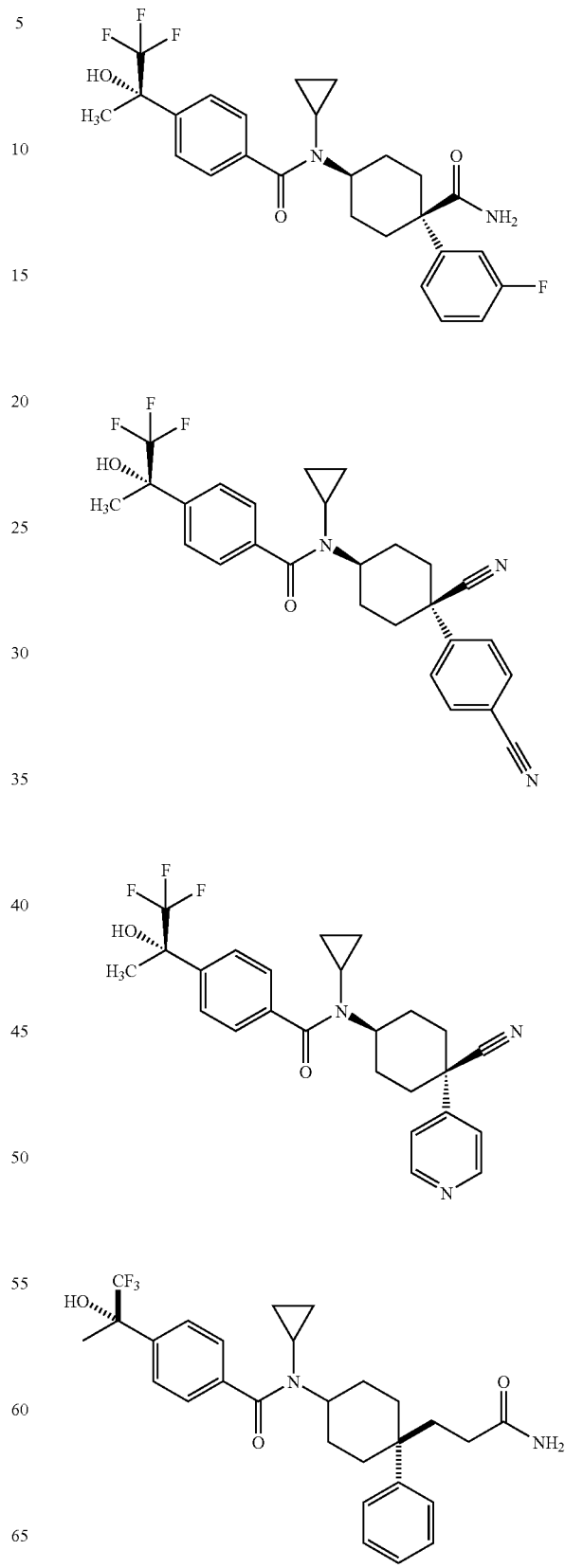

163
-continued
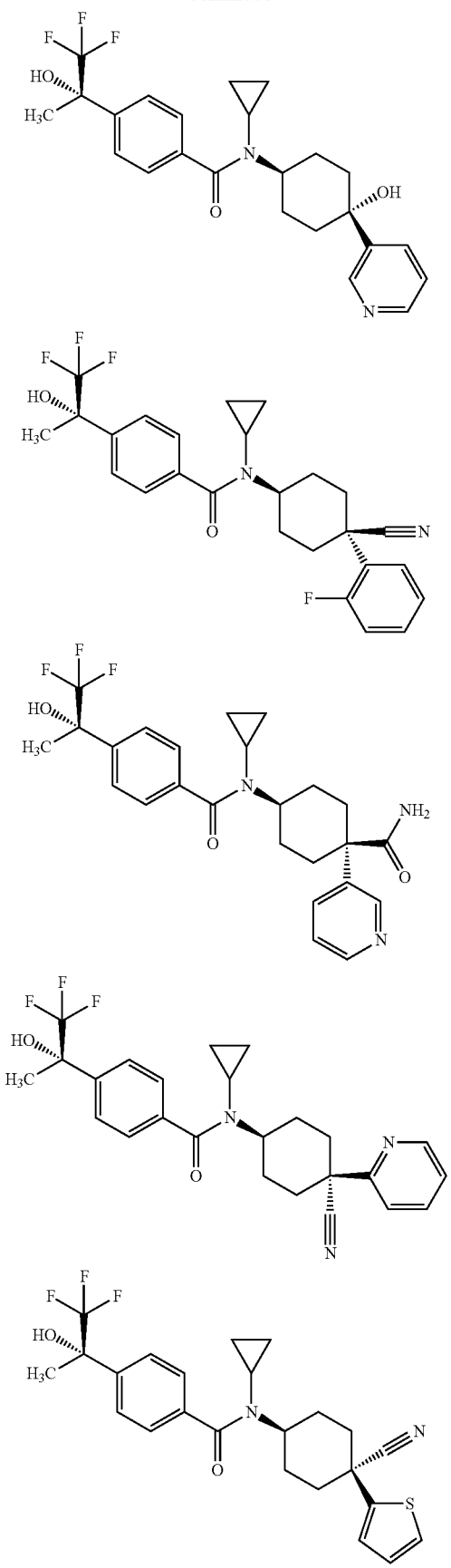
164
-continued
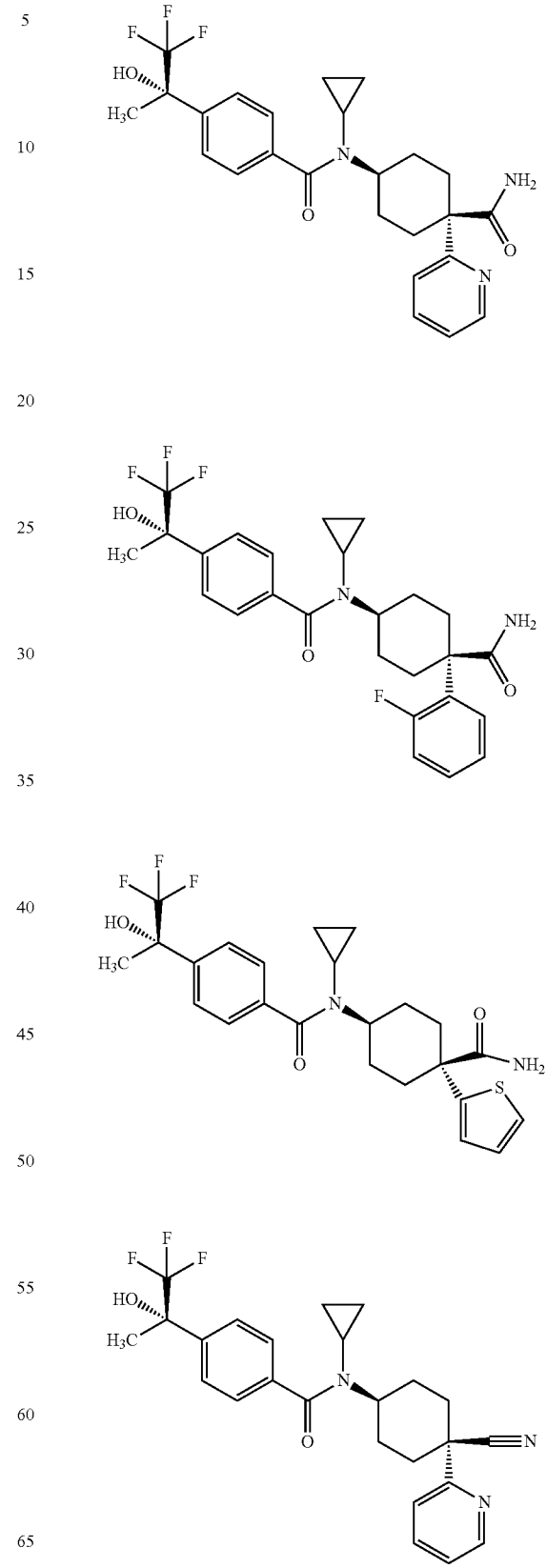

165
-continued
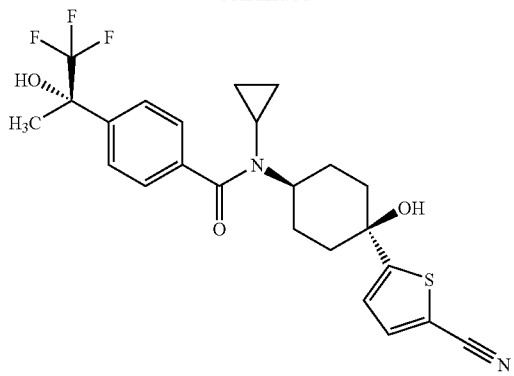
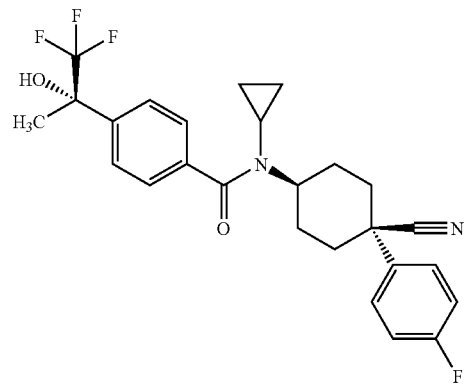
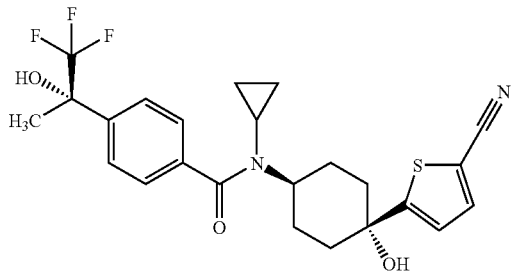
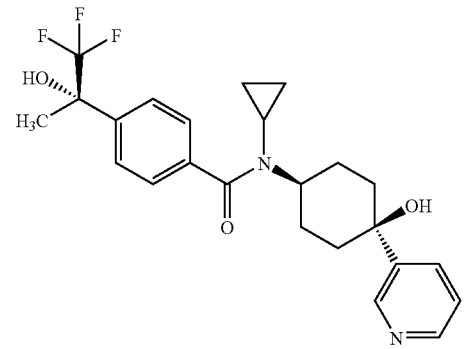
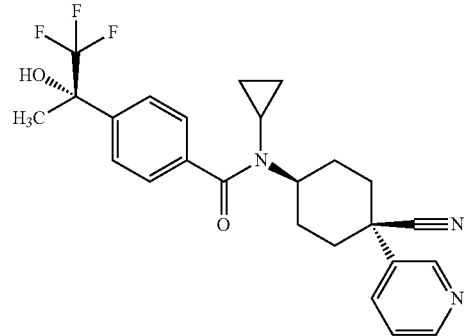
166
-continued
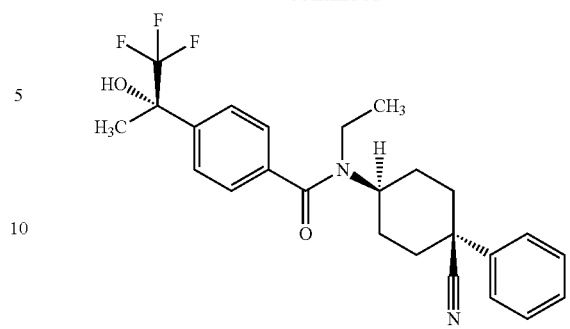
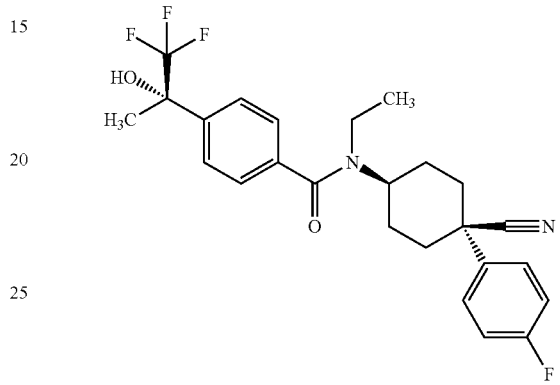
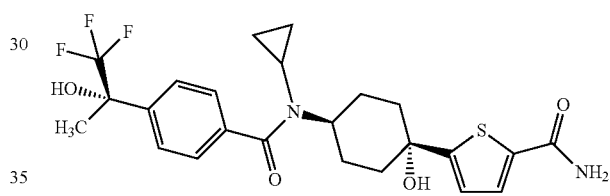
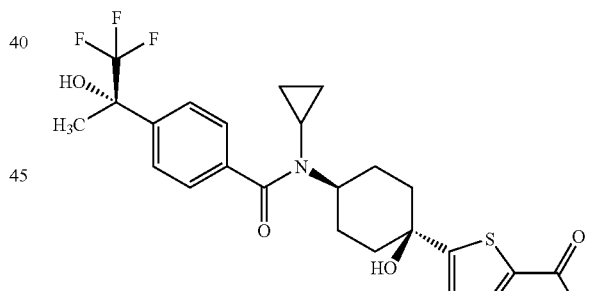
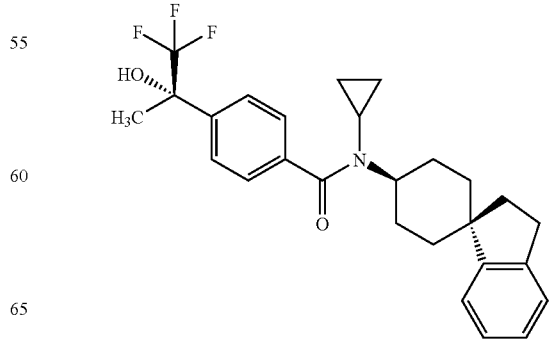

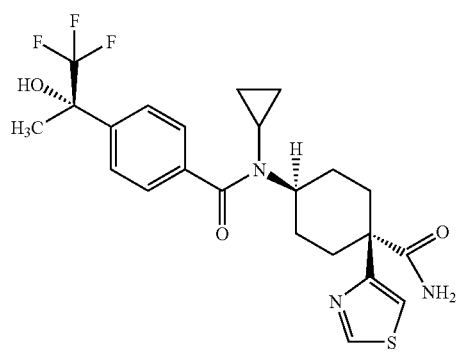
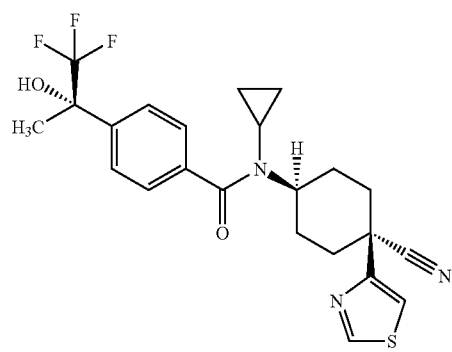
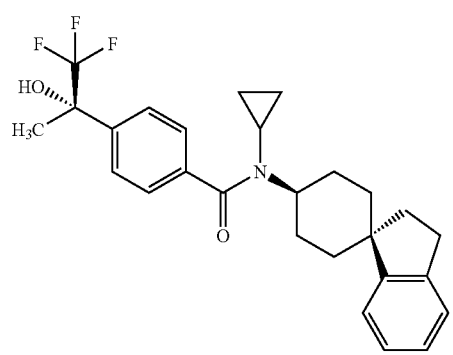
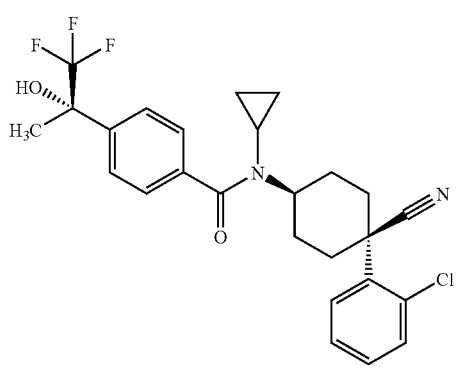
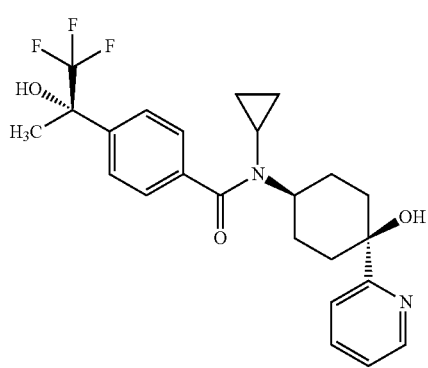
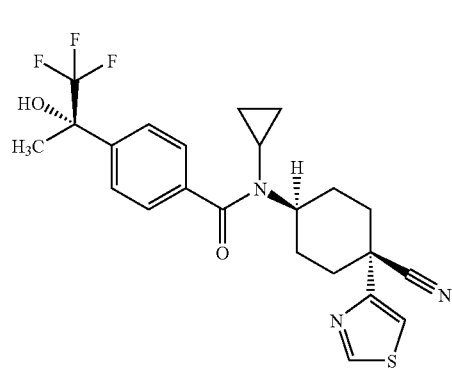
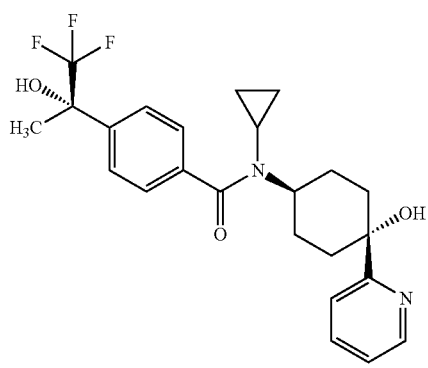
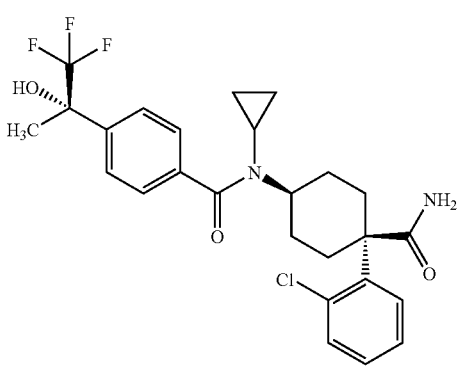

-continued
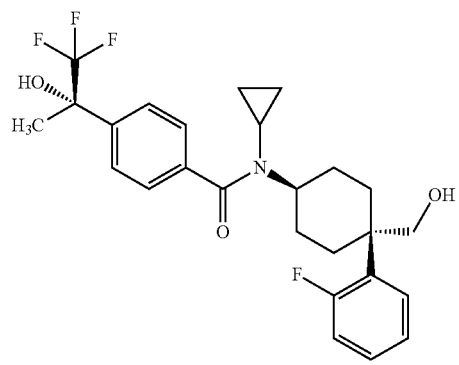
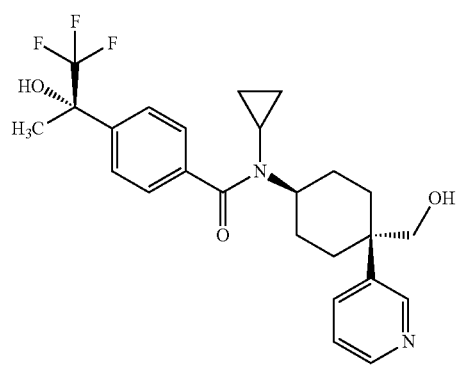
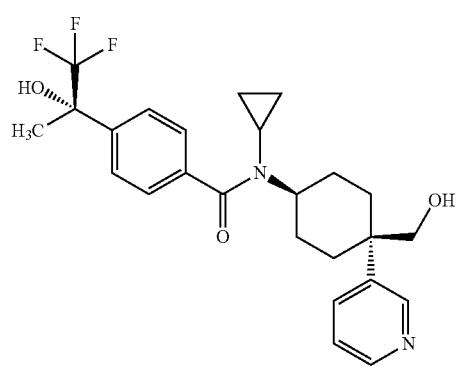
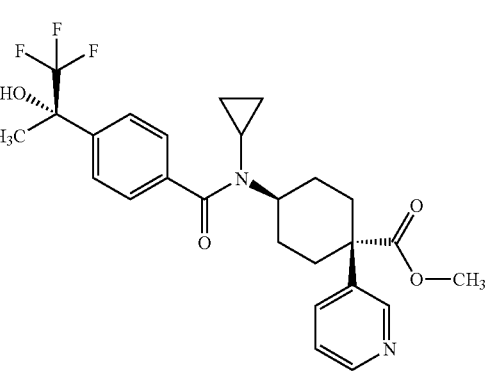
-continued
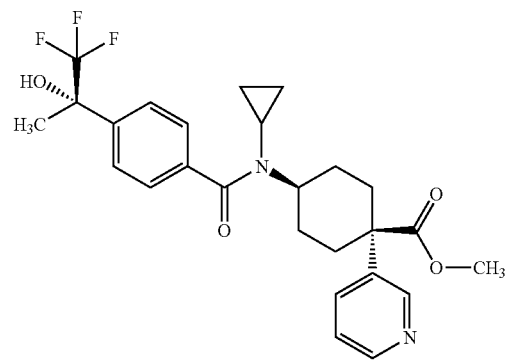
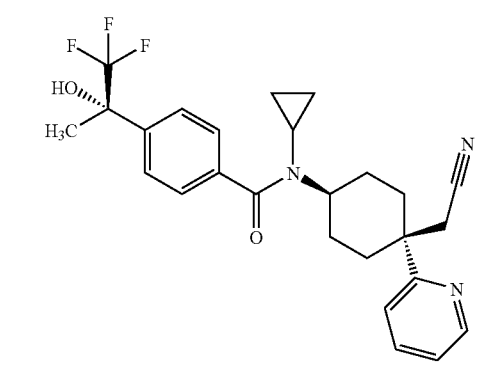
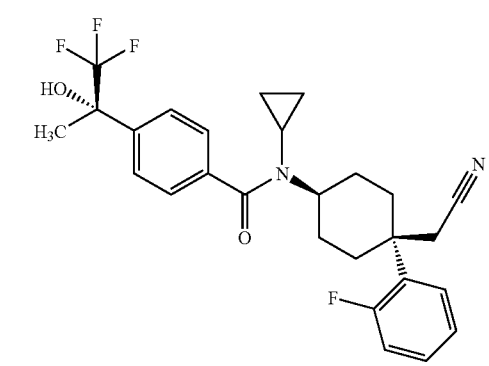
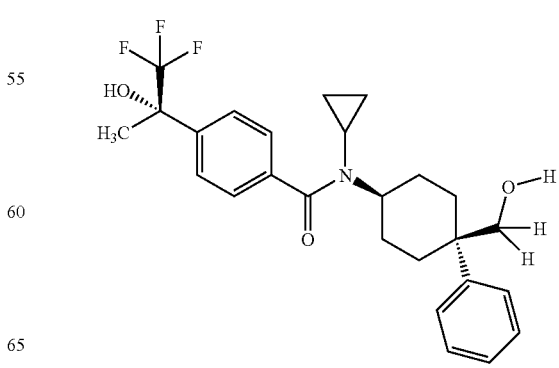

-continued
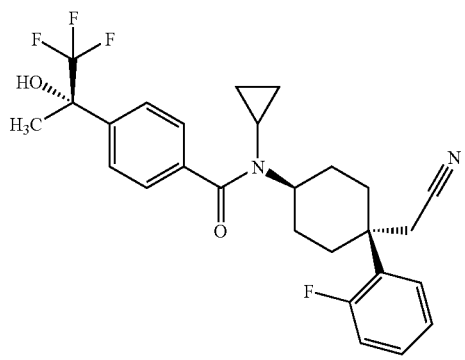
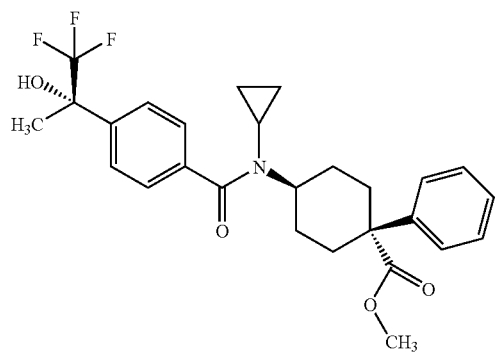
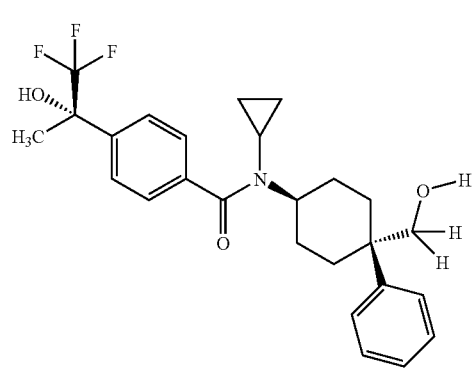
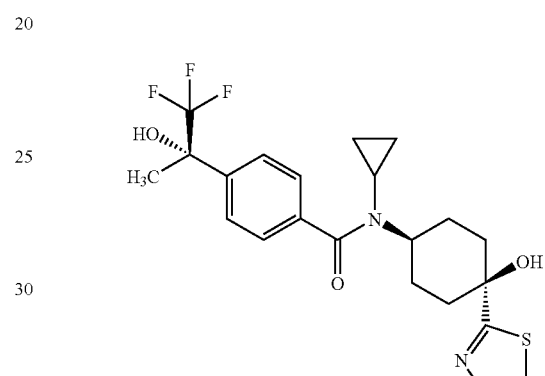
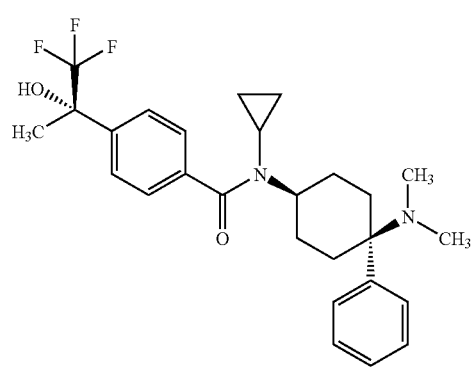
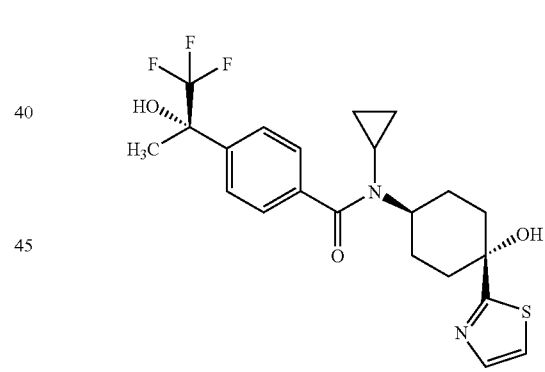
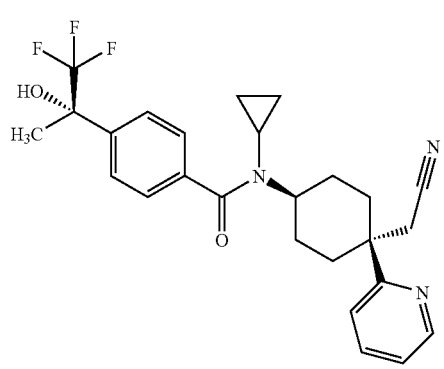
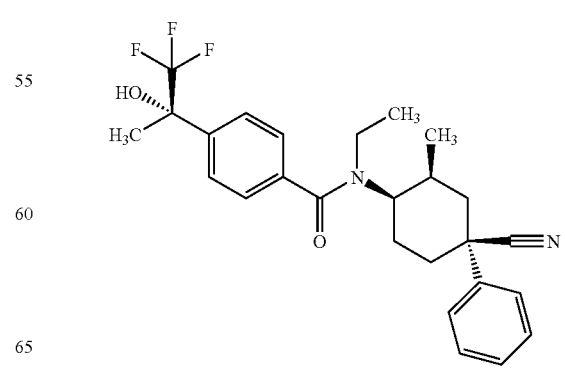

-continued

-continued
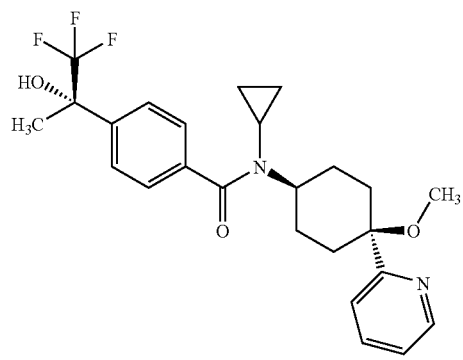
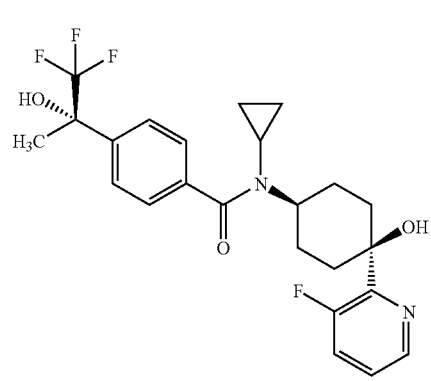
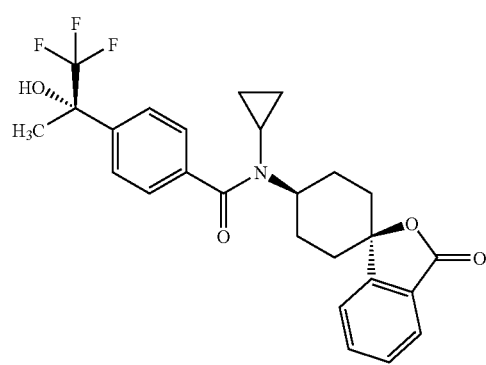
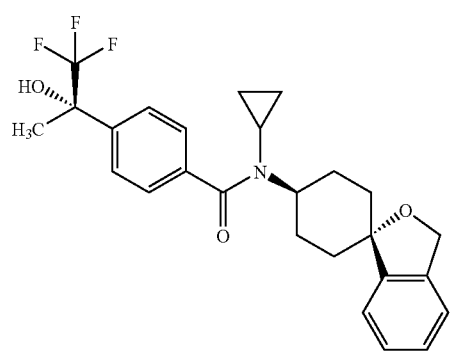
-continued
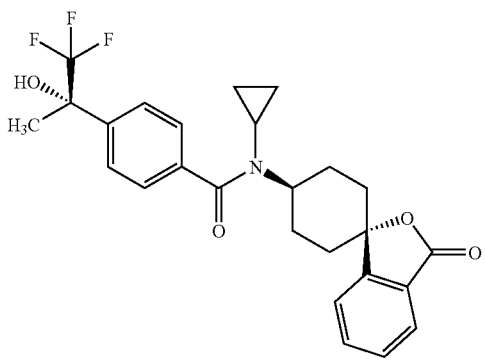
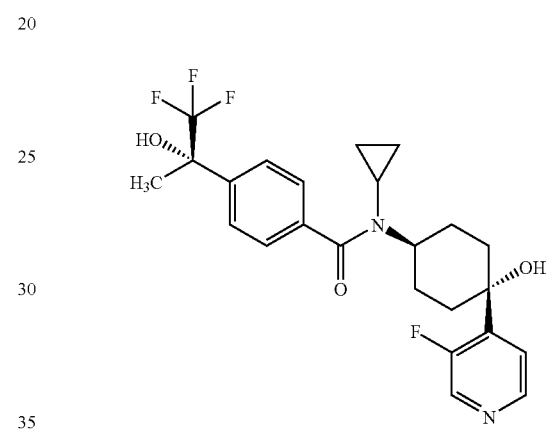
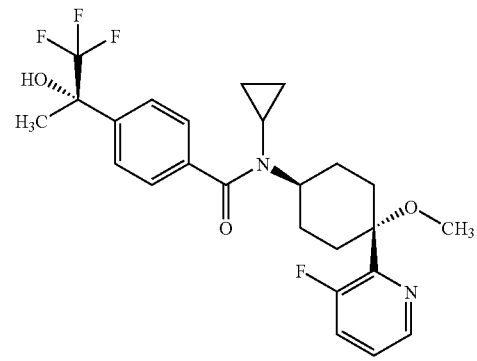
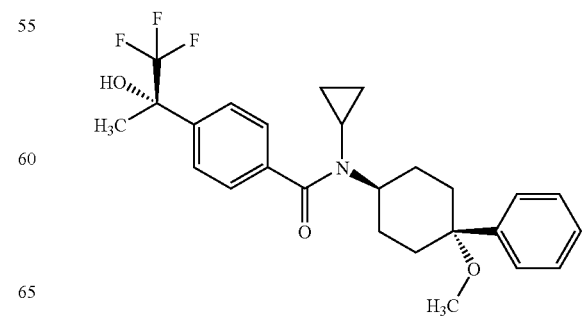

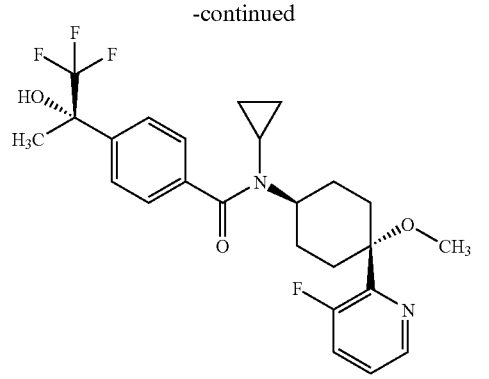
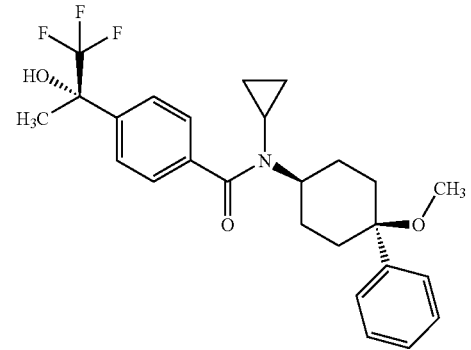
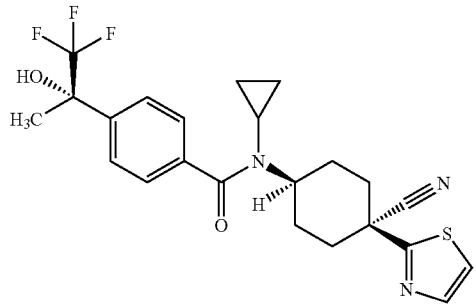
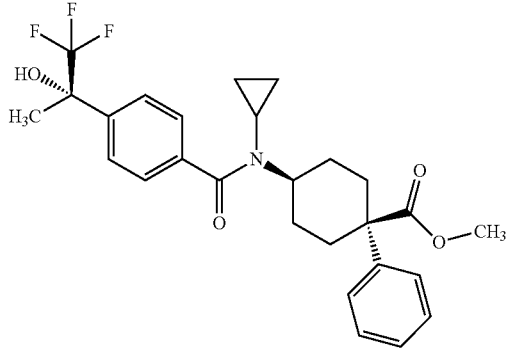
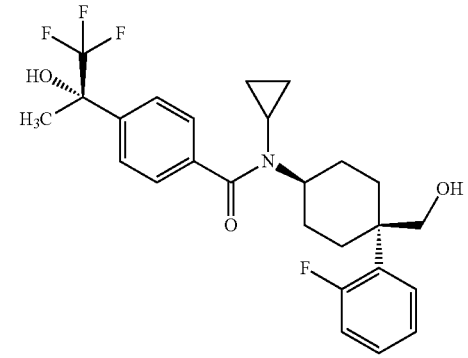
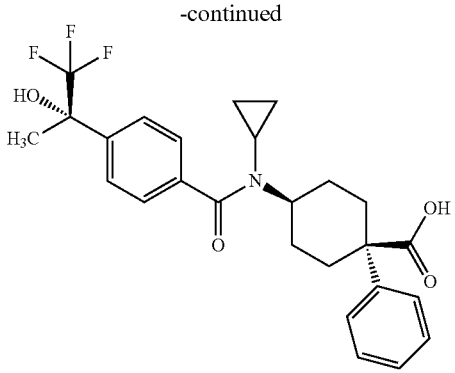
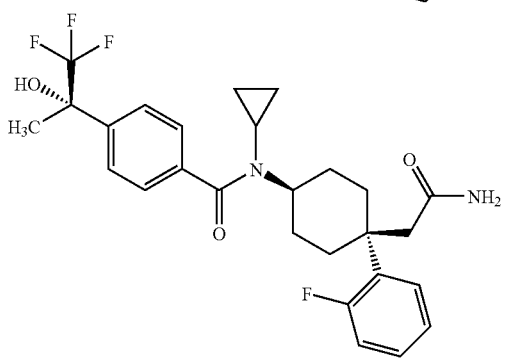
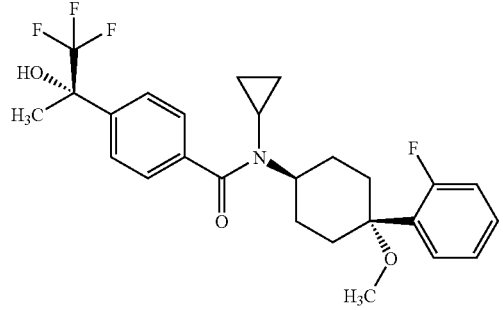
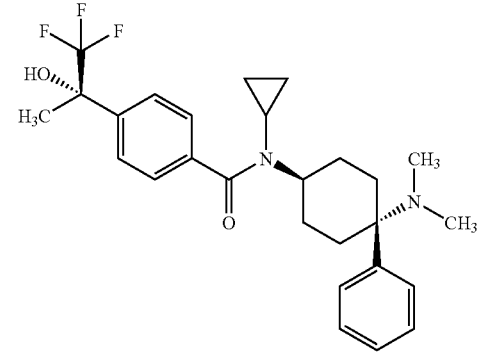
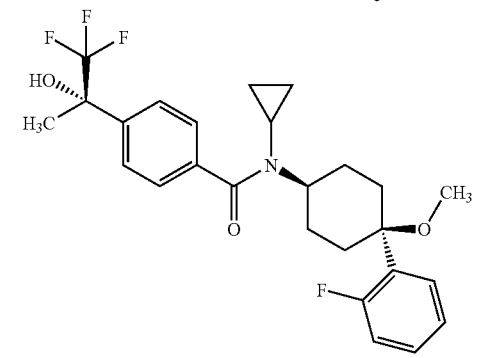

-continued
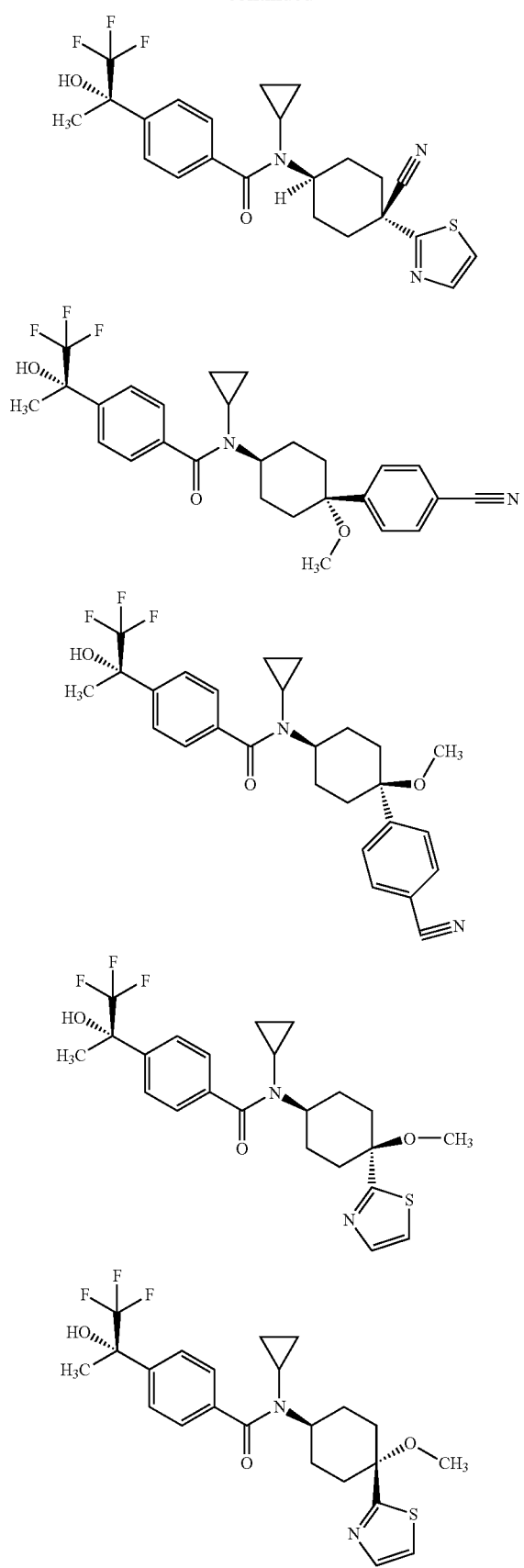
-continued
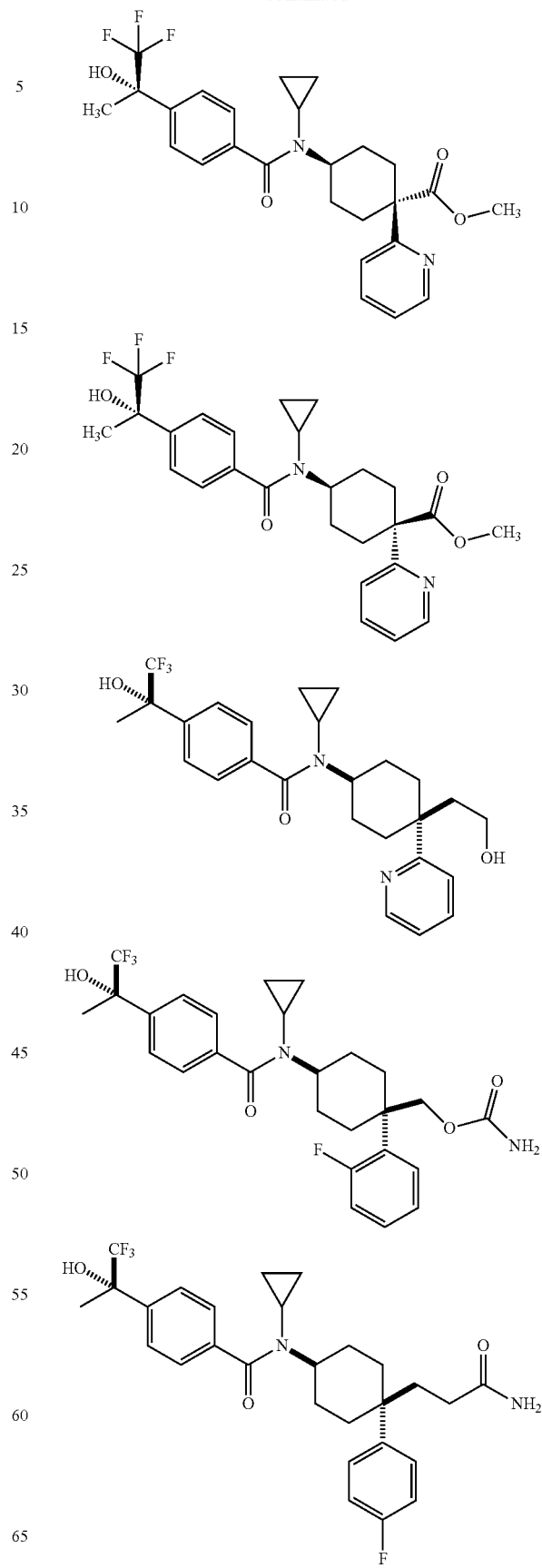

181
-continued
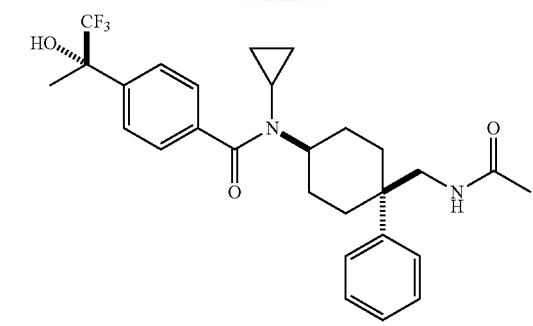
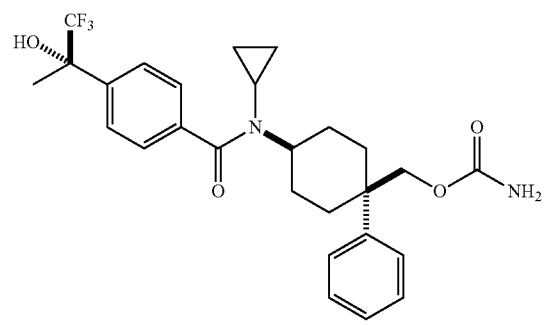
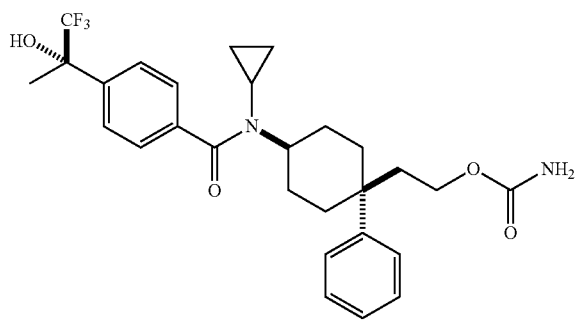
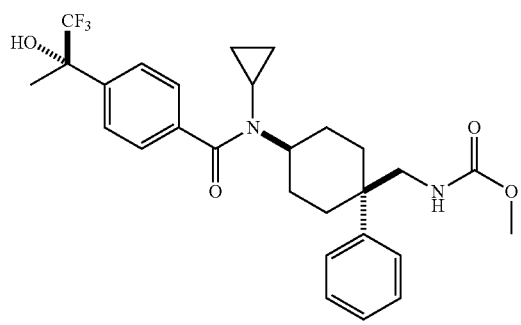
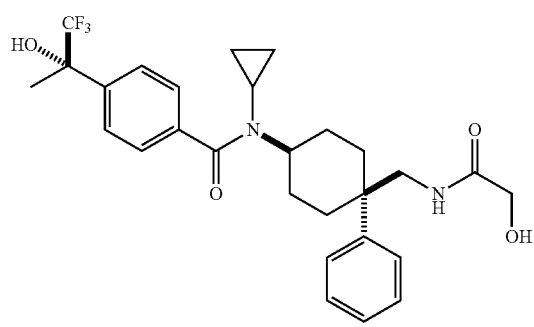
182
-continued
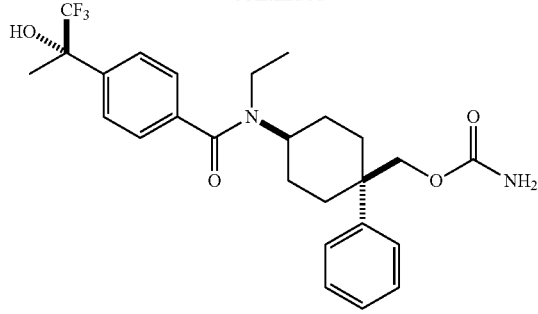
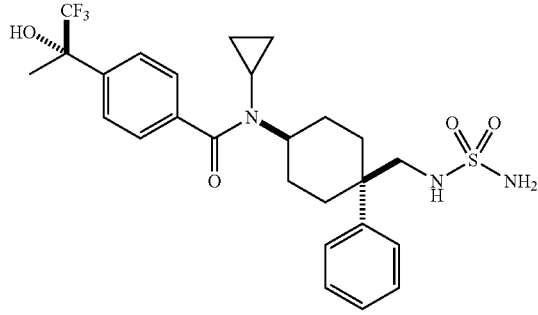
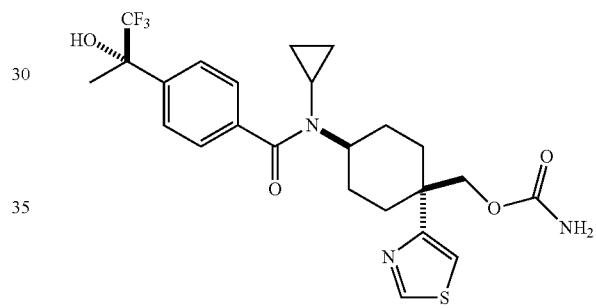
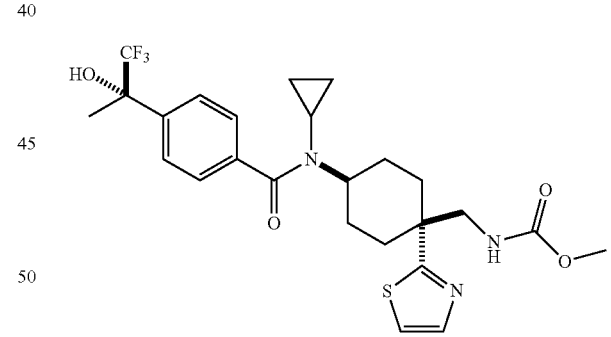
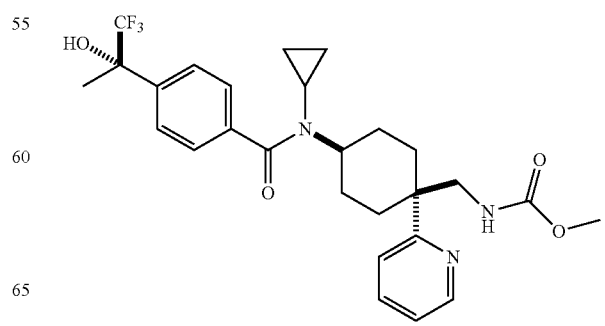

-continued
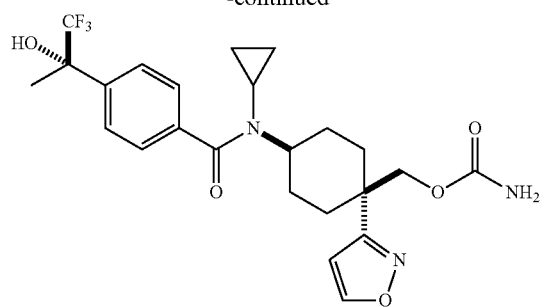
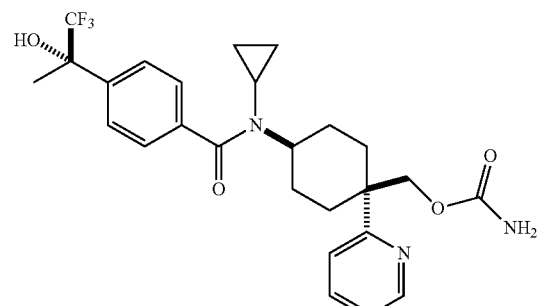
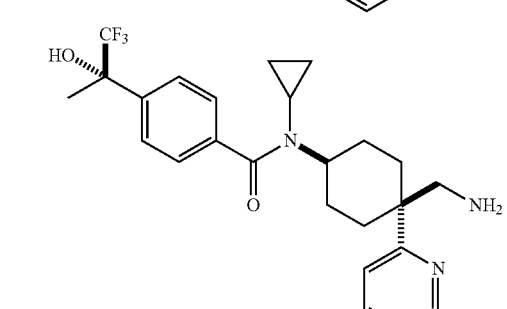
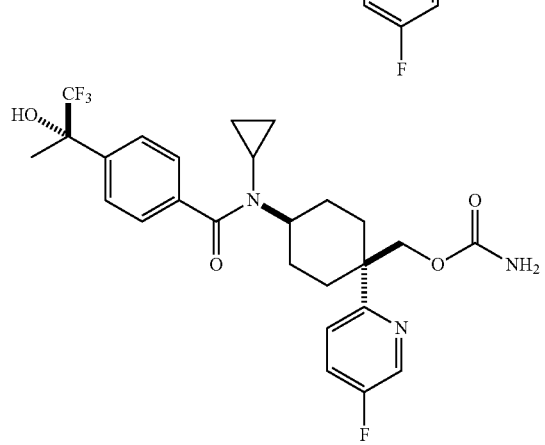
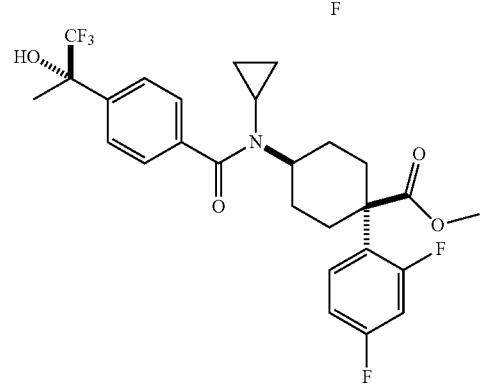
-continued
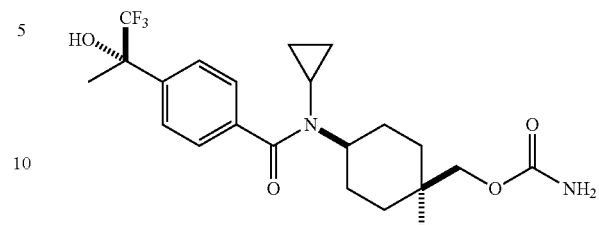
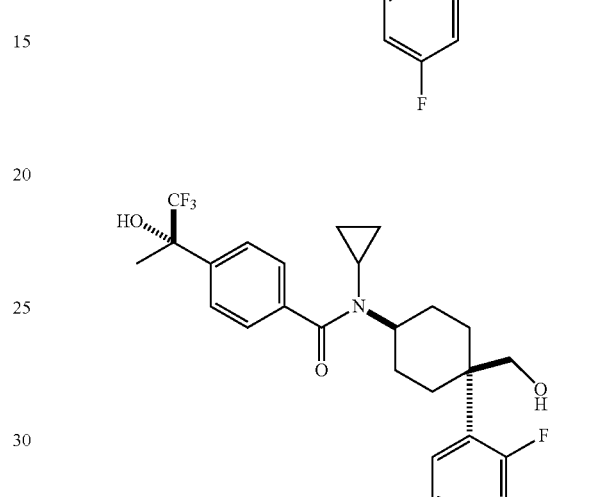
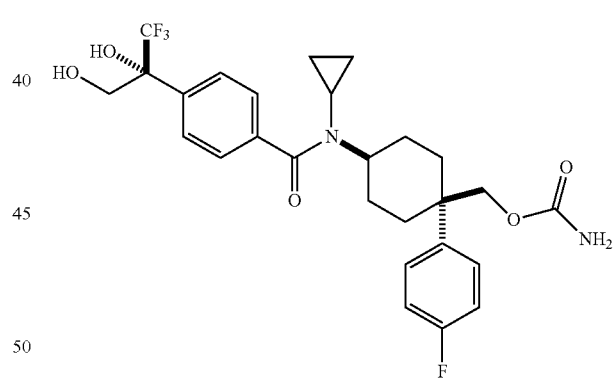
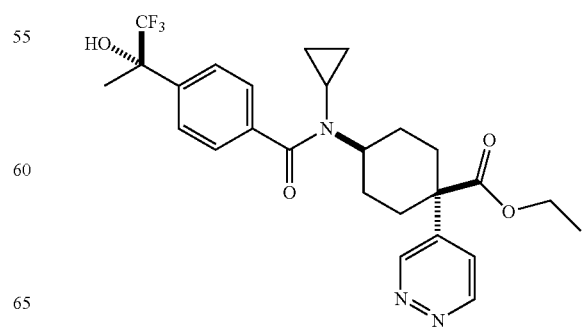

-continued
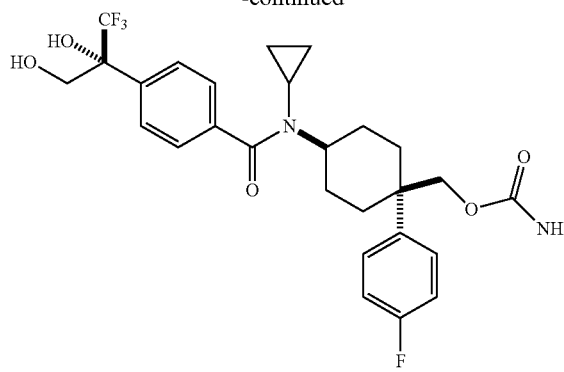
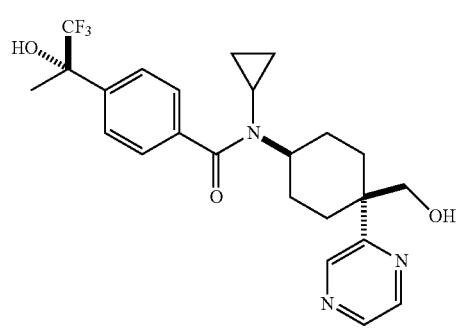
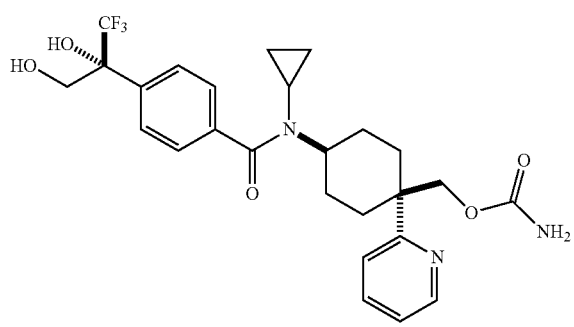
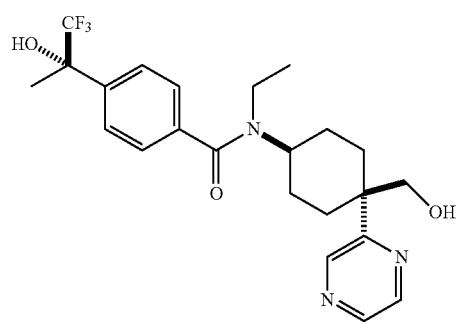
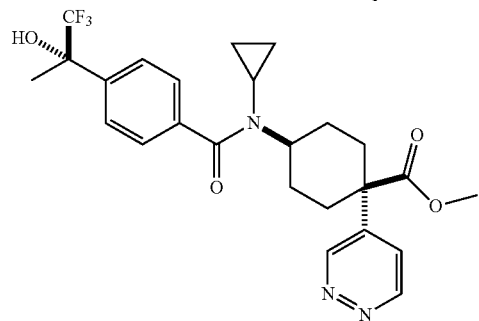
-continued
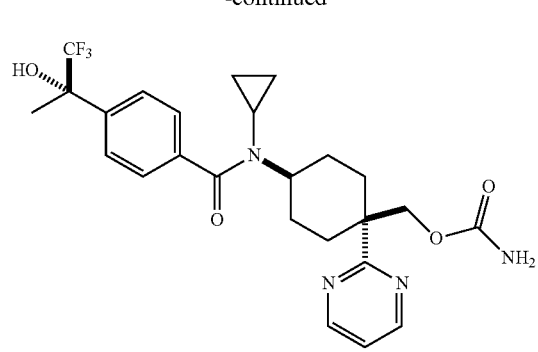
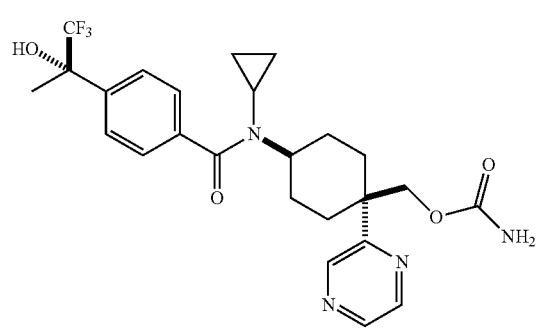
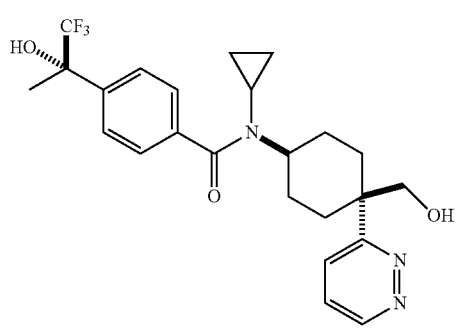
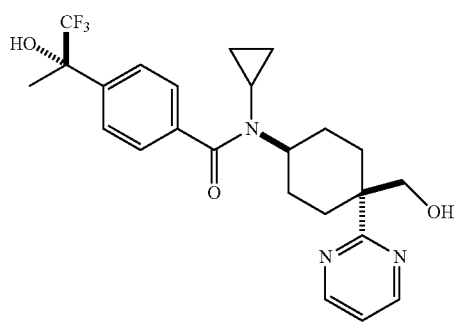
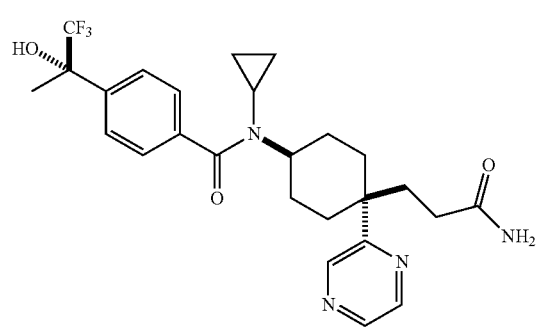

-continued

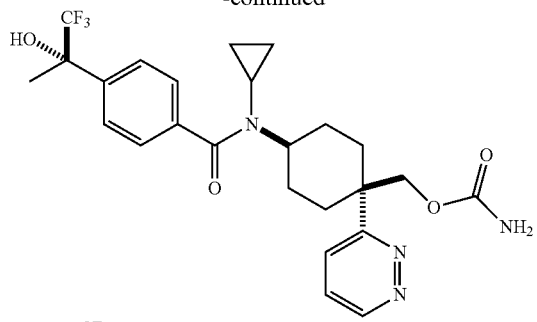

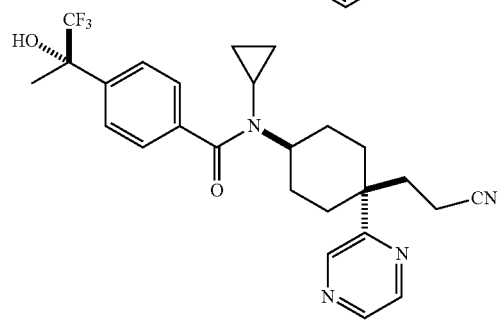

or a pharmaceutically acceptable salt, solvate, stereoisomer or prodrug thereof.

14. The compound according to claim 13, which is

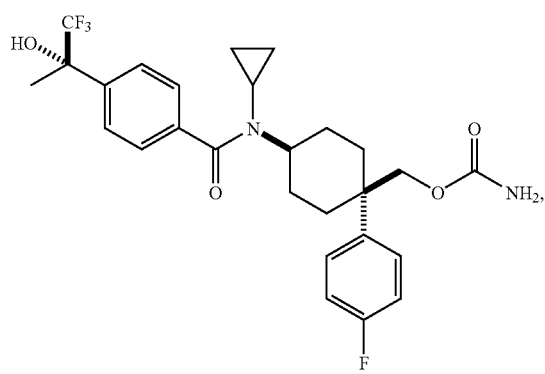

or a pharmaceutically acceptable salt, solvate, stereoisomer or prodrug thereof.

15. The compound according to claim 13, which is

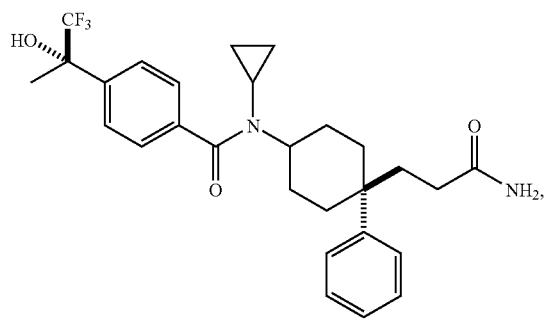

or a pharmaceutically acceptable salt, solvate, stereoisomer or prodrug thereof.

16. The compound according to claim 13, which is

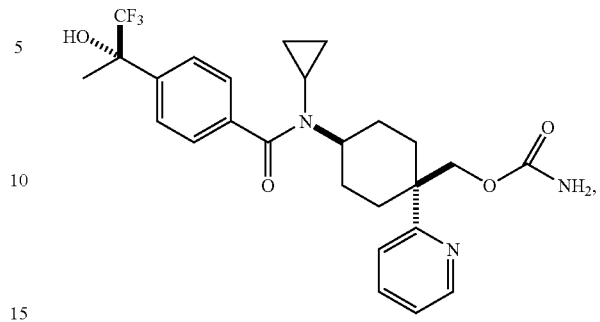

or a pharmaceutically acceptable salt, solvate, stereoisomer or prodrug thereof.

17. The compound according to claim 13, which is

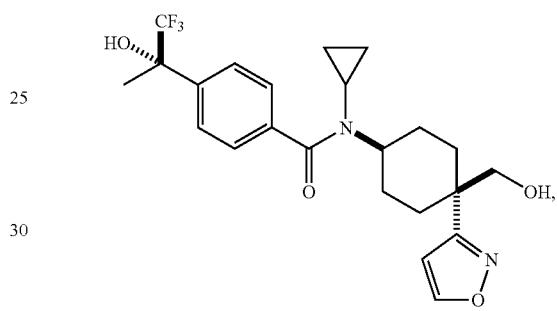

or a pharmaceutically acceptable salt, solvate, stereoisomer or prodrug thereof.

18. The compound according to claim 13, which is

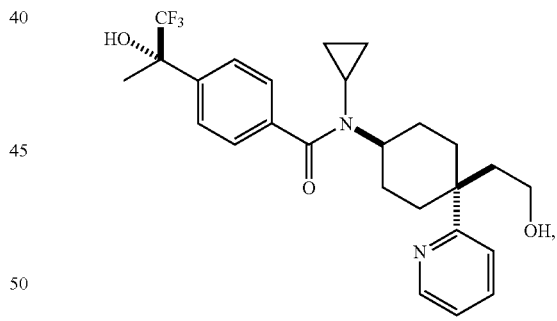

or a pharmaceutically acceptable salt, solvate, stereoisomer or prodrug thereof.

19. A pharmaceutical composition comprising the compound of claim 13, and a pharmaceutically acceptable carrier.

20. A pharmaceutical composition comprising the compound of claim 13, and an additional therapeutic agent.

21. A pharmaceutical composition of claim 20, wherein the additional therapeutic agent is useful for treating a condition or disorder selected from the group consisting of diabetes, syndrome X, obesity, polycystic ovarian disease, an eating disorder, craniopharyngioma, Prader-Willi syndrome, Frohlich's syndrome, hyperlipidemia, dyslipidemia, hypercholesterolemia, hypertriglyceridemia, low HDL levels, high HDL levels, hyperglycemia, insulin resistance, hyperinsulinemia, Cushing's syndrome, hypertension, atherosclerosis, vascular restenosis, retinopathy, nephropathy, neurodegenerative disease, neuropathy, muscle wasting, cognitive disorders, dementia, depression, psoriasis, glaucoma, osteoporosis, a viral infection, an inflammatory disorder and an immune disorder.

22. A method for treating a condition or disorder selected from the group consisting of diabetes, syndrome X, obesity, Cushing's syndrome, and atherosclerosis, comprising administering to a patient in need thereof a therapeutically effective amount of a compound of claim 13.

23. The method of claim 22, wherein the condition or disorder is diabetes or obesity.

\* \* \* \* \*